United States Patent
Adam et al.

(10) Patent No.: US 6,949,542 B2
(45) Date of Patent: Sep. 27, 2005

(54) DIHYDRO-BENZO[B][1,4]DIAZEPIN-2-ONE DERIVATIVES

(75) Inventors: Geo Adam, Schopfheim (DE); Erwin Goetschi, Reinach (CH); Juergen Wichmann, Steinen (DE); Thomas Johannes Woltering, Weil am Rhein (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/350,713

(22) Filed: Jan. 24, 2003

(65) Prior Publication Data
US 2003/0166639 A1 Sep. 4, 2003

(30) Foreign Application Priority Data

Feb. 6, 2002 (EP) ............................................. 02002012

(51) Int. Cl.⁷ ..................... C07D 243/12; C07D 409/04; C07D 417/04; A61K 31/55; A61P 25/18
(52) U.S. Cl. ........................................ 514/221; 540/517
(58) Field of Search ........................... 540/517; 514/221

(56) References Cited

U.S. PATENT DOCUMENTS 5,008,263 A * 4/1991 Cooper et al. .............. 514/220

FOREIGN PATENT DOCUMENTS

| WO | WO 01 29011 | 4/2001 |
|---|---|---|
| WO | WO 01 29012 | 4/2001 |

* cited by examiner

Primary Examiner—Bruck Kifle
(74) Attorney, Agent, or Firm—George W. Johnston; Patricia S. Rocha-Tramaloni

(57) ABSTRACT

This invention relates to dihydro-benzo[b][1,4]diazepin-2-one derivatives of the formula

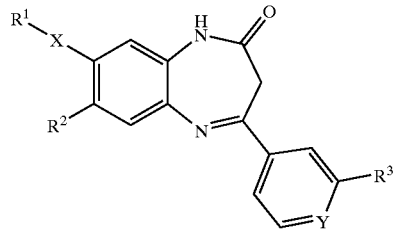

I wherein $R^1$, $R^2$, X and Y are as defined in the specification and $R^3$ is a six-membered aromatic heterocycle containing 1 to 3 nitrogen atoms or a pyridine-N-oxide as further defined in the specification. The invention further relates to medicaments containing these compounds, a process for their preparation as well as their use for preparation of medicaments for the treatment or prevention of acute and/or chronic neurological disorders.

32 Claims, No Drawings

DIHYDRO-BENZO[B][1,4]DIAZEPIN-2-ONE DERIVATIVES

FIELD OF THE INVENTION

The present invention relates dihydro-benzo[b][1,4]diazepin-2-one derivatives of the formula

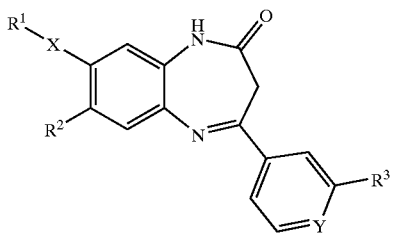

and their pharmaceutically acceptable addition salts.

BACKGROUND OF THE INVENTION

In the central nervous system (CNS) the transmission of stimuli takes place by the interaction of a neurotransmitter, which is sent out by a neuron, with a neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

SUMMARY OF THE INVENTION

It has surprisingly been found that the compounds of formula I are metabotropic glutamate receptor antagonists. Compounds of formula I are distinguished by valuable therapeutic properties.

Formula I is a dihydro-benzo[b][1,4]diazepin-2-one derivative as follows:

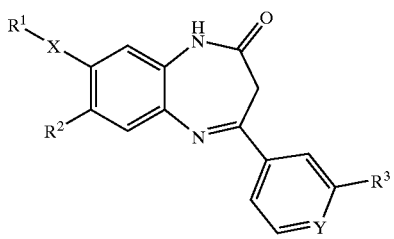

wherein
X is a single bond or an ethynediyl group; and wherein
in case X is a single bond,
$R^1$ is hydrogen,
  cyano,
  halogen,
  lower alkyl,
  lower alkoxy,
  fluoro-lower alkyl,
  fluoro-lower alkoxy,
  pyrrol-1-yl, or
  phenyl, which is unsubstituted or substituted by one or two substituents selected from the group consisting of halogen, lower alkyl or fluoro-lower alkyl;
or in case X is an ethynediyl group,
$R^1$ is phenyl, which is unsubstituted or substituted by one or two substituents selected from the group consisting of halogen, lower alkyl or fluoro-lower alkyl;
and wherein
$R^2$ is hydrogen,
  lower alkyl,
  lower alkenyl
  lower alkoxy,
  halogen,
  —NR'R",
  pyrrolidin-1-yl,
  piperidin-1-yl,
  morpholine-4-yl,
  fluoro-lower alkyl,
  fluoro-lower alkoxy, or
  lower alkoxy-(ethoxy)$_m$;
m is 1,2,3 or 4;
R' is hydrogen, lower alkyl or $C_3$–$C_6$-cycloalkyl;
R" is hydrogen, lower alkyl or $C_3$–$C_6$-cycloalkyl;
Y is —CH= or =N—;
$R^3$ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R",—(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy, whereby R' and R" have the meaning specified above;
n is 0, 1, 2, 3 or 4;

and their pharmaceutically acceptable addition salts.

The present invention provides for compounds of formula I and their pharmaceutically acceptable salts per se and as pharmaceutically active substances, their manufacture, medicaments based on a compound in accordance with the invention and their production, as well as the use of the compounds in accordance with the invention in the control or prevention of illnesses of the aforementioned kind, and, respectively, for the production of corresponding medicaments.

The compounds of formula I can also be used in form of their prodrugs. Examples are esters, N-oxides, phosphate esters, glycoamide esters, glyceride conjugates and the like. The prodrugs may add to the value of the present compounds in absorption, pharmacokinetics in distribution and transport to the brain.

The invention includes all tautomeric forms of the compounds of the invention.

Preferred compounds of formula I in the scope of the present invention are those in which X is a single bond. Further preferred are compounds of formula I, in which X is a single bond and Y is —CH═.

Preferred compounds are those in which $R^3$ is pyridyl, which is unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —$(CH_2)_n$—C(O)—OR", —$(CH_2)_n$—C(O)—NR'R", —$(CH_2)_n$—$SO_2$—NR'R", —$(CH_2)_n$—$C(NH_2)$═NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and R' and R" are independently from each other selected from hydrogen, lower alkyl or $C_3$–$C_6$-cycloalkyl. A pyridyl residue substituted by one or two lower alkyl groups is especially preferred.

A preferred subgroup of these compounds of formula I are those, wherein $R^1$ is hydrogen, halogen, lower alkyl or fluoro-lower alkyl.

Especially preferred are compounds of formula I wherein $R^3$ is pyridyl as defined above and wherein $R^1$ is hydrogen or lower alkyl.

The following compounds are examples thereof:

8-methyl-4-(3-pyridin-3-yl-phenyl)-7-trifluoromethyl-1,3-dihydro-benzo[b][1,4]diazepin-2-one, 8-methyl-4-[3-(2-methyl-pyridin-4-yl)-phenyl]-7-trifluoromethyl-1,3-dihydro benzo[b][1,4]diazepin-2-one, 4-(3-pyridin-3-yl-phenyl)-7-(2,2,2-trifluoro-ethoxy)-1,3-dihydro-benzo[b][1,4]diazepin-2-one, or 4-[3-(2,6-dimethyl-pyridin-4-yl)-phenyl]-8-methyl-7-trifluoromethyl-1,3-dihydro benzo [b][1,4]diazepin-2-one.

Further preferred are compounds of formula I, wherein $R^3$ is pyridyl as defined above and wherein $R^1$ is halogen.

Examples of such compounds are the following:

7,8-dichloro-4-(3-pyridin-3-yl-phenyl)-1,3-dihydro-benzo[b][1,4]diazepin-2-one, 8-chloro-4-(3-pyridin-4-yl-phenyl)-1,3-dihydro-benzo[b][1,4]diazepin-2-one, 7,8-dichloro-4-(3-pyridin-4-yl-phenyl)-1,3-dihydro-benzo[b][1,4]diazepin-2-one, 8-chloro-7-methyl-4-(3-pyridin-3-yl-phenyl)-1,3-dihydro-benzo[b][1,4]diazepin-2-one, 8-chloro-4-(3-pyridin-3-yl-phenyl)-1,3-dihydro-benzo[b][1,4]diazepin-2-one, 8-chloro-4-[3-(6-methyl-pyridin-3-yl)-phenyl]-1,3-dihydro-benzo[b][1,4]diazepin-2-one, 8-chloro-4-[3-(2-methyl-pyridin-3-yl)-phenyl]-1,3-dihydro-benzo[b][1,4]diazepin-2-one, 8-chloro-7-methyl-4-(3-pyridin-4-yl-phenyl)-1,3-dihydro-benzo[b][1,4]diazepin-2-one, 7,8-dichloro-4-[3-(2-methyl-pyridin-4-yl)-phenyl]-1,3-dihydro-benzo[b][1,4]diazepin-2-one, 8-chloro-7-methyl-4-[3-(2-methyl-pyridin-4-yl)-phenyl]-1,3-dihydro-benzo[b][1,4]diazepin-2-one, 8-fluoro-4-[3-(2-methyl-pyridin-4-yl)-phenyl]-1,3-dihydro-benzo[b][1,4]diazepin-2-one, 8-chloro-4-[3-(2-methyl-pyridin-4-yl)-phenyl]-7-trifluoromethyl-1,3-dihydro benzo[b][1,4]diazepin-2-one, 8-chloro-4-[3-(2,6-dimethyl-pyridin-4-yl)-phenyl]-7-methyl-1,3-dihydro-benzo[b][1,4]diazepin-2-one, or 7,8-dichloro-4-[3-(2,6-dimethyl-pyridin-4-yl)-phenyl]-1,3-dihydro-benzo[b][1,4]diazepin-2-one.

Also preferred are compounds of formula I wherein $R^3$ is pyridyl as defined above and wherein $R^1$ is trifluoromethyl.

The following compounds are examples thereof:

7-dimethylamino-4-(3-pyridin-3-yl-phenyl)-8-trifluoromethyl-1,3-dihydro-benzo[b][1,4]diazepin-2-one, 7-dimethylamino-4-(3-pyridin-4-yl-phenyl)-8-trifluoromethyl-1,3-dihydro-benzo[b][1,4]diazepin-2-one, 4-(3-pyridin-4-yl-phenyl)-8-trifluoromethyl-1,3-dihydro-benzo[b][1,4]diazepin-2-one, 4-(3-pyridin-3-yl-phenyl)-8-trifluoromethyl-1,3-dihydro-benzo[b][1,4]diazepin-2-one, 4-(3-pyridin-3-yl-phenyl)-7-(2,2,2-trifluoro-ethoxy)-8-trifluoromethyl-1,3-dihydro-benzo[b][1,4]diazepin-2-one, 7-ethoxy-4-(3-pyridin-4-yl-phenyl)-8-trifluoromethyl-1,3-dihydro-benzo[b][1,4]diazepin-2-one, 4-(3-pyridin-4-yl-phenyl)-7-(2,2,2-trifluoro-ethoxy)-8-trifluoromethyl-1,3-dihydro-benzo[b][1,4]diazepin-2-one, 7-methyl-4-(3-pyridin-4-yl-phenyl)-8-trifluoromethyl-1,3-dihydro-benzo[b][1,4]diazepin-2-one, 8-methyl-4-(3-pyridin-4-yl-phenyl)-7-trifluoromethyl-1,3-dihydro-benzo[b][1,4]diazepin-2-one, 7-chloro-4-(3-pyridin-4-yl-phenyl)-8-trifluoromethyl-1,3-dihydro-benzo[b][1,4]diazepin-2-one, 7-methyl-4-[3-(2-methyl-pyridin-4-yl)-phenyl]-8-trifluoromethyl-1,3-dihydro benzo[b][1,4]diazepin-2-one, 4-[3-(2-methyl-pyridin-4-yl)-phenyl]-8-trifluoromethyl-1,3-dihydro benzo[b][1,4]diazepin-2-one, 7-dimethylamino-4-[3-(2-methyl-pyridin-4-yl)-phenyl]-8-trifluoromethyl-1,3-dihydro benzo[b][1,4]diazepin-2-one, 4-[3-(2,6-dimethyl-pyridin-4-yl)-phenyl]-7-methyl-8-trifluoromethyl-1,3-dihydro benzo[b][1,4]diazepin-2-one, 4-[3-(2,6-dimethyl-pyridin-4-yl)-phenyl]-8-trifluoromethyl-1,3-dihydro benzo[b][1,4]diazepin-2-one, 7-chloro-4-[3-(2,6-dimethyl-pyridin-4-yl)-phenyl]-8-trifluoromethyl-1,3-dihydro benzo[b][1,4]diazepin-2-one, 4-[3-(2,6-dimethyl-pyridin-4-yl)-phenyl]-7-(2,2,2-trifluoroethoxy)-8-trifluoromethyl-1,3-dihydro-benzo[b][1,4]diazepin-2-one, 4-[3-(2,6-dimethyl-pyridin-4-yl)-phenyl]-7-ethoxy-8-trifluoromethyl-1,3-dihydro-benzo[b][1,4]diazepin-2-one, 4-[3-(2-ethyl-pyridin-4-yl)-phenyl]-7-methyl-8-trifluoromethyl-1,3-dihydro benzo[b][1,4]diazepin-2-one, 4-[3-(6-cyclopropyl-pyridin-3-yl)-phenyl]-8-trifluoromethyl-1,3-dihydro-benzo[b][1,4]diazepin-2-one, 7-methyl-4-(3-pyridin-3-yl-phenyl)-8-trifluoromethyl-1,3-dihydro-benzo[b][1,4]diazepin-2-one, 7-methoxy-4-(3-pyridin-3-yl-phenyl)-8-trifluoromethyl-1, 3-dihydro-benzo[b][1,4]diazepin-2-one, 7-ethoxy-4-(3-pyridin-3-yl-phenyl)-8-trifluoromethyl-1,3-dihydro-benzo[b][1,4]diazepin-2-one, 7-cyclopropylmethoxy-4-[3-(2-methyl-pyridin-4-yl)-phenyl]-8-trifluoromethyl-1,3-dihydro-benzo[b][1,4]diazepin-2-one, 7-ethyl-4-[3-(2-methyl-pyridin-4-yl)-phenyl]-8-trifluoromethyl-1,3-dihydro-benzo[b][1,4]diazepin-2-one, 4-[3-(2,6-dimethyl-pyridin-4-yl)-phenyl]-7-ethyl-8-trifluoromethyl-1,3-dihydro-benzo[b][1,4]diazepin-2-one, 4-[3-(2-ethyl-6-methyl-pyridin-4-yl)-phenyl]-7-methyl-8-trifluoromethyl-1,3-dihydro-benzo[b][1,4]diazepin-2-one, or 4-[3-(2-hydroxymethyl-pyridin-4-yl)-phenyl]-7-methyl-8-trifluoromethyl-1,3-dihydro benzo[b][1,4]diazepin-2-one.

Another preferred subgroup of compounds of formula I wherein $R^3$ is pyridyl as defined above, are those compounds, wherein $R^1$ is pyrrol-1-yl or phenyl, which is unsubstituted or substituted by one or two substituents selected from the group consisting of halogen, lower alkyl or fluoro-lower alkyl.

The following compounds are examples thereof:

8-(2-fluoro-phenyl)-4-[3-(2-methyl-pyridin-3-yl)-phenyl]-1,3-dihydro-benzo[b][1,4]diazepin-2-one, 8-(2-fluoro-phenyl)-4-(3-pyridin-4-yl-phenyl)-1,3-dihydro-benzo[b][1,4]diazepin-2-one, 8-(2-fluoro-phenyl)-4-(3-pyridin-3-yl-phenyl)-1,3-dihydro-benzo[b][1,4]diazepin-2-one, or 8-(2-fluoro-phenyl)-4-[3-(2-methyl-pyridin-4-yl)-phenyl]-1,3-dihydro-benzo[b][1,4]diazepin-2-one.

Further preferred are compounds of formula I wherein $R^3$ is pyridyl as defined above, and wherein $R^1$ is fluoro-lower alkoxy.

An example of such a compound is 4-[3-(2-methyl-pyridin-4-yl)-phenyl]-8-trifluoromethoxy-1,3-dihydro-benzo[b][1,4]diazepin-2-one.

Further preferred compounds of formula I are those wherein $R^3$ is pyrazinyl, which is unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, C$_3$–C$_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and wherein R' and R" are independently from each other selected from hydrogen, lower alkyl or C$_3$–C$_6$-cycloalkyl.

Examples of such compounds are the following:

8-chloro-7-methyl-4-(3-pyrazin-2-yl-phenyl)-1,3-dihydro-benzo[b][1,4]diazepin-2-one, 7-methyl-4-(3-pyrazin-2-yl-phenyl)-8-trifluoromethyl-1,3-dihydro-benzo[b][1,4]diazepin-2-one, or 7-(methyl-propyl-amino)-4-(3-pyrazin-2-yl-phenyl)-8-trifluoromethyl-1,3-dihydro-benzo[b][1,4]diazepin-2-one.

Also preferred are compounds of formula I wherein $R^3$ is pyrimidinyl or pyridazinyl, which are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, C$_3$–C$_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and R' and R" are independently from each other selected from hydrogen, lower alkyl or C$_3$–C$_6$-cycloalkyl.

The following are examples of such compounds:

8-chloro-7-methyl-4-(3-pyridazin-4-yl-phenyl)-1,3-dihydro-benzo[b][1,4]diazepin-2-one, 7-methyl-4-(3-pyridazin-4-yl-phenyl)-8-trifluoromethyl-1, 3-dihydro-benzo[b][1,4]diazepin-2-one, 8-(2-fluoro-phenyl)-4-(3-pyrimidin-5-yl-phenyl)-1,3-dihydro-benzo[b][1,4]diazepin-2-one, or 4-[3-(6-methyl-pyrimidin-4-yl)-phenyl]-8-trifluoromethyl-1,3-dihydro-benzo[b][1,4]diazepin-2-one.

Further preferred are compounds of formula I wherein $R^3$ is a pyridine-N-oxide, which is unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, C$_3$–C$_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and R' and R" are independently from each other selected from hydrogen, lower alkyl or C$_3$–C$_6$-cycloalkyl.

Compounds of formula I wherein Y is —N=, are also preferred.

The following compounds are examples thereof:

4-[2,3']bipyridinyl-4-yl-7-methyl-8-trifluoromethyl-1,3-dihydro-benzo[b][1,4]diazepin-2-one, or 7-methyl-4-(2'-methyl-[2,4']bipyridinyl-4-yl)-8-trifluoromethyl-1,3-dihydro-benzo[b][1,4]diazepin-2-one.

Unless otherwise stated, the following terms used in the present description have the definitions given in the following. The term "lower alkyl" denotes straight-chain or branched saturated hydrocarbon residues with 1 to 7 carbon atoms, preferably with 1 to 4 carbon atoms, such as methyl, ethyl, n-propyl, i-propyl and the like.

The term "lower alkenyl" denotes straight-chain or branched unsaturated hydrocarbon residues with 2 to 7 carbon atoms, preferably with 2 to 4 carbon atoms, such as ethenyl or propenyl.

The term "lower alkoxy" denotes a lower alkyl residue in the sense of the foregoing definition bound via an oxygen atom. Examples of "lower alkoxy" residues include methoxy, ethoxy, isopropoxy and the like.

The term "halogen" embraces fluorine, chlorine, bromine and iodine.

The term "fluoro-lower alkyl" means a lower alkyl residue, wherein one or more hydrogen atoms are replaced by fluorine, for example trifluoromethyl. Accordingly, the term "fluoro-lower alkoxy" denotes a lower alkoxy residue as defined before, wherein one or more hydrogen atoms are replaced by fluorine.

"Lower alkoxy-(ethoxy)$_m$" (m is 1, 2, 3 or 4) denotes a lower alkoxy residue in the sense of the foregoing definition bound via 1 to 4 —CH$_2$—CH$_2$—O— groups, for example 2-methoxy-ethoxy.

The term "C$_3$–C$_6$-cycloalkyl" means a cycloalkyl group containing 3 to 6 carbon atoms, such as cyclopropyl, cyclobutyl, cyclopentyl or cyclohexyl.

The term "alkylthio" denotes a lower alkyl residue in the sense of the foregoing definition bound via a sulfur atom, for example methylsulfanyl.

"Carbamoyloxy" means the group —O—CO—NH$_2$.

The expression "six-membered aromatic heterocycle containing 1 to 3 nitrogen atoms" means a six-membered heteroaryl group selected from the group consisting of pyridine, pyridazine, pyrimidine, pyrazine and triazine.

"Pyridine-N-oxide" or "pyridine-1-oxide" means a compound having the following formula:

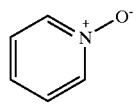

The term "pharmaceutically acceptable addition salt" refers to any salt derived from an inorganic or organic acid or base.

The compounds of formula I and their pharmaceutically acceptable salts can be manufactured according to a process, which comprises
reacting a compound of formula II

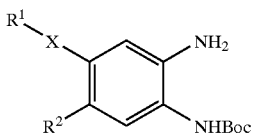

with a compound of formula IV or IVa

IV

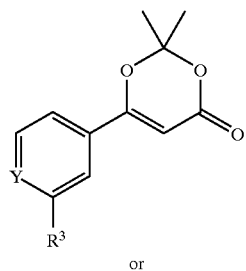

or

IVa wherein R is ethyl or butyl, to a compound of formula III

III which subsequently undergoes deprotection of the amino group and cyclization, to obtain a compound of formula

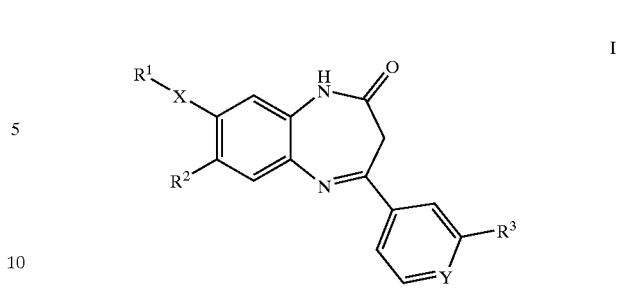

wherein R$^1$, R$^2$, R$^3$, X and Y are as described above, and, if desired, converting the compound obtained into a pharmaceutically acceptable acid addition salt.

DETAILED DESCRIPTION OF THE INVENTION

In more detail, according to scheme A, compounds of formula I, in which X, Y, R$^1$, R$^2$ and R$^3$ are as described above, can be prepared from compounds of formula II via an acylation-deprotection-cyclization sequence:

Scheme A

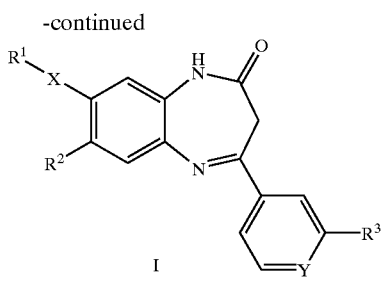

I

Reacting compounds of formula II with a dioxinone IV, in which Y and $R^3$ are as described above, in an inert solvent such as toluene or xylene at elevated temperatures, preferably between 80° C. and 160° C., gives rise to compounds of formula III.

Alternatively, compounds of formula III can also be prepared by, for example, reaction of a compound of formula II with a β-ketoester (formula IVa), in which Y and $R^3$ are as described above, using the same conditions as described for the reaction with the dioxinones. Afterwards, cleaving the BOC (tert-butoxycarbonyl) protecting group in compounds of formula III and concomitant cyclization of the deprotected compound yields the desired compounds of formula I. Any other suitable amino protecting group, such as Fmoc (9-fluorenylmethoxycarbonyl) or benzyloxycarbonyl (Z), can be alternatively used instead of the BOC group.

The deprotection-cyclization step can be carried out by treating the compounds of formula III with for example a Bronsted acid such as trifluoroacetic acid in an inert solvent such as dichloromethane (DCM). The reaction is preferably carried out at temperatures between 0° C. and 50° C. It may be advantageous to use also anisole or 1,3-dimethoxybenzene as a carbocation scavenger in the reaction mixture.

Scheme B

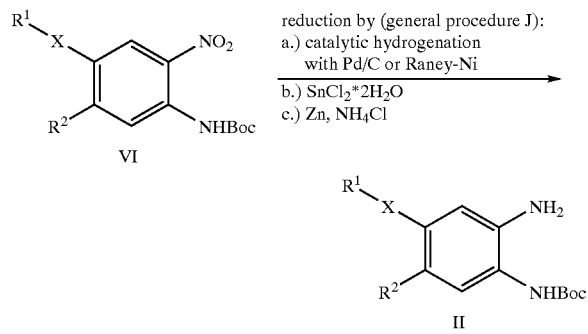

reduction by (general procedure J):
a.) catalytic hydrogenation with Pd/C or Raney-Ni
b.) $SnCl_2 \cdot 2H_2O$
c.) Zn, $NH_4Cl$ Compounds of formula II, in which $R^1$, $R^2$ and X are as described above can be prepared according to scheme B, by reducing the nitro group in compounds of formula VIa to the amino group. The reduction can for example be carried out using hydrogen gas in presence of a suitable catalyst like for example Raney-Nickel or Palladium on carbon.

Another possible reduction method is using stannous(II) chloride ($SnCl_2 \cdot 2H_2O$) in ethanol at temperatures between 70° C. and 80° C. (as described in *Tetrahedron Lett.* 1984, 25, 839), or alternatively in polar aprotic solvents, like DMF, DMA or NMP and the like, optionally in the presence of bases, like for example pyridine or triethylamine and the like, at temperatures between 0° C. and 80° C. Another suitable method is using zinc-powder in the presence of ammonium chloride in protic solvents like for example water or ethanol at temperatures between 20° C. and 80° C. The exact conditions for the respective compounds of formula II can be found in the experimental part.

The protection of the amino function can be applied to a number of commercially available starting materials or compounds synthesized by anyone skilled in the art to produce the corresponding 2-nitroanilines with the formula VI, in which X is a single bond and $R^1$ is as described above.

Scheme C

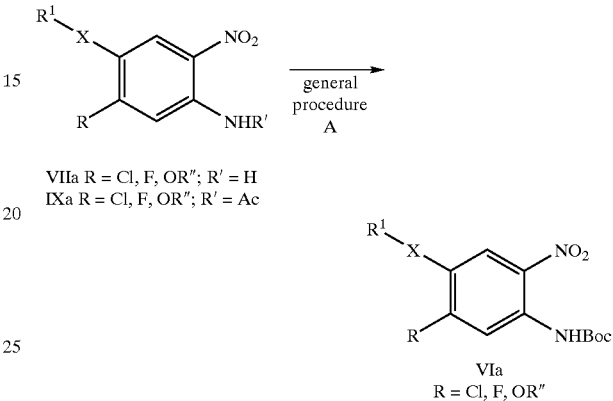

VIIa R = Cl, F, OR″; R′ = H
IXa R = Cl, F, OR″; R′ = Ac

VIa
R = Cl, F, OR″

R′ = H: GP A, method a: diphosgene, EtOAc, 77° C.; then t-BuOH
R′ = H: GP A, method b: $Boc_2O$, $Cs_2CO_3$, 2-butanone, 52° C.
R′ = H: GP A, method c: i) $Boc_2O$, DMAP, THF; ii) TFA, DCM, 0° C.
R′ = Ac: GP A, method d: i) $Boc_2O$, DMAP, THF; ii) $NH_4OH$, THF As described in scheme C, compounds of the formula VIa, in which $R^1$ is as described above, R is chloro, fluoro or substituted oxygen and R′ is hydrogen, can be prepared by protection of the amino group of compounds of the formula VIIa, in which $R^1$ is as described above, R is chloro, fluoro or substituted oxygen and R′ is hydrogen, with a tert-butoxycarbonyl-group (BOC). One possibility for the protection of the amino function is reacting compounds of formula VIIa with di-tert-butyl-carbonate in the presence of a base such as cesium carbonate. The reaction can be carried out in polar solvents such as acetone or butanone and the like at temperatures between 20° C. and 80° C.

Alternatively, the protection of the amino group can be achieved by preparing the intermediate isocyanate by treatment of compounds of the formula VIIa, in which $R^1$ is as described above, R is chloro, fluoro or substituted oxygen and R′ is hydrogen, with diphosgene, preferably in aprotic solvents such as EtOAc or 1,4-dioxane at temperatures from 0° C. to 100° C., and subsequent treatment of the isocyanate with tert-butanol in solvents such as dichloromethane or 1,2-dichloroethane and the like at temperatures between 20° C. and 85° C. to give the desired compounds of formula VIa.

Another suitable method to achieve this protection step is the intermediate formation of a di-BOC compound by treatment of compounds of the formula VIIa, in which $R^1$ is as described above, R is chloro, fluoro or substituted oxygen and R′ is hydrogen, with di-tert-butyl-carbonate in the presence of DMAP in an aprotic solvent such as tetrahydrofuran and the like, followed by selective removal of a single BOC-group by treatment with a Bronsted-acid, like TFA, in aprotic solvents such as dichloro-methane, chloroform or 1,2-dichloroethane at temperatures between 0° C. and 20° C. to give the desired compounds of formula VIa.

Yet another suitable method to produce compounds of formula IXa is the intermediate formation of a N-Ac-BOC compound by treatment of compounds of the formula VIIa, in which R¹ is as described above, R is chloro or fluoro and R' is acetyl, with di-tert-butyl-carbonate in the presence of DMAP in an aprotic solvent such as tetrahydrofuran and the like, followed by selective removal of a single BOC-group by treatment with a Brønsted-base, like aqueous ammonia (NH₄OH), in aprotic solvents such as tetrahydrofuran, diethylether or 1,4-dioxane and the like, at temperatures between 0° C. and 20° C. to give the desired compounds of formula VIa.

Apparently, the protection of the amino function as shown in scheme C can be applied to a number of commercially available starting materials or compounds synthesized by standard transformations [e.g. nitration followed by selective ammonolysis of the halide in ortho-position to the newly introduced nitro-group as described in *J. Med. Chem.* 1994, 37, 467; or ortho-nitration of acetanilide-compounds followed by deacetylation with for example aqueous potassium hydroxide solution or aqueous hydrochloric acid as described in *Org. Synth.* 1945, 25, 78 or in *J. Med. Chem.* 1985, 28, 1387] known to anyone skilled in the art to produce the corresponding 2-nitroanilines with the formula VIIa, in which R¹ is as described above, R is chloro or fluoro and R' is hydrogen, or 2-nitroacetanilides with the formula IXa, in which R¹ is as described above, R is chloro or fluoro and R' is acetyl. The exact conditions for the respective compounds used in this invention can be found in the experimental part.

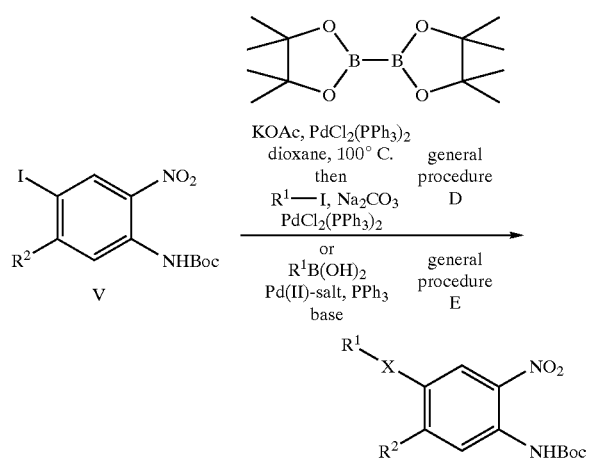

According to scheme D, compounds of formula II in which R¹ is phenyl optionally substituted as described above for compounds where X is a single bond and R² is as described above, can be prepared by different routes depending on the nature of R¹ from the iodo-compounds of formula V, in which R² is as described above. As shown in scheme D, the key step is a coupling reaction of Suzuki-type to produce compounds of the formula VIb.

Compounds of formula V, in which R² is as described above, can be prepared by different routes depending on the individual residue R². For example, a compound of formula V wherein R² is Cl, can be prepared from the commercially available 5-chloro-2-nitroaniline by iodination using iodine monochloride in acetic acid in the presence of sodium acetate at temperatures between 20° C. and 80° C. to give 5-chloro-4-iodo-2-nitroaniline, which in turn can be protected to yield a compound of formula V wherein R² is Cl.

According to scheme E, compounds of formula VIIb, in which R¹ is pyrrol-1-yl, X is a single bond and R is chloride, can be prepared from known 5-chloro-2-nitro-1,4-phenylenediamine [CAS-No. 26196-45-2] by selective condensation of the 4-amino-group with a suitable substituted 2,5-dimethoxy-tetrahydrofuran of the formula VIII, as described in *J. Heterocycl. Chem.* 1988, 25, 1003.

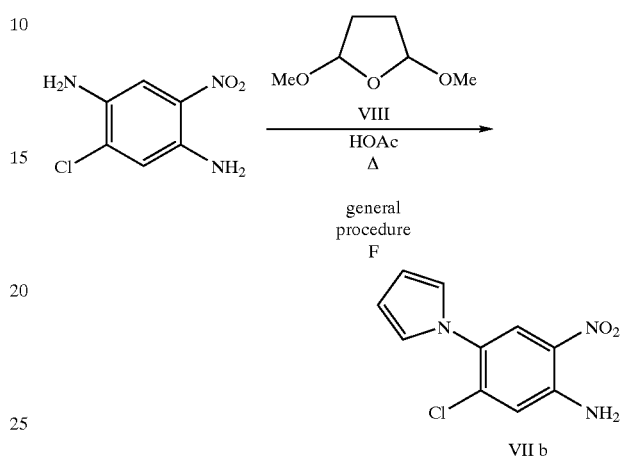

The reaction is preferably carried out in acidic media, for example acetic acid or propionic acid and the like, at temperatures between 40° C. to 100° C. The exact conditions for the respective compounds can be found in the experimental part.

As shown in scheme F, compounds of formula VIc, in which R² is —NR'R", wherein R' and R" are hydrogen, lower alkyl or C₃–C₆-cycloalkyl, or form a pyrrolidin-1-yl, piperidin-1-yl, or morpholine-4-yl, can be prepared from the intermediate compounds with the formula VIc—which individual synthesis can be found in the experimental part—by a nucleophilic substitution reaction with the respective amines in the presence of a suitable base.

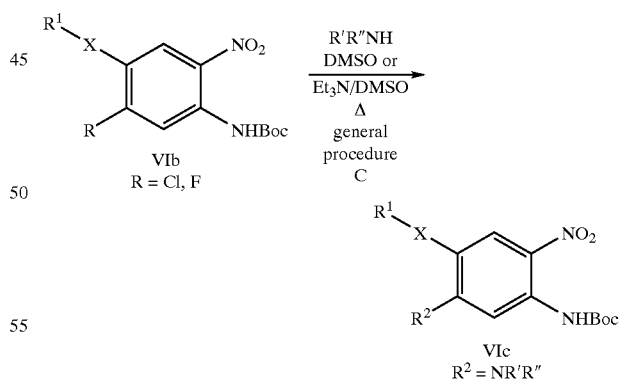

The reaction is preferably carried out in a polar, aprotic solvent such as dimethyl formamide, N-methyl-pyrrolidone or dimethyl sulfoxide and the like. The base can be selected from the sterically hindered amines such as triethylamine or Hünig's base, alkoxides such as sodium methoxide and tert-butoxide, or hydrides such as sodium hydride. The reaction can be performed at temperatures between 20° C. and 110° C., depending on the individual compounds to be synthesized.

Scheme G

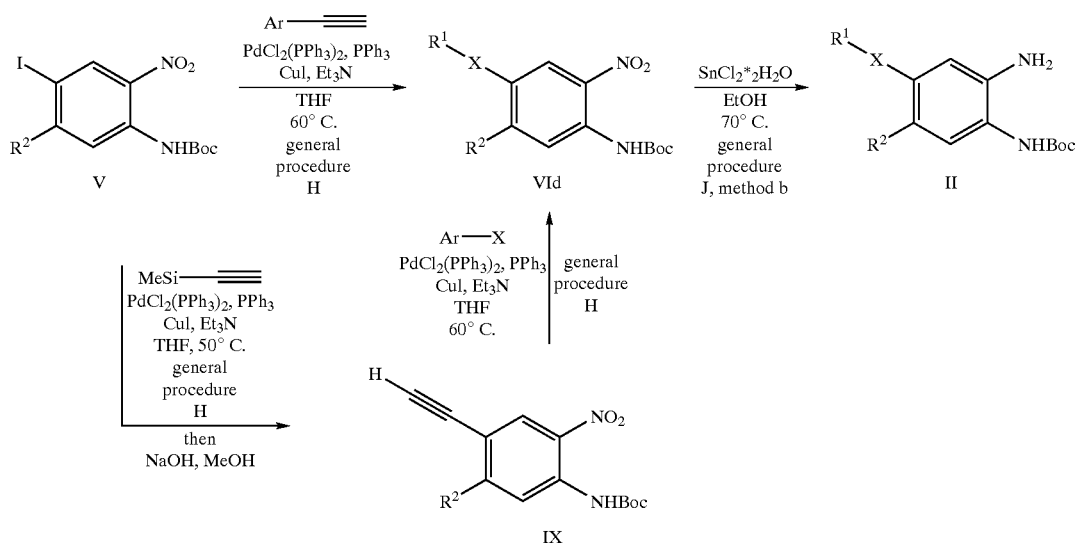

According to scheme G, compounds of formula II in which $R^1$ is as described above for compounds where X is an ethynediyl group can be prepared by different routes from the iodo-compounds V, depending on the nature of $R^1$ and $R^2$. As shown in scheme F, the transformation can for example be carried out a) by directly attaching the $R^1$-alkynediyl-substituent to a compound of formula V via a Sonogashira-type coupling to produce compounds of the formula VId followed by the reduction of the nitro group, or
b) by two stepwise Sonogashira-type couplings, in which first trimethylsilyl-acetylene is coupled to a compound of formula V to yield, after desilylation with sodium hydroxide in methanol, the intermediate X which then can be transformed via a second Sonogashira-type coupling with the appropriate reactant $R^1$-I, $R^1$—Br or $R^1$—$OSO_2CF_3$ into compounds of the formula VId and reduction of the nitro group leads to the desired compounds of formula II. The exact conditions for the respective compounds can be found in the experimental part.

Scheme H

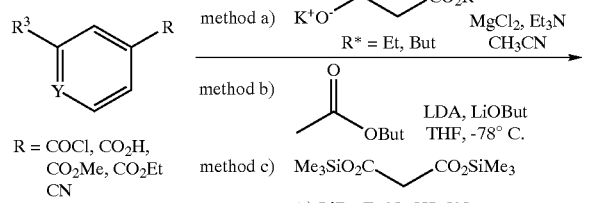

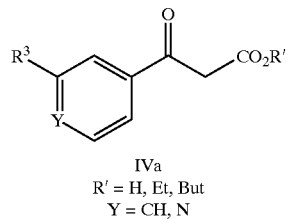

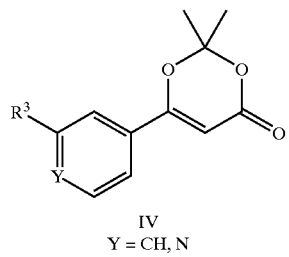

According to Scheme H, the dioxinones and β-keto esters building blocks with the formula IV and IVa can be prepared by methods known to someone skilled in the art from the corresponding carboxylic acid derivatives $R^3$—R, i.e. free acids, methyl or ethyl esters, acid chlorides and nitriles. The exact conditions for the corresponding compounds can be found in the experimental part.

The pharmaceutically acceptable addition salts can be manufactured readily according to methods known per se and taking into consideration the nature of the compound to be converted into a salt. Inorganic or organic acids such as, for example, hydrochloric acid, hydrobromic acid, sulfuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I.

The compounds of formula I and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycaemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia and depression.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g., in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain further therapeutically valuable substances.

As mentioned earlier, medicaments containing a compound of formula I or a pharmaceutically acceptable salt thereof and a therapeutically inert excipient are also an embodiment of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being weighing 70 kg accordingly lies between 0.7–1400 mg per day, preferably between 7 and 700 mg per day.

The present invention relates also to the use of compounds of formula I and of pharmaceutically acceptable salts thereof for the production of medicaments, especially for the control or prevention of acute and/or chronic neurological disorders of the aforementioned kind.

The compounds of the present invention are group II mGlu receptor antagonists. The compounds show activities, as measured in the assay described below, of 0.060 $\mu$M or less, typically 0.025 $\mu$M or less, and ideally of 0.010 $\mu$M or less. In the table below are described some specific Ki values of preferred compounds.

| Compound | $K_i$ mGlu2 ($\mu$M) |
| --- | --- |
| 7,8-Dichloro-4-(3-pyridin-3-yl-phenyl)-1,3-dihydro-benzo[b][1,4]diazepin-2-one | 0.00135 |
| 7,8-Dichloro-4-(3-pyridin-4-yl-phenyl)-1,3-dihydro-benzo[b][1,4]diazepin-2-one | 0.0034 |
| 7-Dimethylamino-4-(3-pyridin-3-yl-phenyl)-8-trifluoromethyl-1,3-dihydro-benzo[b][1,4]diazepin-2-one | 0.0023 |
| 7-Dimethylamino-4-(3-pyridin-4-yl-phenyl)-8-trifluoromethyl-1,3-dihydro-benzo[b][1,4]diazepin-2-one | 0.006 |
| 7,8-Dichloro-4-(3-pyridin-2-yl-phenyl)-1,3-dihydro-benzo[b][1,4]diazepin-2-one | 0.0235 |
| 4-[3-(6-Methyl-pyridin-3-yl)-phenyl]-8-trifluoromethyl-1,3-dihyrdro-benzo[b][1,4]diazepin-2-one | 0.0055 |
| 8-(2-Fluoro-phenyl)-4-[3-(6-methyl-pyridin-3-yl)-phenyl]-1,3-dihydro-benzo[b][1,4]diazepin-2-one | 0.0039 |
| 7-Dimethylamino-4-[3-(2-methyl-pyridin-3-yl)-phenyl]-8-trifluoromethyl-1,3-dihydro-benzo[b][1,4]diazepin-2-one | 0.006 |
| 8-(2-Fluoro-phenyl)-4-[3-(6-methyl-pyridazin-3-yl)-phenyl]-1,3-dihydro-benzo[b][1,4]diazepin-2-one | 0.0165 |
| 8-Methyl-4-(3-pyridin-3-yl-phenyl)-7-trifluoromethyl-1,3-dihydro-benzo[b][1,4]diazepin-2-one | 0.0028 |
| 8-Chloro-4-(3-pyridin-3-yl-phenyl)-1,3-dihydro-benzo[b][1,4]diazepin-2-one | 0.002 |
| 7-Ethoxy-4-(3-pyridin-4-yl-phenyl)-8-trifluoromethyl-1,3-dihydro-benzo[b][1,4]diazepin-2-one | 0.00215 |
| 4-(3-Pyridin-4-yl-phenyl)-7-(2,2,2-trifluoro-ethoxy)-8-trifluoromethyl-1,3-dihydro-benzo[b][1,4]diazepin-2-one | 0.00155 |
| 8-(2-Fluoro-phenyl)-4-[3-(6-methoxy-pyridazin-3-yl)-phenyl]-1,3-dihydro-benzo[b][1,4]diazepin-2-one | 0.0245 |
| 7-Methoxy-4-(3-pyridin-2-yl-phenyl)-8-trifluoromethyl-1,3-dihydro-benzo[b][1,4]diazepin-2-one | 0.027 |
| 7-Dimethylamino-4-[3-(2,6-dimethyl-pyridin-3-yl)-phenyl]-8-trifluoromethyl-1,3-dihydro-benzo[b][1,4]diazepin-2-one | 0.0225 |
| 8-Chloro-7-methyl-4-(3-pyridazin-4-yl-phenyl)-1,3-dihydro-benzo[b][1,4]diazepin-2-one | 0.00935 |
| 4-(3-Pyridin-2-yl-phenyl)-8-pyrrol-1-yl-1,3-dihydro-benzo[b][1,4]diazepin-2-one | 0.0326 |
| 4-(3-Pyridin-3-yl-phenyl)-7-(2,2,2-trifluoro-ethoxy)-1,3-dihydro-benzo[b][1,4]diazepin-2-one | 0.0062 |
| 7-Isobutylamino-4-(3-pyridin-4-yl-phenyl)-8-trifluoromethyl-1,3-dihydro-benzo[b][1,4]diazepin-2-one | 0.019 |
| 8-Chloro-7-methyl-4-(3-pyridin-4-yl-phenyl)-1,3-dihydro-benzo[b][1,4]diazepin-2-one | 0.00155 |
| 8-(2-Fluoro-phenyl)-4-[3-(2-methyl-pyridin-4-yl)-phenyl]-1,3-dihydro-benzo[b][1,4]diazepin-2-one | 0.0018 |
| 8-Chloro-7-methyl-4-[3-(2-methyl-pyridin-4-yl)-phenyl]-1,3-dihydro-benzo[b][1,4]diazepin-2-one | 0.0027 |
| 7-Dimethylamino-4-[3-(2-methyl-pyridin-4-yl)-phenyl]-8-trifluoromethyl-1,3-dihydro benzo[b][1,4]diazepin-2-one | 0.00129 |
| 7-(Methyl-propyl-amino)-4-[3-(2-methyl-pyridin-4-yl)-phenyl]-8-trifluoromethyl-1,3-dihydro benzo[b][1,4]diazepin-2-one | 0.0055 |
| 7-Methyl-4-(3-pyrazin-2-yl-phenyl)-8-trifluoromethyl-1,3-dihydro-benzo[b][1,4]diazepin-2-one | 0.010 |

-continued

| Compound | $K_i$ mGlu2 ($\mu$M) |
|---|---|
| 7,8-Dichloro-4-(3-pyrimidin-5-yl-phenyl)-1,3-dihydro-benzo[b][1,4]diazepin-2-one | 0.0107 |
| 8-Chloro-7-methyl-4-(3-pyrimidin-5-yl-phenyl)-1,3-dihydro-benzo[b][1,4]diazepin-2-one | 0.008 |
| 8-(2-Fluoro-phenyl)-4-(3-pyrimidin-5-yl-phenyl)-1,3-dihydro-benzo[b][1,4]diazepin-2-one | 0.0062 |
| 4-(3-Pyrazin-2-yl-phenyl)-8-pyrrol-1-yl-1,3-dihydro-benzo[b][1,4]diazepin-2-one | 0.0055 |
| 7-Methyl-4-[3-(6-methyl-pyrazin-2-yl)-phenyl]-8-trifluoromethyl-1,3-dihydro-benzo[b][1,4]diazepin-2-one | 0.0031 |
| 4-[3-(2,5-Dimethyl-pyridin-4-yl)-phenyl]-7-(2,2,2-trifluoro-ethoxy)-8-trifluoromethyl-1,3-dihydro-benzo[b][1,4]diazepin-2-one | 0.0036 |
| 8-Chloro-4-[3-(5-ethyl-2-methyl-pyridin-4-yl)-phenyl]-7-methyl-1,3-dihydro-benzo[b][1,4]diazepin-2-one | 0.0045 |
| 7-Dimethylamino-4-[3-(6-methyl-pyridin-2-yl)-phenyl]-8-trifluoromethyl-1,3-dihydro-benzo[b][1,4]diazepin-2-one | 0.0188 |
| 4-[3-(6-Cyclopropyl-pyridin-3-yl)-phenyl]-7-(2,2,2-trifluoro-ethoxy)-1,3-dihydro-benzo[b][1,4]diazepin-2-one | 0.00605 |
| 4-(3-Pyridin-3-yl-phenyl)-8-(2,2,2-trifluoro-ethoxy)-1,3-dihydro-benzo[b][1,4]diazepin-2-one | 0.01 |
| 4-[3-(4-Oxo-7-trifluoromethyl-4,5-dihydro-3H-benzo[b][1,4]diazepin-2-yl)-phenyl]-pyridine-2-carbonitrile | 0.0237 |
| 4-{3-[8-(2-Methoxy-ethoxy)-4-oxo-7-trifluoromethyl-4,5-dihydro-3H-benzo[b][1,4]diazepin-2-yl]-phenyl}-pyridine-2-carbonitrile | 0.0128 |
| 4-[3-(6-Cyclopropyl-4-methyl-pyridin-3-yl)-phenyl]-7-methyl-8-trifluoromethyl-1,3-dihydro-benzo[b][1,4]diazepin-2-one | 0.01695 |
| 4-[2,3']Bipyridinyl-4-yl-7-methyl-8-trifluoromethyl-1,3-dihydro-benzo[b][1,4]diazepin-2-one | 0.005 |
| 7-Dimethylamino-4-[3-(2-methyl-pyrimidin-4-yl)-phenyl]-8-trifluoromethyl-1,3-dihydro-benzo[b][1,4]diazepin-2-one | 0.045 |
| 4-{3-[2-(2-Hydroxy-ethylamino)-6-methyl-pyrimidin-4-yl]-phenyl}-7-methyl-8-trifluoromethyl-1,3-dihydro-benzo[b][1,4]diazepin-2-one | 0.004 |
| 7-Dimethylamino-4-{3-[2-(2-methoxy-ethylamino)-6-methyl-pyrimidin-4-yl]-phenyl}-8-trifluoromethyl-1,3-dihydro-benzo[b][1,4]diazepin-2-one | 0.008 |
| 8-Chloro-7-methyl-4-[3-(6-methyl-2-morpholin-4-yl-pyrimidin-4-yl)-phenyl]-1,3-dihydro-benzo[b][1,4]diazepin-2-one | 0.012 |
| 4-[3-(1-Oxy-pyridin-3-yl)-phenyl]-7-(2,2,2-trifluoro-ethoxy)-8-trifluoromethyl-1,3-dihydro-benzo[b][1,4]diazepin-2-one | 0.0061 |
| 7-Ethoxy-4-[3-(2-methyl-1-oxy-pyridin-4-yl)-phenyl]-8-trifluoromethyl-1,3-dihydro-benzo[b][1,4]diazepin-2-one | 0.0265 |
| 7,8-Dichloro-4-[3-(2,6-dimethyl-1-oxy-pyridin-4-yl)-phenyl]-1,3-dihydro-benzo[b][1,4]diazepin-2-one | 0.0165 |
| 7-Methyl-4-[3-(2-morpholin-4-yl-pyridin-4-yl)-phenyl]-8-trifluoromethyl-1,3-dihydro-benzo[b][1,4]diazepin-2-one | 0.0145 |
| 4-[3-(2-Pyrrolidin-1-yl-pyridin-4-yl)-phenyl]-7-(2,2,2-trifluoro-ethoxy)-8-trifluoromethyl-1,3-dihydro-benzo[b][1,4]diazepin-2-one | 0.0079 |
| 8-Chloro-4-[3-(2,6-dimethyl-pyridin-4-yl)-phenyl]-7-(isobutyl-methyl-amino)-1,3-dihydro-benzo[b][1,4]diazepin-2-one | 0.00325 |

[$^3$H]-LY354740 Binding on mGlu2 Transfected CHO Cell Membranes

Transfection and Cell Culture cDNA encoding the rat mGlu2 receptor protein in pBluescript II was subcloned into the eukaryotic expression vector pcDNA I-amp from Invitrogen (NV Leek, The Netherlands). This vector construct (pcD1mGR2) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (2 mM final concentration) and 10% dialysed foetal calf serum from Gibco BRL (Basel, Switzerland). Selection was made in the presence of G-418 (1000 ug/ml final). Clones were identified by reverse transcription of 5 $\mu$g total RNA, followed by PCR using mGlu2 receptor specific primers 5'-atcactgcttgggtttctggcactg-3' and 5'-agcatcactgtgggtggcataggagc-3' in 60 mM Tris HCl (pH 10), 15 mM $(NH_4)_2SO_4$, 2 mM $MgCl_2$, 25 units/ml Taq Polymerase with 30 cycles annealing at 60° C. for 1 min., extention at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with the same buffer, and once with cold 20 mM HEPES-NaOH buffer containing 0.1 mM EDTA, (pH 7.4). Protein content was measured using the Pierce method (Socochim, Lausanne, Switzerland) using bovine serum albumin as standard.

[$^3$H]-LY354740 Binding

After thawing, the membranes were resuspended in cold 50 mM Tris-HCl buffer containing 2 mM $MgCl_2$ and 2 mM $CaCl_2$, (pH 7) (binding buffer). The final concentration of the membranes in the assays was 25 $\mu$g protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/C glass fiber filters and washed 5 times with cold binding buffer. Non specific binding was measured in the presence of 10 $\mu$M DCG IV. After transfer of the filters into plastic vials containing 10 ml of Ultima-gold scintillation fluid (Packard, Zürich, Switzerland), the radioactivity was measured by liquid scintillation in a Tri-Carb 2500 TR counter (Packard, Zürich, Switzerland).

Data Analysis

The inhibition curves were fitted with a four parameter logistic equation giving $IC_{50}$ values, and Hill coefficients.

EXAMPLES

General Procedure A

Preparation of (2-nitro-phenyl)-carbamic acid tert-butyl esters from 2-nitroanilines or 2-nitroacetanilides Method a (from 2-nitroanilines): To a solution of diphosgene (4.1 mL, 34.1 mmol) in EtOAc (40 mL) at 0° C. was added a solution of the 2-nitroaniline (45.5 mmol) in EtOAc (200–500 mL), and the mixture was heated to reflux for 18 h. The solvent was removed in vacuum to leave a brown solid, which was triturated with hot hexane (200 mL). The solid material was filtered off and the filtrate was concentrated under reduced pressure to leave the pure 2-nitrophenylisocyanate as a yellow solid. This material was refluxed in a mixture of excess tert-BuOH in $CH_2Cl_2$ for 2.5 h. Removal of the solvent left an orange solid which was purified by silica gel column chromatography with hexane/EtOAc to give the (2-nitro-phenyl)-carbamic acid tert-butyl ester as a yellow solid.

Method b (from 2-nitroanilines): To a mixture of the 2-nitroaniline (142 mmol) and cesium carbonate (55.5 g, 170 mmol) in 2-butanone (740 mL) was dropwise added a solution of $Boc_2O$ (37.8 g, 173 mmol) in 2-butanone (170 mL) and the resulting mixture was stirred at 50° C. to 80° C. until tlc indicated complete conversion. The solvent was removed in vacuum, the residue was treated with a mixture of H$_2$O (240 mL) and MeOH (240 mL) and extracted with hexane (3×500 mL). The combined hexane layer was washed with brine (200 mL) and all aqueous layers were reextracted with hexane (300 mL). All combined hexane layers were dried over MgSO$_4$, filtered and the solvent was removed in vacuum to give an orange solid, which was purified by silica gel column chromatography with hexane/EtOAc to give the (2-nitro-phenyl)-carbamic acid tert-butyl ester as a yellow solid.

Method c (from 2-nitroanilines): To a solution of the 2-nitroaniline (550 mmol) and DMAP (1.22 g, 10 mmol) in THF (1000 mL) at 23° C. was dropwise added within 70 min a solution of Boc$_2$O (246 g, 1128 mmol) in THF (500 mL) and stirring was continued at 23° C. for 75 min. The entire mixture was evaporated to dryness and dried at HV to leave a dark brown solid. This material was dissolved in DCM (1100 mL), cooled to 0° C. and TFA (84 mL, 1100 mmol) was added dropwise. The mixture was stirred at 0° C. for 2 h, poured into ice cold sat. NaHCO$_3$-solution, extracted with DCM, washed with brine and dried over MgSO$_4$. Removal of the solvent in vacuum left a dark brown solid which was coated on silica gel and purified by silica gel column chromatography with hexane/EtOAc to give the (2-nitro-phenyl)-carbamic acid tert-butyl ester as a yellow solid.

Method d (from 2-nitroacetanilides): To a solution of the 2-nitroacetanilide (100 mmol) and DMAP (122 mg, 1 mmol) in THF (100 mL) at 23° C. was dropwise added within 15 min a solution of Boc$_2$O (22.92 g, 105 mmol) in THF (100 mL) and stirring was continued at 23° C. until tlc indicated completed conversion. The entire mixture was evaporated to dryness and dried at HV to leave a yellow to dark brown solid. This material was dissolved in THF (200 mL) and 25% NH$_4$OH (77 mL, 500 mmol) was added dropwise. The mixture was stirred at 23° C. until tlc indicated complete conversion, poured into 1N HCl-solution, extracted with EtOAc, washed the organic layer with sat. NaHCO$_3$-solution and brine, dried over MgSO4. Removal of the solvent in vacuum left a yellow to brown solid which was generally pure enough for further transformation or—if necessary— coated on silica gel and purified by silica gel column chromatography with hexane/EtOAc to give the (2-nitro-phenyl)-carbamic acid tert-butyl ester as a yellow solid.

Example A1

(5-Chloro-2-nitro-4-trifluoromethyl-phenyl)-carbamic acid tert-butyl ester

The title compound was prepared via the di-Boc-compound from commercially available 5-chloro-2-nitro-4-trifluoromethyl-phenylamine [CAS-No. 35375-74-7] (22.61 g, 94 mmol) and Boc$_2$O (42.06 g, 193 mmol), followed by treatment with 2 eq. TFA in CH$_2$Cl$_2$ according to the general procedure A (method c). Obtained as a yellow solid (31.82 g, 99%).

MS (ISN) 339.1 [(M−H)$^-$] and 341 [(M+2−H)$^-$]; mp 113–115° C.

Example A2

(5-Fluoro-2-nitro-4-trifluoromethyl-phenyl)-carbamic acid tert-butyl ester

The title compound was prepared via the di-Boc-compound from 5-fluoro-2-nitro-4-trifluoromethyl-phenylamine [which was prepared from commercially available 4-amino-2-fluorobenzotrifluoride by acetylation with Ac$_2$O in toluene at 23° C., followed by nitration with 100% nitric acid from 10–23° C. and deacetylation with 2N NaOH in THF at 50° C.] (5.21 g, 23.2 mmol) and Boc$_2$O (10.63 g, 48.7 mmol). After treatment with 2 eq. TFA in CH$_2$Cl$_2$ according to the general procedure A (method c) (5-fluoro-2-nitro-4-trifluoromethyl-phenyl)-carbamic acid tert-butyl ester was obtained as a light yellow solid (6.33 g, 84%).

MS (ISN) 323 [(M−H)$^-$]; mp 104° C.

Example A3

(4-Fluoro-2-nitro-phenyl)-carbamic acid tert-butyl ester (4-Fluoro-2-nitro-phenyl)-carbamic acid tert-butyl ester was prepared via the di-Boc-compound from commercially available 4-fluoro-2-nitroaniline [CAS-No. 364-78-3] (20 g, 128 mmol) and Boc$_2$O (57.32 g, 263 mmol), followed by treatment with 2 eq. TFA in CH$_2$Cl$_2$ according to the general procedure A (method c). Obtained as a yellow solid (32.81 g, 99%).

MS (EI) 256 (M$^+$); mp 57° C.

Example A4

(2-Nitro-4-trifluoromethyl-phenyl)-carbamic acid tert-butyl ester

The title compound was prepared via the di-Boc-compound from commercially available 4-amino-3-nitrobenzotrifluoride [CAS-No. 400-98-6] (20.61 g, 100 mmol) and Boc$_2$O (44.07 g, 205 mmol), followed by treatment with 2 eq. TFA in CH$_2$Cl$_2$ according to the general procedure A (method c). Obtained as a yellow solid (30.2 g, 99%).

MS (ISN) 305.3 [(M−H)$^-$]; mp 72–76° C.

Example A5

(4-Chloro-2-nitro-phenyl)-carbamic acid tert-butyl ester

The title compound was prepared via the isocyanate from commercially available 4-chloro-2-nitro-phenylamine [CAS-No. 89-63-4] (5.0 g, 29 mmol) with diphosgene (1.75 mL, 14.5 mmol) in EtOAc (60 mL), followed by treatment with tert-BuOH (30 mL) in CH$_2$Cl$_2$ (60 mL) according to the general procedure A (method a). Obtained as a yellow solid (6.2 g, 76%).

MS (EI) 272 (M$^+$) and 274 [(M+2)$^+$]; mp 76–79° C.

Example A6

(4-Chloro-5-fluoro-2-nitro-phenyl)-carbamic acid tert-butyl ester

The title compound was prepared via the di-Boc-compound from 4-chloro-5-fluoro-2-nitro-phenylamine [prepared by chlorination of 5-fluoro-2-nitroaniline [CAS-No. 2369-11-1] with NCS in isopropanol at 60° C. according to Synlett 1999, 1984] (12.94 g, 67.9 mmol) and Boc$_2$O (30.38 g, 139.2 mmol), followed by treatment with 2 eq. TFA in CH$_2$Cl$_2$ according to the general procedure A (method c). Obtained as a yellow solid (17.06 g, 86%).

MS (ISN) 289.0 [(M−H)$^-$] and 291 [(M+2−H)$^-$]; mp 72–73° C.

Example A7

[2-Nitro-5-(2,2,2-trifluoro-ethoxy)-4-trifluoromethyl-phenyl]-carbamic acid tert-butyl ester The title compound was prepared via the di-Boc-compound from 2-nitro-5-(2,2,2-trifluoro-ethoxy)-4- trifluoromethyl-phenylamine [prepared by stirring commercially available 5-chloro-2-nitro-4-trifluoromethyl-phenylamine [CAS-No. 35375-74-7], 2,2,2-trifluoroethanol and KOH in DMSO at 23° C. for 32.5 days] and Boc$_2$O, followed by treatment with 2 eq. TFA in CH$_2$Cl$_2$ according to the general procedure A (method c). Obtained as a yellow solid (18.955 g).

MS (ISN) 403 [(M−H)$^-$].

Example A8

(5-Methoxy-2-nitro-4-trifluoromethyl-phenyl)-carbamic acid tert-butyl ester (5-Methoxy-2-nitro-4-trifluoromethyl-phenyl)-carbamic acid tert-butyl ester was prepared via the di-Boc-compound from 5-methoxy-2-nitro-4-trifluoromethyl-phenylamine [prepared by stirring commercially available 5-chloro-2-nitro-4-trifluoromethyl-phenylamine [CAS-No. 35375-74-7], methanol and KOH in DMSO at 23° C. for 10 days] (4.14 g, 17.5 mmol) and Boc$_2$O (8.04 g, 36.8 mmol), followed by treatment with 2 eq. TFA in CH$_2$Cl$_2$ according to the general procedure A (method c). Obtained as a yellow solid (5.86 g).

MS (ISN) 335 [(M−H)$^-$]; mp 68° C.

Example A9

(5-Ethoxy-2-nitro-4-trifluoromethyl-phenyl)-carbamic acid tert-butyl ester

The title compound was prepared via the di-Boc-compound from 5-ethoxy-2-nitro-4-trifluoromethyl-phenylamine [prepared by stirring commercially available 5-chloro-2-nitro-4-trifluoromethyl-phenylamine [CAS-No. 35375-74-7], ethanol and KOH in DMSO at 60° C. for 7 days] (4.16 g, 16.6 mmol) and Boc$_2$O (7.62 g, 34.9 mmol), followed by treatment with 2 eq. TFA in CH$_2$Cl$_2$ according to the general procedure A (method c). Obtained as a yellow solid (5.54 g).

MS (ISN) 349 [(M−H)$^-$]; mp 67° C.

Example A10

(4-Methoxy-2-nitro-phenyl)-carbamic acid tert-butyl ester

The title compound was prepared via the di-Boc-compound from commercially available 4-methoxy-2-nitroaniline [CAS-No. 96-96-8] and Boc$_2$O, followed by treatment with 2 eq. TFA in CH$_2$Cl$_2$ according to the general procedure A (method c). Obtained as an orange solid (21.868 g).

MS (ISN) 268.2 [(M−H)$^-$]; mp 53° C.

Example A11

(2-Nitro-4-pyrrol-1-yl-phenyl)-carbamic acid tert-butyl ester (2-Nitro-4-pyrrol-1-yl-phenyl)-carbamic acid tert-butyl ester was prepared via the di-Boc-compound from 2-nitro-4-pyrrol-1-yl-phenylamine (Example F1) (13.5 g, 66.4 mmol) and Boc$_2$O (30.45 g, 139 mmol), followed by treatment with 2 eq. TFA in CH$_2$Cl$_2$ according to the general procedure A (method c). Obtained as a yellow solid (16.0 g, 79%).

MS (ISN) 302 [(M−H)$^-$].

Example A12

(5-Methoxy-2-nitro-phenyl)-carbamic acid tert-butyl ester

The title compound was prepared via the di-Boc-compound from 5-methoxy-2-nitro-phenylamine [CAS-No. 16133-49-6] (7.73 g, 46 mmol) and Boc$_2$O (20.60 g, 94.3 mmol), followed by treatment with 2 eq. TFA in CH$_2$Cl$_2$ according to the general procedure A (method c). Obtained as a yellow solid (12.234 g).

MS (EI) 268.2 (M$^+$); mp 109–112° C.

Example A13

[2-Nitro-5-(2,2,2-trifluoro-ethoxy)-phenyl]-carbamic acid tert-butyl ester

The title compound was prepared via the di-Boc-compound from 2-nitro-5-(2,2,2-trifluoro-ethoxy)-phenylamine [CAS-No. 57925-48-1] [prepared by stirring commercially available 5-chloro-2-nitro-phenylamine [CAS-No. 1635-61-6], 2,2,2-trifluoroethanol and KOH in DMSO at 60° C. for 7 days] (11.0 g, 46.6 mmol) and Boc$_2$O (21.35 g, 97.8 mmol), followed by treatment with 2 eq. TFA in CH$_2$Cl$_2$ according to the general procedure A (method c). Obtained as a yellow solid (16.052 g).

MS (ISN) 403 [(M−H)$^-$].

Example A14

(5-Ethoxy-2-nitro-phenyl)-carbamic acid tert-butyl ester (5-Ethoxy-2-nitro-phenyl)-carbamic acid tert-butyl ester was prepared via the di-Boc-compound from 5-ethoxy-2-nitro-phenylamine [CAS-No. 27076-16-0] [prepared by stirring commercially available 5-chloro-2-nitro-phenylamine [CAS-No. 1635-61-6], ethanol and KOH in DMSO at 60° C. for 7 days] (7.78 g, 42.7 mmol) and Boc$_2$O (19.57 g, 89.7 mmol), followed by treatment with 2 eq. TFA in CH$_2$Cl$_2$ according to the general procedure A (method c). Obtained as a yellow solid (8.71 g).

MS (ISN) 281 [(M−H)$^-$]; mp 98° C.

Example A15

(5-Methyl-2-nitro-4-trifluoromethyl-phenyl)-carbamic acid tert-butyl ester

To a suspension of (5-chloro-2-nitro-4-trifluoromethyl-phenyl)-carbamic acid tert-butyl ester (Example A1) (5.00 g, 14.7 mmol), tetrakis(triphenylphosphine)palladium (1.70 g, 1.47 mmol) and potassium carbonate (6.09 g, 44.1 mmol) in dioxane/water (9:1; 50 ml) was added at RT trimethylboroxine (2.04 ml, 14.7 mmol). The reaction mixture was stirred under reflux conditions for 15 h, filtered, evaporated and purified by column chromato-graphy on silica gel (hexane/ethyl acetate 9:1) to yield a light yellow solid (3.25 g, 69%).

MS (ISP) 319.2 [(M−H)$^-$].

Example A16

(4-Chloro-5-methyl-2-nitro-phenyl)-carbamic acid tert-butyl ester

To a suspension of (4,5-dichloro-2-nitro-phenyl)-carbamic acid tert.-butyl ester (Example A20) (10.0 g, 32.6 mmol), tetrakis(triphenylphosphine)palladium (3.76 g, 3.26 mmol) and potassium carbonate (13.5 g, 97.7 mmol) in dioxane/water (9:1; 100 ml) was added at RT trimethylboroxine (4.53 ml, 32.6 mmol). The reaction mixture was stirred under reflux conditions for 15 h, filtered, evaporated and purified by column chromatography on silica gel (hexane/ethyl acetate 19:1) to yield a light yellow solid (4.45 g, 48%).

MS (ISP) 285.0 [(M−H)$^-$].

Example A17

(5-Chloro-4-methyl-2-nitro-phenyl)-carbamic acid tert-butyl ester

The title compound was prepared via the di-Boc compound from commercially available 5-chloro-4-methyl-2-nitroaniline (10.0 g, 53.6 mmol) and $Boc_2O$ (23.9 g, 109 mmol), followed by treatment with 2 eq. TFA in $CH_2Cl_2$ according to the general procedure A (method c). Obtained by column chromatography (toluene/ethylacetate 19:1) as a yellow solid (14.6 g, 95%).

MS (ISN) 285.1 [(M−H)⁻].

Example A18

(4-Methyl-2-nitro-5-trifluoromethyl-phenyl)-carbamic acid tert-butyl ester a) N-(4-Methyl-3-trifluoromethyl-phenyl)-acetamide Acetylation of commercially available 4-methyl-3-trifluoromethyl-aniline (10 g, 57.1 mmol) with acetic acid anhydride in toluene at RT gave N-(4-methyl-3-trifluoromethyl-phenyl)-acetamide (11.9 g, 96%) as a white solid; mp 101° C. [CAS 22957-86-4].

b) N-(4-Methyl-2-nitro-5-trifluoromethyl-phenyl)-acetamide Nitration of N-(4-methyl-3-trifluoromethyl-phenyl)-acetamide (11.6 g, 53.5 mmol) in acetic acid anhydride gave a mixture of N-(4-methyl-2-nitro-5-trifluoromethyl-phenyl)-acetamide and N-(4-methyl-2-nitro-3-trifluoromethyl-phenyl)-acetamide. Separation of this mixture by column chromatography on silica gel (hexane/ethyl acetate 2:1) yielded N-(4-methyl-2-nitro-5-trifluoromethyl-phenyl)-acetamide (5.2 g, 37%) as a yellow solid.

c) (4-methyl-2-nitro-5-trifluoromethyl-phenyl)-carbamic acid tert-butyl ester Reaction of N-(4-methyl-2-nitro-5-trifluoromethyl-phenyl)-acetamide (5.0 g, 19.1 mmol) with Boc-anhydride (4.37 g, 20.0 mmol) according to the general procedure A (method d) and subsequent reaction with ammonium hydroxide (25%; 5.87 ml, 38.1 mmol) gave after aqueous work up and purification by column chromatography on silica gel (hexane/ethyl acetate 4:1) (4-methyl-2-nitro-5-trifluoromethyl-phenyl)-carbamic acid tert-butyl ester (4.84 g, 79%) as a yellow solid.

MS (ISP) 319.2 [(M−H)⁻].

Example A19

(4-Chloro-2-nitro-5-trifluoromethyl-phenyl)-carbamic acid tert-butyl ester

Reaction of N-(4-chloro-2-nitro-5-trifluoromethyl-phenyl)-acetamide [CAS 157554-77-3] (4.02 g, 14.2 mmol) with Boc-anhydride (3.26 g, 14.9 mmol) according to the general procedure A (method c) and subsequent reaction with ammonium hydroxide (25%; 4.38 ml, 28.4 mmol) gave after aqueous work up and purification by column chromatography on silica gel (hexane/ethyl acetate 4:1) (4-chloro-2-nitro-5-trifluoromethyl-phenyl)-carbamic acid tert-butyl ester (3.39 g, 70%) as an orange oil.

MS (ISP) 339.0 [(M−H)⁻].

Example A20

(4,5-Dichloro-2-nitro-phenyl)-carbamic acid tert-butyl ester

The title compound was prepared via the di-Boc compound from commercially available 4,5-dichloro-2-nitroaniline [CAS-No. 6641-64-1] (41.5 g, 200 mmol) and $Boc_2O$ (89.7 g, 411 mmol), followed by treatment with 2 eq. TFA in $CH_2Cl_2$ according to the general procedure A (method c). Obtained by column chromatography (toluene/ethylacetate 19:1) as a pale brown solid (58.9 g, 96%).

MS (ISN) 306.1 [(M−H)⁻].

Example A21

(4-Chloro-5-ethoxy-2-nitro-phenyl)-carbamic acid tert-butyl ester

The title compound was prepared via the di-Boc-compound from 4-chloro-5-ethoxy-2-nitro-phenylamine [prepared by stirring commercially available 4,5-dichloro-2-nitro-phenylamine [CAS-No. 6641-64-1], ethanol and KOH in DMSO at 23° C. for 20 days and at 60° C. for 20 h] (7.38 g, 34.7 mmol) and $Boc_2O$ (15.61 g, 71.5 mmol), followed by treatment with 2 eq. TFA in $CH_2Cl_2$ according to the general procedure A (method c). Obtained as a yellow solid (7.09 g, 66%).

MS (ISN) 315 [(M−H)⁻] and 317 [(M+2−H)⁻]; mp 45–82° C.

Example A22

(2-Nitro-4-trifluoromethoxy-phenyl)-carbamic acid tert-butyl ester

Reaction of commercially available N-(2-nitro-4-trifluoromethoxy-phenyl)-acetamide CAS-No.[787-57-5] (10.0 g, 37.6 mmol) with Boc-anhydride (8.68 g, 39.7 mmol) according to the general procedure A (method c) and subsequent reaction with ammonium hydroxide (25%; 11.7 ml, 75.7 mmol) gave after aqueous work up and purification by column chromatography on silica gel (cyclohexane/ethyl acetate 4:1) the title compound (12.04 g, 99%) as a brown solid.

MS (ISN) 321 [(M−H)⁻].

Example A23

(5-Cyclopropylmethoxy-2-nitro-4-trifluoromethyl-phenyl)-carbamic acid tert-butyl ester The title compound was prepared via the di-Boc-compound from 5-cyclopropyl-methoxy-2-nitro-4-trifluoromethyl-phenylamine [prepared by stirring commercially available 5-chloro-2-nitro-4-trifluoromethyl-phenylamine [CAS-No. 35375-74-7], (hydroxymethyl)cyclopropane and KOH in DMSO at 23° C. for 4 days and at 60° C. for 7 days] (4.49 g, 16.3 mmol) and $Boc_2O$ (7.45 g, 34.1 mmol), followed by treatment with 2 eq. TFA in $CH_2Cl_2$ according to the general procedure A (method c). Obtained as a yellow solid (4.24 g, 85%).

MS (ISN) 375 [(M−H)⁻]; mp 81° C.

Example A24

[2-Nitro-4-(2,2,2-trifluoro-ethoxy)-phenyl]-carbamic acid tert-butyl ester

Reaction of N-[2-nitro-4-(2,2,2-trifluoro-ethoxy)-phenyl]-acetamide CAS-No.[97963-71-8] (4.25 g, 15 mmol) with Boc-anhydride (3.50 g, 16 mmol) according to the general procedure A (method c) and subsequent reaction with ammonium hydroxide (25%; 4.6 ml, 29.8 mmol) gave after aqueous work up and purification by column chromatography on silica gel (cyclohexane/ethyl acetate 4:1) the title compound (3.683 g, 73%) as a yellow solid.

MS (ISN) 335 [(M−H)⁻]; mp 86–87° C.

Example A25

[4-Chloro-2-nitro-5-(2,2,2-trifluoro-ethoxy)-phenyl]-carbamic acid tert-butyl ester The title compound was prepared via the di-Boc-compound from 4-chloro-2-nitro-5-(2,2,2-trifluoro-ethoxy)-phenylamine [prepared by stirring commercially available 4,5-dichloro-2-nitro-phenylamine [CAS-No. 6641-64-1], 2,2,2-trifluoro-ethanol and KOH in DMSO at 60° C. for 5 days] (9.33 g, 34.5 mmol) and Boc$_2$O (15.8 g, 72.4 mmol), followed by treatment with 2 eq. TFA in CH$_2$Cl$_2$ according to the general procedure A (method c). Obtained as a yellow solid (8.80 g, 69%).

MS (ISN) 369.0 [(M−H)$^-$] and 371 [(M+2−H)$^-$]; mp 67–69° C.

Example A26

[5-(2-Methoxy-ethoxy)-2-nitro-4-trifluoromethyl-phenyl]-carbamic acid tert-butyl ester The title compound was prepared via the di-Boc-compound from 5-(2-methoxy-ethoxy)-2-nitro-4-trifluoromethyl-phenylamine [prepared by stirring commercially available 5-chloro-2-nitro-4-trifluoromethyl-phenylamine [CAS-No. 35375-74-7], 2-methoxyethanol and KOH in DMSO at 60° C. for 2 days] (12.3 g, 39 mmol) and Boc$_2$O (20.6 g, 94.5 mmol), followed by treatment with 2 eq. TFA in CH$_2$Cl$_2$ according to the general procedure A (method c). Obtained as a yellow solid (7.906 g, 53%).

MS (ISN) 379 [(M−H)$^-$].

Example A27

(2-Nitro-4-trifluoromethyl-5-vinyl-phenyl)-carbamic acid tert-butyl ester

A suspension of (5-chloro-2-nitro-4-trifluoromethyl-phenyl)-carbamic acid tert-butyl ester (Example A1) (6.8 g, 20 mmol), vinyl boronic acid [CAS-No. 4363-34-2] {Bull. Soc. Chim. Fr. 1966, (8), 2557–64} (4.312 g, 60 mmol) and K$_2$CO$_3$ (8.29 g, 60 mmol) in water (10 mL) and dioxane (50 mL) was purged by Ar-stream at 23° C. for 10 min, then tetrakis(triphenylphosphine)palladium(0) (693 mg, 0.6 mmol) was added and the mixture was heated to 100° C. for 20 h, filtered, evaporated and purified by column chromatography on silica gel (hexane/ethyl acetate 9:1) to yield a light yellow solid (2.476 g, 37%).

MS (ISN) 331 [(M−H)$^-$].

Example A28

(2-Nitro-5-propoxy-4-trifluoromethyl-phenyl)-carbamic acid tert-butyl ester

The title compound was prepared via the di-Boc-compound from 5-(2-methoxy-ethoxy)-2-nitro-4-trifluoromethyl-phenylamine [prepared by stirring commercially available 5-chloro-2-nitro-4-trifluoromethyl-phenylamine [CAS-No. 35375-74-7] (12.03 g, 50 mmol), n-propanol (30 mL) and KOH (7.26 g, 110 mmol) in DMSO (100 mL) at 60° C. for 8 days] (4.83 g, 13.3 mmol) and Boc$_2$O (8.38 g, 38.4 mmol), followed by treatment with 2 eq. TFA in CH$_2$Cl$_2$ according to the general procedure A (method c). Obtained as an orange solid (6.62 g, 99%).

MS (ISN) 363 [(M−H)$^-$]; mp 91° C.

Example A29

(E/Z)-(2-Nitro-5-propenyl-4-trifluoromethyl-phenyl)-carbamic acid tert-butyl ester A suspension of (5-chloro-2-nitro-4-trifluoromethyl-phenyl)-carbamic acid tert-butyl ester (Example A1) (6.8 g, 20 mmol), (E/Z)-1-prop-1-enyl boronic acid [CAS-No. 6336-44-3] {Bull Soc. Chim. Fr. 1966, (8), 2557–64} (5.1 g, 60 mmol) and K$_3$PO$_4$ (12.74 g, 60 mmol) in water (29 mL) and dioxane (65 mL) was purged by Ar-stream at 23° C. for 10 min, then tetrakis(triphenylphosphine)palladium(0) (693 mg, 0.6 mmol) was added and the mixture was heated to 100° C. for 20 h, filtered, evaporated and purified by column chromato-graphy on silica gel (hexane/ethyl acetate 9:1) to yield a light yellow oil (3.946 g, 57%).

MS (ISN) 345 [(M−H)$^-$].

Example A30

(5-Hydroxymethyl-2-nitro-4-trifluoromethyl-phenyl)-carbamic acid tert-butyl ester The title compound was prepared from (5-methyl-2-nitro-4-trifluoromethyl-phenyl)-carbamic acid tert-butyl ester (Example A15) by the following sequence:
1.) A mixture of (5-methyl-2-nitro-4-trifluoromethyl-phenyl)-carbamic acid tert-butyl ester (Example A15) (2.42 g, 7.00 mmol), NBS (1.62 g, 9.10 mmol) and benzoyl peroxide (0.50 g, 1.54 mmol) in CCl$_4$ (50 mL) was refluxed and irradiated with a 500 W sunlamp for 6 h. Cooled to 23° C., filtered the succinimide off and washed with CCl$_4$. After evaporation of the solvent under vacuum, the crude bromide (2.63 g, 6.59 mmol), KOAc (2.94 g, 30 mmol) and TBAHSO$_4$ (100 mg, 0.3 mmol) in DCM (50 mL) were stirred at 23° C. for 17 h.
2.) The obtained acetic acid 5-tert-butoxycarbonylamino-4-nitro-2-trifluoromethyl-benzyl ester (822 mg, 2.17 mmol) was stirred in THF (10 mL), MeOH (1 mL) and 1 M NaOH (6.52 mL, 6.52 mmol) at 23° C. for 2 h. Obtained as yellow oil (493 mg).

MS (ISN) 335 [(M−H)$^-$].

Example A31

(5-Cyclopropyl-2-nitro-4-trifluoromethyl-phenyl)-carbamic acid tert-butyl ester

A mixture of (2-nitro-4-trifluoromethyl-5-vinyl-phenyl)-carbamic acid tert-butyl ester (Example A27) (1.66 g, 5 mmol), trimethylsulfoxonium iodide (2.75 g, 12.5 mmol) and benzyltriethylammonium chloride (200 mg, 0.878 mmol) in NaOH 50% (15 ml) and DCM (25 ml) was stirred at 23° C. for 2 days. The mixture was diluted with EtOAc and washed with 1N HCl, water and brine, dried over MgSO$_4$. Removal of the solvent invacuum left a dark brown oil, which was purified by silica gel column chromatography to give the title compound a yellow solid (659 mg). Residual starting material was removed as follows: To a solution of the obtained material (659 mg, 1.9 mmol) in EtOAc (11.5 ml) and MeCN (11.5 ml), a solution of RuCl$_3$ (30 mg, 0.133 mmol) and NaIO$_4$ (610 mg, 2.85 mmol) in H$_2$O (3.8 ml) was added under vigurous stirring at 0° C. The mixture was being stirred for a further 3 min and then quenched with a sat. sol. of Na$_2$S$_2$O$_3$ (19 ml). The mixture was diluted with EtOAc, the aqueous layer was separated, extracted once with EtOAc. The combined EtOAc layers were washed with brine, dried over MgSO$_4$ and charcoal, filtered over dicalite, evaporated and purified by column chromatography on silica gel (heptane/ethyl acetate 9:1) to yield a yellow solid (630 g, 36%).

MS (ISN) 345.2 [(M−H)$^-$]; mp 117–119° C.

General Procedure C

Preparation of 5-N-substituted-(2-nitro-phenyl)-carbamic acid tert-butyl esters (5-Chloro or -fluoro-2-nitro-phenyl)-carbamic acid tert-butyl ester was stirred with the desired amine optionally with DMSO, DMF, DMA, NMP or THF and/or DIPEA or Et$_3$N at temperatures from 23° C. to 130° C. until tlc indicated complete disappearance of the chloride or fluoride. The reaction was cooled to 23° C., poured into ice-water, the precipitate was filtered off, washed with water and dried in vacuum. In cases were the product did not precipitate, the mixture was extracted with EtOAc, washed with water and brine, dried over Na$_2$SO$_4$. Filtration and removal of the solvent in vacuum left a crude product, which was—if necessary—purified by silica gel column chromatography with hexane/EtOAc to give the pure title compound.

Example C1

(5-Dimethylamino-2-nitro-4-trifluoromethyl-phenyl)-carbamic acid tert-butyl ester The title compound was prepared from (5-fluoro-2-nitro-4-trifluoromethyl-phenyl)-carbamic acid tert-butyl ester (Example A2) (1.62 g, 5.0 mmol) and dimethylamine (5.6 N in EtOH, 4.47 mL, 25.0 mmol) in DMSO (10 mL) at 23° C. according to the general procedure C and obtained as a yellow solid (1.48 g).

MS (ISN) 348 [(M−H)$^−$]; mp 110° C.

Example C2

(2-Dimethylamino-2'-fluoro-5-nitro-biphenyl-4-yl)-carbamic acid tert-butyl ester The title compound was prepared from (2-chloro-2'-fluoro-5-nitro-biphenyl-4-yl)-carbamic acid tert-butyl ester (Example D1) (9.568 g, ca. 26 mmol) and Me$_2$NH (60% in H$_2$O, 12 mL) in DMSO (87 mL) at 23° C. according to the general procedure C. Obtained as a yellow solid (4.54 g).

MS (ISP) 376.3 [(M+H)$^+$].

Example C3

[5-(Cyclopropyl-methyl-amino)-2-nitro-4-trifluoromethyl-phenyl]-carbamic acid tert-butyl ester The title compound was prepared from (5-chloro-2-nitro-4-trifluoromethyl-phenyl)-carbamic acid tert-butyl ester (Example A1) (3.40 g, 10 mmol) and cyclopropyl-methyl-amine hydrochloride (3.22 g, 30 mmol) and Et$_3$N (6.97 mL, 50 mmol) in DMSO (50 mL) at 23° C. according to the general procedure C. Obtained as a yellow solid (3.74 g).

MS (ISP) 374.2 [(M+H)$^+$].

Example C4

(4-Chloro-5-isobutylamino-2-nitro-phenyl)-carbamic acid tert-butyl ester

The title compound was prepared from (4,5-dichloro-2-nitro-phenyl)-carbamic acid tert-butyl ester (Example A20) (3.0 g, 9.77 mmol) and isobutylamine (3.57 g, 48.8 mmol) in DMSO (20 mL) at 55° C. according to the general procedure C. Obtained as a brown solid (2.26 g, 67%).

MS (ISP) 344.2 [(M+H)$^+$].

Example C5

[5-(Methyl-propyl-amino)-2-nitro-4-trifluoromethyl-phenyl]-carbamic acid tert-butyl ester The title compound was prepared from (5-chloro-2-nitro-4-trifluoromethyl-phenyl)-carbamic acid tert-butyl ester (Example A1) (4.00 g, 11.7 mmol), N-methyl-propylamine (1.89 ml, 17.6 mmol) and triethylamine (5.73 ml, 41.1 mmol) in DMSO (30 mL) at RT according to the general procedure C. Obtained as a yellow solid (4.04 g, 91%).

MS (ISP) 378.3 [(M+H)$^+$].

Example C6

(5-Isobutylamino-2-nitro-4-trifluoromethyl-phenyl)-carbamic acid tert-butyl ester The title compound was prepared from (5-chloro-2-nitro-4-trifluoromethyl-phenyl)-carbamic acid tert-butyl ester (Example A1) (5.00 g, 14.7 mmol), isobutyl-amine (7.36 mL, 73.4 mmol) in DMSO (35 mL) at RT according to the general procedure C. Obtained as a yellow solid (5.39 g, 97%).

MS (ISP) 376.3 [(M−H)$^−$].

Example C7

(2-Nitro-5-pyrrolidin-1-yl-4-trifluoromethyl-phenyl)-carbamic acid tert-butyl ester The title compound was prepared from (5-chloro-2-nitro-4-trifluoromethyl-phenyl)-carbamic acid tert-butyl ester (Example A1) (6.81 g, 20 mmol), pyrrolidine (8.27 mL, 100 mmol) in DMSO (70 mL) at RT according to the general procedure C. Obtained as a yellow solid (7.35 g, 98%).

MS (ISN) 374 [(M−H)$^−$]; mp 138–141° C.

Example C8

(5-Morpholin-4-yl-2-nitro-4-trifluoromethyl-phenyl)-carbamic acid tert-butyl ester The title compound was prepared from (5-chloro-2-nitro-4-trifluoromethyl-phenyl)-carbamic acid tert-butyl ester (Example A1) (1.62 g, 5 mmol), morpholine (2.18 mL, 25 mmol) in DMSO (10 mL) at RT according to the general procedure C. Obtained as a yellow solid (1.83 g, 94%).

MS (ISN) 390 [(M−H)$^−$]; mp 75° C.

Example C9

[5-(Isobutyl-methyl-amino)-2-nitro-4-trifluoromethyl-phenyl]-carbamic acid tert-butyl ester The title compound was prepared from (5-chloro-2-nitro-4-trifluoromethyl-phenyl)-carbamic acid tert-butyl ester (Example A1) (4.00 g, 11.7 mmol), N-isobutyl-methyl-amine (1.54 g, 17.6 mmol) and triethylamine (5.73 ml, 41.1 mmol) in DMSO (30 mL) at RT according to the general procedure C. Obtained as a yellow solid (4.18 g, 91%).

MS (ISP) 390.3 [(M−H)$^−$].

Example C10

[5-(Isopropyl-methyl-amino)-2-nitro-4-trifluoromethyl-phenyl]-carbamic acid tert-butyl ester The title compound was prepared from (5-chloro-2-nitro-4-trifluoromethyl-phenyl)-carbamic acid tert-butyl ester (Example A1) (4.00 g, 11.7 mmol), N-isopropyl-methyl-amine (3.67 ml, 35.2 mmol) and triethylamine (5.73 ml, 41.1 mmol) in DMSO (30 mL) at 50° C. according to the general procedure C. Obtained as a yellow solid (3.27 g, 74%).

MS (ISP) 376.3 [(M−H)$^−$].

Example C11

[4-Chloro-5-(isobutyl-methyl-amino)-2-nitro-phenyl]-carbamic acid tert-butyl ester The title compound was prepared from (4,5-dichloro-2-nitro-phenyl)-carbamic acid tert.-butyl ester (Example A20) (5.0 g, 16.3 mmol) and N-isobutyl-methylamine (7.09 g, 81.4 mmol) in DMSO (50 mL) at RT according to the general procedure C. Obtained as a brown oil (5.79 g, 99%).

MS (ISP) 358.2 [(M+H)$^+$].

Example C12

[4-Chloro-5-(isopropyl-methyl-amino)-2-nitro-phenyl]-carbamic acid tert-butyl ester The title compound was prepared from (4,5-dichloro-2-nitro-phenyl)-carbamic acid tert.-butyl ester (Example A20) (5.0 g, 16.3 mmol) and N-isopropyl-methylamine (5.95 g, 81.4 mmol) in DMSO (50 mL) at 75° C. according to the general procedure C. Obtained as a yellow solid (4.07 g, 73%).

MS (ISP) 344.3 [(M+H)$^+$].

General Procedure D

Preparation of (4-aryl-2-nitro-phenyl)-carbamic acid tert-butyl esters by Direct Suzuki-coupling of (4-iodo-2-nitro-phenyl)-carbamic acid tert-butyl esters with arylboronic acids A mixture of the (4-iodo-2-nitro-phenyl)-carbamic acid tert-butyl ester (3.0 mmol), the arylboronic acid (4.5 mmol) and PdCl$_2$(PPh$_3$)$_2$ (2 mol %) was refluxed in 1,4-dioxane (25 mL) and 2M Na$_2$CO$_3$-solution (7.5 mL) [or alternatively with 1M NaHCO$_3$-solution (7.5 mL), LiCl (6.0 mmol) and (Ph$_3$P)$_4$Pd (3 mol %) in DME (30 mL); also possible with Et$_3$N (9.0 mmol), Pd(OAc)$_2$ (3 mol %), PPh$_3$ (6 mol %) in DMF (10 mL) at 100° C.] until tlc indicated complete conversion of the iodide. The mixture was transferred into a separating funnel, H$_2$O (25 mL) was added and the product was extracted with ether or EtOAc (3×30 mL). The combined organic layers were washed with brine (50 mL) and dried over Na$_2$SO$_4$. Removal of the solvent left a brown residue, which was purified by silica gel column chromatography with cyclohexane/ether or cyclohexane/EtOAc to give the title compound.

Example D1

(2-Chloro-2'-fluoro-5-nitro-biphenyl-4-yl)-carbamic acid tert-butyl ester

The title compound was prepared from (5-chloro-4-iodo-2-nitro-phenyl)-carbamic acid tert-butyl ester [CAS-No. 335349-60-5] (30 g, 75.3 mmol) and 2-fluorophenylboronic acid (13.82 g, 98.8 mmol) according to the general procedure D. Obtained as a yellow gum (1.39 g).

MS (ISN) 365.0 [(M−H)$^-$].

General Procedure E

Preparation of (4-aryl-2-nitro-phenyl)-carbamic acid tert-butyl esters by Suzuki-coupling of (4-iodo-2-nitro-phenyl)-carbamic acid tert-butyl esters with bis(pinacolato)diboron and subsequent reaction with aryl halides A mixture of the (4-iodo-2-nitro-phenyl)-carbamic acid tert-butyl ester (2.0 mmol), bis(pinacolato)diboron (2.2 mmol), KOAc (6.0 mmol) and PdCl$_2$(PPh$_3$)$_2$ (3 mol %) in 1,4-dioxane (25 mL) was stirred at 100° C. until tlc indicated complete conversion of the iodide [cf. *Tetr. Lett.* 1997, 38, 3841–3844]. After addition of the aryl halide (4.0 mmol), PdCl$_2$(PPh$_3$)$_2$ (3 mol %) and 2M Na$_2$CO$_3$-solution (7.5 mL) the mixture was stirred at 100° C. until tlc indicated complete conversion of the intermediate boronic ester. The mixture was transferred into a separating funnel, H$_2$O (30 mL) was added and the product was extracted with ether or EtOAc (3×50 mL). The combined organic layers were washed with brine (100 mL) and dried over Na$_2$SO$_4$. Removal of the solvent left a brown residue, which was purified by silica gel column chromatography with cyclohexane/ether or cyclohexane/EtOAc to give the title compound.

General Procedure F

Preparation of 2-nitro-4-pyrrol-1-yl-phenylamines by condensation of 2-nitro-1,4-phenylenediamine with 2,5-dimethoxytetrahydrofuran [cf. *J. Heterocycl. Chem.* 1988, 25, 1003–1005]

A mixture of the 2-nitro-1,4-phenylenediamine (25 mmol) and 2,5-dimethoxytetrahydrofuran (26–32.5 mmol) in HOAc (150 mL) was stirred at 60–120° C. until tlc indicated complete conversion of the phenylenediamine. After cooling to 23° C., the mixture was poured into brine (500 mL) and extracted with EtOAc (3×200 mL). The combined organic layers were washed with brine (300 mL) and dried over MgSO$_4$. Removal of the solvent left a brown residue, which was purified by silica gel column chromatography with cyclohexane/EtOAc to give the title compound.

Example F1

2-Nitro-4-pyrrol-1-yl-phenylamine

The title compound was prepared from 2-nitro-1,4-phenylenediamine [CAS-No. 5307-14-2] (20 g, 131 mmol) and 2,5-dimethoxytetrahydrofuran (18.3 mL, 135 mmol) in HOAc (37 mL) at 95° C. for 3 h according to the general procedure F. Obtained as a red solid (13.5 g).

MS (EI) 203 (M$^+$).

General Procedure G

Preparation of 2,5-dimethoxydihydrofurans by bromination of furans in MeOH [cf. *Tetrahedron* 1971, 27, 1973–1996]

To a solution of the furan (177.5 mmol) in a mixture of anhydrous ether (54 mL) and abs. MeOH (79 mL) kept at −35° C. bromine (10.0 mL, 195 mmol) in MeOH (105 mL) was added gradually with stirring. The reaction mixture was stirred for 30 min, saturated with gaseous NH$_3$ to pH 8, and allowed to warm up to 23° C. Poured into ice-water, extracted with ether (3×400 mL), washed with brine, dried over Na$_2$SO$_4$. Evaporation of the solvent left a yellow liquid, which was purified by vacuum distillation to give the title compound.

General Procedure H

Preparation of (4-alkynyl-2-nitro-phenyl)-carbamic acid tert-butyl esters by Sonogashira-coupling of (4-iodo-2-nitro-phenyl)-carbamic acid tert-butyl esters with acetylenic compounds (also Sonogashira-coupling of (4-ethynyl-2-nitro-phenyl)-carbamic acid tert-butyl esters with aryl halides)

A mixture of the halide (3.0–4.5 mmol), acetylenic compound (3.0–4.5 mmol), Et3N (13.5 mmol), PdCl$_2$(PPh$_3$)$_2$ (5 mol %) and PPh3 (2.5 mol %) in THF (12 mL) [with very insoluble material DMF (up to 12 mL) could be added] was stirred for 20 min at 23° C. while being purged with Argon. CuI (1.2 mol %) was added and stirring was continued at 60° C. under Argon atmosphere until tlc indicated complete conversion of the minor component [cf *J. Org. Chem.* 1998, 63, 8551]. The mixture was transferred into a separating funnel, 5% citric acid (50 mL) was added and the product was extracted with EtOAc (2×100 mL). The combined organic layers were washed with sat. $NaHCO_3$-solution (50 mL) and brine (50 mL), followed by drying over $MgSO_4$. Removal of the solvent left a yellow residue, which was purified by silica gel column chromatography with hexane/EtOAc and/or triturated with hexane or aqueous EtOH to give the title compound.

General Procedure J

Preparation of the (2-amino-phenyl)-carbamic acid tert-butyl esters by reduction of (2-nitro-phenyl)-carbamic acid tert-butyl esters Method a: Catalytic Hydrogenation A mixture of the nitro compound (1.0 mmol) in MeOH or EtOH and THF (1:1 ca. 20 mL) [or solely EtOAc for aromatic chlorides] and 10% pPalladium on carbon (20 mg), Raney-Ni (20 mg) or 5% platinum on carbon was stirred vigorously at 23° C. under hydrogen atmosphere until tlc indicated complete conversion. The catalyst was filtered off, washed thoroughly with MeOH or EtOH and THF (1:1) [or EtOAc], the solvent was removed in vacuum to give the title compound, which was generally pure enough for further transformations, but could be crystallized from hot hexane or cyclohexane if necessary.

Method b: Reduction with $SnCl_2.2H_2O$

A mixture of the nitro compound (1.0 mmol) and $SnCl_2.2H_2O$ (5.0 mmol) was either stirred in EtOH (30 mL) at 70–80° C. or alternatively in pyridine (3 mL) and DMF (12 mL) at 23° C. under Argon atmosphere until tlc indicated complete conversion [cf. *Tetr. Lett.* 1984, 25, 839]. The reaction mixture was brought to pH 8 by addition of sat. $NaHCO_3$-solution and extracted with EtOAc (2×100 mL). The combined organic layers were washed with brine and dried over $Na_2SO_4$. Removal of the solvent left a yellow solid, which—if necessary—can be purified by silica gel column chromatography.

Method c: Reduction with Zn and $NH_4Cl$

To a mixture of the nitro compound (1.0 mmol) in EtOH/THF/sat. $NH_4Cl$-solution (1:1:1, 30 mL) was added Zinc dust (3.0 mmol) and the mixture was stirred at 70° C. under Argon atmosphere until tlc indicated complete conversion. Aqueous workup as described in method b.

Example J1

(2-Amino-5-dimethylamino-4-trifluoromethyl-phenyl)-carbamic acid tert-butyl ester The title compound was prepared from (5-dimethylamino-2-nitro-4-trifluoromethyl-phenyl)-carbamic acid tert-butyl ester (Example C1) by hydrogenation with 10% Pd/C according to the general procedure J (method a). Obtained as an amorphous yellow substance (1.34 g).

MS (ISP) 320 [(M+H)$^+$].

Example J2

(2-Amino-4-fluoro-phenyl)-carbamic acid tert-butyl ester

The title compound was prepared from (4-fluoro-2-nitro-phenyl)-carbamic acid tert-butyl ester (Example A3) (32.54 g, 127 mmol) by hydrogenation with 10% Pd/C according to the general procedure J (method a). Obtained as a light orange solid (25.03 g).

MS (ISP) 227 [(M+H)$^+$]; mp 119–121° C.

Example J3

(2-Amino-4-trifluoromethyl-phenyl)-carbamic acid tert-butyl ester

The title compound was prepared from (2-nitro-4-trifluoromethyl-phenyl)-carbamic acid tert-butyl ester (Example A4) (30.0 g, 98 mmol) by hydrogenation with 10% Pd/C according to the general procedure J (method a). Obtained as a light yellow solid (26.5 g).

MS (ISP) 277.2 [(M+H)$^+$]; mp 133–135° C.

Example J4

(2-Amino-4-chloro-phenyl)-carbamic acid tert-butyl ester

The title compound was prepared from (4-chloro-2-nitro-phenyl)-carbamic acid tert-butyl ester (Example A5) (22.12 g, 85 mmol) by reduction with $SnCl_2.2H_2O$ according to the general procedure J (method b). Obtained as a red solid (13.93 g).

MS (EI) 242 (M$^+$) and 244 [(M+2)$^+$]; mp 127–128° C.

Example J5

(2-Amino-4-chloro-5-fluoro-phenyl)-carbamic acid tert-butyl ester

The title compound was prepared from (4-chloro-5-fluoro-2-nitro-phenyl)-carbamic acid tert-butyl ester (Example A6) (16.48 g, 56.7 mmol) by hydrogenation with 5% Pt/C according to the general procedure J (method a). Obtained as a brown solid (14.78 g).

MS (ISP) 261.2 [(M+H)$^+$] and 263 [(M+2+H)$^+$]; mp 85–87° C.

Example J6

[2-Amino-5-(2,2,2-trifluoro-ethoxy)-4-trifluoromethyl-phenyl]-carbamic acid tert-butyl ester The title compound was prepared from [2-nitro-5-(2,2,2-trifluoro-ethoxy)-4-trifluoromethyl-phenyl]-carbamic acid tert-butyl ester (Example A) by hydrogenation with 5% Pt/C according to the general procedure J (method a). Obtained as a yellow solid (17.374 g).

MS (ISP) 375 [(M+H)$^+$].

Example J7

(2-Amino-5-methoxy-4-trifluoromethyl-phenyl)-carbamic acid tert-butyl ester

The title compound was prepared from (5-methoxy-2-nitro-4-trifluoromethyl-phenyl)-carbamic acid tert-butyl ester (Example A8) (5.79 g, 17.2 mmol) by hydrogenation with 10% Pd/C according to the general procedure J (method a). Obtained as a yellow solid (5.36 g).

MS (ISP) 307 [(M+H)$^+$]; mp 125° C.

Example J8

(2-Amino-5-ethoxy-4-trifluoromethyl-phenyl)-carbamic acid tert-butyl ester

The title compound was prepared from (5-ethoxy-2-nitro-4-trifluoromethyl-phenyl)-carbamic acid tert-butyl ester

Example J9

(2-Amino-4-methoxy-phenyl)-carbamic acid tert-butyl ester

The title compound was prepared from (4-methoxy-2-nitro-phenyl)-carbamic acid tert-butyl ester (Example A10) by hydrogenation with 10% Pd/C according to the general procedure J (method a). Obtained as a white solid (19.377 g).

MS (ISP) 239.3 [(M+H)$^+$]; mp 114–115° C.

Example J10

(5-Amino-2-dimethylamino-2'-fluoro-biphenyl-4-yl)-carbamic acid tert-butyl ester The title compound was prepared from (2-dimethylamino-2'-fluoro-5-nitro-biphenyl-4-yl)-carbamic acid tert-butyl ester (Example C2) (4.54 g, 12.1 mmol) by hydrogenation with 10% Pd/C according to the general procedure J (method a). Obtained as a light brown solid (3.324 g).

MS (ISP) 346.4 [(M+H)$^+$]; mp 118–123° C.

Example J11

(2-Amino-4-pyrrol-1-yl-phenyl)-carbamic acid tert-butyl ester

The title compound was prepared from (2-nitro-4-pyrrol-1-yl-phenyl)-carbamic acid tert-butyl ester (Example A11) by hydrogenation with 5% Pd/C according to the general procedure J (method a). Obtained as a white solid (9.06 g).

MS (ISP) 274 [(M+H)$^+$].

Example J12

(2-Amino-5-methoxy-phenyl)-carbamic acid tert-butyl ester

The title compound was prepared from (5-methoxy-2-nitro-phenyl)-carbamic acid tert-butyl ester (Example A12) (12.234 g, 45.6 mmol) by hydrogenation with 10% Pd/C according to the general procedure J (method a). Obtained as a purple solid (7.185 g).

MS (EI) 238.1 (M$^+$); mp 98–99° C.

Example J13

[2-Amino-5-(2,2,2-trifluoro-ethoxy)-phenyl]-carbamic acid tert-butyl ester

The title compound was prepared from [2-nitro-5-(2,2,2-trifluoro-ethoxy)-phenyl]-carbamic acid tert-butyl ester (Example A13) by hydrogenation with 5% Pt/C according to the general procedure J (method a). Obtained as a light brown solid (13.157 g).

MS (ISP) 307 [(M+H)$^+$].

Example J14

(2-Amino-5-ethoxy-phenyl)-carbamic acid tert-butyl ester

The title compound was prepared from (5-ethoxy-2-nitro-phenyl)-carbamic acid tert-butyl ester (Example A14) (8.65 g, 30.6 mmol) by hydrogenation with 10% Pd/C according to the general procedure J (method a). Obtained as a purple solid (6.45 g).

MS (ISP) 253 [(M+H)$^+$]; mp 60–95° C.

Example J15

[2-Amino-5-(cyclopropyl-methyl-amino)-4-trifluoromethyl-phenyl]-carbamic acid tert-butyl ester The title compound was prepared from [5-(cyclopropyl-methyl-amino)-2-nitro-4-trifluoromethyl-phenyl]-carbamic acid tert-butyl ester (Example C3) (3.74 g, 9.96 mmol) by reduction with SnCl$_2$.2H$_2$O according to the general procedure J (method b). Obtained as an orange semisolid (2.00 g).

MS (ISP) 346.4 [(M+H)$^+$].

Example J16

(2-Amino-4-chloro-5-isobutylamino-phenyl)-carbamic acid tert-butyl ester

The title compound was prepared from (4-chloro-5-isobutylamino-2-nitro-phenyl)-carbamic acid tert-butyl ester (Example C4) (1.93 g, 5.61 mmol) by reduction with SnCl$_2$.2H$_2$O according to the general procedure J (method b). Obtained as a brown solid (1.30 g, 74%).

MS (ISP) 314.3 [(M+H)$^+$].

Example J17

[2-Amino-5-(methyl-propyl-amino)-4-trifluoromethyl-phenyl]-carbamic acid tert-butyl ester The title compound was prepared from [5-(methyl-propyl-amino)-2-nitro-4-trifluoromethyl-phenyl]-carbamic acid tert-butyl ester (Example C5) (3.78 g, 10.0 mmol) by hydrogenation with 10% Pd/C according to the general procedure J (method a). Obtained as a red oil (3.40 g, 98%).

MS (ISP) 248.4 [(M+H)$^+$].

Example J18

[2-Amino-5-(isobutyl-amino)-4-trifluoromethyl-phenyl]-carbamic acid tert-butyl ester The title compound was prepared from [5-(isobutyl-amino)-2-nitro-4-trifluoromethyl-phenyl]-carbamic acid tert-butyl ester (Example C6) (5.28 g, 13.99 mmol) by hydrogenation with 10% Pd/C according to the general procedure J (method a). Obtained as a pale yellow solid (3.69 g, 76%).

MS (ISP) 348.5 [(M+H)$^+$]; mp 141° C.

Example J19

(2-Amino-5-chloro-4-trifluoromethyl-phenyl)-carbamic acid tert-butyl ester

The title compound was prepared from (5-chloro-2-nitro-4-trifluoromethyl-phenyl)-carbamic acid tert-butyl ester (Example A1) (7.00 g, 20.5 mmol) by reduction with SnCl$_2$.2H$_2$O according to the general procedure J (method b). Obtained as a yellow solid (3.13 g, 49%).

MS (ISP) 309.3 [(M−H)$^−$]; mp 170° C.

Example J20

(2-Amino-5-methyl-4-trifluoromethyl-phenyl)-carbamic acid tert-butyl ester

The title compound was prepared from (5-methyl-2-nitro-4-trifluoromethyl-phenyl)-carbamic acid tert-butyl ester (Example A15) (3.40 g, 10.6 mmol) by hydrogenation with 10% Pd/C according to the general procedure J (method a). Obtained as light gray solid (3.0 g, 97%).

MS (ISP) 291.2 [(M+H)⁺]; mp 174° C.

Example J21

(2-Amino-5-chloro-4-methyl-phenyl)-carbamic acid tert-butyl ester (2-Amino-5-chloro-4-methyl-phenyl)-carbamic acid tert-butyl ester was prepared from (5-chloro-4-methyl-2-nitro-phenyl)-carbamic acid tert-butyl ester (Example A16) (11.9 g, 41.4 mmol) by reduction with $SnCl_2.2H_2O$ according to the general procedure J (method b). Obtained as a yellow solid (9.25 g, 87%).

MS (ISP) 257.1 [(M+H)⁺]; mp 147° C.

Example J22

(2-Amino-4-chloro-5-methyl-phenyl)-carbamic acid tert-butyl ester

The title compound was prepared from (4-chloro-5-methyl-2-nitro-phenyl)-carbamic acid tert-butyl ester (Example A17) (4.45 g, 15.5 mmol) by reduction with $SnCl_2.2H_2O$ according to the general procedure J (method b). Obtained as a yellow solid (3.90 g, 98%).

MS (ISP) 257.2 [(M+H)⁺]; mp 171° C.

Example J23

(2-Amino-4-methyl-5-trifluoromethyl-phenyl)-carbamic acid tert-butyl ester

Prepared from (4-methyl-2-nitro-5-trifluoromethyl-phenyl)-carbamic acid tert-butyl ester (Example A18) (4.68 g, 14.6 mmol) by hydrogenation with 10% Pd/C according to the general procedure J (method a). Obtained as a white solid (3.68 g, 87%).

MS (ISP) 291.3 [(M+H)⁺]; mp 144° C.

Example J24

(2-Amino-4-chloro-5-trifluoromethyl-phenyl)-carbamic acid tert-butyl ester

The title compound was prepared from (4-chloro-2-nitro-5-trifluoromethyl-phenyl)-carbamic acid tert-butyl ester (Example A19) (3.37 g, 0.99 mmol) by reduction with $SnCl_2.2H_2O$ according to the general procedure J (method b). Obtained as an orange solid (2.55 g, 83%).

MS (ISP) 309.2 [(M–H)⁻]; mp 137° C.

Example J25

(2-Amino-4-chloro-5-ethoxy-phenyl)-carbamic acid tert-butyl ester

The title compound was prepared from (4-chloro-5-ethoxy-2-nitro-phenyl)-carbamic acid tert-butyl ester (Example A21) (7.04 g, 22.2 mmol) by hydrogenation with 5% Pt/C according to the general procedure J (method a). Obtained as a light yellow solid (6.32 g, 99%).

MS (ISN) 285 [(M–H)⁻] and 287 [(M+2–H)⁻]; mp 148° C.

Example J26

(2-Amino-4-trifluoromethoxy-phenyl)-carbamic acid tert-butyl ester

The title compound was prepared from (2-nitro-4-trifluoromethoxy-phenyl)-carbamic acid tert-butyl ester (Example A22) (10.38 g, 32.2 mmol) by hydrogenation with 10% Pd/C according to the general procedure J (method a). Obtained as a light brown solid (8.76 g, 93%).

MS (ISN) 293 [(M–H)⁻]; mp 90° C.

Example J27

(2-Amino-5-pyrrolidin-1-yl-4-trifluoromethyl-phenyl)-carbamic acid tert-butyl ester The title compound was prepared from (2-nitro-5-pyrrolidin-1-yl-4-trifluoromethyl-phenyl)-carbamic acid tert-butyl ester (Example C7) (7.45 g, 19.75 mmol) by hydrogenation with 10% Pd/C according to the general procedure J (method a). Obtained as a light orange solid (6.75 g, 99%).

MS (ISP) 346 [(M+H)⁺]; mp 101–103° C.

Example J28

(2-Amino-5-morpholin-4-yl-4-trifluoromethyl-phenyl)-carbamic acid tert-butyl ester The title compound was prepared from (5-morpholin-4-yl-2-nitro-4-trifluoromethyl-phenyl)-carbamic acid tert-butyl ester (Example C8) (1.83 g, 4.68 mmol) by hydrogenation with 10% Pd/C according to the general procedure J (method a). Obtained as an amorphous red substance (1.72 g, 102%).

MS (ISP) 362 [(M+H)⁺].

Example J29

(2-Amino-5-cyclopropylmethoxy-4-trifluoromethyl-phenyl)-carbamic acid tert-butyl ester The title compound was prepared from (5-cyclopropylmethoxy-2-nitro-4-trifluoromethyl-phenyl)-carbamic acid tert-butyl ester (Example A23) (5.18 g, 13.8 mmol) by hydrogenation with 10% Pd/C according to the general procedure J (method a). Obtained as a light brown solid (3.80 g, 80%).

MS (ISP) 347 [(M+H)⁺]; mp 127° C.

Example J30

[2-Amino-4-(2,2,2-trifluoro-ethoxy)-phenyl]-carbamic acid tert-butyl ester

The title compound was prepared from [2-nitro-4-(2,2,2-trifluoro-ethoxy)-phenyl]-carbamic acid tert-butyl ester (Example A24) (3.65 g, 11 mmol) by hydrogenation with 10% Pd/C according to the general procedure J (method a). Obtained as a light brown solid (3.16 g, 94%).

MS (ISP) 307 [(M+H)⁺]; mp 127–128° C.

Example J31

[2-Amino-4-chloro-5-(2,2,2-trifluoro-ethoxy)-phenyl]-carbamic acid tert-butyl ester The title compound was prepared from ([4-chloro-2-nitro-5-(2,2,2-trifluoro-ethoxy)-phenyl]-carbamic acid tert-butyl ester (Example A25) (8.70 g, 23.5 mmol) by hydrogenation with 5% Pt/C according to the general procedure J (method a). Obtained as a yellow solid (7.94 g, 99%).

MS (ISP) 341.2 [(M+H)⁺] and 343 [(M+2+H)⁺]; mp 91–93° C.

Example J32

[2-Amino-5-(2-methoxy-ethoxy)-4-trifluoromethyl-phenyl]-carbamic acid tert-butyl ester The title compound was prepared from [5-(2-methoxy-ethoxy)-2-nitro-4-trifluoromethyl-phenyl]-carbamic acid tert-butyl ester (Example A26) (7.90 g, 20.8 mmol) by hydrogenation with 10% Pd/C according to the general procedure J (method a). Obtained as a yellow solid (7.00 g, 96%).

MS (ISP) 351 [(M+H)⁺]; mp 96–100° C.

Example J33

(2-Amino-5-ethyl-4-trifluoromethyl-phenyl)-carbamic acid tert-butyl ester

The title compound was prepared from (2-nitro-4-trifluoromethyl-5-vinyl-phenyl)-carbamic acid tert-butyl ester (Example A27) (1.20 g, 3.6 mmol) by hydrogenation with 10% Pd/C according to the general procedure J (method a). Obtained as a white solid (1.289 g, 100%).

MS (EI) 304 (M⁺); mp 133–139° C.

Example J34

(2-Amino-4-trifluoromethyl-5-vinyl-phenyl)-carbamic acid tert-butyl ester

The title compound was prepared from (2-nitro-4-trifluoromethyl-5-vinyl-phenyl)-carbamic acid tert-butyl ester (Example A27) (1.01 g, 3.0 mmol) by reduction with $SnCl_2.2H_2O$ according to the general procedure J (method b). Obtained as an orange solid (669 mg, 74%).

MS (ISP) 303 [(M+H)⁺].

Example J35

(2-Amino-5-propoxy-4-trifluoromethyl-phenyl)-carbamic acid tert-butyl ester

The title compound was prepared from (2-nitro-5-propoxy-4-trifluoromethyl-phenyl)-carbamic acid tert-butyl ester (Example A28) (6.46 g, 17.7 mmol) by hydrogenation with 10% Pd/C according to the general procedure J (method a). Obtained as a white solid (0.93 g, 16%).

MS (ISP) 335 [(M+H)⁺]; mp 120° C.

Example J36

(2-Amino-5-propyl-4-trifluoromethyl-phenyl)-carbamic acid tert-butyl ester

The title compound was prepared from (E/Z)-(2-nitro-5-propenyl-4-trifluoromethyl-phenyl)-carbamic acid tert-butyl ester (Example A29) (3.0 g, 8.7 mmol) by hydrogenation with 5% Pt/C according to the general procedure J (method a). Obtained as a yellow solid (2.984 g, 100%).

MS (ISN) 317 [(M−H)⁻].

Example J37

(2-Amino-5-fluoro-4-trifluoromethyl-phenyl)-carbamic acid tert-butyl ester

The title compound was prepared from (5-fluoro-2-nitro-4-trifluoromethyl-phenyl)-carbamic acid tert-butyl ester (Example A2) (3.34 g, 10.3 mmol) by hydrogenation with 10% Pd/C according to the general procedure J (method a). Obtained as a yellow solid (2.93 g, 97%).

MS (ISP) 295.2 [(M+H)⁺]; mp 107–109° C.

Example J38

[2-Amino-5-(tetrahydro-pyran-2-yloxymethyl)-4-trifluoromethyl-phenyl]-carbamic acid tert-butyl ester The title compound was prepared from [2-nitro-5-(tetrahydro-pyran-2-yloxymethyl)-4-trifluoromethyl-phenyl]-carbamic acid tert-butyl ester [prepared from (5-hydroxymethyl-2-nitro-4-trifluoromethyl-phenyl)-carbamic acid tert-butyl ester (Example A30) (476 mg, 1.42 mmol) by treatment with 3,4-dihydro-2H-pyran (0.19 mL, 2.12 mmol) and p-TsOH (5 mg, 0.03 mmol) in DCM at 0° C., stirring at 0° C. for 15 min and at 23° C. for 18 h.] (0.58 g, 1.38 mmol) reduction with $SnCl_2.2H_2O$ according to the general procedure J (method b). Obtained as an amorphous yellow substance (414 mg, 77%).

MS (ISP) 391 [(M+H)⁺].

Example J39

(2-Amino-5-cyclopropyl-4-trifluoromethyl-phenyl)-carbamic acid tert-butyl ester

The title compound was prepared from (5-cyclopropyl-2-nitro-4-trifluoromethyl-phenyl)-carbamic acid tert-butyl ester (Example A31) (460 mg, 1.33 mmol) by reduction with $SnCl_2.2H_2O$ according to the general procedure J (method b). Obtained as an orange solid (300 mg, 71%).

MS (ISP) 317.1 [(M+H)⁺]; mp 134–137° C.

Example J40

[2-Amino-5-(isobutyl-methyl-amino)-4-trifluoromethyl-phenyl]-carbamic acid tert-butyl ester The title compound was prepared from [5-(isobutyl-methyl-amino)-2-nitro-4-trifluoromethyl-phenyl]-carbamic acid tert-butyl ester (Example C9) (3.88 g, 9.91 mmol) by hydrogenation with 10% Pd/C according to the general procedure J (method a). Obtained as a orange oil (2.70 g, 75%).

MS (ISP) 362.3 [(M+H)⁺].

Example J41

[2-Amino-5-(isopropyl-methyl-amino)-4-trifluoromethyl-phenyl]-carbamic acid tert-butyl ester The title compound was prepared from [5-(isopropyl-methyl-amino)-2-nitro-4-trifluoromethyl-phenyl]-carbamic acid tert-butyl ester (Example C10) (2.98 g, 7.90 mmol) by hydrogenation with 10% Pd/C according to the general procedure J (method a). Obtained as a orange oil (2.42 g, 88%).

MS (ISP) 348.5 [(M+H)⁺].

Example J42

[2-Amino-4-chloro-5-(isobutyl-methyl-amino)-1-phenyl]-carbamic acid tert-butyl ester The title compound was prepared from [4-chloro-5-(isobutyl-methyl-amino)-2-nitro-phenyl]-carbamic acid tert-butyl ester (Example C24) (5.55 g, 15.5 mmol) by reduction with $SnCl_2.2H_2O$ according to the general procedure J (method b). Obtained as a pale brown solid (3.98 g, 78%).

MS (ISP) 328.3 [(M+H)⁺].

Example J43

[2-Amino-4-chloro-5-(isopropyl-methyl-amino)-phenyl]-carbamic acid tert-butyl ester The title compound was prepared from [4-chloro-5-(isopropyl-methyl-amino)-2-nitro-phenyl]-carbamic acid tert-butyl ester (Example C12) (4.07 g, 11.8 mmol) by reduction with SnCl$_2$·2H$_2$O according to the general procedure J (method b). Obtained as a pale brown solid (3.08 g, 83%).

MS (ISP) 314.3 [(M+H)$^+$]; mp 116° C.

The following methods relate to the preparation of the ethyl or tert-butyl 3-aryl-3-oxo-propionates (formula IVa), which serve as building blocks in the synthesis of the target compounds (Synthetic Scheme G).

General Procedure K

Method a): Preparation of ethyl or tert-butyl 3-aryl-3-oxo-propionates

The ethyl or tert-butyl 3-aryl-3-oxo-propionates were prepared from the aryl acid chlorides and ethyl or tert-butyl malonate potassium salt [CAS-no. 6148-64-7 and 75486-33-8] with Et$_3$N and MgCl$_2$ in CH$_3$CN at 0° C. to 23° C. according to *Synthesis* 1993, 290. If the free aryl carboxylic acid was employed in this reaction, it was activated by treatment with ethyl chloroformate and Et$_3$N in THF/CH$_3$CN at 0° C. prior to reaction with the malonate salt.

Method b): Preparation of tert-butyl 3-aryl-3-oxo-propionates

The tert-butyl 3-aryl-3-oxo-propionates were alternatively prepared from the methyl or ethyl aryl esters by treatment with lithium tert-butyl acetate [prepared by treatment of tert-butyl acetate with lithium diisopropylamide in THF at −78° C.] in the presence of lithium tert-butoxide according to *Synthesis* 1985, 45. If the product contained residual starting material after workup, thus could be removed by selective saponification with LiOH in THF/MeOH/H$_2$O at 23° C.

Method c): Preparation of 3-aryl-3-oxo-propionic acids

The 3-aryl-3-oxo-propionic acids were prepared from the aryl acid chlorides and bis(trimethylsilyl)malonate with Et$_3$N and LiBr in CH$_3$CN at 0° C. according to *Synth. Commun.* 1985, 15, 1039 (method c1) or with n-BuLi in ether at −60° C. to 0° C. according to *Synthesis* 1979, 787 (method c2).

Method d): Preparation of ethyl or tert-butyl 3-aryl-3-oxo-propionates

The ethyl or tert-butyl 3-aryl-3-oxo-propionates were prepared from aryl nitriles and ethyl or tert-butyl bromoacetate [CAS-No. 105-36-2 and 5292-43-3] with activated Zinc dust in THF at reflux, followed by treatment of the obtained enamino ester with 10% HCl in THF at 23° C. according to *J. Org. Chem.* 1983, 48, 3835.

Example K1

3-Oxo-3-(3-pyridin-3-yl-phenyl)-propionic acid tert-butyl ester

The title compound was prepared from 3-pyridin-3-yl-benzoic acid methyl ester [CAS-No. 79601-27-7] (1.00 g, 4.69 mmol) by treatment with lithium tert-butyl acetate according to general procedure K (method b). Obtained as an orange oil (673 mg).

MS (ISP) 298.4 [(M+H)$^+$].

Example K2

3-Oxo-3-(3-pyridin-4-yl-phenyl)-propionic acid tert-butyl ester

The title compound was prepared from 3-pyridin-4-yl-benzoic acid methyl ester [CAS-No. 126179-78-0] (3.60 g, 16.88 mmol) by treatment with lithium tert-butyl acetate according to general procedure K (method b). Obtained as a yellow oil (3.88 g).

MS (ISN) 296.3 [(M−H)$^−$].

Example K3

3-Oxo-3-(3-pyridin-2-yl-phenyl)-propionic acid tert-butyl ester

The title compond was prepared from 3-pyridin-2-yl-benzoic acid methyl ester [CAS-No. 98061-20-2] (9.42 g, 44.18 mmol) by treatment with lithium tert-butyl acetate according to general procedure K (method b). Obtained as a yellow oil (8.35 g).

MS (ISP) 298.4 [(M+H)$^+$].

Example K4

3-[3-(6-Methyl-pyridin-3-yl)-phenyl]-3-oxo-propionic acid tert-butyl ester

The title compound was prepared from 3-(6-methyl-pyridin-3-yl)-benzoic acid methyl ester [prepared by the following procedure: A mixture of 3-carboxyphenylboronic acid (4.82 g, 29.07 mmol) and 3-bromo-2-methylpyridine (5.00 g, 29.07 mmol) in acetonitrile (145 mL) and 0.4M Na$_2$CO$_3$-solution (145 mL) was degassed and Pd(Ph$_3$P)$_4$ (1.68 g, 5 mol %) was added. The reaction mixture was refluxed for 16 h, evaporated to dryness (cf. *Synlett* 2000, 829). The residue was suspended in MeOH (400 mL) and SOCl$_2$ (10.5 mL, 145 mmol) was added dropwise at 23° C. and the reaction mixture was refluxed for 4 h. Evaporated to dryness, taken up in EtOAc, washed with sat. NaHCO$_3$-solution and brine, dried over Na$_2$SO$_4$. Removal of the solvent in vacuum left a brown oil, which was purified by silica gel column chromatography with cyclohexane/EtOAc.] (3.87 g, 17.0 mmol) by treatment with lithium tert-butyl acetate according to general procedure K (method b). Obtained as a yellow oil (4.73 g).

MS (ISP) 312 [(M+H)$^+$].

Example K5

3-[3-(2-Methyl-pyridin-3-yl)-phenyl]-3-oxo-propionic acid tert-butyl ester

The title compound was prepared from 3-(2-methyl-pyridin-3-yl)-benzoic acid methyl ester [prepared by the following procedure: A mixture of 3-carboxyphenylboronic acid (3.96 g, 23.85 mmol), 3-bromo-2-methylpyridine (5.23 g, 21.68 mmol) and K$_3$PO$_4$ (7.60 g, 35.78 mmol) in dioxane (112 mL) was degassed and Pd(Ph$_3$P)$_4$ (1.37 g, 1.2 mmol) was added. The reaction mixture was refluxed for 5 h, evaporated to dryness. The residue was suspended in MeOH (320 mL) and SOCl$_2$ (7.87 mL, 108.4 mmol) was added dropwise at 23° C. and the reaction mixture was refluxed for 16 h. Evaporated to dryness, taken up in EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (2.65 g, 11.66 mmol) by treatment with lithium tert-butyl acetate according to general procedure K (method b). Obtained as a colorless oil (2.62 g).

MS (ISN) 310.2 [(M−H)$^−$].

Example K6

3-[3-(6-Methyl-pyridazin-3-yl)-phenyl]-3-oxo-propionic acid tert-butyl ester

The title compound was prepared from 3-(6-methyl-pyridazin-3-yl)-benzoic acid methyl ester [prepared by the following procedure: A mixture of 3-carboxyphenylboronic acid (2.24 g, 13.5 mmol) and 3-chloro-6-methylpyridazine (1.79 g, 13.5 mmol) in acetonitrile (67 mL) and 0.4M $Na_2CO_3$-solution (67 mL) was degassed and $Pd(Ph_3P)_4$ (0.78 g, 5 mol %) was added. The reaction mixture was refluxed for 16 h, evaporated to dryness (cf. *Synlett* 2000, 829). The residue was suspended in MeOH (200 mL) and $SOCl_2$ (4.9 mL, 67.5 mmol) was added dropwise at 23° C. and the reaction mixture was refluxed for 16 h. Evaporated to dryness, taken up in EtOAc, washed with sat. $NaHCO_3$-solution and brine, dried over $Na_2SO_4$. Removal of the solvent in vacuum left a brown oil, which was purified by silica gel column chromatography with cyclohexane/ EtOAc.] (2.57 g, 11.26 mmol) by treatment with lithium tert-butyl acetate according to general procedure K (method b). Obtained as a light yellow solid (2.68 g).

MS (ISP) 313 [(M+H)$^+$]; mp 68° C.

Example K7

3-[3-(6-Methoxy-pyridazin-3-yl)-phenyl]-3-oxo-propionic acid tert-butyl ester

The title compound was prepared from 3-(6-methoxy-pyridazin-3-yl)-benzoic acid methyl ester [prepared by the following procedure: A mixture of 3-carboxyphenyl-boronic acid (7.11 g, 42.8 mmol) and 3-chloro-6-methoxy-pyridazine [CAS-No. 1722-10-7] (6.19 g, 42.8 mmol) in acetonitrile (212 mL) and 0.4M $Na_2CO_3$-solution (212 mL) was degassed and $Pd(Ph_3P)_4$ (2.47 g, 5 mol %) was added. The reaction mixture was refluxed for 16 h, evaporated to dryness (cf. *Synlett* 2000, 829). The residue was suspended in MeOH (630 mL) and $SOCl_2$ (15.5 mL, 214.1 mmol) was added dropwise at 23° C. and the reaction mixture was refluxed for 4 h. Evaporated to dryness, taken up in EtOAc, washed with sat. $NaHCO_3$-solution and brine, dried over $Na_2SO_4$. Removal of the solvent in vacuum left a brown oil, which was purified by silica gel column chromatography with cyclohexane/EtOAc.] (5.41 g, 22.15 mmol) by treatment with lithium tert-butyl acetate according to general procedure K (method b). Obtained as a yellow oil (6.39 g).

MS (ISP) 329 [(M+H)$^+$].

Example K8

3-[3-(2,6-Dimethyl-pyridin-3-yl)-phenyl]-3-oxo-propionic acid tert-butyl ester

The title compound was obtained from 3-(2,6-dimethyl-pyridin-3-yl)-benzonitrile [prepared by the following procedure: A mixture of 3-cyanophenylboronic acid [CAS-No. 150255-96-2] (4.74 g, 32.25 mmol), 3-bromo-2,6-dimethylpyridine [CAS-No. 3430-31-7] (5.00 g, 26.87 mmol) and $K_3PO_4$ (8.56 g, 35.78 mmol) in dioxane (126 mL) was degassed and $Pd(Ph_3P)_4$ (1.53 g, 1.37 mmol) was added. The reaction mixture was stirred at 90° C. for 18 h. Evaporated to dryness, taken up in EtOAc, washed with sat. $NaHCO_3$-solution and brine, dried over $Na_2SO_4$. Removal of the solvent in vacuum left a brown solid, which was purified by silica gel column chromatography with cyclohexane/EtOAc.] (2.2 g, 10.6 mmol) by treatment with tert-butyl bromoacetate and activated zinc, followed by hydrolysis with 10% HCl according to general procedure K (method d). Obtained as an orange oil (2.61 g).

MS (ISP) 326.4 [(M+H)$^+$].

Example K9

3-Oxo-3-(3-pyridazin-4-yl-phenyl)-propionic acid tert-butyl ester

The title compound was prepared from 3-pyridazin-4-yl-benzoic acid methyl ester [prepared by the following sequence: i.) An equimolar mixture of glyoxylic acid and m-tolyl-acetaldehyde [CAS-No. 72927-80-1] was heated to 135° C. for 17 h. ii.) The obtained crude 5-hydroxy-4-(m-tolyl)-2(5H)-furanone and hydrazine hydrate in BuOH were refluxed for 18 h according to *J. Med. Chem.* 1987, 30, 239. iii.) The obtained 5-m-tolyl-2H-pyridazin-3-one was heated with excess phosphorous oxychloride to 95° C. for 4 h. iv.) The obtained 3-chloro-5-m-tolyl-pyridazine was hydrogenated in MeOH and EtOAc over 5% Pd/C in the presence of NaOAc at 23° C. v.) The obtained 4-m-tolyl-pyridazine was oxidized with $KMnO_4$ in aqueous HOAc at 100° C. for 4 h. vi.) The obtained 3-pyridazin-4-yl-benzoic acid was esterified with $SOCl_2$ in MeOH at 60° C.] by treatment with lithium tert-butyl acetate according to general procedure K (method b). Obtained as a yellow oil (554 mg).

MS (ISN) 297 [(M−H)$^-$].

Example K10

3-[3-(6-Methoxy-pyridin-3-yl)-phenyl]-3-oxo-propionic acid tert-butyl ester

The title compound was obtained from 3-(6-methoxy-pyridin-3-yl)-benzonitrile [prepared by the following procedure: A mixture of 3-cyanophenylboronic acid [CAS-No. 150255-96-2] (6.47 g, 44 mmol), 5-bromo-2-methoxypyridine [CAS-No. 13472-85-0] (5.18 mL, 40 mmol) and $K_3PO_4$ (12.74 g, 60 mmol) in dioxane (200 mL) was degassed and $Pd(Ph_3P)_4$ (2.31 g, 5 mol %) was added. The reaction mixture was stirred at 90° C. for 4.5 h. Evaporated to dryness, taken up in EtOAc, washed with sat. $NaHCO_3$-solution and brine, dried over $Na_2SO_4$. Removal of the solvent in vacuum left a brown solid, which was purified by silica gel column chromatography with cyclohexane/EtOAc.] (1.95 g, 9.28 mmol) by treatment with tert-butyl bromoacetate and activated zinc, followed by hydrolysis with 10% HCl according to general procedure K (method d). Obtained as a brown oil (2.81 g).

MS (ISN) 326.2 [(M−H)$^-$].

Example K11

3-[3-(6-Methyl-pyridin-2-yl)-phenyl]-3-oxo-propionic acid tert-butyl ester

The title compound was prepared from 3-(6-methyl-pyridin-2-yl)-benzonitrile [prepared by the following procedure: A mixture of 3-cyanophenylboronic acid [CAS-No. 150255-96-2] (11.10 g, 75.6 mmol), 2-bromo-6-methylpyridine [CAS-No. 5315-25-3] (10.0 g, 58.1 mmol) and $K_3PO_4$ (21.22 g, 100 mmol) in dioxane (250 mL) was degassed and $Pd(Ph_3P)_4$ (3.36 g, 5 mol %) was added. The reaction mixture was stirred at 90° C. for 38 h. Evaporated to dryness, taken up in EtOAc, washed with sat. $NaHCO_3$-solution and brine, dried over $Na_2SO_4$. Removal of the solvent in vacuum left a brown solid, which was purified by silica gel column chromatography with cyclohexane/ EtOAc.] (6.36 g, 32.7 mmol) by treatment with tert-butyl bromoacetate and activated zinc, followed by hydrolysis with 10% HCl according to general procedure K (method d). Obtained as a yellow oil (7.84 g).

MS (ISN) 311 [(M−H)$^-$].

Example K12

3-[3-(2-Methyl-pyridin-4-yl)-phenyl]-3-oxo-propionic acid tert-butyl ester

The title compound was prepared from 3-(2-methyl-pyridin-4-yl)-benzoic acid methyl ester [prepared by the following procedure: A mixture of 3-carboxyphenylboronic acid (7.13 g, 43.0 mmol) and 4-bromo-2-methylpyridine [*Chem. Pharm. Bull.* 1990, 38 (9), 2446–2458] (7.40 g, 43.0 mmol) in acetonitrile (215 ml) and 0.4M $Na_2CO_3$-solution (215 ml) was degassed and $Pd(Ph_3P)_4$ (5.0 g, 0.43 mmol) was added. The reaction mixture was refluxed for 18 h and evaporated to dryness [*Synlett* 2000 (6), 829–831]. The residue was suspended in MeOH (215 ml), $SOCl_2$ (15.6 ml, 215 mmol) was added dropwise at RT and the reaction mixture was refluxed for 4h. Aqueous work-up and further purification by column chromatography as described in example K4] (10.1 g, 44.4 mmol) by treatment with tert-butyl acetate according to general procedure K (method b). Obtained as a light yellow oil (9.50 g, 69%).

MS (ISP) 312.3 [(M+H)$^+$].

Example K13

3-Oxo-3-(3-pyrimidin-5-yl-phenyl)-propionic acid tert-butyl ester

The title compound was obtained from 3-(3-pyrimidin-5-yl)-benzoic acid methyl ester [prepared by the following procedure: A mixture of 3-carboxyphenylboronic acid (7.13 g, 43.0 mmol) and commercially available 5-bromo-pyrimidine (6.84 g, 43.0 mmol) in acetonitrile (215 ml) and 0.4M $Na_2CO_3$-solution (215 ml) was degassed and $Pd(Ph_3P)_4$ (5.0 g, 0.43 mmol) was added. The reaction mixture was refluxed for 4 h and evaporated to dryness [*Synlett* 2000 (6) 829–831]. The residue was suspended in MeOH (215 ml), $SOCl_2$ (15.6 ml, 215 mmol) was added dropwise at RT and the reaction mixture was refluxed for 4h. Aqueous work-up and further purification by column chromatography as described in example K4] (7.63 g, 35.6 mmol) by treatment with tert-butyl acetate according to general procedure K (method b). Obtained as a light yellow oil (6.17 g, 58%).

MS (ISP) 299.4 [(M+H)$^+$].

Example K14

3-Oxo-3-(3-pyrazin-2-yl-phenyl)-propionic acid tert-butl ester

The title compound was prepared from 3-(3-pyrazin-2-yl)-benzoic acid methyl ester [prepared by the following procedure: A mixture of 3-carboxyphenylboronic acid (7.13 g, 43.0 mmol) and commercially available 2-chloro-pyrazine (4.93 g, 43.0 mmol) in acetonitrile (215 ml) and 0.4M $Na_2CO_3$-solution (215 ml) was degassed and $Pd(Ph_3P)_4$ (5.0 g, 0.43 mmol) was added. The reaction mixture was refluxed for 4 h and evaporated to dryness [*Synlett* 2000 (6), 829–831]. The residue was suspended in MeOH (215 ml), $SOCl_2$ (15.6 ml, 215 mmol) was added dropwise at RT and the reaction mixture was refluxed for 5 h. Aqueous work-up and further purification by column chromatography as described in example K4] (6.79 g, 31.7 mmol) by treatment with tert-butyl acetate according to general procedure K (method b). Obtained as an orange oil (4.57 g, 48%).

MS (ISP) 299.4 [(M+H)$^+$].

Example K15

3-[3-(2,6-Dimethyl-pyridin-4-yl)-phenyl]-3-oxo-propionic acid tert-butyl ester

The title compound was prepared from commercially available 3-cyanophenylboronic acid [CAS-No. 150255-96-2] and 4-bromo-2,6-dimethylpyridine [*Chem. Pharm. Bull.* 1990, 38, 2446 and *J. Org. Chem.* 1962, 27, 1665] according to general procedure K (method d, example K8). Obtained as an orange oil.

MS (ISP) 326.4 [(M+H)$^+$].

Example K16

3-[3-(6-Methyl-pyrazin-2-yl)-phenyl]-3-oxo-propionic acid tert-butyl ester

The title compound was prepared from commercially available 3-cyanophenylboronic acid [CAS-No. 150255-96-2] and commercially available 2-chloro-6-methylpyrazine according to general procedure K (method d; example K8). Obtained as a light brown oil.

MS (ISP) 313.3 [(M+H)$^+$].

Example K17

3-[3-(2,5-Dimethyl-pyridin-4-yl)-phenyl]-3-oxo-propionic acid tert-butyl ester

The title compound was prepared from commercially available 3-cyanophenylboronic acid [CAS-No. 150255-96-2] and 4-bromo-2,5-dimethyl-pyridine [CAS-No. 17117-23-6] according to general procedure K (method d; example K8). Obtained as a light yellow oil.

MS (ISP) 326.2 [(M+H)$^+$].

Example K18

3-[3-(2,3-Dimethyl-pyridin-4-yl)-phenyl]-3-oxo-propionic acid tert-butyl ester

The title compound was prepared from commercially available 3-cyanophenylboronic acid [CAS-No. 150255-96-2] and 4-bromo-2,3-dimethyl-pyridine [CAS-No. 259807-91-5] according to general procedure K (method d; example K8). Obtained as an orange oil.

MS (ISP) 326.3 [(M+H)$^+$].

Example K19

3-[3-(5-Ethyl-2-methyl-pyridin-4-yl)-phenyl]-3-oxo-propionic acid tert-butyl ester The title compound was prepared from commercially available 3-cyanophenylboronic acid [CAS-No. 150255-96-2] and 4-bromo-5-ethyl-2-methyl-pyridine [CAS-No. 98488-99-4] according to general procedure K (method d; example K8). Obtained as an orange oil.

MS (ISP) 340.2 [(M+H)$^+$].

Example K20

3-[3-(2-Ethyl-pyridin-4-yl)-phenyl]-3-oxo-propionic acid tert-butyl ester

The title compound was prepared from commercially available 3-cyanophenylboronic acid [CAS-No. 150255-96-2] and 4-bromo-2-ethyl-pyridine [CAS-No. 156761-88-5] according to general procedure K (method d; example K8). Obtained as a light brown oil.

MS (ISP) 326.2 [(M+H)$^+$].

Example K21

3-[3-(6-Cyclopropyl-pyridin-3-yl)-phenyl]-3-oxo-propionic acid tert-butyl ester

The title compound was obtained from 3-(6-cyclopropyl-pyridin-3-yl)-benzonitrile [prepared by the following procedure: A mixture of 3-cyanophenylboronic acid [CAS-No. 150255-96-2] (8.82 g, 60 mmol), crude 5-bromo-2-cyclopropylpyridine {prepared by the following procedure: A mixture of 2,5-dibromopyridine (11.85 g, 50 mmol), cyclopropylzinc chloride (0.4 M in THF, 160 mL, 64 mmol), Pd(PPh$_3$)$_4$ (578 mg, 1 mol %) in THF (55 mL) was stirred under Argon atmosphere at 70° C. for 1.5 h. Cooled to rt, poured into sat. NaHCO$_3$-solution, extracted with ether, washed with brine, dried over Na$_2$SO$_4$. Removal of the solvent in vacuum left a brown oil (12.36 g).} (ca. 60 mmol), Pd(PPh$_3$)$_4$ (1.733 g, 3 mol %) and K$_2$CO$_3$ (13.82 g, 100 mmol) in toluene (250 mL), EtOH (22 mL) and H$_2$O (50 mL) was stirred at 80° C. for 14 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (9.88 g, 44.87 mmol) by treatment with tert-butyl bromoacetate and activated zinc, followed by hydrolysis with 10% HCl according to general procedure K (method d). Obtained as a light yellow solid (9.65 g, 64%).

MS (ISP) 338.3 [(M+H)$^+$]; mp 72° C.

Example K22

3-[3-(6-Isopropyl-pyridin-3-yl)-phenyl]-3-oxo-propionic acid tert-butyl ester

The title compound was obtained from 3-(6-isopropyl-pyridin-3-yl)-benzonitrile [prepared by the following procedure: A mixture of 3-cyanophenylboronic acid [CAS-No. 150255-96-2] (5.78 g, 39.3 mmol), crude 5-bromo-2-isopropenyl-pyridine {prepared by the following procedure: A solution of dried ZnCl$_2$ (6.81 g, 50 mmol) in THF (71 mL) was added dropwise to isopropenyl magnesiumbromide-solution 0.5 M (100 mL, 50 mmol) at −75° C. and the mixture was allowed to warm up to 23° C. A solution of 2,5-dibromopyridine (9.12 g, 35.5 mmol) and Pd(PPh$_3$)$_4$ (450 mg, 0.39 mmol) in THF (50 mL) was added dropwise at 23° C. and the reaxtion mixture was refluxed for 20 h. Cooled to room temperature, poured into sat. NaHCO$_3$-solution, extracted with ether, washed with brine, dried over Na$_2$SO$_4$. Removal of the solvent in vacuum left a brown liquid (10.98 g).} (ca. 36 mmol), Pd(PPh$_3$)$_4$ (1.24 g, 3 mol %) and K$_3$PO$_4$ (11.38 g, 53.1 mmol) in dioxane (180 mL) was stirred at 90° C. for 18 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc to obtain a yellow solid (4.91 g, 22.3 mmol). This material was hydrogenated with Pd/C 10% (0.89 g, 0.84 mmol) in EtOAc (210 mL) at 23° C. for 28 h.] (4.71 g, 21.2 mmol) by treatment with tert-butyl bromoacetate and activated zinc, followed by hydrolysis with 10% HCl according to general procedure K (method d). Obtained as a light yellow oil (4.95 g, 69%).

MS (ISP) 340 [(M+H)$^+$].

Example K23

3-[3-(6-Ethyl-pyridin-3-yl)-phenyl]-3-oxo-propionic acid tert-butyl ester

The title compound was obtained from 3-(6-ethyl-pyridin-3-yl)-benzonitrile [prepared by the following procedure: A mixture of 3-cyanophenylboronic acid [CAS-No. 150255-96-2] (2.77 g, 18.8 mmol), 5-bromo-2-ethyl-pyridine [CAS-No. 38749-90-5] (3.24 g, 15.7 mmol), Pd(PPh$_3$)$_4$ (906 mg, 3 mol %) and K$_3$PO$_4$ (4.99 g, 23.5 mmol) in dioxane (77 mL) was stirred at 90° C. for 18 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc to obtain a yellow liquid.] (1.94 g, 9.32 mmol) by treatment with tert-butyl bromoacetate and activated zinc, followed by hydrolysis with 10% HCl according to general procedure K (method d). Obtained as a light yellow oil (2.23 g, 74%).

MS (ISP) 326 [(M+H)$^+$].

Example K24

3-[3-(2-Cyano-pyridin-4-yl)-phenyl]-3-oxo-propionic acid tert-butyl ester

The title compound was prepared from 3-(2-cyano-pyridin-4-yl)-benzoic acid ethyl ester [prepared by the following sequence: 1.) A mixture of 3-pyridin-4-yl-benzoic acid ethyl ester [CAS-No. 4385-74-4] (4.711 g, 20.7 mmol) and hydrogen peroxide (3.4 mL, 33.2 mmol) was heated at 70° C. for 8 days {after 4 days further hydrogen peroxide (2.1 mL, 20.7 mmol) was added}, then solvent was removed, water (twice 15 mL) was added and volatile compounds were again removed. 2.) The obtained 3-(1-oxy-pyridin-4-yl)-benzoic acid ethyl ester (4.763 g, 19.58 mmol), trimethylsilyl cyanide (7.35 mL, 58.7 mmol) and triethylamine (5.46 mL, 39.2 mmol) in acetonitrile (20 mL) was refluxed for 22.5 h. After evaporation of the solvent, the residue was made alkaline with 3N Na$_2$CO$_3$ (130 mL) and extracted five times with dichloromethane (120 mL). The combined organic layers were washed with H$_2$O (100 ml) and brine (100 mL), dried over Na$_2$SO$_4$. Removal of the solvent in vacuum left a brown residue, which was purified by silica gel column chromatography with cyclohexane/EtOAc.] (4.51 g, 17.88 mmol) by treatment with lithium tert-butyl acetate according to general procedure K (method b). Obtained as a yellow oil (2.53 g).

MS (ISN) 321.3 [(M−H)$^-$].

Example K25

3-[3-(6-Amino-pyridin-3-yl)-phenyl]-3-oxo-propionic acid tert-butyl ester

The title compound was obtained from 3-(6-amino-pyridin-3-yl)-benzonitrile [prepared by the following procedure: A mixture of 3-cyanophenylboronic acid [CAS-No. 150255-96-2] (17.0 g, 115.7 mmol), 2-amino-5-bromo-pyridine [CAS-No. 1072-97-5] (15.64 g, 90.4 mmol), Pd(PPh$_3$)$_4$ (5.0 g, 5 mol %) and 0.4 M Na$_2$CO$_3$-solution (450 mL) in acetonitrile (450 mL) was stirred at 90° C. for 2 days. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc to obtain a yellow solid.] (4.34 g, 22.23 mmol) by treatment with tert-butyl bromoacetate and activated zinc, followed by hydrolysis with 10% HCl according to general procedure K (method d). Obtained as a light brown solid (4.41 g, 63%).

MS (ISN) 311.1 [(M−H)$^-$]; mp 78–80° C.

Example K26

3-[3-(6-Cyano-pyridin-3-yl)-phenyl]-3-oxo-propionic acid tert-butyl ester

The title compound was prepared from 3-(6-cyano-pyridin-3-yl)-benzoic acid methyl ester [prepared by the following procedure: A mixture of 3-carboxyphenylboronic acid (2.08 g, 12.51 mmol) and 5-bromo-pyridine-2-carbonitrile [CAS-No. 97483-77-7] (2.08 g, 11.37 mmol) in acetonitrile (55 ml) and 0.4M $Na_2CO_3$-solution (55 ml) was degassed and $Pd(Ph_3P)_4$ (657 mg, 0.57 mmol) was added. The reaction mixture was refluxed for 18 h and evaporated to dryness [*Synlett* 2000 (6), 829–831]. The residue was suspended in MeOH (300 ml), $SOCl_2$ (2.61 ml, 36 mmol) was added dropwise at 23° C. and the reaction mixture was stirred at 23° C. for 3 days. Concentrated in vacuum to about 100 mL, diluted with EtOAc, washed with sat. $NaHCO_3$-solution and brine, dried over $Na_2SO_4$. Removal of the solvent in vacuum left a brown residue, which was purified by silica gel column chromatography with cyclohexane/EtOAc.] (1.38 g, 5.79 mmol) by treatment with lithium tert-butyl acetate according to general procedure K (method b). Obtained as an orange oil (530 mg).

MS (ISN) 323.3 [(M–H)$^-$].

Example K27

3-Oxo-3-(3-pyridazin-3-yl-phenyl)-propionic acid tert-butyl ester

The title compound was prepared from 3-pyridazin-3-yl-benzoic acid methyl ester [prepared by the following procedure: A mixture of 3-carboxyphenylboronic acid (6.98 g, 42.06 mmol) and 3-chloropyridazine [CAS-No. 1120-95-2] (4.817 g, 42.06 mmol) in acetonitrile (210 ml) and 0.4M $Na_2CO_3$-solution (210 ml) was degassed and $Pd(Ph_3P)_4$ (2.43 g, 2.1 mmol) was added. The reaction mixture was refluxed for 15 h and evaporated to dryness [*Synlett* 2000 (6), 829–831]. The residue was suspended in MeOH (500 ml), $SOCl_2$ (15.3 ml, 211 mmol) was added dropwise at 23° C. and the reaction mixture was stirred at reflux for 16 h. Concentrated in vacuum to about 100 mL, diluted with EtOAc, washed with sat. $NaHCO_3$-solution and brine, dried over $Na_2SO_4$. Removal of the solvent in vacuum left a brown residue, which was purified by silica gel column chromatography with cyclohexane/EtOAc.] (7.35 g, 34.32 mmol) by treatment with lithium tert-butyl acetate according to general procedure K (method b). Obtained as a yellow oil (8.306 g, 81%).

MS (ISP) 299.3 [(M+H)$^+$].

Example K28

3-[3-(6-Dimethylamino-pyridin-3-yl)-phenyl]-3-oxo-propionic acid tert-butyl ester The title compound was obtained from 3-(6-dimethylamino-pyridin-3-yl)-benzonitrile [prepared by the following procedure: A mixture of 3-cyanophenylboronic acid [CAS-No. 150255-96-2] (6.994 g, 47.6 mmol), (5-bromo-pyridin-2-yl)-dimethylamine [CAS-No. 26163-07-5] (7.326 g, 36.6 mmol), $Pd(PPh_3)_4$ (2.116 g, 1.83 mmol) and $K_3PO_4$ (12.436 g, 58.6 mmol) in dioxane (180 mL) was stirred at 90° C. for 24 h. Cooled to room temperature, diluted with EtOAc, washed with sat. $NaHCO_3$-solution and brine, dried over $Na_2SO_4$. Removal of the solvent in vacuum left a brown solid, which was purified by silica gel column chromatography with cyclohexane/EtOAc to obtain a yellow solid.] (1.157 g, 5.2 mmol) by treatment with tert-butyl bromoacetate and activated zinc, followed by hydrolysis with 10% HCl according to general procedure K (method d). Obtained as a yellow oil (1.382 g, 78%).

MS (ISP) 341 [(M+H)$^+$].

Example K29

3-[3-(2-Cyclopropyl-pyridin-3-yl)-phenyl]-3-oxo-propionic acid tert-butyl ester

The title compound was obtained from 3-(2-cyclopropyl-pyridin-3-yl)-benzonitrile [prepared by the following procedure: A mixture of 3-cyanophenylboronic acid [CAS-No. 150255-96-2] (8.82 g, 60 mmol), crude trifluoro-methanesulfonic acid 2-cyclo-propyl-pyridin-3-yl ester {prepared by the following procedure: A mixture of trifluoro-methanesulfonic acid 2-bromo-pyridin-3-yl ester [CAS-No. 157373-97-2] (5.45 g, 17.81 mmol), cyclopropylzinc chloride (0.4 M in THF, 60 mL, 24 mmol), $Pd(PPh_3)_4$ (200 mg, 1 mol %) in THF (20 mL) was stirred under argon atmosphere at 70° C. for 1.5 h. Cooled to room temperature, poured into sat. $NaHCO_3$-solution, extracted with ether, washed with brine, dried over $Na_2SO_4$. Removal of the solvent in vacuum left a yellow oil (5.88 g).} (ca. 18 mmol), $Pd(PPh_3)_4$ (617 mg, 3 mol %) and $K_2CO_3$ (4.92 g, 32 mmol) in toluene (90 mL), EtOH (8 mL) and $H_2O$ (18 mL) was stirred at 80° C. for 13 h. Cooled to room temperature, diluted with EtOAc, washed with sat. $NaHCO_3$-solution and brine, dried over $Na_2SO_4$. Removal of the solvent in vacuum left a brown solid, which was purified by silica gel column chromatography with cyclohexane/EtOAc.] (3.69 g, 16.75 mmol) by treatment with tert-butyl bromoacetate and activated zinc, followed by hydrolysis with 10% HCl according to general procedure K (method d). Obtained as a yellow oil (4.32 g, 76%).

MS (ISN) 336.1 [(M–H)$^-$].

Example K30

3-[3-(4-Methyl-pyridin-3-yl)-phenyl]-3-oxo-propionic acid tert-butyl ester

The title compound was obtained from 3-(4-methyl-pyridin-3-yl)-benzonitrile [prepared by the following procedure: A mixture of 3-cyanophenylboronic acid [CAS-No. 150255-96-2] (8.82 g, 60 mmol), 3-bromo-4-methylpyridine [CAS-No. 3430-22-6] (8.60 g, 50 mmol), $Pd(PPh_3)_4$ (1.73 g, 3 mol %) and 2M $K_2CO_3$-solution (50 mL) in toluene (250 mL) and EtOH (22 mL) was stirred at 80° C. for 3 h. Cooled to room temperature, diluted with EtOAc, washed with sat. $NaHCO_3$-solution and brine, dried over $Na_2SO_4$. Removal of the solvent in vacuum left a brown solid, which was purified by silica gel column chromatography with cyclohexane/EtOAc.] (8.90 g, 45.8 mmol) by treatment with tert-butyl bromoacetate and activated zinc, followed by hydrolysis with 10% HCl according to general procedure K (method d). Obtained as an orange oil (12.22 g, 86%).

MS (ISP) 312.3 [(M–H)$^-$].

Example K31

3-[3-(2-Ethyl-pyridin-3-yl)-phenyl]-3-oxo-propionic acid tert-butyl ester

The title compound was obtained from 3-(2-ethyl-pyridin-3-yl)-benzonitrile [prepared by the following procedure: A mixture of 3-cyanophenylboronic acid [CAS-No. 150255-96-2] (3.53 g, 24 mmol), crude trifluoro-methanesulfonic acid 2-ethyl-pyridin-3-yl ester {prepared by the following procedure: A mixture of trifluoro-methanesulfonic acid 2-bromo-pyridin-3-yl ester [CAS-No. 157373-97-2] (6.12 g, 20 mmol), diethylzinc (1.1 M in toluene, 11 mL, 12 mmol), $Pd(PPh_3)_4$ (230 mg, 1 mol %) in THF (90 mL) was stirred under argon atmosphere at 70° C. for 1 h. Cooled to room temperature, poured into sat. $NaHCO_3$-solution, extracted with ether, washed with brine, dried over $Na_2SO_4$. Removal of the solvent in vacuum left a yellow oil (5.10 g).} (ca. 20 mmol), $Pd(PPh_3)_4$ (690 mg, 3 mol %) and $K_2CO_3$ (5.53 g, 40 mmol) in toluene (100 mL), EtOH (9 mL) and $H_2O$ (20 mL) was stirred at 80° C. for 4.5 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (3.44 g, 16.5 mmol) by treatment with tert-butyl bromoacetate and activated zinc, followed by hydrolysis with 10% HCl according to general procedure K (method d). Obtained as a yellow oil (1.11 g, 21%).

MS (ISP) 326 [(M+H)$^+$].

Example K32

3-[3-(4,6-Dimethyl-pyridin-3-yl)-phenyl]-3-oxo-propionic acid tert-butyl ester

The title compound was obtained from 3-(4,6-dimethyl-pyridin-3-yl)-benzonitrile [prepared by the following procedure: A mixture of 3-cyanophenylboronic acid [CAS-No. 150255-96-2] (8.82 g, 60 mmol), 5-bromo-2,4-dimethyl-pyridine [CAS-No. 27063-92-9] (9.3 g, 50 mmol), Pd(PPh$_3$)$_4$ (1.73 g, 3 mol %) and 2M K$_2$CO$_3$-solution (50 mL) in dioxane (250 mL) and EtOH (22 mL) was stirred at 80° C. for 3.5 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (8.90 g, 42.7 mmol) by treatment with tert-butyl bromoacetate and activated zinc, followed by hydrolysis with 10% HCl according to general procedure K (method d). Obtained as a yellow oil (2.73 g, 20%).

MS (EI) 325.1 (M$^+$).

Example K33

3-[3-(6-Cyclopropyl-4-methyl-pyridin-3-yl)-phenyl]-3-oxo-propionic acid tert-butyl ester The title compound was obtained from 3-(6-cyclopropyl-4-methyl-pyridin-3-yl)-benzonitrile [prepared by the following procedure: A mixture of 3-cyanophenylboronic acid [CAS-No. 150255-96-2] (5.15 g, 35 mmol), 5-bromo-2-cyclopropyl-4-methyl-pyridine {prepared by the following procedure: A mixture of 2,5-dibromo-4-methyl-pyridine [CAS-No. 3430-26-0] (12.55 g, 50 mmol), cyclopropylzinc chloride (0.4 M in THF, 156 mL, 62.5 mmol), Pd(PPh$_3$)$_4$ (580 mg, 1 mol %) in THF (55 mL) was stirred under argon atmosphere at 70° C. for 1 h. Cooled to room temperature, poured into sat. NaHCO$_3$-solution, extracted with ether, washed with brine, dried over Na$_2$SO$_4$. Removal of the solvent in vacuum left a yellow oil (6.24 g).} (6.19 g, 29.2 mmol), Pd(PPh$_3$)$_4$ (1.01 g, 3 mol %) and 2M K$_2$CO$_3$-solution (29 mL) in toluene (146 mL) and EtOH (13 mL) was stirred at 80° C. for 3 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (5.11 g, 21.8 mmol) by treatment with tert-butyl bromoacetate and activated zinc, followed by hydrolysis with 10% HCl according to general procedure K (method d). Obtained as an off-white solid (1.93 g, 25%).

MS (EI) 351 (M$^+$); mp 65–73° C.

Example K34

3-[3-(2-Ethyl-6-methyl-pyridin-4-yl)-phenyl]-3-oxo-propionic acid tert-butyl ester The title compound was obtained from 3-(2-ethyl-6-methyl-pyridin-4-yl)-benzonitrile [prepared by the following procedure: A mixture of 3-cyanophenylboronic acid [CAS-No. 150255-96-2] (11.31 g, 76.9 mmol), 4-bromo-2-ethyl-6-methyl-pyridine [CAS-No. 155887-27-7] (12.83 g, 64.1 mmol), Pd(PPh$_3$)$_4$ (2.22 g, 3 mol %) and K$_2$CO$_3$ (17.73 g, 128.2 mmol) in toluene (360 mL), EtOH (29 mL) and H2O (72 mL) was stirred at 80° C. for 2 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (12.34 g, 55.5 mmol) by treatment with tert-butyl bromoacetate and activated zinc, followed by hydrolysis with 10% HCl according to general procedure K (method d). Obtained as a yellow oil (15.21 g, 81%).

MS (EI) 339 (M$^+$).

Example K35

3-[3-(6-Ethyl-4-methyl-pyridin-3-yl)-phenyl]-3-oxo-propionic acid tert-butyl ester The title compound was obtained from 3-(6-ethyl-4-methyl-pyridin-3-yl)-benzonitrile [prepared by the following procedure: A mixture of 3-cyanophenylboronic acid [CAS-No. 150255-96-2] (3.53 g, 24 mmol), 5-bromo-2-ethyl-4-methyl-pyridine {prepared by the following procedure: A mixture of 2,5-dibromo-4-methyl-pyridine [CAS-No. 3430-26-0] (5.0 g, 20 mmol), diethylzinc (1.1 M in toluene, 10.9 mL, 12 mmol), Pd(PPh$_3$)$_4$ (231 mg, 1 mol %) in THF (90 mL) was stirred under argon atmosphere at 70° C. for 0.5 h. Cooled to room temperature, poured into sat. NaHCO$_3$-solution, extracted with ether, washed with brine, dried over Na$_2$SO$_4$. Removal of the solvent in vacuum followed by silica gel column chromatography with cyclohexane/EtOAc left a colorless oil (5.321 g).} (5.321 g, 20 mmol), Pd(PPh$_3$)$_4$ (693 mg, 3 mol %) and K$_2$CO$_3$ (5.53 g, 40 mmol) in toluene (100 mL), EtOH (9 mL) and H$_2$O (20 mL) was stirred at 80° C. for 3.5 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (2.330 g, 10.5 mmol) by treatment with tert-butyl bromoacetate and activated zinc, followed by hydrolysis with 10% HCl according to general procedure K (method d). Obtained as a brown oil (2.926 g, 82%).

MS (EI) 339 (M$^+$).

Example K36

3-[3-(2-Cyclopropyl-6-methyl-pyridin-4-yl)-phenyl]-3-oxo-propionic acid tert-butyl ester The title compound was obtained from 3-(2-cyclopropyl-6-methyl-pyridin-4-yl)-benzonitrile [prepared by the following procedure: A mixture of 3-cyanophenylboronic acid [CAS-No. 150255-96-2] (0.71 g, 4.8 mmol), 4-bromo-2-cyclopropyl-6-methyl-pyridine {prepared by the following procedure: A mixture of 2,4-dibromo-6-methyl-pyridine [CAS-No. 79055-52-0] (1.00 g, 4.0 mmol), cyclopropylzinc chloride (0.4 M in THF, 12.5 mL, 5 mmol), Pd(PPh$_3$)$_4$ (46 mg, 1 mol %) in THF (4.4 mL) was stirred under argon atmosphere at 70° C. for 1 h. Cooled to room temperature, poured into sat. NaHCO$_3$-solution, extracted with ether, washed with brine, dried over Na$_2$SO$_4$. Removal of the solvent in vacuum left a brown oil.} (ca. 4 mmol), Pd(PPh$_3$)$_4$ (139 mg, 3 mol %) and K$_2$CO$_3$ (1.11 g, 8.0 mmol) in toluene (22 mL), EtOH (1.8 mL) and H$_2$O (4.5 mL) was stirred at 80° C. for 2 h. Cooled to room temperature, diluted with EtOAc, washed with sat. NaHCO$_3$-solution and brine, dried over Na$_2$SO$_4$. Removal of the solvent in vacuum left a brown solid, which was purified by silica gel column chromatography with cyclohexane/EtOAc.] (0.94 g, 4.0 mmol) by treatment with tert-butyl bromoacetate and activated zinc, followed by hydrolysis with 10% HCl according to general procedure K (method d). Obtained as a yellow oil (1.17 g, 83%).

MS (ISP) 352 [(M+H)$^+$].

Example K37

3-[3-(2-Isobutyl-pyridin-4-yl)-phenyl]-3-oxo-propionic acid tert-butyl ester

The title compound was prepared from commercially available 3-cyanophenylboronic acid [CAS-No. 150255-96-2] and 4-chloro-2-isobutyl-pyridine [D. L. Comins; *J. Org. Chem.* 50 (1985) 4410] according to general procedure K (method d; example K8). Obtained as a yellow oil.

MS (ISP) 354.3 [(M+H)$^+$].

Example K38

3-Oxo-3-[3-(2-trifluoromethyl-pyridin-4-yl)-phenyl]-propionic acid tert-butyl ester The title compound was prepared from commercially available 3-cyanophenylboronic acid [CAS-No. 150255-96-2] and 4-chloro-2-trifluoromethyl-pyridine [CAS-No. 131748-14-6] according to general procedure K (method d; example K8). Obtained as an orange oil.

MS (ISP) 364.0 [(M−H)$^-$].

Example K39

3-[3-(2-Isopropyl-pyridin-4-yl)-phenyl]-3-oxo-propionic acid tert-butyl ester

The title compound was prepared from commercially available 3-cyanophenylboronic acid [CAS-No. 150255-96-2] and 4-chloro-2-isopropyl-pyridine [CAS-No. 98420-91-8] according to general procedure K (method d; example K8). Obtained as a light brown oil.

MS (ISP) 340.3 [(M+H)$^+$].

Example K40

(RS)-3-Oxo-3-{3-[2-(tetrahydro-pyran-2-yloxymethyl)-pyridin-4-yl]-phenyl}-propionic acid tert-butyl ester a) Oxidation of 3-(2-methyl-pyridin-4-yl)-benzoic acid methyl ester (26.2 g, 0.11 mol; example K12) with H$_2$O$_2$ (30%, 31.5 ml, 0.31 mol) in acetic acid (117 ml) at 70° C. for 27 h and subsequent reaction of the N-oxide in acetic acid anhydride (22 ml) at 135° C. for 30 min yielded after aqueous work-up 3-(2-acetoxymethyl-pyridin-4-yl)-benzoic acid methyl ester (25.3 g, 82%) as a brown oil.

b) Hydrolysis of crude 3-(2-acetoxymethyl-pyridin-4-yl)-benzoic acid methyl ester (25.3 g, 0.09 mmol) with sodium methanolate (5.4M in methanol, 5 ml) in methanol (100 ml) at RT for 48 h led after aqueous work-up and purification by column chromatography (ethyl acetate) to 3-(2-hydroxymethyl-pyridin-4-yl)-benzoic acid methyl ester (brown oil, 14.7 g, 68%), which by reaction with 3,4-dihydro-2H-pyrane (9.3 ml, 0.10 mol) in dichloromethane (165 ml) at RT for 22h gave after aqueous work-up and purification by column chromatography (ethyl acetate) un-reacted material (9.46 g) and (RS)-3-[2-(tetrahydro-pyran-2-yloxymethyl)-pyridin-4-yl]-benzoic acid methyl ester (7.88 g, 35%) as a light brown oil.

c) Reaction of (RS)-3-[2-(tetrahydro-pyran-2-yloxymethyl)-pyridin-4-yl]-benzoic acid methyl ester with tert-butyl acetate according to general procedure K (method d; example K8) yielded the title compound as a light yellow oil.

MS (ISP) 412.2 [(M+H)$^+$].

Example K41

3-[3-(6-Methyl-pyrimidin-4-yl)-phenyl]-3-oxo-propionic acid tert-butyl ester

The title compound was prepared from 3-(6-methyl-pyrimidin-4-yl)-benzoic acid methyl ester ester [prepared by the following procedure: A solution of 3-chlorocarbonyl-benzoic acid methyl ester (19.9 g, 0.1 mol) in Et$_2$O (20 ml) was added at 5° C. to a solution of 3-oxo-butyric acid tert-butyl ester magnesium salt [prepared from 3-oxo-butyric acid tert-butyl ester (13.4 ml, 82 mmol) and freshly prepared magnesium ethoxide [from Mg (2.65 g, 109 mol) in ethanol (25 ml)/CCl4 (0.5 ml)] according to *Helv. Chim. Acta* 1952, 35, 2280]. The mixture was stirred at RT for 15 h and then poured on sat. NH$_4$Cl-sol. The pH was set to 1.6 by the addition of 25% HCl and the mixture was extracted with Et$_2$O. The orange oil (27 g) obtained was heated in toluene (400 ml) in the presence of p-TsOH monohydrate (0.69 g, 3.6 mmol) to 100° C. for 4 h. After cooling, the solvent was evaporated in vacuum and the residue was dissolved in AcOEt. The solution was washed with sat. NaHCO$_3$-sol. and brine, dried over Na$_2$SO$_4$ and evaporated in vacuum to give 3-(3-oxo-butyryl)-benzoic acid methyl ester (15.6 g). A sample of this material (3.0 g, 13.6 mmol) was stirred with 2N KOH (40 ml) at RT for 10 min. The mixture was acidified to pH 1 with 3N HCl and the precipitate was isolated by filtration and triturated with AcOEt to give 3-(3-oxo-butyryl)-benzoic acid (2.3 g). A solution of this material (2.2 g, 11.0 mmol) in formamide (5.3 ml, 132 mmol) was heated to 180° C. for 1 h. The mixture was cooled and partitioned between AcOEt and sat. NaHCO$_3$-sol. The aqueous phase was acidified with 3N HCl to pH 2.6 and extracted with AcOEt and the crude product obtained was esterified by heating in MeOH (12 ml)/4N HCl-Et$_2$O (3 ml) for 18 h at 40° C. to give the methyl ester as white crystals (0.33 g).] (0.8 g, 3.5 mmol) by treatment with lithium tert-butyl acetate according to general procedure K (method b). Obtained as a light yellow oil (1.34 g, crude product).

Example K42

3-[3-(2-Methyl-pyrimidin-4-yl)-phenyl]-3-oxo-propionic acid tert-butyl ester

The title compound was prepared from 3-(2-methyl-pyrimidin-4-yl)-benzoic acid methyl ester [prepared by the following procedure: A mixture of 3-acetyl-benzoic acid (0.82 g, 5 mmol), N-(bis-acetylamino-methyl)-acetamide (0.94 g, 5 mmol) and conc. H$_2$SO$_4$ (0.01 ml) was heated to 155° C. for 6 h. The cooled mixture was diluted with H$_2$O (20 ml) and the precipitate was collected, dried and esterified by heating in MeOH (12 ml)/4N HCl-Et$_2$O (3 ml) for 20 h at 40° C.; white crystals (0.27 g).] (0.80 g, 3.5 mmol by treatment with lithium tert-butyl acetate according to general procedure K (method b). Obtained as a yellow solid (1.36 g, crude product).

MS (ISP) 313.3 [(M+H)$^+$].

Example K43

3-Oxo-3-(3-pyrimidin-4-yl-phenyl)-propionic acid tert-butyl ester

The title compound was prepared from 3-pyrimidin-4-yl-benzoic acid methyl ester [prepared by the following procedure: A mixture of 3-acetyl-benzoic acid (2.46 g, 15 mmol), N-(bis-formylamino-methyl)-formamide (2.18 g, 15 mmol) and conc. $H_2SO_4$ (0.1 ml) were heated to 155° C. for 3 h. The cooled mixture was diluted with $H_2O$ (20 ml) and the precipitate was collected, dried and esterified by heating in MeOH (12 ml)/4N HCl-$Et_2O$ (3 ml) for 20 h at 40° C.; white solid (1.06 g).] (0.90 g, 4.2 mmol) by treatment with lithium tert-butyl acetate according to general procedure K (method b). Obtained as a light yellow oil (1.58 g, crude product).

MS (ISP) 299.4 [(M+H)$^+$].

Example K44

3-Oxo-3-(3-pyrimidin-2-yl-phenyl)-propionic acid tert-butyl ester

The title compound was prepared from 3-pyrimidin-2-yl-benzoic acid methyl ester [prepared by the following procedure: 3-Pyrimidin-2-yl-benzoic acid (3.0 g) was esterified by heating in MeOH (160 ml)/4N HCl-$Et_2O$ (40 ml) for 16 h at 40° C.; white crystals (1.99 g).] (1.99 g, 9.3 mmol) by treatment with lithium tert-butyl acetate according to general procedure K (method b). Obtained as a light yellow oil (3.24 g, crude product).

MS (ISP) 299.4 [(M+H)$^+$].

Example K45

3-[3-(2-Amino-6-methyl-pyrimidin-4-yl)-phenyl]-3-oxo-propionic acid tert-butyl ester The title compound was prepared from 3-(2-amino-6-methyl-pyrimidin-4-yl)-benzoic acid methyl ester [prepared by the following procedure: To a solution of 3-(3-oxo-butyryl)-benzoic acid (2.06 g, 10 mmol) and guanidine hydrochloride (0.96 g, 10 mmol) in $H_2O$ (10 ml) was added 2N NaOH (3 ml) and the mixture was stirred at 100° C. for 72 h, the pH of the mixture being maintained at 6–7 by occasional addition of 2N NaOH. After cooling to RT, the pH was set to 3 with 3N HCl and the precipitate was collected, dried and esterified by stirring in 1N HCl-MeOH (40 ml) for 3 d at RT. The crude product was purified by chromatography (silica gel, AcOEt) to give the methyl ester as yellow solid (0.61 g).] (0.73 g, 3 mmol) by treatment with lithium tert-butyl acetate according to general procedure K (method b). Obtained as a light yellow oil (0.85 g).

MS (ISP) 328.4 [(M+H)$^+$].

Example K46

3-[3-(3-Methyl-[1,2,4]triazin-6-yl)-phenyl]-3-oxo-propionic acid tert-butyl ester The title compound was prepared from 3-(3-methyl-[1,2,4]triazin-6-yl)-benzoic acid methyl ester [prepared by the following procedure: To a solution of 3-bromoacetyl-benzoic acid (2.43 g, 10 mmol) in DMSO (17 ml) was added 48% aqueous HBr (3.4 ml) and the mixture was stirred at 55° C. for 0.5 h. The cooled mixture was partitioned between AcOEt and $H_2O$, the organic layer was washed with brine, dried and evaporated in vacuum and the solid residue was triturated with $Et_2O$/hexane to give 3-oxoacetyl-benzoic acid (1.08 g) as a white solid. A solution of this material (3.92 g, 20 mmol) and acetyl hydrazide (1.63 g, 22 mmol) in MeOH (20 ml) was stirred at RT for 1 h. The mixture was evaporated in vacuum and the residue was heated in an autoclave in 5N $NH_3$-MeOH (30 ml) at 150° C. for 3 h. The mixture was cooled and partitionned between AcOEt and sat. $NaHCO_3$-solution. The aqueous phase was acidified to pH 3 with 3N HCl and extracted with AcOEt. The crude product obtained from the AcOEt extract was esterified by heating in 1N HCl-MeOH (80 ml) for 18 h at 50° C. and the crude ester obtained was purified by chromatography (silica gel, AcOEt) to give the methyl ester as light-yellow solid (0.45 g).] (0.8 g, 3.5 mmol) by treatment with lithium tert-butyl acetate according to general procedure K (method b). Obtained as a yellow solid (1.34 g, crude product).

MS (ISP) 314.3 [(M+H)$^+$].

Example K47

3-[3-(5,6-Dimethyl-[1,2,4]triazin-3-yl)-phenyl]-3-oxo-propionic acid tert-butyl ester The title compound was prepared from 3-(5,6-dimethyl-[1,2,4]triazin-3-yl)-benzoic acid methyl ester [prepared by the following procedure: A solution of 3-chlorocarbonyl-benzoic acid methyl ester (31.6 g, 0.15 mol) in $Et_2O$ (0.15 l) was added over 15 min at 0–5° C. to a solution of hydrazinecarboxylic acid tert-butyl ester (19.9 g, 0.1 mol) and pyridine (13.3 ml, 0.165 mol) in $Et_2O$ (0.6 l). The mixture was stirred for 1 h at 0° C. and for 1 h at RT, diluted with AcOEt and washed successively with 1N HCl, sat. $NaHCO_3$-sol. and brine. The organic layer was dried and evaporated to give 3-(N'-tert-butoxycarbonyl-hydrazinocarbonyl)-benzoic acid (31.5 g) as white solid. A sample of this material (29.4 g, 0.1 mol) was stirred in a mixture of MeOH (0.1 l) and 1 N KOH (0.2 l) for 18 h at RT The solution was concentrated in vacuum and then washed with AcOEt. The aqueous phase was acidified to pH 1 with 3N HCl and the precipitate formed was isolated by filtration, dried and then stirred with TFA (0.3 l) at RT for 40 min. The mixture was evaporated in vacuum and the residue was triturated with $Et_2O$/EtOH (10:1) to give 3-hydrazinocarbonyl-benzoic acid as a white solid (16.2 g). A solution of this material (3.6 g, 20 mmol) and 1,3-butandione (1.89 g, 22 mmol) in MeOH (20 ml) was stirred at RT for 1 h. The mixture was evaporated in vacuum and the residue was heated in an autoclave in 5N $NH_3$-MeOH (30 mL) at 150° C. for 3 h. The mixture was cooled and partitionned between AcOEt and sat. $NaHCO_3$-solution. The aqueous phase was acidified to pH 3 with 3N HCl and extracted with AcOEt. The crude product obtained from the AcOEt extract was esterified by heating in 1N HCl-MeOH (80 mL) for 18 h at 50° C. The crude product was purified by chromatography (silica gel, AcOEt) to give the methyl ester as light yellow solid (1.21 g).] (1.21 g, 5 mmol) by treatment with lithium tert-butyl acetate according to general procedure K (method b). Obtained as a light brown solid (1.78 g, crude product).

MS (ISP) 328.4 [(M+H)$^+$].

Example K48

3-[3-(6-Methyl-dimethylamino-pyrimidin-4-yl)-phenyl]-3-oxo-propionic acid tert-butyl ester The title compound was prepared from 3-(2-dimethylamino-6-methyl-pyrimidin-4-yl)-benzoic acid methyl ester [prepared by the following procedure: A mixture of NaH (50% dispersion in mineral oil, 1.56 g, 32.5 mmol) in 2-propanol (45 ml) was stirred at 50° C. for 10 min. N-methylguanidine hydrochloride (3.3 g, 30 mmol) was added and stirring was continued for 10 min. After the addition of 3-(3-oxo-butyryl)-benzoic acid (3.1 g, 15 mmol), the mixture was stirred at 80° C. for 48 h. After cooling to RT, $H_2O$ (100 ml) was added and the mixture was concentrated in vacuum to a volume of ca. 80 ml. The pH was set to 2.5 with 25% HCl and the precipitate was collected, dried and then esterified by stirring in 1N HCl-MeOH (30 ml) for 60 h at RT The crude product was purified by chromatography (silica gel, AcOEt) to give the methyl ester as light yellow solid (0.27 g).] (0.26 g, 1 mmol) by treatment with lithium tert-butyl acetate according to general procedure K (method b). Obtained as a light yellow oil (0.38 g, crude product).

Example K49

3-[3-(6-Methyl-2-dimethylamino-pyrimidin-4-yl)-phenyl]-3-oxo-propionic acid tert-butyl ester The title compound was prepared from 3-(2-methylamino-6-methyl-pyrimidin-4-yl)-benzoic acid methyl ester [prepared by the following procedure: A mixture of NaH (50% dispersion in mineral oil, 1.56 g, 32.5 mmol) in 2-propanol (45 ml) was stirred at 50° C. for 10 min. 1,1-Dimethylguanidine sulfate (4.08 g, 15 mmol) was added and stirring was continued for 10 min. After the addition of 3-(3-oxo-butyryl)-benzoic acid (3.1 g, 15 mmol), the mixture was stirred at 80° C. for 40 h. After cooling to RT, $H_2O$ (100 ml) was added and the mixture was concentrated in vacuum to a volume of ca. 80 ml. The pH was set to 2.8 with 25% HCl and the precipitate formed was collected, dried and then esterified by stirring in 1N HCl-MeOH (30 mL) for 18 h at RT The crude product was purified by chromatography (silica gel, AcOEt) to give the methyl ester as white solid (0.49 g).] (0.48 g, 1.77 mmol) by treatment with lithium tert-butyl acetate according to general procedure K (method b). Obtained as a yellow oil (0.70 g, crude product).

MS (ISP) 356.2 [(M+H)$^+$].

Example K50

3-{3-[2-(2-Hydroxy-ethylamino)-6-methyl-pyrimidin-4-yl]-phenyl}-3-oxo-propionic acid tert-butyl ester The title compound was prepared from rac-3-{6-methyl-2-[2-(tetrahydro-pyran-2-yloxy)-ethylamino]-pyrimidin-4-yl}-benzoic acid methyl ester [prepared by the following procedure: A mixture of 3-carboxyphenylboronic acid (8.3 g, 50.0 mmol), 2,4-dichloro-6-methylpyrimidine (8.15 g, 50.0 mmol) and $Na_2CO_3$ (9.5 g, 90 mmol) in acetonitrile (160 ml)/$H_2O$ (80 ml) was degassed and Pd(PPh$_3$)$_4$ (0.87 g, 0.75 mmol) was added. The mixture was stirred for 18 h at 85° C. in an atmosphere of nitrogen and then concentrated in vacuum to a volume of ca.100 ml $H_2O$ (100 ml) was added and the mixture was washed with AcOEt (50 ml). The pH of the aqueous phase was set to 2.5 by addition of 25% HCl and the precipitate was collected and dried to give 3-(2-chloro-6-methyl-pyrimidin-4-yl)-benzoic acid (9.1 g) as a white solid. A sample of this material (1.49 g, 6 mmol) was heated in 2-amino-ethanol (3.6 ml) at 80° C. for 1 h. The mixture was evaporated in vacuum and the residual oil was stirred in 1N HCl-MeOH (20 ml) for 18 h at 40° C. The crude product (1.36 g) and 3,4-dihydro-2H-pyran (0.86 ml, 9.5 mmol) were stirred in AcOEt (10 mL)/4N HCl-Et$_2$O (1.3 ml) for 4 h at RT The mixture was diluted with AcOEt and washed with sat. NaHCO$_3$-sol. and brine. The organic layer was dried over $Na_2SO_4$, evaporated in vacuum, and the residue was purified by chromatography (silica gel, AcOEt/hexane 1:1) to give the methyl ester as light yellow oil (1.53 g).] (1.53 g, 4.1 mmol) by treatment with lithium tert-butyl acetate according to general procedure K (method b). Obtained as a light yellow oil (1.62 g).

MS (ISP) 456.4 [(M+H)$^+$].

Example K51

3-{3-[2-(2-Methoxy-ethylamino)-6-methyl-pyrimidin-4-yl]-phenyl}-3-oxo-propionic acid tert-butyl ester The title compound was prepared from 3-[2-(2-methoxy-ethylamino)-6-methyl-pyrimidin-4-yl]-benzoic acid methyl ester [prepared by the following procedure: 3-(2-Chloro-6-methyl-pyrimidin-4-yl)-benzoic acid (1.49 g, 6 mmol) was heated in 2-methoxy-ethylamine (5.2 ml) to 80° C. for 2.5 h. The mixture was evaporated in vacuum and the residual oil was stirred in 1N HCl-MeOH (20 ml) for 18 h at 40° C. to give the methyl ester as light yellow solid (1.29 g).] (1.29 g, 4.3 mmol) by treatment with lithium tert-butyl acetate according to general procedure K (method b). Obtained as a light yellow oil (1.44 g).

MS (ISP) 386.3 [(M+H)$^+$].

Example K52

3-[3-(6-Methyl-2-morpholin-4-yl-pyrimidin-4-yl)-phenyl]-3-oxo-propionic acid tert-butyl ester The title compound was prepared from 3-(2-morpholin-4-yl-pyrimidin-4-yl)-benzoic acid methyl ester [prepared by the following procedure: 3-(2-Chloro-6-methyl-pyrimidin-4-yl)-benzoic acid (1.49 g, 6 mmol) was heated in morpholine (5.2 ml) to 120° C. for 16 h. The mixture was evaporated in vacuum and the residual oil was stirred in 1N HCl-MeOH (20 ml) for 20 h at 40° C. to give the methyl ester as light yellow solid (1.19 g).] (1.13 g, 4.3 mmol) by treatment with lithium tert-butyl acetate according to general procedure K (method b). Obtained as a light yellow solid (1.66 g).

MS (ISP) 398.5 [(M+H)$^+$].

Example K53

3-[3-(6-Amino-pyrimidin-4-yl)-phenyl]-3-oxo-propionic acid tert-butyl ester

The title compound was prepared from rac-3-(2-amino-pyrimidin-4-yl)-benzoic acid methyl ester [prepared by the following procedure: A mixture of 3-carboxyphenylboronic acid (8.3 g, 50 mmol), 4,6-dichloro-pyrimidine (7.45 g, 50 mmol) and $Na_2CO_3$ (9.5 g, 90 mmol) in CH$_3$CN (160 ml)/$H_2O$ (80 ml) was degassed and Pd(PPh$_3$)$_4$ (1.16 g, 1.0 mmol) was added. The mixture was stirred for 18 h at 85° C. in an atmosphere of nitrogen and then concentrated in vacuum to a volume of ca. 100 ml. $H_2O$ (100 ml) was added and the mixture was washed with AcOEt (50 ml). The pH of the aqueous phase was set to 4.2 by addition of 25% HCl and the precipitate formed was collected and dried to give 3-(6-chloro-pyrimidin-4-yl)-benzoic acid (8.84 g) as a white solid. A sample of this material (0.75 g, 3.2 mmol) was stirred in 25% aqueous NH$_3$ (5 ml) for 24 h at RT The mixture was evaporated in vacuum and the residue was stirred in 1N HCl-MeOH (10 ml) for 72 h at 50° C. The crude product was purified by chromatography (silica gel, AcOEt/hexane 1:1) to give the methyl ester as yellow solid (0.54 g).] (0.62 g, 2.7 mmol) by treatment with lithium tert-butyl acetate according to general procedure K (method b). Obtained as a light yellow solid (0.29 g).

MS (ISP) 314.2 [(M+H)$^+$].

Example K54

3-[3-(6-Methylamino-pyrimidin-4-yl)-phenyl]-3-oxo-propionic acid tert-butyl ester The title compound was prepared from 3-[6-methylamino-pyrimidin-4-yl]-benzoic acid methyl ester [prepared by the following procedure: 3-(6-Chloro-pyrimidin-4-yl)-benzoic acid (1.49 g, 6 mmol) was heated in 40% aqueous methylamine (5 ml) to 80° C. for 14 h. The mixture was evaporated in vacuum and the residual oil was stirred in 1N HCl-MeOH (10 ml) for 36 h at 50° C. The crude product was purified by chromatography (silica gel, AcOEt) to give the methyl ester as yellow solid (0.62 g).] (0.60 g, 2.4 mmol) by treatment with lithium tert-butyl acetate according to general procedure K (method b). Obtained as a white solid (0.72 g).

MS (ISP) 328.4 [(M+H)$^+$].

Example K55

3-[3-(6-Dimethylamino-pyrimidin-4-yl)-phenyl]-3-oxo-propionic acid tert-butyl ester The title compound was prepared from 3-(2-morpholin-4-yl-pyrimidin-4-yl)-benzoic acid methyl ester [prepared by the following procedure: 3-(6-Chloro-pyrimidin-4-yl)-benzoic acid (1.0 g, 4.3 mmol) was heated in 5.6M dimethylamine-EtOH (5 ml) to 80° C. for 1.5 h. The mixture was evaporated in vacuum and the residual oil was stirred in 1N HCl-MeOH (10 ml) for 72 h at 50° C. The crude product was purified by chromatography (silica gel, AcOEt) to give the methyl ester as yellow solid (0.43 g).] (0.39 g, 1.5 mmol) by treatment with lithium tert-butyl acetate according to general procedure K (method b). Obtained as a light yellow solid (0.45 g).

MS (ISP) 342.3 [(M+H)$^+$].

Example K56

3-{3-[6-(2-Methoxy-ethylamino)-pyrimidin-4-yl]-phenyl}-3-oxo-propionic acid tert-butyl ester The title compound was prepared from 3-[6-(2-methoxy-ethylamino)-pyrimidin-4-yl]-benzoic acid methyl ester [prepared by the following procedure: 3-(6-Chloro-pyrimidin-4-yl)-benzoic acid (1.0 g, 4.3 mmol) was heated in 2-methoxy-ethylamine (5 ml) to 80° C. for 1 h. The mixture was evaporated in vacuum and the residual oil was stirred in 1N HCl-MeOH (25 mL) for 18 h at 50° C. The crude product was purified by chromatography (silica gel, AcOEt-hexane 1:1) to give the methyl ester as light yellow solid (0.67 g).] (0.66 g, 2.3 mmol) by treatment with lithium tert-butyl acetate according to general procedure K (method b). Obtained as a light yellow oil (0.93 g, not pure).

MS (ISP) 372.3 [(M+H)$^+$].

Example K57

3-[2,3']Bipyridinyl-4-yl-3-oxo-propionic acid tert-butyl ester

The title compound was prepared from [2,3']bipyridinyl-4-carboxylic acid methyl ester [prepared by the following procedure: A mixture of pyridine-3-boronic acid (0.7 g, 5.7 mmol), 2-bromo-isonicotinic acid (1.15 g, 5.7 mmol) and K$_2$CO$_3$ (0.63 g, 4.6 mmol) in CH$_3$CN (120 mL)/H$_2$O (10 mL) was degassed and Pd(PPh$_3$)$_4$ (0.13 g, 0.11 mmol) was added. The mixture was stirred for 24 h at 80° C. in an atmosphere of nitrogen and then concentrated in vacuum to a volume of about 10 ml. The pH was set to 6 by addition of 3N HCl and the solution was then evaporated in vacuum to dryness. The residue was stirred in 1N HCl-MeOH (23 ml) for 65 h at 50° C. The crude product was purified by chromatography (silica gel, AcOEt/cyclohexane 1:1) to give the methyl ester as light yellow oil (0.37 g).] (044 g, 2.1 mmol) by treatment with lithium tert-butyl acetate according to general procedure K (method b). Obtained as a light yellow oil (0.62 g, crude product).

MS (ISP) 299.3 [(M+H)$^+$].

Example K58

3-[2,4']Bipyridinyl-4-yl-3-oxo-propionic acid tert-butyl ester

The title compound was prepared from [2,4']bipyridinyl-4-carboxylic acid methyl ester [prepared by the following procedure: A mixture of pyridine-4-boronic acid (0.7 g, 5.7 mmol), 2-bromo-isonicotinic acid (1.15 g, 5.7 mmol) and K$_2$CO$_3$ (0.63 g, 4.6 mmol) in CH$_3$CN (120 ml)/H$_2$O (10 ml) was degassed and Pd(PPh$_3$)$_4$ (0.13 g, 0.11 mmol) was added. The mixture was stirred for 24 h at 80° C. in an atmosphere of nitrogen and then concentrated in vacuum to a volume of about 10 ml. The pH was set to 6 by addition of 3N HCl and the solution was then evaporated in vacuum to dryness. The residue was stirred in 1N HCl-MeOH (23 ml) for 65 h at 50° C. The crude product was purified by chromatography (silica gel, AcOEt/cyclohexane 1:1) to give the methyl ester as light yellow oil (0.37 g).] (0.21 g, 1.0 mmol) by treatment with lithium tert-butyl acetate according to general procedure K (method b). Obtained as a light yellow oil (0.45 g, crude product).

MS (ISP) 299.3 [(M+H)$^+$].

Example K59

3-(2'-Methyl-[2,4']bipyridinyl-4-yl)-3-oxo-propionic acid tert-butyl ester

The title compound was prepared from 2'-methyl-[2,4'] bipyridinyl-4-carboxylic acid methyl ester [prepared by the following procedure: A cooled solution of 4-bromo-2-methyl-pyridine (2.75 g) in Et$_2$O (26 ml) was added at −78° C. over to a solution of 1.6 M butyl lithium/hexane (12 ml) in Et$_2$O (50 ml). The solution was stirred for 20 min at −78° C. Triisopropylborate (4.8 ml, 20.8 mmol) was added and the mixture was allowed to warm up to RT over 1 hour and subsequently stirred for 18 h. H$_2$O (13 ml) was added and the layers were separated. The organic layer was extracted with 0.5N NaOH (25 ml) and the combined aqueous layers were acidified to pH 6 with 2N HCl and then extracted with AcOEt (200 ml). The organic extract was dried and evaporated in vacuum and the residue was triturated with Et$_2$O to give pyridine-2-methyl-4-boronic acid (0.36 g). A mixture of this material (0.36 g, 2.6 mmol), 2-bromo-isonicotinic acid (0.53 g, 2.6 mmol) and K$_2$CO$_3$ (0.29 g, 2.1 mmol) in CH$_3$CN (9 ml)/H$_2$O (4.5 ml) was degassed and Pd(PPh$_3$)$_4$ (0.12 g, 0.1 mmol) was added. The mixture was stirred for 70 h at 80° C. in an atmosphere of nitrogen and then concentrated in vacuum to a volume of ca. 5 ml. The pH was set to 6 by addition of 3N HCl and the solution was then evaporated to dryness in vacuum. The residue was stirred in 1N HCl-MeOH (30 ml) for 20 h at 50° C. The crude product was purified by chromatography (silica gel, AcOEt/cyclohexane 1:1) to give the methyl ester as light yellow oil (0.22 g).] (0.16 g, 0.71 mmol) by treatment with lithium tert-butyl acetate according to general procedure K (method b). Obtained as a white solid (0.38 g).

MS (ISP) 313.3 [(M+H)+].

Example K60

3-[3-(2-Cyclopropyl-pyridin-4-yl)-phenyl]-3-oxo-propionic acid tert-butyl ester

The title compound was obtained from 3-(2-cyclopropyl-pyridin-4-yl)-benzonitrile [prepared by the following sequence: 1.) A mixture of 3-cyanophenylboronic acid [CAS-No. 150255-96-2] (23.14 g, 158 mmol), 2-chloro-4-iodo-pyridine [CAS-No. 153034-86-7] (35.92 g, 150 mmol), NaHCO$_3$ (30.24 g, 360 mmol) and PPh$_3$ (1.31 g, 3.3 mol %) in DME (750 mL) and H$_2$O (360 mL) was thoroughly degassed at 23° C. before Pd(OAc)$_2$ (337 mg, 1 mol %) was added and the mixture was refluxed for 5 h. Poured onto ice, saturated with solid NaCl, extracted with EtOAc (2×1000 mL), dried the combined organic layer over Na$_2$SO$_4$. Removal of the solvent in vacuum left a yellow solid. Dissolved in hot EtOAc (ca. 200 mL), added heptane (ca. 350 mL), allowed to cool to RT, filtered precipitate off, washed with heptane/EtOAc 3:2, dried in HV to give a light yellow solid (28.11 g). 2.) A mixture of the resulting 3-(2-chloro-pyridin-4-yl)-benzonitrile (4.29 g, 20 mmol), cyclopropylzinc chloride (0.4 M in THF, 62.5 mL, 25 mmol), Pd(PPh$_3$)$_4$ (690 mg, 3 mol %) in THF (22 mL) was stirred under argon atmosphere at 70° C. for 2 h. Cooled to room temperature, poured into sat. NaHCO$_3$-solution, extracted with ether, washed with brine, dried over Na$_2$SO$_4$. Removal of the solvent in vacuum left a light yellow solid (2.98 g).] (3.19 g, 14.5 mmol) by treatment with tert-butyl bromoacetate and activated zinc, followed by hydrolysis with 10% HCl according to general procedure K (method d). Obtained as a yellow oil (3.37 g, 69%).

MS (ISN) 336 [(M−H)−].

Example K61

3-[3-(2-Cyclopentyl-pyridin-4-yl)-phenyl]-3-oxo-propionic acid tert-butyl ester

The title compound was obtained from 3-(2-cyclopentyl-pyridin-4-yl)-benzonitrile [prepared by the following procedure: A mixture of 3-(2-chloro-pyridin-4-yl)-benzonitrile (cf. Example K60) (4.29 g, 20 mmol), cyclopentylzinc bromide (0.5 M in THF, 50 mL, 25 mmol), Pd(PPh$_3$)$_4$ (690 mg, 3 mol %) in THF (20 mL) was stirred under argon atmosphere at 70° C. for 2 h. Cooled to room temperature, poured into sat. NaHCO$_3$-solution, extracted with ether, washed with brine, dried over Na$_2$SO$_4$. Removal of the solvent in vacuum followed by silica gel column chromatography left an orange oil (1.63 g).] (1.60 g, 6.44 mmol) by treatment with tert-butyl bromoacetate and activated zinc, followed by hydrolysis with 10% HCl according to general procedure K (method d). Obtained as a yellow oil (1.45 g, 62%).

MS (ISN) 364.3 [(M−H)−].

Example K62

3-[3-(2-Morpholin-4-yl-pyridin-4-yl)-phenyl]-3-oxo-propionic acid tert-butyl ester The title compound was obtained from 3-(2-morpholin-4-yl-pyridin-4-yl)-benzonitrile [prepared by the following procedure: A mixture of 3-(2-chloro-pyridin-4-yl)-benzonitrile (cf. Example K60) (3×800 mg, 11.81 mmol) and morpholine (3×4 mL, 137.74 mmol) was irradiated in the microwave at 200° C. for 15 min each. The mixtures were poured into water and extracted with EtOAc, the organic layer was washed with brine and dried over MgSO$_4$. Removal of the solvent in vacuum followed by silica gel column chromatography left a white solid (2.08 g).] (2.00 g, 7.54 mmol) by treatment with tert-butyl bromoacetate and activated zinc, followed by hydrolysis with 10% HCl according to general procedure K (method d). Obtained as a yellow oil (2.60 g, 90%).

MS (ISP) 383.3 [(M+H)+].

Example K63

3-Oxo-3-[3-(2-pyrrolidin-1-yl-pyridin-4-yl)-phenyl]-propionic acid tert-butyl ester The title compound was obtained from 3-(2-pyrrolidin-1-yl-pyridin-4-yl)-benzonitrile [prepared by the following procedure: A mixture of 3-(2-chloro-pyridin-4-yl)-benzonitrile (cf. Example K60) (3.59 g, 16.72 mmol) and pyrrolidine (15 mL) was irradiated in the microwave at 200° C. for 4–15 min. The mixtures were poured into water and extracted with EtOAc, the organic layer was washed with brine and dried over MgSO$_4$. Removal of the solvent in vacuum followed by silica gel column chromatography left a light yellow solid.] (1.18 g, 4.73 mmol) by treatment with tert-butyl bromoacetate and activated zinc, followed by hydrolysis with 10% HCl according to general procedure K (method d). Obtained as a yellow oil (1.31 g, 76%).

MS (ISP) 367 [(M+H)+].

Example K64

(RS)-3-{3-[2-Methyl-6-(tetrahydro-pyran-2-yloxymethyl)-pyridin-4-yl]-phenyl}-3-oxo-propionic acid tert-butyl ester a) Oxidation of 3-(2,6-dimethyl-pyridin-4-yl)-benzoic acid methyl ester (28.8 g, 0.12 mol; prepared from commercially available 3-carboxyphenylboronic acid [CAS-No. 25487-66-5] and 4-bromo-2,6-dimethylpyridine [*Chem. Pharm. Bull.* 38 (1990) 2446 and *J. Org. Chem.* 27 (1962) 1665] as described for 3-(2-methyl-pyridin-4-yl)-benzoic acid methyl ester in example K12) with H$_2$O$_2$ (30%, 36.5 ml, 0.36 mol) in acetic acid (117 ml) at 70° C. for 27 h and subsequent reaction of the N-oxide in acetic acid anhydride (31 ml) at 135° C. for 30 min yielded after aqueous work-up 3-(2-acetoxymethyl-6-methyl-pyridin-4-yl)-benzoic acid methyl ester (29.2 g, 82%) as a brown oil.

b) Hydrolysis of crude 3-(2-acetoxymethyl-6-methyl-pyridin-4-yl)-benzoic acid methyl ester (17.5 g, 58.5 mmol) with sodium methanolate (5.4M in methanol, 3.2 ml) in methanol (65 ml) at RT for 24 h led after aqueous work-up and purification by column chromatography (ethyl acetate) to 3-(2-hydroxymethyl-6-methyl-pyridin-4-yl)-benzoic acid methyl ester (yellow solid, mp 147° C.; 9.52 g, 63%), which by reaction with 3,4-dihydro-2H-pyrane (15 ml, 166 mmol) in THF (90 ml) at RT for 5 d gave after aqueous work-up and purification by column chromatography (ethyl acetate) (RS)-3-[2-methyl-6-(tetrahydro-pyran-2-yloxymethyl)-pyridin-4-yl]-benzoic acid methyl ester (12.4 g, 98%) as a yellow oil.

c) Reaction of (RS)-3-[2-methyl-6-(tetrahydro-pyran-2-yloxymethyl)-pyridin-4-yl]-benzoic acid methyl ester with tert.-butyl acetate according to general procedure K (method d; example K8) yielded the title compound as a yellow oil.

MS (ISP) 426.6 [(M+H)+].

The following methods relate to the preparation of the 6-aryl-2,2-dimethyl-[1,3]dioxin-4-ones (formula IV), which serve as building blocks in the synthesis of the target compounds (Synthetic Scheme H).

General Procedure L

Preparation of 6-aryl-2,2-dimethyl-[1,3]dioxin-4-ones

Method a)

The 6-aryl-2,2-dimethyl-[1,3]dioxin-4-ones were prepared from 3-aryl-3-oxo-propionic acids and catalytic amount of conc. $H_2SO_4$ or trifluoroacetic acid (TFA) in isopropenyl acetate at 23° C. according to *Chem. Pharm. Bull.* 1983, 31, 1896. The final products were purified by silica gel column chromatography with hexane/EtOAc.

Method b)

The 6-aryl-2,2-dimethyl-[1,3]dioxin-4-ones were prepared from the tert-butyl 3-aryl-3-oxo-propionates by treatment with trifluoroacetic anhydride (TFAA) in a mixture of TFA and acetone at 23° C. according to *Tetrahedron Lett.* 1998, 39, 2253. The final products were if necessary purified by silica gel column chromatography with hexane/EtOAc.

General Procedure M

Preparation of {2-[3-aryl-3-oxo-propionylamino]-phenyl}-carbamic acid tert-butyl esters by reaction of (2-amino-phenyl)-carbamic acid tert-butyl esters with ethyl or tert-butyl 3-aryl-3-oxo-propionates or 6-aryl-2,2-dimethyl-[1,3]dioxin-4-ones A mixture of the (2-amino-phenyl)-carbamic acid tert-butyl ester or (1.0–1.2 mmol) and (1.0–1.5 mmol) of the ethyl or tert-butyl 3-aryl-3-oxo-propionate or 6-aryl-2,2-dimethyl-[1,3]dioxin-4-one was heated in toluene or xylene (4–8 mL) to 80° C. to 150° C. until tlc indicated complete consumption of the minor component. The solution was allowed to cool to 23° C., whereupon the product generally crystallized (in cases where crystallization failed to appear it was induced by addition of hexane or ether, alternatively the reaction mixture was directly subjected to silica gel column chromatography). The solid was filtered off, washed with ether or mixtures of ether/hexane and dried in vacuum to give the {2-[3-aryl-3-oxo-propionylamino]-phenyl}-carbamic acid tert-butyl esters, which was used directly in the following step or—if necessary—was purified by recrystallization or by silica gel column chromatography.

Example M1

{5-Dimethylamino-2-[3-oxo-3-(3-pyridin-3-yl-phenyl)-propionylamino]-4-trifluoromethyl-phenyl}-carbamic acid tert-butyl ester The title compound was prepared from (2-amino-5-dimethylamino-4-trifluoromethyl-phenyl)-carbamic acid tert-butyl ester (Example J1) (262 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a pink foam (335 mg).

MS (ISP) 543.3 [(M+H)+].

Example M2

{5-Dimethylamino-2-[3-oxo-3-(3-pyridin-4-yl-phenyl)-propionylamino]-4-trifluoromethyl-phenyl}-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-oxo-3-(3-pyridin-4-yl-phenyl)-propionic acid tert-butyl ester (Example K2) (223 mg, 0.75 mmol) according to the general procedure M. Obtained as an orange solid (324 mg).

MS (ISN) 541 [(M–H)−]; mp 161° C.

Example M3

{5-Dimethylamino-2-[3-oxo-3-(3-pyridin-2-yl-phenyl)-propionylamino]-4-trifluoromethyl-phenyl}-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as a pink solid (295 mg).

MS (ISN) 541.0 [(M–H)−]; mp 169° C.

Example M4

{4-Fluoro-2-[3-oxo-3-(3-pyridin-3-yl-phenyl)-propionylamino]-phenyl}-carbamic acid tert-butyl ester The title compound was prepared from (2-amino-4-fluoro-phenyl)-carbamic acid tert-butyl ester (Example J2) (83 mg, 0.37 mmol) and 3-oxo-3-(3-pyridin-3-yl-phenyl)-propionic acid tert-butyl ester (Example K1) (109 mg, 0.37 mmol) according to the general procedure M. Obtained as a light yellow amorphous substance (127 mg).

MS (ISP) 450 [(M+H)+].

Example M5

{4-Fluoro-2-[3-oxo-3-(3-pyridin-4-yl-phenyl)-propionylamino]-phenyl}-carbamic acid tert-butyl ester The title compound was prepared from (2-amino-4-fluoro-phenyl)-carbamic acid tert-butyl ester (Example J2) (170 mg, 0.75 mmol) and 3-oxo-3-(3-pyridin-4-yl-phenyl)-propionic acid tert-butyl ester (Example K2) (223 mg, 0.75 mmol) according to the general procedure M. Obtained as an off-white solid (251 mg).

MS (ISP) 450.4 [(M+H)+]; mp 110–115° C.

Example M6

(2-{3-[3-(6-Methyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as a white solid (399 mg).

MS (ISN) 512.2 [(M–H)−]; mp 74–76° C.

Example M7

(5-Dimethylamino-2-{3-[3-(6-methyl-pyridin-3-yl)-phenyl]-3-oxo-propionylamino}-4-trifluoromethyl-phenyl)-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as a pink solid (358 mg).

MS (ISN) 555.1 [(M−H)−].

Example M8

(4-Fluoro-2-{3-[3-(6-methyl-pyridin-3-yl)-phenyl]-3-oxo-propionylamino}-phenyl)-carbamic acid tert-butyl ester The title compound was prepared from (2-amino-4-fluoro-phenyl)-carbamic acid tert-butyl ester (Example J2) (170 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as a light yellow solid (323 mg).

MS (ISN) 462.5 [(M−H)−].

Example M9

(2'-Fluoro-3-{3-[3-(6-methyl-pyridin-3-yl)-phenyl]-3-oxo-propionylamino}-biphenyl-4-yl)-carbamic acid tert-butyl ester The title compound was prepared from (3-amino-2'-fluoro-biphenyl-4-yl)-carbamic acid tert-butyl ester [CAS-No. 335255-65-7] (227 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as a yellow solid (347 mg).

MS (ISN) 538.2 [(M−H)−]; mp 86–88° C.

Example M10

(5-Dimethylamino-2-{3-[3-(2-methyl-pyridin-3-yl)-phenyl]-3-oxo-propionylamino}-4-trifluoromethyl-phenyl)-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-[3-(2-methyl-pyridin-3-yl)-phenyl]-3-oxo-propionic acid tert-butyl ester (Example K5) (234 mg, 0.75 mmol) according to the general procedure M. Obtained as a pink solid (389 mg).

Mp 87–91° C.

Example M11

(2-{3-[3-(6-Methyl-pyridazin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(6-methyl-pyridazin-3-yl)-phenyl]-3-oxo-propionic acid tert-butyl ester (Example K6) (234 mg, 0.75 mmol) according to the general procedure M. Obtained as an off-white solid (332 mg).

MS (ISP) 515 [(M+H)+]; mp 174° C.

Example M12

(5-Dimethylamino-2-{3-[3-(6-methyl-pyridazin-3-yl)-phenyl]-3-oxo-propionylamino}-4-trifluoromethyl-phenyl)-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-[3-(6-methyl-pyridazin-3-yl)-phenyl]-3-oxo-propionic acid tert-butyl ester (Example K6) (234 mg, 0.75 mmol) according to the general procedure M. Obtained as an off-white solid (254 mg).

MS (ISP) 558 [(M+H)+]; mp 145° C.

Example M13

(2'-Fluoro-3-{3-[3-(6-methyl-pyridazin-3-yl)-phenyl]-3-oxo-propionylamino}-biphenyl-4-yl)-carbamic acid tert-butyl ester The title compound was prepared from (3-amino-2'-fluoro-biphenyl-4-yl)-carbamic acid tert-butyl ester [CAS-No. 335255-65-7] (227 mg, 0.75 mmol) and 3-[3-(6-methyl-pyridazin-3-yl)-phenyl]-3-oxo-propionic acid tert-butyl ester (Example K6) (234 mg, 0.75 mmol) according to the general procedure M. Obtained as an amorphous yellow substance (330 mg).

MS (ISP) 541 [(M+H)+].

Example M14

(2-{3-[3-(2-Methyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2-methyl-pyridin-3-yl)-phenyl]-3-oxo-propionic acid tert-butyl ester (Example K5) (234 mg, 0.75 mmol) according to the general procedure M. Obtained as a light yellow oil (322 mg).

MS (ISP) 514.3 [(M+H)+].

Example M15

(4-Fluoro-2-{3-[3-(2-methyl-pyridin-3-yl)-phenyl]-3-oxo-propionylamino}-phenyl)-carbamic acid tert-butyl ester The title compound was prepared from (2-amino-4-fluoro-phenyl)-carbamic acid tert-butyl ester (Example J2) (170 mg, 0.75 mmol) and 3-[3-(2-methyl-pyridin-3-yl)-phenyl]-3-oxo-propionic acid tert-butyl ester (Example K5) (234 mg, 0.75 mmol) according to the general procedure M. Obtained as a light yellow solid (308 mg).

MS (ISP) 462.2 [(M+H)+]; mp 74–78° C.

Example M16

(2'-Fluoro-3-{3-[3-(2-methyl-pyridin-3-yl)-phenyl]-3-oxo-propionylamino}-biphenyl-4-yl)-carbamic acid tert-butyl ester The title compound was prepared from (3-amino-2'-fluoro-biphenyl-4-yl)-carbamic acid tert-butyl ester [CAS-No. 335255-65-7] (227 mg, 0.75 mmol) and 3-[3-(2-methyl-pyridin-3-yl)-phenyl]-3-oxo-propionic acid tert-butyl ester (Example K5) (234 mg, 0.75 mmol) according to the general procedure M. Obtained as a yellow solid (381 mg).

MS (ISP) 538.2 [(M+H)+]; mp 48–54° C.

Example M17

{2-[3-Oxo-3-(3-pyridin-4-yl-phenyl)-propionylamino]-4-trifluoromethyl-phenyl}-carbamic acid tert-butyl ester The title compound was prepared from (2-amino-4-trifluoromethyl-phenyl)-carbamic acid tert-butyl ester (Example J3) and 3-oxo-3-(3-pyridin-4-yl-phenyl)-propionic acid tert-butyl ester (Example K2) according to the general procedure M. Obtained as a white solid (275 mg).

MS (ISP) 500 [(M+H)$^+$].

Example M18

{2'-Fluoro-3-[3-oxo-3-(3-pyridin-4-yl-phenyl)-propionylamino]-biphenyl-4-yl}-carbamic acid tert-butyl ester The title compound was prepared from (3-amino-2'-fluoro-biphenyl-4-yl)-carbamic acid tert-butyl ester [CAS-No. 335255-65-7] and 3-oxo-3-(3-pyridin-4-yl-phenyl)-propionic acid tert-butyl ester (Example K2) according to the general procedure M. Obtained as a yellow solid (410 mg).

MS (ISP) 526 [(M+H)$^+$].

Example M19

{4-Chloro-2-[3-oxo-3-(3-pyridin-4-yl-phenyl)-propionylamino]-phenyl}-carbamic acid tert-butyl ester Prepared from (2-amino-4-chloro-phenyl)-carbamic acid tert-butyl ester (Example J4) and 3-oxo-3-(3-pyridin-4-yl-phenyl)-propionic acid tert-butyl ester (Example K2) according to the general procedure M. Obtained as a yellow solid (270 mg).

MS (ISP) 466 [(M+H)$^+$] and 468 [(M+2+H)$^+$].

Example M20

(4-Chloro-5-fluoro-2-{3-[3-(6-methyl-pyridin-3-yl)-phenyl]-3-oxo-propionylamino}-

The title compound was prepared from (2-amino-4-chloro-5-fluoro-phenyl)-carbamic acid tert-butyl ester (Example J5) (235 mg, 0.9 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as an off-white foam (257 mg).

MS (ISN) 496.1 [(M–H)$^-$] and 498 [(M+2–H)$^-$]; mp 76–80° C.

Example M21

{4-Chloro-5-fluoro-2-[3-oxo-3-(3-pyridin-4-yl-phenyl)-propionylamino]-phenyl}-carbamic acid tert-butyl ester The title compound was prepared from (2-amino-4-chloro-5-fluoro-phenyl)-carbamic acid tert-butyl ester (Example J5) (235 mg, 0.9 mmol) and 3-oxo-3-(3-pyridin-4-yl-phenyl)-propionic acid tert-butyl ester (Example K2) (223 mg, 0.75 mmol) according to the general procedure M. Obtained as a pink powder (272 mg).

MS (ISN) 482.2 [(M–H)$^-$] and 484 [(M+2–H)$^-$]; mp 170–174° C.

Example M22

{4-Methyl-2-[3-oxo-3-(3-pyridin-3-yl-phenyl)-propionylamino]-5-trifluoromethyl-phenyl}-carbamic acid tert-butyl ester The title compound was prepared from (2-amino-4-methyl-5-trifluoromethyl-phenyl)-carbamic acid tert-butyl ester (Example J23) and 3-oxo-3-(3-pyridin-3-yl-phenyl)-propionic acid tert-butyl ester (Example K1) according to the general procedure M. Obtained as a white solid (229 mg).

MS (ISN) 512 [(M–H)$^-$].

Example M23

{4-Chloro-5-methyl-2-[3-oxo-3-(3-pyridin-3-yl-phenyl)-propionylamino]-phenyl}-carbamic acid tert-butyl ester The title compound was prepared from (2-amino-4-chloro-5-methyl-phenyl)-carbamic acid tert-butyl ester (Example J22) and 3-oxo-3-(3-pyridin-3-yl-phenyl)-propionic acid tert-butyl ester (Example K1) according to the general procedure M. Obtained as a yellow solid (310 mg).

MS (ISP) 480 [(M+H)$^+$] and 482 [(M+2+H)$^+$].

Example M24

{2-[3-Oxo-3-(3-pyridin-3-yl-phenyl)-propionylamino]-4-trifluoromethyl-phenyl}-carbamic acid tert-butyl ester The title compound was prepared from (2-amino-4-trifluoromethyl-phenyl)-carbamic acid tert-butyl ester (Example J3) and 3-oxo-3-(3-pyridin-3-yl-phenyl)-propionic acid tert-butyl ester (Example K1) according to the general procedure M. Obtained as a light brown solid (303 mg).

MS (ISP) 500 [(M+H)$^+$].

Example M25

{4-Chloro-2-[3-oxo-3-(3-pyridin-3-yl-phenyl)-propionylamino]-phenyl}-carbamic acid tert-butyl ester The title compound was prepared from (2-amino-4-chloro-phenyl)-carbamic acid tert-butyl ester (Example J4) and 3-oxo-3-(3-pyridin-3-yl-phenyl)-propionic acid tert-butyl ester (Example K1) according to the general procedure M. Obtained as a light brown solid (227 mg).

MS (ISP) 466 [(M+H)$^+$] and 468 [(M+2+H)$^+$].

Example M26

{2'-Fluoro-3-[3-oxo-3-(3-pyridin-3-yl-phenyl)-propionylamino]-biphenyl-4-yl}-carbamic The title compound was prepared from (3-amino-2'-fluoro-biphenyl-4-yl)-carbamic acid tert-butyl ester [CAS-No. 335255-65-7] and 3-oxo-3-(3-pyridin-3-yl-phenyl)-propionic acid tert-butyl ester (Example K1) according to the general procedure M. Obtained as a light brown solid (198 mg).

MS (ISP) 526 [(M+H)$^+$].

Example M27

[2-[3-Oxo-3-(3-pyridin-3-yl-phenyl)-propionylamino]-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) and 3-oxo-3-(3-pyridin-3-yl-phenyl)-propionic acid tert-butyl ester (Example K1) according to the general procedure M. Obtained as a light yellow solid (331 mg).

MS (ISP) 598 [(M+H)⁺].

Example M28

(4-Chloro-2-{3-[3-(6-methyl-pyridin-3-yl)-phenyl]-3-oxo-propionylamino}-phenyl)-carbamic acid tert-butyl ester The title compound was prepared from (2-amino-4-chloro-phenyl)-carbamic acid tert-butyl ester (Example J4) (182 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as an amorphous light brown substance (316 mg).

MS (ISN) 480 [(M−H)⁻] and 482 [(M+2−H)⁻].

Example M29

(4-Chloro-2-{3-[3-(2-methyl-pyridin-3-yl)-phenyl]-3-oxo-propionylamino}-phenyl)-carbamic acid tert-butyl ester The title compound was prepared from (2-amino-4-chloro-phenyl)-carbamic acid tert-butyl ester (Example J4) (182 mg, 0.75 mmol) and 3-[3-(2-methyl-pyridin-3-yl)-phenyl]-3-oxo-propionic acid tert-butyl ester (Example K5) (234 mg, 0.75 mmol) according to the general procedure M. Obtained as an amorphous light brown substance (286 mg).

MS (ISN) 480 [(M−H)⁻] and 482 [(M+2−H)⁻].

Example M30

{2-[3-Oxo-3-(3-pyridin-2-yl-phenyl)-propionylamino]-4-trifluoromethyl-phenyl}-carbamic acid tert-butyl ester The title compound was prepared from (2-amino-4-trifluoromethyl-phenyl)-carbamic acid tert-butyl ester (Example J3) (207 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as a white solid (284 mg).

MS (ISN) 498.1 [(M−H)⁻]; mp 70–73° C.

Example M31

{5-Methoxy-2-[3-oxo-3-(3-pyridin-4-yl-phenyl)-propionylamino]-4-trifluoromethyl-phenyl}-carbamic acid tert-butyl ester The title compound was prepared from (2-amino-5-methoxy-4-trifluoromethyl-phenyl)-carbamic acid tert-butyl ester (Example J7) and 3-oxo-3-(3-pyridin-4-yl-phenyl)-propionic acid tert-butyl ester (Example K2) according to the general procedure M. Obtained as a light yellow solid (271 mg).

MS (ISP) 530.2 [(M+H)⁺]; mp 179° C. (dec.).

Example M32

{5-Ethoxy-2-[3-oxo-3-(3-pyridin-4-yl-phenyl)-propionylamino]-4-trifluoromethyl-phenyl}-carbamic acid tert-butyl ester The title compound was prepared from (2-amino-5-ethoxy-4-trifluoromethyl-phenyl)-carbamic acid tert-butyl ester (Example J8) and 3-oxo-3-(3-pyridin-4-yl-phenyl)-propionic acid tert-butyl ester (Example K2) according to the general procedure M. Obtained as a light yellow solid (271 mg).

MS (ISP) 544.2 [(M+H)⁺]; mp 165° C. (dec.).

Example M33

[2-[3-Oxo-3-(3-pyridin-4-yl-phenyl)-propionylamino]-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) and 3-oxo-3-(3-pyridin-4-yl-phenyl)-propionic acid tert-butyl ester (Example K2) according to the general procedure M. Obtained as a light yellow solid (299 mg).

MS (ISP) 598.0 [(M+H)⁺]; mp 173° C. (dec.).

Example M34

{4-Methoxy-2-[3-oxo-3-(3-pyridin-4-yl-phenyl)-propionylamino]-phenyl}-carbamic acid tert-butyl ester The title compound was prepared from (2-amino-4-methoxy-phenyl)-carbamic acid tert-butyl ester (Example J9) and 3-oxo-3-(3-pyridin-4-yl-phenyl)-propionic acid tert-butyl ester (Example K2) according to the general procedure M. Obtained as a light yellow solid (258 mg).

MS (ISP) 462.3 [(M+H)⁺]; mp 148–150° C.

Example M35

{2-Dimethylamino-2'-fluoro-5-[3-oxo-3-(3-pyridin-4-yl-phenyl)-propionylamino]-biphenyl-4-yl}-carbamic acid tert-butyl ester The title compound was prepared from (5-amino-2-dimethylamino-2'-fluoro-biphenyl-4-yl)-carbamic acid tert-butyl ester (Example J10) (271 mg, 0.78 mmol) and 3-oxo-3-(3-pyridin-4-yl-phenyl)-propionic acid tert-butyl ester (Example K2) (194 mg, 0.65 mmol) according to the general procedure M. Obtained as a yellow solid (316 mg).

MS (ISN) 567.1 [(M−H)⁻]; mp 105–110° C.

Example M36

(5-Dimethylamino-2-{3-[3-(6-methoxy-pyridazin-3-yl)-phenyl]-3-oxo-propionylamino}-4-trifluoromethyl-phenyl)-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-[3-(6-methoxy-pyridazin-3-yl)-phenyl]-3-oxo-propionic acid tert-butyl ester (Example K7) (246 mg, 0.75 mmol) according to the general procedure M. Obtained as an off-white solid (317 mg).

MS (ISP) 574 [(M+H)⁺]; mp 100–145° C.

Example M37

(2'-Fluoro-3-{3-[3-(6-methoxy-pyridazin-3-yl)-phenyl]-3-oxo-propionylamino}-biphenyl-4-yl)-carbamic acid tert-butyl ester The title compound was prepared from (3-amino-2'-fluoro-biphenyl-4-yl)-carbamic acid tert-butyl ester [CAS- No. 335255-65-7] (227 mg, 0.75 mmol) and 3-[3-(6-methoxy-pyridazin-3-yl)-phenyl]-3-oxo-propionic acid tert-butyl ester (Example K7) (246 mg, 0.75 mmol) according to the general procedure M. Obtained as an off-white amorphous substance (352 mg).

MS (ISP) 557 [(M+H)$^+$].

Example M38

{5-Methoxy-2-[3-oxo-3-(3-pyridin-2-yl-phenyl)-propionylamino]-4-trifluoromethyl-phenyl}-carbamic acid tert-butyl ester The title compound was prepared from (2-amino-5-methoxy-4-trifluoromethyl-phenyl)-carbamic acid tert-butyl ester (Example J7) (230 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as an off-white solid (240 mg).

MS (ISN) 528 [(M–H)$^-$]; mp 164° C.

Example M39

{5-Ethoxy-2-[3-oxo-3-(3-pyridin-2-yl-phenyl)-propionylamino]-4-trifluoromethyl-phenyl}-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as an off-white solid (234 mg).

MS (ISN) 542 [(M–H)$^-$]; mp 128–144° C.

Example M40

[2-[3-Oxo-3-(3-pyridin-2-yl-phenyl)-propionylamino]-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as an off-white solid (199 mg).

MS (ISN) 596 [(M–H)$^-$]; mp 68–71° C.

Example M41

{4-Chloro-5-methyl-2-[3-oxo-3-(3-pyridin-2-yl-phenyl)-propionylamino]-phenyl}-carbamic acid tert-butyl ester The title compound was prepared from (2-amino-4-chloro-5-methyl-phenyl)-carbamic acid tert-butyl ester (Example J22) (193 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as a light yellow foam (320 mg).

MS (ISN) 478.2 [(M–H)$^-$] and 480 [(M+2–H)$^-$]; mp 135–137° C.

Example M42

{5-Methyl-2-[3-oxo-3-(3-pyridin-2-yl-phenyl)-propionylamino]-4-trifluoromethyl-phenyl}-carbamic acid tert-butyl ester The title compound was obtained from (2-amino-5-methyl-4-trifluoromethyl-phenyl)-carbamic acid tert-butyl ester (Example J20) (218 mg, 0.75 mmol) and 3-oxo-3-(3-pyridin-2-yl-phenyl)-propionic acid tert-butyl ester (Example K3) (223 mg, 0.75 mmol) according to the general procedure M as a white foam (283 mg).

MS (ISN) 512.2 [(M–H)$^-$]; mp 76–77° C.

Example M43

(5-Dimethylamino-2-{3-[3-(2,6-dimethyl-pyridin-3-yl)-phenyl]-3-oxo-propionylamino}-4-trifluoromethyl-phenyl)-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-[3-(2,6-dimethyl-pyridin-3-yl)-phenyl]-3-oxo-propionic acid tert-butyl ester (Example K8) (244 mg, 0.75 mmol) according to the general procedure M. Obtained as an amorphous brown substance (201 mg).

MS (ISN) 569.1 [(M–H)$^-$].

Example M44

{4-Chloro-5-methyl-2-[3-oxo-3-(3-pyridazin-4-yl-phenyl)-propionylamino]-phenyl}-carbamic acid tert-butyl ester The title compound was prepared from (2-amino-4-chloro-5-methyl-phenyl)-carbamic acid tert-butyl ester (Example J22) and 3-oxo-3-(3-pyridazin-4-yl-phenyl)-propionic acid tert-butyl ester (Example K9) according to the general procedure M. Obtained as a light yellow solid (184 mg).

MS (ISN) 479 [(M–H)$^-$] and 481 [(M+2–H)$^-$].

Example M45

{5-Methyl-2-[3-oxo-3-(3-pyridazin-4-yl-phenyl)-propionylamino]-4-trifluoromethyl-phenyl}-carbamic acid tert-butyl ester The title compound was obtained from (2-amino-5-methyl-4-trifluoromethyl-phenyl)-carbamic acid tert-butyl ester (Example J20) and 3-oxo-3-(3-pyridazin-4-yl-phenyl)-propionic acid tert-butyl ester (Example K9) according to the general procedure M as a light yellow solid (175 mg).

MS (ISN) 513 [(M–H)$^-$].

Example M46

(2-{3-[3-(6-Methoxy-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (249 mg, 0.9 mmol) and 3-[3-(6-methoxy-pyridin-3-yl)-phenyl]-3-oxo-propionic acid tert-butyl ester (Example K10) (350 mg, 1.07 mmol) according to the general procedure M. Obtained as an orange foam (284 mg).

MS (ISN) 528 [(M–H)$^-$].

Example M47

(4-Chloro-2-{3-[3-(6-methoxy-pyridin-3-yl)-phenyl]-3-oxo-propionylamino}-phenyl)-carbamic acid tert-butyl ester The title compound was obtained from (2-amino-4-chloro-phenyl)-carbamic acid tert-butyl ester (Example J4)

(196 mg, 0.81 mmol) and 3-[3-(6-methoxy-pyridin-3-yl)-phenyl]-3-oxo-propionic acid tert-butyl ester (Example K10) (312 mg, 0.95 mmol) according to the general procedure M as a brown oil (285 mg).

MS (ISN) 494.1 [(M–H)$^-$] and 496 [(M+2–H)$^-$].

Example M48

{4-Chloro-5-fluoro-2-[3-oxo-3-(3-pyridin-2-yl-phenyl)-propionylamino]-phenyl}-carbamic acid tert-butyl ester The title compound was prepared from (2-amino-4-chloro-5-fluoro-phenyl)-carbamic acid tert-butyl ester (Example J5) (205 mg, 0.79 mmol) and 3-oxo-3-(3-pyridin-2-yl-phenyl)-propionic acid tert-butyl ester (Example K3) (302 mg, 0.97 mmol) according to the general procedure M. Obtained as a pink foam (340 mg).

MS (ISN) 482.2 [(M–H)$^-$] and 484 [(M+2–H)$^-$].

Example M49

{2'-Fluoro-3-[3-oxo-3-(3-pyridin-2-yl-phenyl)-propionylamino]-biphenyl-4-yl}-carbamic acid tert-butyl ester The title compound was prepared from (3-amino-2'-fluoro-biphenyl-4-yl)-carbamic acid tert-butyl ester [CAS-No. 335255-65-7] (227 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as a light yellow viscous oil (356 mg).

MS (ISN) 524 [(M–H)$^-$].

Example M50

{2-[3-Oxo-3-(3-pyridin-2-yl-phenyl)-propionylamino]-4-pyrrol-1-yl-phenyl}-carbamic acid tert-butyl ester The title compound was obtained from (2-amino-4-pyrrol-1-yl-phenyl)-carbamic acid tert-butyl ester (Example J11) (205 mg, 0.75 mmol) and 3-oxo-3-(3-pyridin-2-yl-phenyl)-propionic acid tert-butyl ester (Example K3) (223 mg, 0.75 mmol) according to the general procedure M as a yellow solid (300 mg).

MS (ISN) 495 [(M–H)$^-$].

Example M51

{5-Methoxy-2-[3-oxo-3-(3-pyridin-3-yl-phenyl)-propionylamino]-phenyl}-carbamic acid tert-butyl ester The title compound was prepared from (2-Amino-5-methoxy-phenyl)-carbamic acid tert-butyl ester (Example J12) (179 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light brown foam (256 mg).

MS (ISN) 460.3 [(M–H)$^-$].

Example M52

[2-[3-Oxo-3-(3-pyridin-2-yl-phenyl)-propionylamino]-5-(2,2,2-trifluoro-ethoxy)-phenyl]-carbamic acid tert-butyl ester The title compound was obtained from [2-amino-5-(2,2,2-trifluoro-ethoxy)-phenyl]-carbamic acid tert-butyl ester (Example J13) (230 mg, 0.75 mmol) and 3-oxo-3-(3-pyridin-2-yl-phenyl)-propionic acid tert-butyl ester (Example K3) (223 mg, 0.75 mmol) according to the general procedure M as an orange oil (388 mg).

MS (ISN) 528 [(M–H)$^-$].

Example M53

[2-[3-Oxo-3-(3-pyridin-3-yl-phenyl)-propionylamino]-5-(2,2,2-trifluoro-ethoxy)-phenyl]-carbamic acid tert-butyl ester The title compound was prepared from [2-amino-5-(2,2,2-trifluoro-ethoxy)-phenyl]-carbamic acid tert-butyl ester (Example J13) (230 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light brown solid (362 mg).

MS (ISN) 528 [(M–H)$^-$].

Example M54

[2-[3-Oxo-3-(3-pyridin-4-yl-phenyl)-propionylamino]-5-(2,2,2-trifluoro-ethoxy)-phenyl]-carbamic acid tert-butyl ester The title compound was prepared from [2-amino-5-(2,2,2-trifluoro-ethoxy)-phenyl]-carbamic acid tert-butyl ester (Example J13) (230 mg, 0.75 mmol) and 3-oxo-3-(3-pyridin-4-yl-phenyl)-propionic acid tert-butyl ester (Example K2) (223 mg, 0.75 mmol) according to the general procedure M. Obtained as a light brown solid (258 mg).

MS (ISN) 528 [(M–H)$^-$].

Example M55

(5-Ethoxy-2-{3-[3-(2-methyl-pyridin-4-yl)-phenyl]-3-oxo-propionylamino}-phenyl)-carbamic acid tert-butyl ester The title compound was obtained from (2-amino-5-ethoxy-phenyl)-carbamic acid tert-butyl ester (Example J14) (189 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as a light yellow amorphous substance (247 mg).

MS (ISN) 488 [(M–H)$^-$].

Example M56

(5-Ethoxy-2-{3-[3-(2-methyl-pyridin-4-yl)-phenyl]-3-oxo-propionylamino}-phenyl)-carbamic acid tert-butyl ester The title compound was obtained from (2-amino-5-ethoxy-phenyl)-carbamic acid tert-butyl ester (Example J14) (189 mg, 0.75 mmol) and 3-[3-(4-methyl-pyridin-3-yl)-phenyl]-3-oxo-propionic acid tert-butyl ester (Example K4) (234 mg, 0.75 mmol) according to the general procedure M as a light yellow amorphous substance (247 mg).

MS (ISN) 488 [(M–H)$^-$].

Example M57

(5-Ethoxy-2-{3-[3-(2-methyl-pyridin-4-yl)-phenyl]-3-oxo-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as a light yellow solid (358 mg).

MS (ISN) 556 [(M−H)⁻]; mp 135–149° C.

Example M58

{5-(Cyclopropyl-methyl-amino)-2-[3-oxo-3-(3-pyridin-3-yl-phenyl)-propionylamino]-4-trifluoromethyl-phenyl}-carbamic acid tert-butyl ester The title compound was prepared from [2-amino-5-(cyclopropyl-methyl-amino)-4-trifluoromethyl-phenyl]-carbamic acid tert-butyl ester (Example J15) (259 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a yellow foam (393 mg).

MS (ISN) 567.1 [(M−H)⁻].

Example M59

{5-Isobutylamino-2-[3-oxo-3-(3-pyridin-4-yl-phenyl)-propionylamino]-4-trifluoromethyl-phenyl}-carbamic acid tert-butyl ester The title compound was prepared from [2-amino-5-(isobutyl-amino)-4-trifluoromethyl-phenyl]-carbamic acid tert-butyl ester (Example J18) (347 mg, 1.0 mmol) and 3-oxo-3-(3-pyridin-4-yl-phenyl)-propionic acid tert-butyl ester (Example K2) (297 mg, 1.0 mmol) according to the general procedure M. Obtained as a light yellow solid (570 mg, 100%).

MS (ISP) 571.2 [(M+H)⁺].

Example M60

{5-Methyl-2-[3-oxo-3-(3-pyridin-4-yl-phenyl)-propionylamino]-4-trifluoromethyl-

The title compound was obtained from (2-amino-5-methyl-4-trifluoromethyl-phenyl)-carbamic acid tert-butyl ester (Example J20) (290 mg, 1.0 mmol) and 3-oxo-3-(3-pyridin-4-yl-phenyl)-propionic acid tert-butyl ester (Example K2) (297 mg, 1.0 mmol) according to the general procedure M as a white solid (340 mg, 66%).

MS (ISP) 512.2 [(M−H)⁻]; mp 173° C.

Example M61

{4-Methyl-2-[3-oxo-3-(3-pyridin-4-yl-phenyl)-propionylamino]-5-trifluoromethyl-phenyl}-carbamic acid tert-butyl ester The title compound was prepared from (2-amino-4-methyl-5-trifluoromethyl-phenyl)-carbamic acid tert-butyl ester (Example J23) (290 mg, 1.0 mmol) and 3-oxo-3-(3-pyridin-4-yl-phenyl)-propionic acid tert-butyl ester (Example K2) (297 mg, 1.0 mmol) according to the general procedure M. Obtained as a white solid (276 mg, 54%).

MS (ISP) 512.2 [(M−H)⁻]; mp 158° C.

Example M62

{4-Chloro-5-methyl-2-[3-oxo-3-(3-pyridin-4-yl-phenyl)-propionylamino]-phenyl}-carbamic acid tert-butyl ester The title compound was obtained from (2-amino-4-chloro-5-methyl-phenyl)-carbamic acid tert-butyl ester (Example J22) (257 mg, 1.0 mmol) and 3-oxo-3-(3-pyridin-4-yl-phenyl)-propionic acid tert-butyl ester (Example K2) (297 mg, 1.0 mmol) according to the general procedure M as a light yellow foam (370 mg, 77%).

MS (ISP) 478.2 [(M−H)⁻].

Example M63

{5-Chloro-4-methyl-2-[3-oxo-3-(3-pyridin-4-yl-phenyl)-propionylamino]-phenyl}-carbamic acid tert-butyl ester The title compound was prepared from (2-amino-5-chloro-4-methyl-phenyl)-carbamic acid tert-butyl ester (Example J21) (257 mg, 1.0 mmol) and 3-oxo-3-(3-pyridin-4-yl-phenyl)-propionic acid tert-butyl ester (Example K2) (297 mg, 1.0 mmol) according to the general procedure M. Obtained as an off-white foam (370 mg, 77%).

MS (ISP) 478.2 [(M−H)⁻].

Example M64

{5-Chloro-2-[3-oxo-3-(3-pyridin-4-yl-phenyl)-propionylamino]-4-trifluoromethyl-phenyl}-carbamic acid tert-butyl ester The title compound was prepared from (2-amino-5-chloro-4-trifluoromethyl-phenyl)-carbamic acid tert-butyl ester (Example J19) (311 mg, 1.0 mmol) and 3-oxo-3-(3-pyridin-4-yl-phenyl)-propionic acid tert-butyl ester (Example K2) (297 mg, 1.0 mmol) according to the general procedure M. Obtained as a light yellow foam (400 mg, 75%).

MS (ISP) 534.3 [(M+H)⁺].

Example M65

(2'-Fluoro-3-{3-[3-(2-methyl-pyridin-4-yl)-phenyl]-3-oxo-propionylamino}-biphenyl-4-yl)-carbamic acid tert-butyl ester The title compound was prepared from (3-amino-2'-fluoro-biphenyl-4-yl)-carbamic acid tert-butyl ester [CAS 335255-65-7] (302 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as an off-white foam (480 mg, 89%).

MS (ISP) 540.3 [(M+H)⁺].

Example M66

(4-Chloro-5-methyl-2-{3-[3-(2-methyl-pyridin-4-yl)-phenyl]-3-oxo-propionylamino}-phenyl)-carbamic acid tert-butyl ester The title compound was prepared from (2-amino-4-chloro-5-methyl-phenyl)-carbamic acid tert-butyl ester (Example J22) (257 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as an off-white foam (470 mg, 95%).

MS (ISP) 492.1 [(M−H)⁻].

Example M67

(4-Chloro-2-{3-[3-(2-methyl-pyridin-4-yl)-phenyl]-3-oxo-propionylamino}-phenyl)-carbamic acid tert-butyl ester The title compound was obtained from (2-amino-4-chloro-phenyl)-carbamic acid tert-butyl ester (Example J4)

(243 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as a light brown foam (410 mg, 85%).

MS (ISP) 478.2 [(M−H)⁻].

Example M68

(5-Methyl-2-{3-[3-(2-methyl-pyridin-4-yl)-phenyl]-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (290 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as a white foam (430 mg, 82%).

MS (ISP) 526.0 [(M−H)⁻].

Example M69

(2-{3-[3-(2-methyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (276 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as a light brown foam (420 mg, 82%).

MS (ISP) 512.2 [(M−H)⁻].

Example M70

(4-Methyl-2-{3-[3-(2-methyl-pyridin-4-yl)-phenyl]-3-oxo-propionylamino}-5-trifluoromethyl-phenyl)-carbamic acid tert-butyl ester The title compound was prepared from (2-amino-4-methyl-5-trifluoromethyl-phenyl)-carbamic acid tert-butyl ester (Example J23) (290 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as a light yellow foam (330 mg, 63%).

MS (ISP) 526.1 [(M−H)⁻].

Example M71

(5-Dimethylamino-2-{3-[3-(2-methyl-pyridin-4-yl)-phenyl]-3-oxo-propionylamino}-4-trifluoromethyl-phenyl)-carbamic acid tert-butyl ester The title compound was prepared from (2-amino-5-dimethylamino-4-trifluoromethyl-phenyl)-carbamic acid tert-butyl ester (Example J1) (319 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as a pale pink foam (460 mg, 83%).

MS (ISP) 555.1 [(M−H)⁻].

Example M72

(4-Chloro-5-isobutylamino-2-{3-[3-(2-methyl-pyridin-4-yl)-phenyl]-3-oxo-propionylamino}-phenyl)-carbamic acid tert-butyl ester The title compound was prepared from (2-amino-4-chloro-5-isobutylamino-phenyl)-carbamic acid tert-butyl ester (Example J16) (314 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as a yellow foam (480 mg, 87%).

MS (ISP) 549.1 [(M−H)⁻].

Example M73

(5-(Methyl-propyl-amino)-2-{3-[3-(2-methyl-pyridin-4-yl)-phenyl]-3-oxo-propionylamino}-4-trifluoromethyl-phenyl)-carbamic acid tert-butyl ester The title compound was obtained from [2-amino-5-(methyl-propyl-amino)-4-trifluoromethyl-phenyl]-carbamic acid tert-butyl ester (Example J17) (347 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as a light red foam (470 mg, 80%).

MS (ISP) 583.1 [(M−H)⁻].

Example M74

{5-(Methyl-propyl-amino)-2-[3-oxo-3-(3-pyridin-4-yl-phenyl)-propionylamino]-4-trifluoromethyl-phenyl}-carbamic acid tert-butyl ester The title compound was prepared from [2-amino-5-(methyl-propyl-amino)-4-trifluoromethyl-phenyl]-carbamic acid tert-butyl ester (Example J17) (347 mg, 1.0 mmol) and 3-oxo-3-(3-pyridin-4-yl-phenyl)-propionic acid tert-butyl ester (Example K2) (297 mg, 1.0 mmol) according to the general procedure M. Obtained as a light red foam (550 mg, 96%).

MS (ISP) 569.1 [(M−H)⁻].

Example M75

(5-Chloro-2-{3-[3-(2-methyl-pyridin-4-yl)-phenyl]-3-oxo-propionylamino}-4-trifluoromethyl-phenyl)-carbamic acid tert-butyl ester The title compound was obtained from (2-amino-5-chloro-4-trifluoromethyl-phenyl)-carbamic acid tert-butyl ester (Example J19) (311 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as an off-white solid (345 mg, 63%).

MS (ISP) 546.0 [(M−H)⁻]; mp 177° C.

Example M76

(4-Fluoro-2-{3-[3-(2-methyl-pyridin-4-yl)-phenyl]-3-oxo-propionylamino}-phenyl)-carbamic acid tert-butyl ester The compound was prepared from (2-amino-4-fluoro-phenyl)-carbamic acid tert-butyl ester (Example J2) (226 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as an off-white foam (390 mg, 84%).

MS (ISP) 462.2 [(M−H)⁻].

Example M77

(5-Chloro-4-methyl-2-{3-[3-(2-methyl-pyridin-4-yl)-phenyl]-3-oxo-propionylamino}-phenyl)-carbamic acid tert-butyl ester The title compound was prepared from (2-amino-5-chloro-4-methyl-phenyl)-carbamic acid tert-butyl ester (Example J21) (257 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as a white solid (372 mg, 75%).

MS (ISP) 492.2 [(M–H)⁻]; mp 171° C.

Example M78

{5-Dimethylamino-2-[3-oxo-3-(3-pyrimidin-5-yl-phenyl)-propionylamino]-4-trifluoromethyl-phenyl}-carbamic acid tert-butyl ester The title compound was obtained from (2-amino-5-dimethylamino-4-trifluoromethyl-phenyl)-carbamic acid tert-butyl ester (Example J1) (319 mg, 1.0 mmol) and 3-oxo-3-(3-pyrimidin-5-yl-phenyl)-propionic acid tert-butyl ester (Example K13) (298 mg, 1.0 mmol) according to the general procedure M as an off-white solid (370 mg, 68%).

MS (ISP) 542.1 [(M–H)⁻]; mp 144° C.

Example M79

{4-Chloro-5-methyl-2-[3-oxo-3-(3-pyrazin-2-yl-phenyl)-propionylamino]-phenyl}-carbamic acid tert-butyl ester The title compound was prepared from (2-amino-4-chloro-5-methyl-phenyl)-carbamic acid tert-butyl ester (Example J22) (257 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as a white foam (320 mg, 67%).

MS (ISP) 479.2 [(M–H)⁻].

Example M80

{5-Methyl-2-[3-oxo-3-(3-pyrazin-2-yl-phenyl)-propionylamino]-4-trifluoromethyl-phenyl}-carbamic acid tert-butyl ester The title compound was prepared from (2-amino-5-methyl-4-trifluoromethyl-phenyl)-carbamic acid tert-butyl ester (Example J20) (290 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as a white foam (350 mg, 68%).

MS (ISP) 513.1 [(M–H)⁻].

Example M81

{2-[3-Oxo-3-(3-pyrazin-2-yl-phenyl)-propionylamino]-4-trifluoromethyl-phenyl}-carbamic acid tert-butyl ester The title compound was obtained from (2-amino-4-trifluoromethyl-phenyl)-carbamic acid tert-butyl ester (Example J3) (276 mg, 1.0 mmol) and 3-oxo-3-(3-pyrazin-2-yl-phenyl)-propionic acid tert-butyl ester (Example K14) (298 mg, 1.0 mmol) according to the general procedure M as a light brown foam (340 mg, 68%).

MS (ISP) 499.1 [(M–H)⁻].

Example M82

{5-Dimethylamino-2-[3-oxo-3-(3-pyrazin-2-yl-phenyl)-propionylamino]-4-trifluoromethyl-phenyl}-carbamic acid tert-butyl ester The title compound was prepared from (2-amino-5-dimethylamino-4-trifluoromethyl-phenyl)-carbamic acid tert-butyl ester (Example J1) (319 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as a light brown foam (370 mg, 68%).

MS (ISP) 542.1 [(M–H)⁻].

Example M83

{5-Chloro-2-[3-oxo-3-(3-pyrazin-2-yl-phenyl)-propionylamino]-4-trifluoromethyl-phenyl}-carbamic acid tert-butyl ester The title compound was obtained from (2-amino-5-chloro-4-trifluoromethyl-phenyl)-carbamic acid tert-butyl ester (Example J19) (311 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as an off-white foam (180 mg, 34%).

MS (ISP) 533.1 [(M–H)⁻].

Example M84

{2'-Fluoro-3-[3-oxo-3-(3-pyrazin-2-yl-phenyl)-propionylamino]-biphenyl-4-yl}-carbamic The title compound was prepared from (3-amino-2'-fluoro-biphenyl-4-yl)-carbamic acid tert-butyl ester [CAS 335255-65-7] (302 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as an off-white foam (350 mg, 66%).

MS (ISP) 525.1 [(M–H)⁻].

Example M85

{4-Methyl-2-[3-oxo-3-(3-pyrazin-2-yl-phenyl)-propionylamino]-5-trifluoromethyl-phenyl}-carbamic acid tert-butyl ester The title compound was prepared from (2-amino-4-methyl-5-trifluoromethyl-phenyl)-carbamic acid tert-butyl ester (Example J23) (290 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as a white foam (290 mg, 56%).

MS (ISP) 513.2 [(M–H)⁻].

Example M86

{4-Chloro-2-[3-oxo-3-(3-pyrimidin-5-yl-phenyl)-propionylamino]-phenyl}-carbamic acid tert-butyl ester The title compound was prepared from (2-amino-4-chloro-phenyl)-carbamic acid tert-butyl ester (Example J4) (243 mg, 1.0 mmol) and 3-oxo-3-(3-pyrimidin-5-yl-phenyl)-propionic acid tert-butyl ester (Example K13) (298 mg, 1.0 mmol) according to the general procedure M. Obtained as a light brown solid (350 mg, 75%).

MS (ISP) 479.2 [(M–H)⁻]; mp 169° C.

Example M87

{5-Chloro-2-[3-oxo-3-(3-pyrimidin-5-yl-phenyl)-propionylamino]-4-trifluoromethyl-phenyl}-carbamic acid tert-butyl ester The title compound was prepared from (2-amino-5-chloro-4-trifluoromethyl-phenyl)-carbamic acid tert-butyl ester (Example J19) (311 mg, 1.0 mmol) and 3-oxo-3-(3-pyrimidin-5-yl-phenyl)-propionic acid tert-butyl ester (Example K13) (298 mg, 1.0 mmol) according to the general procedure M. Obtained as a yellow oil (420 mg, 79%).

MS (ISP) 533.1 [(M–H)⁻].

Example M88

{4-Chloro-5-isobutylamino-2-[3-oxo-3-(3-pyrimidin-5-yl-phenyl)-propionylamino]-phenyl}-carbamic acid tert-butyl ester The title compound was prepared from (2-amino-4-chloro-5-isobutylamino-phenyl)-carbamic acid tert-butyl ester (Example J16) (235 mg, 0.75 mmol) and 3-oxo-3-(3-pyrimidin-5-yl-phenyl)-propionic acid tert-butyl ester (Example K13) (224 mg, 0.75 mmol) according to the general procedure M. Obtained as an off-white foam (260 mg, 64%).

MS (ISP) 536.2 [(M–H)⁻].

Example M89

{5-Methyl-2-[3-oxo-3-(3-pyrimidin-5-yl-phenyl)-propionylamino]-4-trifluoromethyl-phenyl}-carbamic acid tert-butyl ester The title compound was prepared from (2-amino-5-methyl-4-trifluoromethyl-phenyl)-carbamic acid tert-butyl ester (Example J20) (290 mg, 1.0 mmol) and 3-oxo-3-(3-pyrimidin-5-yl-phenyl)-propionic acid tert-butyl ester (Example K13) (298 mg, 1.0 mmol) according to the general procedure M. Obtained as an off-white foam (290 mg, 56%).

MS (ISP) 515.3 [(M+H)⁺].

Example M90

{5-(Methyl-propyl-amino)-2-[3-oxo-3-(3-pyrimidin-5-yl-phenyl)-propionylamino]-4-trifluoromethyl-phenyl}-carbamic acid tert-butyl ester The title compound was prepared from [2-amino-5-(methyl-propyl-amino)-4-trifluoromethyl-phenyl]-carbamic acid tert-butyl ester (Example J17) (347 mg, 1.0 mmol) and 3-oxo-3-(3-pyrimidin-5-yl-phenyl)-propionic acid tert-butyl ester (Example K13) (298 mg, 1.0 mmol) according to the general procedure M. Obtained as a red oil (370 mg, 65%).

MS (ISP) 570.2 [(M–H)⁻].

Example M91

(4-Chloro-2-{3-[3-(2-methyl-pyridin-4-yl)-phenyl]-3-oxo-propionylamino}-5-trifluoromethyl-phenyl)-carbamic acid tert-butyl ester The title compound was prepared from (2-amino-4-chloro-5-trifluoromethyl-phenyl)-carbamic acid tert-butyl ester (Example J24) (466 mg, 1.5 mmol) and 3-[3-(2-methyl-pyridin-4-yl)-phenyl]-3-oxo-propionic acid tert-butyl ester (Example K12) (467 mg, 1.5 mmol) according to the general procedure M. Obtained as an orange oil (360 mg, 44%).

MS (ISP) 546.1 [(M–H)⁻].

Example M92

{4-Chloro-2-[3-oxo-3-(3-pyridin-4-yl-phenyl)-propionylamino]-5-trifluoromethyl-phenyl}-carbamic acid tert-butyl ester The title compound was obtained from (2-amino-4-chloro-5-trifluoromethyl-phenyl)-carbamic acid tert-butyl ester (Example J24) (466 mg, 1.5 mmol) and 3-oxo-3-(3-pyridin-4-yl-phenyl)-propionic acid tert-butyl ester (Example K2) (446 mg, 1.5 mmol) according to the general procedure M as a light yellow oil (440 mg, 55%).

MS (ISP) 532.1 [(M–H)⁻].

Example M93

{5-(Methyl-propyl-amino)-2-[3-oxo-3-(3-pyrazin-2-yl-phenyl)-propionylamino]-4-trifluoromethyl-phenyl}-carbamic acid tert-butyl ester The title compound was prepared from [2-amino-5-(methyl-propyl-amino)-4-trifluoromethyl-phenyl]-carbamic acid tert-butyl ester (Example J17) (347 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as a light red foam (350 mg, 61%).

MS (ISP) 570.1 [(M–H)⁻].

Example M94

{5-Chloro-4-methyl-2-[3-oxo-3-(3-pyrazin-2-yl-phenyl)-propionylamino]-phenyl}-carbamic acid tert-butyl ester The title compound was prepared from (2-amino-5-chloro-4-methyl-phenyl)-carbamic acid tert-butyl ester (Example J21) (257 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as a white solid (390 mg, 81%).

MS (ISP) 479.2 [(M–H)⁻].

Example M95

{4-Chloro-5-methyl-2-[3-oxo-3-(3-pyrimidin-5-yl-phenyl)-propionylamino]-phenyl}-carbamic acid tert-butyl ester The title compound was obtained from (2-amino-4-chloro-5-methyl-phenyl)-carbamic acid tert-butyl ester (Example J22) (257 mg, 1.0 mmol) and 3-oxo-3-(3-pyrimidin-5-yl-phenyl)-propionic acid tert-butyl ester (Example K13) (298 mg, 1.0 mmol) according to the general procedure M as a light yellow oil (440 mg, 91%).

MS (ISP) 479.2 [(M–H)⁻].

Example M96

{2'-Fluoro-3-[3-oxo-3-(3-pyrimidin-5-yl-phenyl)-propionylamino]-biphenyl-4-yl}-carbamic acid tert-butyl ester The title compound was prepared from (3-amino-2'-fluoro-biphenyl-4-yl)-carbamic acid tert-butyl ester [CAS 335255-65-7] (302 mg, 1.0 mmol) and 3-oxo-3-(3-pyrimidin-5-yl-phenyl)-propionic acid tert-butyl ester (Example K13) (298 mg, 1.0 mmol) according to the general procedure M. Obtained as a light yellow oil (420 mg, 80%).

MS (ISP) 525.0 [(M–H)⁻].

Example M97

{4-Methyl-2-[3-oxo-3-(3-pyrimidin-5-yl-phenyl)-propionylamino]-5-trifluoromethyl-phenyl}-carbamic acid tert-butyl ester The title compound was prepared from (2-amino-4-methyl-5-trifluoromethyl-phenyl)-carbamic acid tert-butyl ester (Example J23) (290 mg, 1.0 mmol) and 3-oxo-3-(3-pyrimidin-5-yl-phenyl)-propionic acid tert-butyl ester (Example K13) (298 mg, 1.0 mmol) according to the general procedure M. Obtained as a light yellow oil (430 mg, 84%).

MS (ISP) 513.2 [(M−H)⁻].

Example M98

{4-Chloro-2-[3-oxo-3-(3-pyridin-2-yl-phenyl)-propionylamino]-5-trifluoromethyl-phenyl}-carbamic acid tert-butyl ester The title compound was prepared from (2-amino-4-chloro-5-trifluoromethyl-phenyl)-carbamic acid tert-butyl ester (Example J24) (466 mg, 1.5 mmol) and 3-oxo-3-(3-pyridin-2-yl-phenyl)-propionic acid tert-butyl ester (Example K3) (446 mg, 1.5 mmol) according to the general procedure M. Obtained as an orange oil (310 mg, 39%).

MS (ISP) 532.0 [(M−H)⁻].

Example M99

(2-{3-[3-(2-Methyl-pyridin-4-yl)-phenyl]-3-oxo-propionylamino}-4-pyrrol-1-yl-phenyl)-carbamic acid tert-butyl ester The title compound was obtained from (2-amino-4-pyrrol-1-yl-phenyl)-carbamic acid tert-butyl ester (Example J11) (273 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as a yellow oil (490 mg, 96%).

MS (ISN) 509.3 [(M−H)⁻].

Example M100

{2-[3-Oxo-3-(3-pyrazin-2-yl-phenyl)-propionylamino]-4-pyrrol-1-yl-phenyl}-carbamic acid tert-butyl ester The title compound was obtained from (2-amino-4-pyrrol-1-yl-phenyl)-carbamic acid tert-butyl ester (Example J11) (273 mg, 1.0 mmol) and 3-oxo-3-(3-pyrazin-2-yl-phenyl)-propionic acid tert-butyl ester (Example K14) (298 mg, 1.0 mmol) according to the general procedure M as a light brown solid (370 mg, 74%).

MS (ISN) 496.1 [(M−H)⁻]; mp 143° C.

Example M101

{4-Chloro-2-[3-oxo-3-(3-pyrazin-2-yl-phenyl)-propionylamino]-5-trifluoromethyl-phenyl}-carbamic acid tert-butyl ester The title compound was prepared from (2-amino-4-chloro-5-trifluoromethyl-phenyl)-carbamic acid tert-butyl ester (Example J24) (310 mg, 1.0 mmol) and 3-oxo-3-(3-pyrazin-2-yl-phenyl)-propionic acid tert-butyl ester (Example K14) (298 mg, 1.0 mmol) according to the general procedure M. Obtained as a yellow oil (280 mg, 52%).

MS (ISP) 533.0 [(M−H)⁻].

Example M102

{4-Chloro-2-[3-oxo-3-(3-pyrimidin-5-yl-phenyl)-propionylamino]-5-trifluoromethyl-phenyl}-carbamic acid tert-butyl ester The title compound was prepared from (2-amino-4-chloro-5-trifluoromethyl-phenyl)-carbamic acid tert-butyl ester (Example J24) (311 mg, 1.0 mmol) and 3-oxo-3-(3-pyrimidin-5-yl-phenyl)-propionic acid tert-butyl ester (Example K13) (298 mg, 1.0 mmol) according to the general procedure M. Obtained as a yellow oil (320 mg, 60%).

MS (ISP) 533.1 [(M−H)⁻].

Example M103

[2-[3-Oxo-3-(3-pyrazin-2-yl-phenyl)-propionylamino]-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-oxo-3-(3-pyrazin-2-yl-phenyl)-propionic acid tert-butyl ester (Example K14) (224 mg, 0.75 mmol) according to the general procedure M. Obtained as an orange foam (370 mg, 82%).

MS (ISP) 596.9 [(M−H)⁻].

Example M104

{4-Chloro-2-[3-oxo-3-(3-pyridin-3-yl-phenyl)-propionylamino]-5-trifluoromethyl-phenyl}-carbamic acid tert-butyl ester The title compound was prepared from (2-amino-4-chloro-5-trifluoromethyl-phenyl)-carbamic acid tert-butyl ester (Example J24) (230 mg, 0.74 mmol) and 3-oxo-3-(3-pyridin-3-yl-phenyl)-propionic acid tert-butyl ester (Example K1) (220 mg, 0.74 mmol) according to the general procedure M. Obtained as a light yellow solid (260 mg, 66%).

MS (ISP) 532.1 [(M−H)⁻]; mp 158° C.

Example M105

[2-{3-[3-(2-Methyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (374 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M. Obtained as an orange oil (450 mg, 74%).

MS (ISP) 609.9 [(M−H)⁻].

Example M106

(4-Chloro-2-{3-[3-(2,6-dimethyl-pyridin-4-yl)-phenyl]-5-methyl-3-oxo-propionylamino}-phenyl)-carbamic acid tert-butyl ester The title compound was prepared from (2-amino-4-chloro-5-methyl-phenyl)-carbamic acid tert-butyl ester (Example J22) (174 mg, 0.68 mmol) and 3-[3-(2,6-dimethyl-pyridin-4-yl)-phenyl]-3-oxo-propionic acid tert-butyl ester (Example K15) (220 mg, 0.68 mmol) according to the general procedure M. Obtained as a white foam (290 mg, 84%).

MS (ISP) 506.2 [(M−H)⁻].

Example M107

(4-Chloro-2-{3-[3-(2,6-dimethyl-pyridin-4-yl)-phenyl]-3-oxo-propionylamino}-phenyl)-carbamic acid tert-butyl ester The title compound was prepared from (2-amino-4-chloro-phenyl)-carbamic acid tert-butyl ester (Example J4)

Example M108

(2-{3-[3-(2,6-Dimethyl-pyridin-4-yl)-phenyl]-5-methyl-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (196 mg, 0.68 mmol) and 3-[3-(2,6-dimethyl-pyridin-4-yl)-phenyl]-3-oxo-propionic acid tert-butyl ester (Example K15) (220 mg, 0.68 mmol) according to the general procedure M. Obtained as an off-white foam (300 mg, 82%).

MS (ISP) 540.2 [(M–H)⁻].

Example M109

(2-{3-[3-(2,6-Dimethyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (187 mg, 0.68 mmol) and 3-[3-(2,6-dimethyl-pyridin-4-yl)-phenyl]-3-oxo-propionic acid tert-butyl ester (Example K15) (220 mg, 0.68 mmol) according to the general procedure M. Obtained as an off-white foam (270 mg, 76%).

MS (ISP) 526.0 [(M–H)⁻].

Example M110

(2-{3-[3-(2,6-Dimethyl-pyridin-4-yl)-phenyl]-4-methyl-3-oxo-propionylamino}-5-trifluoromethyl-phenyl)-carbamic acid tert-butyl ester The title compound was prepared from (2-amino-4-methyl-5-trifluoromethyl-phenyl)-carbamic acid tert-butyl ester (Example J23) (196 mg, 0.68 mmol) and 3-[3-(2,6-dimethyl-pyridin-4-yl)-phenyl]-3-oxo-propionic acid tert-butyl ester (Example K15) (220 mg, 0.68 mmol) according to the general procedure M. Obtained as a light yellow foam (300 mg, 82%).

MS (ISP) 540.2 [(M–H)⁻].

Example M111

(5-Chloro-2-{3-[3-(2,6-dimethyl-pyridin-4-yl)-phenyl]-3-oxo-propionylamino}-4-trifluoromethyl-phenyl)-carbamic acid tert-butyl ester The title compound was prepared from (2-amino-5-chloro-4-trifluoromethyl-phenyl)-carbamic acid tert-butyl ester (Example J19) (210 mg, 0.68 mmol) and 3-[3-(2,6-dimethyl-pyridin-4-yl)-phenyl]-3-oxo-propionic acid tert-butyl ester (Example K15) (220 mg, 0.68 mmol) according to the general procedure M. Obtained as a white foam (260 mg, 68%).

MS (ISP) 560.1 [(M–H)⁻].

Example M112

(5-Chloro-2-{3-[3-(2,6-dimethyl-pyridin-4-yl)-phenyl]-4-methyl-3-oxo-propionylamino}-phenyl)-carbamic acid tert-butyl ester The title compound was prepared from (2-amino-5-chloro-4-methyl-phenyl)-carbamic acid tert-butyl ester (Example J21) (174 mg, 0.68 mmol) and 3-[3-(2,6-dimethyl-pyridin-4-yl)-phenyl]-3-oxo-propionic acid tert-butyl ester (Example K15) (220 mg, 0.68 mmol) according to the general procedure M. Obtained as a white foam (290 mg, 84%).

MS (ISP) 506.2 [(M–H)⁻].

Example M113

(4-Chloro-2-{3-[3-(2,6-dimethyl-pyridin-4-yl)-phenyl]-3-oxo-propionylamino}-5-trifluoromethyl-phenyl)-carbamic acid tert-butyl ester The title compound was prepared from (2-amino-4-chloro-5-trifluoromethyl-phenyl)-carbamic acid tert-butyl ester (Example J24) (311 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M. Obtained as a light yellow oil (356 mg, 63%).

MS (ISP) 560.1 [(M–H)⁻].

Example M114

[2-{3-[3-(2,6-Dimethyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (374 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M. Obtained as a light brown foam (510 mg, 82%).

MS (ISP) 624.0 [(M–H)⁻].

Example M115

5-Ethoxy-[2-{3-[3-(2,6-dimethyl-pyridin-4-yl)-phenyl]-3-oxo-propionylamino}-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J8) (320 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M. Obtained as a light yellow foam (530 mg, 93%).

MS (ISP) 570.1 [(M–H)⁻].

Example M116

(4-Chloro-5-methyl-2-{3-[3-(6-methyl-pyrazin-2-yl)-phenyl]-3-oxo-propionylamino}-phenyl)-carbamic acid tert-butyl ester The title compound was prepared from (2-amino-4-chloro-5-methyl-phenyl)-carbamic acid tert-butyl ester (Example J22) (257 mg, 1.0 mmol) and 3-[3-(6-methyl-pyrazin-2-yl)-phenyl]-3-oxo-propionic acid tert-butyl ester (Example K16) (312 mg, 1.0 mmol) according to the general procedure M. Obtained as a light brown foam (470 mg, 95%).

MS (ISP) 493.1 [(M–H)⁻].

Example M117

(5-Methyl-2-{3-[3-(6-methyl-pyrazin-2-yl)-phenyl]-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (290 mg, 1.0 mmol) and 3-[3-(6-methyl-pyrazin-2-yl)-phenyl]-3-oxo-propionic acid tert-butyl ester (Example K16) (312 mg, 1.0 mmol) according to the general procedure M. Obtained as a light brown foam (460 mg, 87%).

MS (ISP) 527.0 [(M–H)$^-$].

Example M118

(4-Methyl-2-{3-[3-(6-methyl-pyrazin-2-yl)-phenyl]-3-oxo-propionylamino}-5-trifluoromethyl-phenyl)-carbamic acid tert-butyl ester The title compound was prepared from (2-amino-4-methyl-5-trifluoromethyl-phenyl)-carbamic acid tert-butyl ester (Example J23) (290 mg, 1.0 mmol) and 3-[3-(6-methyl-pyrazin-2-yl)-phenyl]-3-oxo-propionic acid tert-butyl ester (Example K16) (312 mg, 1.0 mmol) according to the general procedure M. Obtained as a light brown foam (400 mg, 76%).

MS (ISP) 527.0 [(M–H)$^-$].

Example M119

(5-Chloro-4-methyl-2-{3-[3-(6-methyl-pyrazin-2-yl)-phenyl]-3-oxo-propionylamino}-phenyl)-carbamic acid tert-butyl ester The title compound was prepared from (2-amino-5-chloro-4-methyl-phenyl)-carbamic acid tert-butyl ester (Example J21) (257 mg, 1.0 mmol) and 3-[3-(6-methyl-pyrazin-2-yl)-phenyl]-3-oxo-propionic acid tert-butyl ester (Example K16) (312 mg, 1.0 mmol) according to the general procedure M. Obtained as a light brown foam (400 mg, 81%).

MS (ISP) 493.1 [(M–H)$^-$].

Example M120

(4-Chloro-2-{3-[3-(2,5-dimethyl-pyridin-4-yl)-phenyl]-5-methyl-3-oxo-propionylamino}-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(2,5-dimethyl-pyridin-4-yl)-phenyl]-3-oxo-propionic acid tert-butyl ester (Example K17) (244 mg, 0.75 mmol) according to the general procedure M. Obtained as an off-white solid (250 mg, 66%).

MS (ISP) 506.2 [(M–H)$^-$]; mp 169° C.

Example M121

(2-{3-[3-(2,5-Dimethyl-pyridin-4-yl)-phenyl]-5-methyl-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2,5-dimethyl-pyridin-4-yl)-phenyl]-3-oxo-propionic acid tert-butyl ester (Example K17) (244 mg, 0.75 mmol) according to the general procedure M. Obtained as a light yellow foam (360 mg, 89%).

MS (ISP) 540.2 [(M–H)$^-$].

Example M122

(5-Chloro-2-{3-[3-(2,5-dimethyl-pyridin-4-yl)-phenyl]-3-oxo-propionylamino}-4-trifluoromethyl-phenyl)-carbamic acid tert-butyl ester The title compound was prepared from (2-amino-5-chloro-4-trifluoromethyl-phenyl)-carbamic acid tert-butyl ester (Example J19) (233 mg, 0.75 mmol) and 3-[3-(2,5-dimethyl-pyridin-4-yl)-phenyl]-3-oxo-propionic acid tert-butyl ester (Example K17) (244 mg, 0.75 mmol) according to the general procedure M. Obtained as an off-white foam (240 mg, 57%).

MS (ISP) 560.1 [(M–H)$^-$].

Example M123

[2-{3-[3-(2,5-Dimethyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2,5-dimethyl-pyridin-4-yl)-phenyl]-3-oxo-propionic acid tert-butyl ester (Example K17) (244 mg, 0.75 mmol) according to the general procedure M. Obtained as an off-white solid (300 mg, 64%).

MS (ISP) 624.0 [(M–H)$^-$]; mp 178° C.

Example M124

5-Ethoxy-[2-{3-[3-(2,5-dimethyl-pyridin-4-yl)-phenyl]-3-oxo-propionylamino}-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J8) (240 mg, 0.75 mmol) and 3-[3-(2,5-dimethyl-pyridin-4-yl)-phenyl]-3-oxo-propionic acid tert-butyl ester (Example K17) (244 mg, 0.75 mmol) according to the general procedure M. Obtained as a light yellow foam (250 mg, 58%).

MS (ISP) 570.1 [(M–H)$^-$].

Example M125

(4-Chloro-2-{3-[3-(2,3-dimethyl-pyridin-4-yl)-phenyl]-5-methyl-3-oxo-propionylamino}-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(2,3-dimethyl-pyridin-4-yl)-phenyl]-3-oxo-propionic acid tert-butyl ester (Example K18) (244 mg, 0.75 mmol) according to the general procedure M. Obtained as an orange foam (280 mg, 73%).

MS (ISP) 506.2 [(M–H)$^-$].

Example M126

(2-{3-[3-(2,3-Dimethyl-pyridin-4-yl)-phenyl]-5-methyl-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2,3-dimethyl-pyridin-4-yl)-phenyl]-3-oxo-propionic acid tert-butyl ester (Example K18) (244 mg, 0.75 mmol) according to the general procedure M. Obtained as a light yellow oil (320 mg, 79%).

MS (ISP) 540.2 [(M–H)$^-$].

Example M127

(2-{3-[3-(2,3-Dimethyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2,3-dimethyl-pyridin-4-yl)-phenyl]-3-oxo-propionic acid tert-butyl ester (Example K18) (244 mg, 0.75 mmol) according to the general procedure M. Obtained as a light yellow oil (310 mg, 78%).

MS (ISP) 526.1 [(M−H)⁻].

Example M128

(5-Chloro-2-{3-[3-(2,3-dimethyl-pyridin-4-yl)-phenyl]-3-oxo-propionylamino}-4-trifluoromethyl-phenyl)-carbamic acid tert-butyl ester The title compound was prepared from (2-amino-5-chloro-4-trifluoromethyl-phenyl)-carbamic acid tert-butyl ester (Example J19) (233 mg, 0.75 mmol) and 3-[3-(2,3-dimethyl-pyridin-4-yl)-phenyl]-3-oxo-propionic acid tert-butyl ester (Example K18) (244 mg, 0.75 mmol) according to the general procedure M. Obtained as a light yellow oil (340 mg, 81%).

MS (ISP) 560.2 [(M−H)⁻].

Example M129

[2-{3-[3-(2,3-Dimethyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2,3-dimethyl-pyridin-4-yl)-phenyl]-3-oxo-propionic acid tert-butyl ester (Example K18) (244 mg, 0.75 mmol) according to the general procedure M. Obtained as an orange foam (330 mg, 70%).

MS (ISP) 624.2 [(M−H)⁻].

Example M130

5-Ethoxy-[2-{3-[3-(2,3-dimethyl-pyridin-4-yl)-phenyl]-3-oxo-propionylamino}-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J8) (240 mg, 0.75 mmol) and 3-[3-(2,3-dimethyl-pyridin-4-yl)-phenyl]-3-oxo-propionic acid tert-butyl ester (Example K18) (244 mg, 0.75 mmol) according to the general procedure M. Obtained as a light yellow oil (350 mg, 82%).

MS (ISP) 570.3 [(M−H)⁻].

Example M131

(4-Chloro-2-{3-[3-(5-ethyl-2-methyl-pyridin-4-yl)-phenyl]-5-methyl-3-oxo-propionylamino}-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(5-ethyl-2-methyl-pyridin-4-yl)-phenyl]-3-oxo-propionic acid tert-butyl ester (Example K19) (255 mg, 0.75 mmol) according to the general procedure M. Obtained as an off-white solid (330 mg, 84%).

MS (ISP) 520.2 [(M−H)⁻]; mp 172° C.

Example M132

(2-{3-[3-(5-ethyl-2-methyl-pyridin-4-yl)-phenyl]-5-methyl-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(5-ethyl-2-methyl-pyridin-4-yl)-phenyl]-3-oxo-propionic acid tert-butyl ester (Example K19) (255 mg, 0.75 mmol) according to the general procedure M. Obtained as an off-white solid (300 mg, 72%).

MS (ISP) 554.3 [(M−H)⁻]; mp 173° C.

Example M133

(2-{3-[3-(5-Ethyl-2-methyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(5-ethyl-2-methyl-pyridin-4-yl)-phenyl]-3-oxo-propionic acid tert-butyl ester (Example K19) (255 mg, 0.75 mmol) according to the general procedure M. Obtained as a light brown solid (260 mg, 64%).

MS (ISP) 540.3 [(M−H)⁻].

Example M134

[2-{3-[3-(5-Ethyl-2-methyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(5-ethyl-2-methyl-pyridin-4-yl)-phenyl]-3-oxo-propionic acid tert-butyl ester (Example K19) (255 mg, 0.75 mmol) according to the general procedure M. Obtained as an off-white solid (300 mg, 63%).

MS (ISP) 638.2 [(M−H)⁻]; mp 183° C.

Example M135

5-Ethoxy-[2-{3-[3-(5-ethyl-2-methyl-pyridin-4-yl)-phenyl]-3-oxo-propionylamino}-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J8) (240 mg, 0.75 mmol) and 3-[3-(5-ethyl-2-methyl-pyridin-4-yl)-phenyl]-3-oxo-propionic acid tert-butyl ester (Example K19) (255 mg, 0.75 mmol) according to the general procedure M. Obtained as an off-white solid (310 mg, 71%).

MS (ISP) 584.2 [(M−H)⁻]; mp 180° C.

Example M136

(4-Chloro-2-{3-[3-(2-ethyl-pyridin-4-yl)-phenyl]-5-methyl-3-oxo-propionylamino}-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(2-ethyl-pyridin-4-yl)-phenyl]-3-oxo-propionic acid tert-butyl ester (Example K20) (244 mg, 0.75 mmol) according to the general procedure M. Obtained as an off-white solid (274 mg, 72%).

MS (ISP) 506.2 [(M−H)⁻]; mp 147° C.

Example M137

(2-{3-[3-(2-Ethyl-pyridin-4-yl)-phenyl]-5-methyl-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-ethyl-pyridin-4-yl)-phenyl]-3-oxo-propionic acid tert-butyl ester (Example K20) (244 mg, 0.75 mmol) according to the general procedure M. Obtained as an off-white solid (295 mg, 73%).

MS (ISP) 540.3 [(M−H)⁻]; mp 158° C.

Example M138

(2-{3-[3-(2-Ethyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2-ethyl-pyridin-4-yl)-phenyl]-3-oxo-propionic acid tert-butyl ester (Example K20) (244 mg, 0.75 mmol) according to the general procedure M. Obtained as an off-white solid (275 mg, 70%).

MS (ISP) 526.1 [(M−H)⁻]; mp 150° C.

Example M139

(5-Chloro-2-{3-[3-(2-ethyl-pyridin-4-yl)-phenyl]-3-oxo-propionylamino}-4-trifluoromethyl-phenyl)-carbamic acid tert-butyl ester The title compound was prepared from (2-amino-5-chloro-4-trifluoromethyl-phenyl)-carbamic acid tert-butyl ester (Example J19) (233 mg, 0.75 mmol) and 3-[3-(2-ethyl-pyridin-4-yl)-phenyl]-3-oxo-propionic acid tert-butyl ester (Example K20) (244 mg, 0.75 mmol) according to the general procedure M. Obtained as an off-white solid (288 mg, 67%).

MS (ISP) 560.3 [(M−H)⁻]; mp 116° C.

Example M140

[2-{3-[3-(2-Ethyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-ethyl-pyridin-4-yl)-phenyl]-3-oxo-propionic acid tert-butyl ester (Example K20) (244 mg, 0.75 mmol) according to the general procedure M. Obtained as an off-white solid (346 mg, 74%).

MS (ISP) 624.2 [(M−H)⁻]; mp 161° C.

Example M141

5-Ethoxy-[2-{3-[3-(2-ethyl-pyridin-4-yl)-phenyl]-3-oxo-propionylamino}-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J6) (240 mg, 0.75 mmol) and 3-[3-(2-ethyl-pyridin-4-yl)-phenyl]-3-oxo-propionic acid tert-butyl ester (Example K20) (244 mg, 0.75 mmol) according to the general procedure M. Obtained as an off-white solid (339 mg, 79%).

MS (ISP) 570.3 [(M−H)⁻]; mp 151° C.

Example M142

(5-Dimethylamino-2-{3-[3-(6-methyl-pyridin-2-yl)-phenyl]-3-oxo-propionylamino}-4-trifluoromethyl-phenyl)-carbamic acid tert-butyl ester The title compound was prepared from (2-amino-5-dimethylamino-4-trifluoromethyl-phenyl)-carbamic acid tert-butyl ester (Example J1) (239 mg, 0.75 mmol) and 3-[3-(6-methyl-pyridin-2-yl)-phenyl]-3-oxo-propionic acid tert-butyl ester (Example K11) (234 mg, 0.75 mmol) according to the general procedure M. Obtained as an amorphous light brown substance (339 mg, 67%).

MS (ISN) 555 [(M−H)⁻].

Example M143

(4-Chloro-2-{3-[3-(6-cyclopropyl-pyridin-3-yl)-phenyl]-3-oxo-propionylamino}-5-methyl-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a light yellow foam (342 mg, 88%).

MS (ISN) 518.1 [(M−H)⁻] and 520 [(M+2−H)⁻].

Example M144

{5-Ethoxy-2-[3-oxo-3-(3-pyridin-3-yl-phenyl)-propionylamino}-phenyl]-carbamic acid tert-butyl ester The title compound was prepared from (2-amino-5-ethoxy-phenyl)-carbamic acid tert-butyl ester (Example J14) (194 mg, 0.77 mmol) and 3-oxo-3-(3-pyridin-3-yl-phenyl)-propionic acid tert-butyl ester (Example K1) (224 mg, 0.75 mmol) according to the general procedure M. Obtained as a light yellow foam (203 mg, 55%).

MS (ISN) 474.2 [(M−H)⁻].

Example M145

{5-Ethoxy-2-[3-oxo-3-(3-pyridin-4-yl-phenyl)-propionylamino]-phenyl}-carbamic acid tert-butyl ester The title compound was prepared from (2-amino-5-ethoxy-phenyl)-carbamic acid tert-butyl ester (Example J14) (193 mg, 0.76 mmol) and 3-oxo-3-(3-pyridin-4-yl-phenyl)-propionic acid tert-butyl ester (Example K2) (221 mg, 0.74 mmol) according to the general procedure M. Obtained as an off-white foam (227 mg, 65%).

MS (ISN) 474.2 [(M−H)⁻].

Example M146

{2-[3-Oxo-3-(3-pyridin-2-yl-phenyl)-propionylamino}-4-phenylethynyl-phenyl]-carbamic acid tert-butyl ester The title compound was prepared from (2-amino-4-phenylethynyl-phenyl)-carbamic acid tert-butyl ester {CAS-No. [335255-26-0]} (231 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as an off-white solid (313 mg, 44%).

MS (ISN) 474.2 [(M−H)⁻]; mp 198° C.

Example M147

{4-(4-Fluoro-phenylethynyl)-2-[3-oxo-3-(3-pyridin-2-yl-phenyl)-propionylamino}-phenyl]-carbamic acid tert-butyl ester The title compound was prepared from [2-amino-4-(4-fluoro-phenylethynyl)-phenyl]-carbamic acid tert-butyl ester {CAS-No. [335255-58-0]} (245 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as an amorphous light brown substance (325 mg, 79%).

MS (ISN) 548 [(M–H)⁻].

Example M148

[2-{3-[3-(6-Cyclopropyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a yellow foam (344 mg, 72%).

MS (ISN) 635.9 [(M–H)⁻].

Example M149

(2-{3-[3-(6-Cyclopropyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a yellow solid (325 mg, 78%).

MS (ISN) 552 [(M–H)⁻]; mp 150–153° C.

Example M150

(2-{3-[3-(6-Methoxy-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (232 mg, 0.80 mmol) and 3-[3-(6-methoxy-pyridin-3-yl)-phenyl]-3-oxo-propionic acid tert-butyl ester (Example K10) (270 mg, 0.82 mmol) according to the general procedure M. Obtained as a yellow foam (287 mg, 66%).

MS (ISN) 542.1 [(M–H)⁻].

Example M151

[2-{3-[3-(6-Methoxy-pyridin-3-yl)-phenyl]-3-oxo-propionylamino}-5-(2,2,2-trifluoro-ethoxy)-phenyl]-carbamic acid tert-butyl ester The title compound was prepared from [2-amino-5-(2,2,2-trifluoro-ethoxy)-phenyl]-carbamic acid tert-butyl ester (Example J13) (240 mg, 0.78 mmol) and 3-[3-(6-methoxy-pyridin-3-yl)-phenyl]-3-oxo-propionic acid tert-butyl ester (Example K10) (293 mg, 0.89 mmol) according to the general procedure M. Obtained as a red foam (288 mg, 66%).

MS (ISN) 558.1 [(M–H)⁻].

Example M152

[2-{3-[3-(6-Methoxy-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (296 mg, 0.79 mmol) and 3-[3-(6-methoxy-pyridin-3-yl)-phenyl]-3-oxo-propionic acid tert-butyl ester (Example K10) (289 mg, 0.88 mmol) according to the general procedure M. Obtained as an orange foam (402 mg, 81%).

MS (ISN) 625.9 [(M–H)⁻].

Example M153

(2-{3-[3-(6-Cyclopropyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a yellow foam (311 mg, 77%).

MS (ISN) 538.1 [(M–H)⁻].

Example M154

{5-Methyl-2-[3-oxo-3-(3-pyridin-3-yl-phenyl)-propionylamino]-4-trifluoromethyl-phenyl}-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light yellow foam (270 mg, 70%).

MS (ISN) 512.2 [(M–H)⁻].

Example M155

{5-Methoxy-2-[3-oxo-3-(3-pyridin-3-yl-phenyl)-propionylamino]-4-trifluoromethyl-phenyl}-carbamic acid tert-butyl ester The title compound was prepared from (2-amino-5-methoxy-4-trifluoromethyl-phenyl)-carbamic acid tert-butyl ester (Example J7) (230 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a yellow foam (326 mg, 82%).

MS (ISN) 528.0 [(M–H)⁻].

Example M156

{4-(4-Fluoro-phenylethynyl)-2-[3-oxo-3-(3-pyridin-3-yl-phenyl)-propionylamino]-phenyl}-carbamic acid tert-butyl ester The title compound was prepared from [2-amino-4-(4-fluoro-phenylethynyl)-phenyl]-carbamic acid tert-butyl ester {CAS-No. [335255-58-0]} (245 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as an orange foam (304 mg, 74%).

MS (ISN) 548.1 [(M–H)⁻].

Example M157

{2-[3-Oxo-3-(3-pyridin-3-yl-phenyl)-propionylamino]-4-phenylethynyl-phenyl}-carbamic acid tert-butyl ester The title compound was prepared from (2-amino-4-phenylethynyl-phenyl)-carbamic acid tert-butyl ester {CAS- No. [335255-26-0]]} (231 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a yellow foam (322 mg, 81%).

MS (ISN) 530.1 [(M−H)⁻].

Example M158

[2-{3-[3-(5-Cyclopropyl-pyridin-2-yl)-phenyl]-3-oxo-propionylamino}-5-(2,2,2-trifluoro-ethoxy)-phenyl]-carbamic acid tert-butyl ester The title compound was prepared from [2-amino-5-(2,2,2-trifluoro-ethoxy)-phenyl]-carbamic acid tert-butyl ester (Example J13) (230 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a light brown foam (323 mg, 76%).

MS (ISN) 568.0 [(M−H)⁻].

Example M159

(2-{3-[3-(6-Isopropyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(6-isopropyl-pyridin-3-yl)-phenyl]-3-oxo-propionic acid tert-butyl ester (Example K22) (255 mg, 0.75 mmol) according to the general procedure M. Obtained as an amorphous brown substance (266 mg, 65%).

MS (ISN) 538.1 [(M−H)⁻].

Example M160

[2-{3-[3-(6-Isopropyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(6-isopropyl-pyridin-3-yl)-phenyl]-3-oxo-propionic acid tert-butyl ester (Example K22) (255 mg, 0.75 mmol) according to the general procedure M. Obtained as an amorphous light brown substance (368 mg, 77%).

MS (ISN) 638 [(M−H)⁻].

Example M161

(4-Chloro-2-{3-[3-(6-isopropyl-pyridin-3-yl)-phenyl]-3-oxo-propionylamino}-5-methyl-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(6-isopropyl-pyridin-3-yl)-phenyl]-3-oxo-propionic acid tert-butyl ester (Example K22) (255 mg, 0.75 mmol) according to the general procedure M. Obtained as an off-white solid (160 mg, 41%).

MS (ISN) 520 [(M−H)⁻] and 522 [(M+2−H)⁻]; mp 168° C.

Example M162

(2-{3-[3-(6-Isopropyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(6-isopropyl-pyridin-3-yl)-phenyl]-3-oxo-propionic acid tert-butyl ester (Example K22) (255 mg, 0.75 mmol) according to the general procedure M. Obtained as an off-white solid (197 mg, 47%).

MS (ISN) 554 [(M−H)⁻]; mp 154° C.

Example M163

{4-Chloro-5-ethoxy-2-[3-oxo-3-(3-pyridin-3-yl-phenyl)-propionylamino]-phenyl}-carbamic acid tert-butyl ester The title compound was prepared from (2-amino-4-chloro-5-ethoxy-phenyl)-carbamic acid tert-butyl ester (Example J25) (215 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as an off-white solid (142 mg, 37%).

MS (ISN) 508 [(M−H)⁻] and 510 [(M+2−H)⁻]; mp 100° C.

Example M164

(4-Chloro-5-ethoxy-2-{3-[3-(2-methyl-pyridin-4-yl)-phenyl]-3-oxo-propionylamino}-phenyl)-carbamic acid tert-butyl ester The title compound was prepared from (2-amino-4-chloro-5-ethoxy-phenyl)-carbamic acid tert-butyl ester (Example J25) (215 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as an off-white solid (280 mg, 71%).

MS (ISN) 522.0 [(M−H)⁻] and 524 [(M+2−H)⁻]; mp 184° C.

Example M165

{5-Chloro-2-[3-oxo-3-(3-pyridin-3-yl-phenyl)-propionylamino]-4-trifluoromethyl-phenyl}-carbamic acid tert-butyl ester The title compound was prepared from (2-amino-5-chloro-4-trifluoromethyl-phenyl)-carbamic acid tert-butyl ester (Example J19) (233 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light yellow foam (261 mg, 65%).

MS (ISN) 532.2 [(M−H)⁻] and 534 [(M+2−H)⁻].

Example M166

{5-Ethoxy-2-[3-oxo-3-(3-pyridin-3-yl-phenyl)-propionylamino]-4-trifluoromethyl-phenyl}-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light yellow solid (271 mg, 66%).

MS (ISN) 542 [(M−H)⁻].

Example M167

{2-[3-Oxo-3-(3-pyridin-3-yl-phenyl)-propionylamino]-4-trifluoromethoxy-phenyl}-carbamic acid tert-butyl ester The title compound was prepared from (2-amino-4-trifluoromethoxy-phenyl)-carbamic acid tert-butyl ester (Example J26) (219 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as an amorphous light yellow substance (271 mg, 70%).

MS (ISN) 514 [(M–H)⁻].

Example M168

(2-{3-[3-(2-Methyl-pyridin-4-yl)-phenyl]-3-oxo-propionylamino}-4-trifluoromethoxy-phenyl)-carbamic acid tert-butyl ester The title compound was prepared from (2-amino-4-trifluoromethoxy-phenyl)-carbamic acid tert-butyl ester (Example J26) (219 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as an amorphous light yellow substance (275 mg, 69%).

MS (ISN) 528 [(M–H)⁻].

Example M169

{2-[3-Oxo-3-(3-pyridin-3-yl-phenyl)-propionylamino]-5-pyrrolidin-1-yl-4-trifluoromethyl-phenyl}-carbamic acid tert-butyl ester The title compound was prepared from (2-amino-5-pyrrolidin-1-yl-4-trifluoromethyl-phenyl)-carbamic acid tert-butyl ester (Example J27) (259 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a yellow foam (259 mg, 61%).

MS (ISN) 567.1 [(M–H)⁻].

Example M170

{5-Morpholin-4-yl-2-[3-oxo-3-(3-pyridin-3-yl-phenyl)-propionylamino]-4-trifluoromethyl-phenyl}-carbamic acid tert-butyl ester The title compound was prepared from (2-amino-5-morpholin-4-yl-4-trifluoromethyl-phenyl)-carbamic acid tert-butyl ester (Example J28) (271 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light yellow foam (346 mg, 79%).

MS (ISN) 583.0 [(M–H)⁻].

Example M171

(4-Chloro-2-{3-[3-(6-ethyl-pyridin-3-yl)-phenyl]-3-oxo-propionylamino}-5-methyl-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(6-ethyl-pyridin-3-yl)-phenyl]-3-oxo-propionic acid tert-butyl ester (Example K23) (244 mg, 0.75 mmol) according to the general procedure M. Obtained as a light yellow foam (307 mg, 81%).

MS (ISN) 506.2 [(M–H)⁻] and 508 [(M+2–H)⁻].

Example M172

(5-Ethoxy-2-{3-[3-(6-ethyl-pyridin-3-yl)-phenyl]-3-oxo-propionylamino}-4-trifluoromethyl-phenyl)-carbamic acid tert-butyl ester The title compound was prepared from [2-amino-5-ethoxy-4-trifluoromethyl-phenyl]-carbamic acid tert-butyl ester (Example J8) (240 mg, 0.75 mmol) and 3-[3-(6-ethyl-pyridin-3-yl)-phenyl]-3-oxo-propionic acid tert-butyl ester (Example K23) (244 mg, 0.75 mmol) according to the general procedure M. Obtained as a yellow solid (324 mg, 76%).

MS (ISN) 570.1 [(M–H)⁻]; mp 123–126° C.

Example M173

(2-{3-[3-(6-Ethyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(6-ethyl-pyridin-3-yl)-phenyl]-3-oxo-propionic acid tert-butyl ester (Example K23) (244 mg, 0.75 mmol) according to the general procedure M. Obtained as an amorphous yellow substance (296 mg, 75%).

MS (ISN) 526 [(M–H)⁻].

Example M174

(2-{3-[3-(6-Ethyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(6-ethyl-pyridin-3-yl)-phenyl]-3-oxo-propionic acid tert-butyl ester (Example K23) (244 mg, 0.75 mmol) according to the general procedure M. Obtained as an amorphous yellow substance (324 mg, 80%).

MS (ISN) 540 [(M–H)⁻].

Example M175

[2-{3-[3-(6-Ethyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(6-ethyl-pyridin-3-yl)-phenyl]-3-oxo-propionic acid tert-butyl ester (Example K23) (244 mg, 0.75 mmol) according to the general procedure M. Obtained as an amorphous yellow substance (422 mg, 90%).

MS (ISN) 624 [(M–H)⁻].

Example M176

{5-Cyclopropylmethoxy-2-[3-oxo-3-(3-pyridin-3-yl-phenyl)-propionylamino]-4-trifluoromethyl-phenyl}-carbamic acid tert-butyl ester The title compound was prepared from (2-amino-5-cyclopropylmethoxy-4-trifluoromethyl-phenyl)-carbamic acid tert-butyl ester (Example J29) (260 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as an amorphous yellow substance (311 mg, 73%).

MS (ISN) 568 [(M–H)⁻].

Example M177

(5-Cyclopropylmethoxy-2-{3-[3-(2-methyl-pyridin-4-yl)-phenyl]-3-oxo-propionylamino}-4-trifluoromethyl-phenyl)-carbamic acid tert-butyl ester The title compound was prepared from (2-amino-5-cyclopropylmethoxy-4-trifluoromethyl-phenyl)-carbamic acid tert-butyl ester (Example J29) (260 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as an amorphous yellow substance (325 mg, 74%).

MS (ISN) 582 [(M−H)⁻].

Example M178

(5-Cyclopropylmethoxy-2-{3-[3-(6-cyclopropyl-pyridin-3-yl)-phenyl]-3-oxo-propionylamino}-4-trifluoromethyl-phenyl)-carbamic acid tert-butyl ester The title compound was prepared from (2-amino-5-cyclopropylmethoxy-4-trifluoromethyl-phenyl)-carbamic acid tert-butyl ester (Example J29) (260 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as an amorphous yellow substance (283 mg, 62%).

MS (ISN) 608 [(M−H)⁻].

Example M179

[2-[3-Oxo-3-(3-pyridin-3-yl-phenyl)-propionylamino]-4-(2,2,2-trifluoro-ethoxy)-phenyl]-carbamic acid tert-butyl ester The title compound was prepared from [2-amino-4-(2,2,2-trifluoro-ethoxy)-phenyl]-carbamic acid tert-butyl ester (Example J30) (230 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as an amorphous yellow substance (298 mg, 75%).

MS (ISN) 528 [(M−H)⁻].

Example M180

(2-{3-[3-(2-Cyano-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2-cyano-pyridin-4-yl)-phenyl]-3-oxo-propionic acid tert-butyl ester (Example K24) (242 mg, 0.75 mmol) according to the general procedure M. Obtained as an orange foam (314 mg, 80%).

MS (ISN) 523.0 [(M−H)⁻].

Example M181

(2-{3-[3-(2-Cyano-pyridin-4-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-cyano-pyridin-4-yl)-phenyl]-3-oxo-propionic acid tert-butyl ester (Example K24) (242 mg, 0.75 mmol) according to the general procedure M. Obtained as a white solid (275 mg, 68%).

MS (ISN) 537.1 [(M−H)⁻]; mp 97–99° C.

Example M182

[4-Chloro-2-[3-oxo-3-(3-pyridin-3-yl-phenyl)-propionylamino]-5-(2,2,2-trifluoro-ethoxy)-phenyl]-carbamic acid tert-butyl ester The title compound was prepared from [2-amino-4-chloro-5-(2,2,2-trifluoro-ethoxy)-phenyl]-carbamic acid tert-butyl ester (Example J31) (256 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light yellow foam (282 mg, 67%).

MS (ISN) 562.1 [(M−H)⁻] and 564 [(M+2−H)⁻].

Example M183

[4-Chloro-2-{3-[3-(2-cyano-pyridin-4-yl)-phenyl]-3-oxo-propionylamino}-5-(2,2,2-trifluoro-ethoxy)-phenyl]-carbamic acid tert-butyl ester The title compound was prepared from [2-amino-4-chloro-5-(2,2,2-trifluoro-ethoxy)-phenyl]-carbamic acid tert-butyl ester (Example J31) (256 mg, 0.75 mmol) and 3-[3-(2-cyano-pyridin-4-yl)-phenyl]-3-oxo-propionic acid tert-butyl ester (Example K24) (242 mg, 0.75 mmol) according to the general procedure M. Obtained as a colorless solid (249 mg, 53%).

MS (ISN) 587.0 [(M−H)⁻] and 589 [(M+2−H)⁻]; mp 116–120° C.

Example M184

(2-{3-[3-(6-Cyano-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(6-cyano-pyridin-3-yl)-phenyl]-3-oxo-propionic acid tert-butyl ester (Example K26) (242 mg, 0.75 mmol) according to the general procedure M. Obtained as a light yellow foam (305 mg, 78%).

MS (ISN) 523.1 [(M−H)⁻].

Example M185

{2-[3-Oxo-3-(3-pyridazin-3-yl-phenyl)-propionylamino]-4-trifluoromethyl-phenyl}-carbamic acid tert-butyl ester The title compound was prepared from (2-amino-4-trifluoromethyl-phenyl)-carbamic acid tert-butyl ester (Example J3) (207 mg, 0.75 mmol) and 3-oxo-3-(3-pyridazin-3-yl-phenyl)-propionic acid tert-butyl ester (Example K27) (224 mg, 0.75 mmol) according to the general procedure M. Obtained as a white solid (250 mg, 67%).

MS (ISN) 499.1 [(M−H)⁻]; mp 146–149° C.

Example M186

{2-[3-Oxo-3-(3-pyridin-2-yl-phenyl)-propionylamino]-4-trifluoromethoxy-phenyl}-carbamic acid tert-butyl ester The title compound was prepared from (2-amino-4-trifluoromethoxy-phenyl)-carbamic acid tert-butyl ester (Example J26) (219 mg, 0.75 mmol) and 3-oxo-3-(3-pyridin-2-yl-phenyl)-propionic acid tert-butyl ester (Example K3) (223 mg, 0.75 mmol) according to the general procedure M. Obtained as a yellow solid (271 mg, 69%).

MS (ISN) 514.1 [(M−H)⁻]; mp 128–130° C.

Example M187

(2-{3-[3-(6-Cyclopropyl-pyridin-3-yl)-phenyl]-3-oxo-propionylamino}-4-trifluoromethoxy-phenyl)-carbamic acid tert-butyl ester The title compound was prepared from (2-amino-4-trifluoromethoxy-phenyl)-carbamic acid tert-butyl ester (Example J26) (219 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a yellow foam (252 mg, 60%).

MS (ISN) 554.0 [(M−H)⁻].

Example M188

{5-(2-Methoxy-ethoxy)-2-[3-oxo-3-(3-pyridin-3-yl-phenyl)-propionylamino]-4-trifluoromethyl-phenyl}-carbamic acid tert-butyl ester The title compound was prepared from [2-amino-5-(2-methoxy-ethoxy)-4-trifluoromethyl-phenyl]-carbamic acid tert-butyl ester (Example J32) (263 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light yellow solid (257 mg, 60%).

MS (ISN) 572 [(M−H)⁻]; mp 148–150° C.

Example M189

[2-{3-[3-(2-Cyano-pyridin-4-yl)-phenyl]-3-oxo-propionylamino}-5-(2-methoxy-ethoxy)-4-trifluoromethyl-phenyl]-carbamic acid tert-butyl ester The title compound was prepared from [2-amino-5-(2-methoxy-ethoxy)-4-trifluoromethyl-phenyl]-carbamic acid tert-butyl ester (Example J32) (263 mg, 0.75 mmol) and 3-[3-(2-cyano-pyridin-4-yl)-phenyl]-3-oxo-propionic acid tert-butyl ester (Example K24) (242 mg, 0.75 mmol) according to the general procedure M. Obtained as a light yellow solid (278 mg, 61%).

MS (ISN) 597 [(M−H)⁻]; mp 125–130° C.

Example M190

(2-{3-[3-(2-Cyano-pyridin-4-yl)-phenyl]-3-oxo-propionylamino}-5-ethyl-4-trifluoromethyl-phenyl)-carbamic acid tert-butyl ester The title compound was prepared from (2-amino-5-ethyl-4-trifluoromethyl-phenyl)-carbamic acid tert-butyl ester (Example J33) (228 mg, 0.75 mmol) and 3-[3-(2-cyano-pyridin-4-yl)-phenyl]-3-oxo-propionic acid tert-butyl ester (Example K24) (242 mg, 0.75 mmol) according to the general procedure M. Obtained as a light brown solid (308 mg, 74%).

MS (ISN) 551 [(M−H)⁻]; mp 86° C.

Example M191

{5-Ethyl-2-[3-oxo-3-(3-pyridin-3-yl-phenyl)-propionylamino]-4-trifluoromethyl-phenyl}-carbamic acid tert-butyl ester The title compound was prepared from (2-amino-5-ethyl-4-trifluoromethyl-phenyl)-carbamic acid tert-butyl ester (Example J33) (228 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a light yellow oil (373 mg, 94%).

MS (ISN) 526 [(M−H)⁻].

Example M192

(2-{3-[3-(6-Methoxy-pyridin-3-yl)-phenyl]-3-oxo-propionylamino}-4-trifluoromethoxy-phenyl)-carbamic acid tert-butyl ester The title compound was prepared from (2-amino-4-trifluoromethoxy-phenyl)-carbamic acid tert-butyl ester (Example J26) (219 mg, 0.75 mmol) and 3-[3-(6-methoxy-pyridin-3-yl)-phenyl]-3-oxo-propionic acid tert-butyl ester (Example K10) (246 mg, 0.75 mmol) according to the general procedure M. Obtained as an orange foam (226 mg, 71%).

MS (ISN) 544.0 [(M−H)⁻].

Example M193

(2-{3-[3-(2,6-Dimethyl-pyridin-4-yl)-phenyl]-3-oxo-propionylamino}-4-trifluoromethoxy-phenyl)-carbamic acid tert-butyl ester The title compound was prepared from (2-amino-4-trifluoromethoxy-phenyl)-carbamic acid tert-butyl ester (Example J26) (219 mg, 0.75 mmol) and 3-[3-(2,6-dimethyl-pyridin-4-yl)-phenyl]-3-oxo-propionic acid tert-butyl ester (Example K15) (244 mg, 0.75 mmol) according to the general procedure M. Obtained as a light yellow foam (240 mg, 59%).

MS (ISN) 542.1 [(M−H)⁻].

Example M194

{2-[3-Oxo-3-(3-pyridin-3-yl-phenyl)-propionylamino]-4-trifluoromethyl-5-vinyl-phenyl}-carbamic acid tert-butyl ester The title compound was prepared from (2-amino-4-trifluoromethyl-5-vinyl-phenyl)-carbamic acid tert-butyl ester (Example J34) (227 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a yellow oil (290 mg, 60%).

MS (ISN) 524 [(M−H)⁻].

Example M195

{2-[3-Oxo-3-(3-pyridin-3-yl-phenyl)-propionylamino]-5-propoxy-4-trifluoromethyl-phenyl}-carbamic acid tert-butyl ester The title compound was prepared from (2-amino-5-propoxy-4-trifluoromethyl-phenyl)-carbamic acid tert-butyl ester (Example J35) (251 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a yellow foam (369 mg, 88%).

MS (ISN) 556.0 [(M−H)⁻].

Example M196

(2-{3-[3-(6-Cyclopropyl-pyridin-3-yl)-phenyl]-3-oxo-propionylamino}-5-propoxy-4-trifluoromethyl-phenyl)-carbamic acid tert-butyl ester The title compound was prepared from (2-amino-5-propoxy-4-trifluoromethyl-phenyl)-carbamic acid tert-butyl ester (Example J35) (251 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a yellow foam (372 mg, 83%).

MS (ISN) 596.1 [(M−H)⁻].

Example M197

(2-{3-[3-(6-Dimethylamino-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(6-dimethylamino-pyridin-3-yl)-phenyl]-3-oxo-propionic acid tert-butyl ester (Example K28) (255 mg, 0.75 mmol) according to the general procedure M. Obtained as a light yellow solid (309 mg, 74%).

MS (ISP) 557 [(M+H)$^+$]; mp 187–188° C.

Example M198

[2-{3-[3-(6-Dimethylamino-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(6-dimethylamino-pyridin-3-yl)-phenyl]-3-oxo-propionic acid tert-butyl ester (Example K28) (255 mg, 0.75 mmol) according to the general procedure M. Obtained as a light brown solid (409 mg, 85%).

MS (ISP) 641 [(M+H)$^+$]; mp 167–169° C.

Example M199

(2-{3-[3-(2,6-Dimethyl-pyridin-4-yl)-phenyl]-3-oxo-propionylamino}-5-propoxy-4-trifluoromethyl-phenyl)-carbamic acid tert-butyl ester The title compound was prepared from (2-amino-5-propoxy-4-trifluoromethyl-phenyl)-carbamic acid tert-butyl ester (Example J35) (251 mg, 0.75 mmol) and 3-[3-(2,6-dimethyl-pyridin-4-yl)-phenyl]-3-oxo-propionic acid tert-butyl ester (Example K15) (244 mg, 0.75 mmol) according to the general procedure M. Obtained as a light yellow solid (172 mg, 49%).

MS (ISN) 596.1 [(M−H)$^−$].

Example M200

(2-{3-[3-(2-Cyclopropyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2-cyclopropyl-pyridin-3-yl)-phenyl]-3-oxo-propionic acid tert-butyl ester (Example K29) (253 mg, 0.75 mmol) according to the general procedure M. Obtained as a yellow oil (223 mg, 58%).

MS (ISN) 538.1 [(M−H)$^−$].

Example M201

(2-{3-[3-(2-Cyclopropyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-cyclopropyl-pyridin-3-yl)-phenyl]-3-oxo-propionic acid tert-butyl ester (Example K29) (253 mg, 0.75 mmol) according to the general procedure M. Obtained as a yellow oil (255 mg, 61%).

MS (ISN) 552.0 [(M−H)$^−$].

Example M202

(2-{3-[3-(2-Methyl-pyridin-4-yl)-phenyl]-3-oxo-propionylamino}-5-propyl-4-trifluoromethyl-phenyl)-carbamic acid tert-butyl ester The title compound was prepared from (2-amino-5-propyl-4-trifluoromethyl-phenyl)-carbamic acid tert-butyl ester (Example J36) (239 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as a light yellow foam (292 mg, 70%).

MS (ISN) 554 [(M−H)$^−$].

Example M203

(5-Ethyl-2-{3-[3-(2-methyl-pyridin-4-yl)-phenyl]-3-oxo-propionylamino}-4-trifluoromethyl-phenyl)-carbamic acid tert-butyl ester The title compound was prepared from (2-amino-5-ethyl-4-trifluoromethyl-phenyl)-carbamic acid tert-butyl ester (Example J33) (152 mg, 0.5 mmol) and 3-[3-(2-methyl-pyridin-4-yl)-phenyl]-3-oxo-propionic acid tert-butyl ester (Example K12) (156 mg, 0.5 mmol) according to the general procedure M. Obtained as a light yellow foam (213 mg, 79%).

MS (ISN) 540 [(M−H)$^−$].

Example M204

(2-{3-[3-(6-Cyclopropyl-pyridin-3-yl)-phenyl]-3-oxo-propionylamino}-5-propyl-4-trifluoromethyl-phenyl)-carbamic acid tert-butyl ester The title compound was prepared from (2-amino-5-propyl-4-trifluoromethyl-phenyl)-carbamic acid tert-butyl ester (Example J36) (239 mg, 0.75 mmol) and 3-[3-(6-cyclopropyl-pyridin-3-yl)-phenyl]-3-oxo-propionic acid tert-butyl ester (Example K21) (253 mg, 0.75 mmol) according to the general procedure M. Obtained as a yellow solid (274 mg, 63%).

MS (ISN) 580 [(M−H)$^−$].

Example M205

(2-{3-[3-(6-Cyclopropyl-pyridin-3-yl)-phenyl]-3-oxo-propionylamino}-5-ethyl-4-trifluoromethyl-phenyl)-carbamic acid tert-butyl ester The title compound was prepared from (2-amino-5-ethyl-4-trifluoromethyl-phenyl)-carbamic acid tert-butyl ester (Example J33) (152 mg, 0.5 mmol) and 3-[3-(6-cyclopropyl-pyridin-3-yl)-phenyl]-3-oxo-propionic acid tert-butyl ester (Example K21) (169 mg, 0.5 mmol) according to the general procedure M. Obtained as a light yellow foam (211 mg, 74%).

MS (ISN) 566 [(M−H)$^−$].

Example M206

(2-{3-[3-(4-Methyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(4-methyl-pyridin-3-yl)-phenyl]-3-oxo-propionic acid tert-butyl ester (Example K30) (234 mg, 0.75 mmol) according to the general procedure M. Obtained as a light yellow foam (276 mg, 72%).

MS (ISN) 512.2 [(M−H)$^−$].

Example M207

(2-{3-[3-(2-Cyclopropyl-pyridin-3-yl)-phenyl]-3-oxo-propionylamino}-5-ethoxy-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(2-cyclopropyl-pyridin-3-yl)-phenyl]-3-oxo-propionic acid tert-butyl ester (Example K29) (253 mg, 0.75 mmol) according to the general procedure M. Obtained as a yellow foam (210 mg, 48%).

MS (ISN) 582.0 [(M−H)⁻].

Example M208

(2-{3-[3-(2,6-Dimethyl-pyridin-4-yl)-phenyl]-3-oxo-propionylamino}-5-ethyl-4-trifluoromethyl-phenyl)-carbamic acid tert-butyl ester The title compound was prepared from (2-amino-5-ethyl-4-trifluoromethyl-phenyl)-carbamic acid tert-butyl ester (Example J33) (152 mg, 0.5 mmol) and 3-[3-(2,6-dimethyl-pyridin-4-yl)-phenyl]-3-oxo-propionic acid tert-butyl ester (Example K15) (163 mg, 0.5 mmol) according to the general procedure M. Obtained as a white solid (185 mg, 67%).

MS (ISP) 556 [(M+H)⁺].

Example M209

(2-{3-[3-(2,6-Dimethyl-pyridin-4-yl)-phenyl]-3-oxo-propionylamino}-5-propyl-4-trifluoromethyl-phenyl)-carbamic acid tert-butyl ester The title compound was prepared from (2-amino-5-propyl-4-trifluoromethyl-phenyl)-carbamic acid tert-butyl ester (Example J36) (239 mg, 0.75 mmol) and 3-[3-(2,6-dimethyl-pyridin-4-yl)-phenyl]-3-oxo-propionic acid tert-butyl ester (Example K15) (244 mg, 0.75 mmol) according to the general procedure M. Obtained as a white solid (325 mg, 76%).

MS (ISN) 568 [(M−H)⁻].

Example M210

{2-[3-Oxo-3-(3-pyridin-3-yl-phenyl)-propionylamino]-5-propyl-4-trifluoromethyl-phenyl}-carbamic acid tert-butyl ester The title compound was prepared from (2-amino-5-propyl-4-trifluoromethyl-phenyl)-carbamic acid tert-butyl ester (Example J36) (239 mg, 0.75 mmol) and 3-oxo-3-(3-pyridin-3-yl-phenyl)-propionic acid tert-butyl ester (Example K1) (223 mg, 0.75 mmol) according to the general procedure M. Obtained as a yellow oil (180 mg, 44%).

MS (ISN) 540 [(M−H)⁻].

Example M211

(5-Ethoxy-2-{3-[3-(4-methyl-pyridin-3-yl)-phenyl]-3-oxo-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(4-methyl-pyridin-3-yl)-phenyl]-3-oxo-propionic acid tert-butyl ester (Example K30) (234 mg, 0.75 mmol) according to the general procedure M. Obtained as a yellow foam (314 mg, 75%).

MS (ISN) 556.0 [(M−H)⁻].

Example M212

[2-{3-[3-(4-Methyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(4-methyl-pyridin-3-yl)-phenyl]-3-oxo-propionic acid tert-butyl ester (Example K30) (234 mg, 0.75 mmol) according to the general procedure M. Obtained as a light yellow foam (380 mg, 83%).

MS (ISN) 609.9 [(M−H)⁻].

Example M213

(5-Methyl-2-{3-[3-(4-methyl-pyridin-3-yl)-phenyl]-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(4-methyl-pyridin-3-yl)-phenyl]-3-oxo-propionic acid tert-butyl ester (Example K30) (234 mg, 0.75 mmol) according to the general procedure M. Obtained as a white solid (301 mg, 76%).

MS (ISN) 526.0 [(M−H)⁻]; mp 167–169° C.

Example M214

(2-{3-[3-(2-Ethyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-ethyl-pyridin-3-yl)-phenyl]-3-oxo-propionic acid tert-butyl ester (Example K31) (244 mg, 0.75 mmol) according to the general procedure M. Obtained as an amorphous off-white substance (346 mg, 85%).

MS (ISN) 540 [(M−H)⁻].

Example M215

(5-Ethoxy-2-{3-[3-(2-ethyl-pyridin-3-yl)-phenyl]-3-oxo-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(2-ethyl-pyridin-3-yl)-phenyl]-3-oxo-propionic acid tert-butyl ester (Example K31) (244 mg, 0.75 mmol) according to the general procedure M. Obtained as an amorphous yellow substance (294 mg, 69%).

MS (ISN) 570 [(M−H)⁻].

Example M216

[2-{3-[3-(2-Ethyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-ethyl-pyridin-3-yl)-phenyl]-3-oxo-propionic acid tert-butyl ester (Example K31) (244 mg, 0.75 mmol) according to the general procedure M. Obtained as an amorphous yellow substance (373 mg, 80%).

MS (ISN) 624 [(M−H)⁻].

Example M217

(5-Methyl-2-{3-[3-(6-methyl-pyridin-3-yl)-phenyl]-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as an amorphous off-white substance (331 mg, 84%).

MS (ISN) 526 [(M−H)⁻].

Example M218

(5-Ethoxy-2-{3-[3-(6-methyl-pyridin-3-yl)-phenyl]-3-oxo-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as an amorphous yellow substance (301 mg, 72%).

MS (ISN) 556 [(M−H)⁻].

Example M219

[2-{3-[3-(6-Methyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(6-methyl-pyridin-3-yl)-phenyl]-3-oxo-propionic acid tert-butyl ester (Example K4) (234 mg, 0.75 mmol) according to the general procedure M. Obtained as an amorphous light brown substance (231 mg, 50%).

MS (ISN) 610 [(M−H)⁻].

Example M220

(2-{3-[3-(2,6-Dimethyl-pyridin-4-yl)-phenyl]-3-oxo-propionylamino}-5-fluoro-4-trifluoromethyl-phenyl)-carbamic acid tert-butyl ester The title compound was prepared from (2-amino-5-fluoro-4-trifluoromethyl-phenyl)-carbamic acid tert-butyl ester (Example J37) (221 mg, 0.75 mmol) and 3-[3-(2,6-dimethyl-pyridin-4-yl)-phenyl]-3-oxo-propionic acid tert-butyl ester (Example K15) (244 mg, 0.75 mmol) according to the general procedure M. Obtained as a light yellow foam (301 mg, 74%).

MS (ISP) 544.1 [(M+H)⁺].

Example M221

(2-{3-[3-(2,6-Dimethyl-pyridin-4-yl)-phenyl]-3-oxo-propionylamino}-4-trifluoromethyl-5-vinyl-phenyl)-carbamic acid tert-butyl ester The title compound was prepared from (2-amino-4-trifluoromethyl-5-vinyl-phenyl)-carbamic acid tert-butyl ester (Example J34) (227 mg, 0.75 mmol) and 3-[3-(2,6-dimethyl-pyridin-4-yl)-phenyl]-3-oxo-propionic acid tert-butyl ester (Example K15) (244 mg, 0.75 mmol) according to the general procedure M. Obtained as a yellow solid (199 mg, 48%).

MS (ISN) 552.0 [(M−H)⁻]; mp 169° C. (dec.).

Example M222

(5-(2-Methoxy-ethoxy)-2-{3-[3-(2-methyl-pyridin-4-yl)-phenyl]-3-oxo-propionylamino}-4-trifluoromethyl-phenyl)-carbamic acid tert-butyl ester The title compound was prepared from [2-amino-5-(2-methoxy-ethoxy)-4-trifluoromethyl-phenyl]-carbamic acid tert-butyl ester (Example J32) (263 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as a light yellow solid (351 mg, 80%).

MS (ISN) 586 [(M−H)⁻].

Example M223

[2-{3-[3-(2,6-Dimethyl-pyridin-4-yl)-phenyl]-3-oxo-propionylamino}-5-(2-methoxy-ethoxy)-4-trifluoromethyl-phenyl]-carbamic acid tert-butyl ester The title compound was prepared from [2-amino-5-(2-methoxy-ethoxy)-4-trifluoromethyl-phenyl]-carbamic acid tert-butyl ester (Example J32) (263 mg, 0.75 mmol) and 3-[3-(2,6-dimethyl-pyridin-4-yl)-phenyl]-3-oxo-propionic acid tert-butyl ester (Example K15) (244 mg, 0.75 mmol) according to the general procedure M. Obtained as a light yellow solid (337 mg, 75%).

MS (ISN) 600 [(M−H)⁻].

Example M224

(2-{3-[3-(2-Methyl-pyridin-4-yl)-phenyl]-3-oxo-propionylamino}-4-trifluoromethyl-5-vinyl-phenyl)-carbamic acid tert-butyl ester The title compound was prepared from (2-amino-4-trifluoromethyl-5-vinyl-phenyl)-carbamic acid tert-butyl ester (Example J34) (227 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as a light yellow solid (313 mg, 77%).

MS (ISN) 538 [(M−H)⁻].

Example M225

(2-{3-[3-(4,6-Dimethyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(4,6-dimethyl-pyridin-3-yl)-phenyl]-3-oxo-propionic acid tert-butyl ester (Example K32) (244 mg, 0.75 mmol) according to the general procedure M. Obtained as a light yellow foam (322 mg, 79%).

MS (ISN) 540.3 [(M−H)⁻].

Example M226

(2-{3-[3-(6-Cyclopropyl-4-methyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(6-cyclopropyl-4-methyl-pyridin-3-yl)-phenyl]-3-oxo-propionic acid tert-butyl ester (Example K33) (264 mg, 0.75 mmol) according to the general procedure M. Obtained as an amorphous light yellow substance (318 mg, 75%).

MS (ISN) 566 [(M−H)⁻].

Example M227

(2-{3-[3-(6-Cyclopropyl-4-methyl-pyridin-3-yl)-phenyl]-3-oxo-propionylamino}-5-ethoxy-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(6-cyclopropyl-4-methyl-pyridin-3-yl)-phenyl]-3-oxo-propionic acid tert-butyl ester (Example K33) (264 mg, 0.75 mmol) according to the general procedure M. Obtained as an amorphous light yellow substance (345 mg, 77%).

MS (ISN) 596 [(M−H)⁻].

Example M228

[2-{3-[3-(6-Cyclopropyl-4-methyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(6-cyclopropyl-4-methyl-pyridin-3-yl)-phenyl]-3-oxo-propionic acid tert-butyl ester (Example K33) (264 mg, 0.75 mmol) according to the general procedure M. Obtained as an amorphous light yellow substance (353 mg, 72%).

MS (ISN) 650 [(M−H)⁻].

Example M229

(2-{3-[3-(2-Ethyl-6-methyl-pyridin-4-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-ethyl-6-methyl-pyridin-4-yl)-phenyl]-3-oxo-propionic acid tert-butyl ester (Example K34) (255 mg, 0.75 mmol) according to the general procedure M. Obtained as an amorphous light yellow substance (332 mg, 80%).

MS (ISN) 554 [(M−H)⁻].

Example M230

(5-Ethoxy-2-{3-[3-(2-ethyl-6-methyl-pyridin-4-yl)-phenyl]-3-oxo-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(2-ethyl-6-methyl-pyridin-4-yl)-phenyl]-3-oxo-propionic acid tert-butyl ester (Example K34) (255 mg, 0.75 mmol) according to the general procedure M. Obtained as an amorphous light yellow substance (336 mg, 77%).

MS (ISN) 584 [(M−H)⁻].

Example M231

[2-{3-[3-(2-Ethyl-6-methyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-ethyl-6-methyl-pyridin-4-yl)-phenyl]-3-oxo-propionic acid tert-butyl ester (Example K34) (255 mg, 0.75 mmol) according to the general procedure M. Obtained as an amorphous light yellow substance (421 mg, 88%).

MS (ISN) 638 [(M−H)⁻].

Example M232

(2-{3-[3-(4,6-Dimethyl-pyridin-3-yl)-phenyl]-3-oxo-propionylamino}-5-ethoxy-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(4,6-dimethyl-pyridin-3-yl)-phenyl]-3-oxo-propionic acid tert-butyl ester (Example K32) (244 mg, 0.75 mmol) according to the general procedure M. Obtained as a light yellow foam (350 mg, 82%).

MS (ISN) 570.3 [(M−H)⁻].

Example M233

[2-{3-[3-(4,6-Dimethyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(4,6-dimethyl-pyridin-3-yl)-phenyl]-3-oxo-propionic acid tert-butyl ester (Example K32) (244 mg, 0.75 mmol) according to the general procedure M. Obtained as a light brown foam (388 mg, 83%).

MS (ISN) 624.2 [(M−H)⁻].

Example M234

(2-{3-[3-(6-Ethyl-4-methyl-pyridin-3-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(6-ethyl-4-methyl-pyridin-3-yl)-phenyl]-3-oxo-propionic acid tert-butyl ester (Example K35) (255 mg, 0.75 mmol) according to the general procedure M. Obtained as an amorphous red substance (184 mg, 44%).

MS (ISN) 554 [(M−H)⁻].

Example M235

(5-Ethoxy-2-{3-[3-(6-ethyl-4-methyl-pyridin-3-yl)-phenyl]-3-oxo-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(6-ethyl-4-methyl-pyridin-3-yl)-phenyl]-3-oxo-propionic acid tert-butyl ester (Example K35) (255 mg, 0.75 mmol) according to the general procedure M. Obtained as an amorphous red substance (184 mg, 42%).

MS (ISN) 584 [(M−H)⁻].

Example M236

[2-{3-[3-(6-Ethyl-4-methyl-pyridin-3-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(6-ethyl-4-methyl-pyridin-3-yl)-phenyl]-3-oxo-propionic acid tert-butyl ester (Example K35) (255 mg, 0.75 mmol) according to the general procedure M. Obtained as an amorphous red substance (229 mg, 48%).

MS (ISN) 638 [(M−H)⁻].

Example M237

(2-{3-[3-(2-Cyclopropyl-6-methyl-pyridin-4-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-cyclopropyl-6-methyl-pyridin-4-yl)-phenyl]-3-oxo-propionic acid tert-butyl ester (Example K36) (264 mg, 0.75 mmol) according to the general procedure M. Obtained as an amorphous yellow substance (309 mg, 73%).

MS (ISP) 568 [(M+H)+].

Example M238

(2-{3-[3-(2-Cyclopropyl-6-methyl-pyridin-4-yl)-phenyl]-3-oxo-propionylamino}-5-ethoxy-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(2-cyclopropyl-6-methyl-pyridin-4-yl)-phenyl]-3-oxo-propionic acid tert-butyl ester (Example K36) (264 mg, 0.75 mmol) according to the general procedure M. Obtained as an amorphous yellow substance (282 mg, 63%).

MS (ISP) 598 [(M+H)+].

Example M239

[2-{3-[3-(2-Cyclopropyl-6-methyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-cyclopropyl-6-methyl-pyridin-4-yl)-phenyl]-3-oxo-propionic acid tert-butyl ester (Example K36) (264 mg, 0.75 mmol) according to the general procedure M. Obtained as an amorphous yellow substance (347 mg, 71%).

MS (ISP) 650 [(M+H)+].

Example M240

(5-Methyl-2-{3-[3-(2-methyl-pyridin-3-yl)-phenyl]-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (357 mg, 1.23 mmol) and 3-[3-(2-methyl-pyridin-3-yl)-phenyl]-3-oxo-propionic acid tert-butyl ester (Example K5) (383 mg, 1.23 mmol) according to the general procedure M. Obtained as a light yellow foam (426 mg, 66%).

MS (ISN) 526.1 [(M−H)−].

Example M241

[2-{3-[3-(2-Methyl-pyridin-4-yl)-phenyl]-3-oxo-propionylamino}-5-(tetrahydro-pyran-2-yloxymethyl)-4-trifluoromethyl-phenyl]-carbamic acid tert-butyl ester The title compound was prepared from [2-amino-5-(tetrahydro-pyran-2-yloxymethyl)-4-trifluoromethyl-phenyl]-carbamic acid tert-butyl ester (Example J38) (293 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as an amorphous yellow substance (168 mg, 36%).

MS (ISN) 626 [(M−H)−].

Example M242

(2-{3-[3-(2-Isobutyl-pyridin-4-yl)-phenyl]-5-methyl-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (203 mg, 0.70 mmol) and 3-[3-(2-isobutyl-pyridin-4-yl)-phenyl]-3-oxo-propionic acid tert-butyl ester (Example K37) (247 mg, 0.70 mmol) according to the general procedure M. Obtained as an off-white solid (290 mg, 73%).

MS (ISP) 568.3 [(M−H)−]; mp 129° C.

Example M243

[2-{3-[3-(2-Isobutyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (262 mg, 0.70 mmol) and 3-[3-(2-isobutyl-pyridin-4-yl)-phenyl]-3-oxo-propionic acid tert-butyl ester (Example K37) (247 mg, 0.70 mmol) according to the general procedure M. Obtained as a light brown oil (320 mg, 70%).

MS (ISP) 652.2 [(M−H)−].

Example M244

(4-Chloro-5-methyl-2-{3-oxo-3-[3-(2-trifluoromethyl-pyridin-4-yl)-phenyl]-

The title compound was prepared from (2-amino-4-chloro-5-methyl-phenyl)-carbamic acid tert-butyl ester (Example J22) (180 mg, 0.70 mmol) and 3-oxo-3-[3-(2-trifluoromethyl-pyridin-4-yl)-phenyl]-propionic acid tert-butyl ester (Example K38) (256 mg, 0.70 mmol) according to the general procedure M. Obtained as an off-white solid (270 mg, 70%).

MS (ISP) 546.2 [(M−H)−]; mp 188° C.

Example M245

(5-Methyl-2-{3-oxo-3-[3-(2-trifluoromethyl-pyridin-4-yl)-phenyl]-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (203 mg, 0.70 mmol) and 3-oxo-3-[3-(2-trifluoromethyl-pyridin-4-yl)-phenyl]-propionic acid tert-butyl ester (Example K38) (256 mg, 0.70 mmol) according to the general procedure M. Obtained as an off-white solid (290 mg, 71%).

MS (ISP) 580.2 [(M−H)−]; mp 117° C.

Example M246

(5-Chloro-2-{3-oxo-3-[3-(2-trifluoromethyl-pyridin-4-yl)-phenyl]-propionylamino}-4-trifluoromethyl-phenyl)-carbamic acid tert-butyl ester The title compound was prepared from (2-amino-5-chloro-4-trifluoromethyl-phenyl)-carbamic acid tert-butyl ester (Example J19) (218 mg, 0.70 mmol) and 3-oxo-3-[3-(2-trifluoromethyl-pyridin-4-yl)-phenyl]-propionic acid tert-butyl ester (Example K38) (256 mg, 0.70 mmol) according to the general procedure M. Obtained as a light brown solid (260 mg, 62%).

MS (ISP) 600.1 [(M–H)⁻]; mp 132° C.

Example M247

[2-{3-Oxo-3-[3-(2-trifluoromethyl-pyridin-4-yl)-phenyl]-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (262 mg, 0.70 mmol) and 3-oxo-3-[3-(2-trifluoromethyl-pyridin-4-yl)-phenyl]-propionic acid tert-butyl ester (Example K38) (256 mg, 0.70 mmol) according to the general procedure M. Obtained as a light brown foam (440 mg, 94%).

MS (ISP) 624.2 [(M–H)⁻].

Example M248

(5-Ethoxy-2-{3-oxo-3-[3-(2-trifluoromethyl-pyridin-4-yl)-phenyl]-propionylamino}-4-trifluoromethyl-phenyl)-carbamic acid tert-butyl ester The title compound was prepared from [2-amino-5-ethoxy-4-trifluoromethyl-phenyl]-carbamic acid tert-butyl ester (Example J6) (224 mg, 0.70 mmol) and 3-oxo-3-[3-(2-trifluoromethyl-pyridin-4-yl)-phenyl]-propionic acid tert-butyl ester (Example K38) (256 mg, 0.70 mmol) according to the general procedure M. Obtained as an off-white solid (320 mg, 75%).

MS (ISP) 610.1 [(M–H)⁻]; mp 140° C.

Example M249

(4-Chloro-2-{3-[3-(2-isopropyl-pyridin-4-yl)-phenyl]-5-methyl-3-oxo-propionylamino}-phenyl)-carbamic acid tert-butyl ester The title compound was prepared from (2-amino-4-chloro-5-methyl-phenyl)-carbamic acid tert-butyl ester (Example J22) (193 mg, 0.75 mmol) and 3-[3-(2-isopropyl-pyridin-4-yl)-phenyl]-3-oxo-propionic acid tert-butyl ester (Example K39) (255 mg, 0.75 mmol) according to the general procedure M. Obtained as an off-white solid (340 mg, 87%).

MS (ISP) 520.2 [(M–H)⁻]; mp 168° C.

Example M250

(2-{3-[3-(2-Isopropyl-pyridin-4-yl)-phenyl]-5-methyl-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-isopropyl-pyridin-4-yl)-phenyl]-3-oxo-propionic acid tert-butyl ester (Example K39) (255 mg, 0.75 mmol) according to the general procedure M. Obtained as an off-white solid (230 mg, 55%).

MS (ISP) 554.2 [(M–H)⁻]; mp 150° C.

Example M251

(2-{3-[3-(2-Isopropyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2-isopropyl-pyridin-4-yl)-phenyl]-3-oxo-propionic acid tert-butyl ester (Example K39) (255 mg, 0.75 mmol) according to the general procedure M. Obtained as an off-white solid (250 mg, 62%).

MS (ISP) 540.3 [(M–H)⁻]; mp 127° C.

Example M252

(5-Chloro-2-{3-[3-(2-isopropyl-pyridin-4-yl)-phenyl]-3-oxo-propionylamino}-4-trifluoromethyl-phenyl)-carbamic acid tert-butyl ester The title compound was prepared from (2-amino-5-chloro-4-trifluoromethyl-phenyl)-carbamic acid tert-butyl ester (Example J19) (233 mg, 0.75 mmol) and 3-[3-(2-isopropyl-pyridin-4-yl)-phenyl]-3-oxo-propionic acid tert-butyl ester (Example K39) (255 mg, 0.75 mmol) according to the general procedure M. Obtained as an off-white solid (240 mg, 56%).

MS (ISP) 574.2 [(M–H)⁻]; mp 144° C.

Example M253

[2-{3-[3-(2-Isopropyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-isopropyl-pyridin-4-yl)-phenyl]-3-oxo-propionic acid tert-butyl ester (Example K39) (255 mg, 0.75 mmol) according to the general procedure M. Obtained as a light brown solid (360 mg, 75%).

MS (ISP) 638.2 [(M–H)⁻]; mp 151° C.

Example M254

5-Ethoxy-[2-{3-[3-(2-isopropyl-pyridin-4-yl)-phenyl]-3-oxo-propionylamino}-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J6) (240 mg, 0.75 mmol) and 3-[3-(2-isopropyl-pyridin-4-yl)-phenyl]-3-oxo-propionic acid tert-butyl ester (Example K39) (255 mg, 0.75 mmol) according to the general procedure M. Obtained as an off-white solid (340 mg, 77%).

MS (ISP) 584.3 [(M–H)⁻]; mp 154° C.

Example M255

(5-Chloro-2-{3-[3-(2-isobutyl-pyridin-4-yl)-phenyl]-3-oxo-propionylamino}-4-trifluoromethyl-phenyl)-carbamic acid tert-butyl ester The title compound was prepared from (2-amino-5-chloro-4-trifluoromethyl-phenyl)-carbamic acid tert-butyl ester (Example J19) (218 mg, 0.70 mmol) and 3-[3-(2-isobutyl-pyridin-4-yl)-phenyl]-3-oxo-propionic acid tert-butyl ester (Example K37) (247 mg, 0.70 mmol) according to the general procedure M. Obtained as an off-white solid (320 mg, 77%).

MS (ISP) 588.3 [(M–H)⁻]; mp 125° C.

Example M256

(4-Chloro-2-{3-[3-(2-isobutyl-pyridin-4-yl)-phenyl]-5-methyl-3-oxo-propionylamino}-phenyl)-carbamic acid tert-butyl ester The title compound was prepared from (2-amino-4-chloro-5-methyl-phenyl)-carbamic acid tert-butyl ester (Example J22) (180 mg, 0.70 mmol) and 3-[3-(2-isobutyl-pyridin-4-yl)-phenyl]-3-oxo-propionic acid tert-butyl ester (Example K37) (247 mg, 0.70 mmol) according to the general procedure M. Obtained as an off-white solid (310 mg, 83%).

MS (ISP) 534.3 [(M–H)⁻]; mp 143° C.

Example M257

5-Ethoxy-[2-{3-[3-(2-isobutyl-pyridin-4-yl)-phenyl]-3-oxo-propionylamino}-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J6) (224 mg, 0.70 mmol) and 3-[3-(2-isobutyl-pyridin-4-yl)-phenyl]-3-oxo-propionic acid tert-butyl ester (Example K37) (247 mg, 0.70 mmol) according to the general procedure M. Obtained as an off-white solid (310 mg, 74%).

MS (ISP) 598.2 [(M–H)⁻]; mp 151° C.

Example M258

(2-{3-[3-(2-Isobutyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (193 mg, 0.70 mmol) and 3-[3-(2-isobutyl-pyridin-4-yl)-phenyl]-3-oxo-propionic acid tert-butyl ester (Example K37) (247 mg, 0.70 mmol) according to the general procedure M. Obtained as an off-white solid (260 mg, 67%).

MS (ISP) 554.3 [(M–H)⁻]; mp 110° C.

Example M259

(RS)-[4-Chloro-5-methyl-2-(3-oxo-3-{3-[2-(tetrahydro-pyran-2-yloxymethyl)-pyridin-4-yl]-phenyl}-propionylamino)-phenyl]-carbamic acid tert-butyl ester The title compound was prepared from (2-amino-4-chloro-5-methyl-phenyl)-carbamic acid tert-butyl ester (Example J22) (257 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M. Obtained as a light brown solid (510 mg, 86%).

MS (ISP) 592.3 [(M–H)⁻]; mp 64° C.

Example M260

(RS)-[5-Methyl-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester The title compound was prepared from (2-amino-5-methyl-4-trifluoromethyl-phenyl)-carbamic acid tert-butyl ester (Example J20) (4.40 g, 15.0 mmol) and (RS)-3-oxo-3-{3-[2-(tetrahydro-pyran-2-yloxymethyl)-pyridin-4-yl]-phenyl}-propionic acid tert-butyl ester (Example K40) (6.24 g, 15.0 mmol) according to the general procedure M. Obtained as a light yellow foam (6.20 g, 65%).

MS (ISP) 626.3 [(M–H)⁻].

Example M261

(RS)-[5-Chloro-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester The title compound was prepared from (2-amino-5-chloro-4-trifluoromethyl-phenyl)-carbamic acid tert-butyl ester (Example J19) (311 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M. Obtained as a light yellow solid (550 mg, 85%).

MS (ISP) 646.2 [(M–H)⁻]; mp 81° C.

Example M262

(RS)-[2-(3-Oxo-3-{3-[2-(tetrahydro-pyran-2-yloxymethyl)-pyridin-4-yl]-phenyl}-propionylamino)-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (374 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M. Obtained as a light brown solid (500 mg, 70%).

MS (ISP) 710.2 [(M–H)⁻]; mp 168° C.

Example M263

(RS)-[5-Ethoxy-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J6) (320 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M. Obtained as an off-white solid (500 mg, 76%).

MS (ISP) 656.3 [(M–H)⁻]; mp 127° C.

Example M264

(2-{3-[3-(6-Cyclopropyl-4-methyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(6-cyclopropyl-4-methyl-pyridin-3-yl)-phenyl]-3-oxo-propionic acid tert-butyl ester (Example K33) (264 mg, 0.75 mmol) according to the general procedure M. Obtained as an amorphous off-white substance (297 mg, 72%).

MS (ISN) 552 [(M–H)⁻].

Example M265

(2-{3-[3-(4,6-Dimethyl-pyridin-3-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(4,6-dimethyl-pyridin-3-yl)-phenyl]-3-oxo-propionic acid tert-butyl ester (Example K32) (244 mg, 0.75 mmol) according to the general procedure M. Obtained as a white foam (320 mg, 81%).

MS (ISN) 526.1 [(M–H)⁻].

Example M266

(2-{3-[3-(2-Cyclopropyl-pyridin-4-yl)-phenyl]-3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2-cyclopropyl-pyridin-4-yl)-phenyl]-3-oxo-propionic acid tert-butyl ester (Example K60) (253 mg, 0.75 mmol) according to the general procedure M. Obtained as an amorphous white substance (315 mg, 75%).

MS (ISN) 538 [(M−H)−].

Example M267

(2-{3-[3-(2-Cyclopropyl-pyridin-4-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-cyclopropyl-pyridin-4-yl)-phenyl]-3-oxo-propionic acid tert-butyl ester (Example K60) (253 mg, 0.75 mmol) according to the general procedure M. Obtained as an amorphous off-white substance (328 mg, 79%).

MS (ISN) 552 [(M−H)−].

Example M268

(2-{3-[3-(2-Cyclopropyl-pyridin-4-yl)-phenyl]-3-oxo-propionylamino}-5-ethoxy-4-trifluoromethyl-phenyl)-carbamic acid tert-butyl ester The title compound was prepared (2-amino-5-ethoxy-4-trifluoromethyl-phenyl)-carbamic acid tert-butyl ester (Example J8) (240 mg, 0.75 mmol) and 3-[3-(2-cyclopropyl-pyridin-4-yl)-phenyl]-3-oxo-propionic acid tert-butyl ester (Example K60) (253 mg, 0.75 mmol) according to the general procedure M. Obtained as an amorphous off-white substance (337 mg, 77%).

MS (ISN) 582 [(M−H)−].

Example M269

[2-{3-[3-(2-Cyclopropyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-cyclopropyl-pyridin-4-yl)-phenyl]-3-oxo-propionic acid tert-butyl ester (Example K60) (253 mg, 0.75 mmol) according to the general procedure M. Obtained as an amorphous off-white substance (391 mg, 82%).

MS (ISN) 636 [(M−H)−].

Example M270

(5-Cyclopropyl-2-{3-[3-(2-methyl-pyridin-4-yl)-phenyl]-3-oxo-propionylamino}-4-trifluoromethyl-phenyl)-carbamic acid tert-butyl ester The title compound was prepared (2-amino-5-cyclopropyl-4-trifluoromethyl-phenyl)-carbamic acid tert-butyl ester (Example J39) (289 mg, 0.914 mmol) and 3-[3-(2-methyl-pyridin-4-yl)-phenyl]-3-oxo-propionic acid tert-butyl ester (Example K12) (284 mg, 0.914 mmol) according to the general procedure M. Obtained as a yellow foam (368 mg, 73%).

MS (ISN) 552.2 [(M−H)−].

Example M271

(2-{3-[3-(2-Cyclopentyl-pyridin-4-yl)-phenyl]-3-oxo-propionylamino}-5-methyl-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-cyclopentyl-pyridin-4-yl)-phenyl]-3-oxo-propionic acid tert-butyl ester (Example K61) (274 mg, 0.75 mmol) according to the general procedure M. Obtained as a light yellow foam (369 mg, 86%).

MS (ISN) 580.4 [(M−H)−].

Example M272

(2-{3-[3-(2-Cyclopentyl-pyridin-4-yl)-phenyl]3-oxo-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (207 mg, 0.75 mmol) and 3-[3-(2-cyclopentyl-pyridin-4-yl)-phenyl]-3-oxo-propionic acid tert-butyl ester (Example K61) (274 mg, 0.75 mmol) according to the general procedure M. Obtained as a light yellow foam (320 mg, 75%).

MS (ISN) 566.4 [(M−H)−].

Example M273

(2-{3-[3-(2-Cyclopentyl-pyridin-4-yl)-phenyl]-3-oxo-propionylamino}-5-ethoxy-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(2-cyclopentyl-pyridin-4-yl)-phenyl]-3-oxo-propionic acid tert-butyl ester (Example K61) (274 mg, 0.75 mmol) according to the general procedure M. Obtained as a light yellow solid (366 mg, 80%).

MS (ISN) 610.4 [(M−H)−]; mp 154–156° C.

Example M274

[2-{3-[3-(2-Cyclopentyl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-cyclopentyl-pyridin-4-yl)-phenyl]-3-oxo-propionic acid tert-butyl ester (Example K61) (274 mg, 0.75 mmol) according to the general procedure M. Obtained as a light yellow foam (410 mg, 82%).

MS (ISN) 664.3 [(M−H)−].

Example M275

(5-(Isobutyl-methyl-amino)-2-{3-[3-(2-methyl-pyridin-4-yl)-phenyl]-3-oxo-propionylamino}-4-trifluoromethyl-phenyl)-carbamic acid tert-butyl ester The title compound was obtained from [2-amino-5-(isobutyl-methyl-amino)-4-trifluoromethyl-phenyl]- carbamic acid tert-butyl ester (Example J40) (361 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as a pink solid (450 mg, 75%).

MS (ISP) 599.4 [(M+H)$^+$]; mp 123° C.

Example M276

(5-(Isopropyl-methyl-amino)-2-{3-[3-(2-methyl-pyridin-4-yl)-phenyl]-3-oxo-propionylamino}-4-trifluoromethyl-phenyl)-carbamic acid tert-butyl ester The title compound was obtained from [2-amino-5-(isopropyl-methyl-amino)-4-trifluoromethyl-phenyl]-carbamic acid tert-butyl ester (Example J41) (347 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as a light brown solid (450 mg, 77%).

MS (ISP) 585.4 [(M+H)$^+$]; mp 146° C.

Example M277

(4-Chloro-5-(isobutyl-methyl-amino)-2-{3-[3-(2-methyl-pyridin-4-yl)-phenyl]-3-oxo-propionylamino}-phenyl)-carbamic acid tert-butyl ester The title compound was obtained from [2-amino-4-chloro-5-(isobutyl-methyl-amino)-1-phenyl]-carbamic acid tert-butyl ester (Example J42) (328 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as an off-white solid (410 mg, 73%).

MS (ISP) 563.4 [(M–H)$^-$]; mp 109° C.

Example M278

(2-{3-[3-(2-Methyl-pyridin-4-yl)-phenyl]-3-oxo-propionylamino}-5-pyrrolidin-1-yl-4-trifluoromethyl-phenyl)-carbamic acid tert-butyl ester The title compound was obtained from (2-amino-5-pyrrolidine-1-yl-4-trifluoromethyl-phenyl)-carbamic acid tert-butyl ester (Example J27) (345 mg, 1.0 mmol) and 3-[3-(2-methyl-pyridin-4-yl)-phenyl]-3-oxo-propionic acid tert-butyl ester (Example K12) (311 mg, 1.0 mmol) according to the general procedure M as a yellow solid (350 mg, 60%).

MS (ISP) 581.4 [(M–H)$^-$]; mp 114° C.

Example M279

(RS)-[5-(Isobutyl-methyl-amino)-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester The title compound was obtained from [2-amino-5-(isobutyl-methyl-amino)-4-trifluoromethyl-phenyl]-carbamic acid tert-butyl ester (Example J40) (4.39 g, 12.1 mmol) and (RS)-3-oxo-3-{3-[2-(tetrahydro-pyran-2-yloxymethyl)-pyridin-4-yl]-phenyl}-propionic acid tert-butyl ester (Example K40) (5.0 g, 12.1 mmol) according to the general procedure M as a light brown foam (5.83 g, 69%).

MS (ISP) 699.5 [(M+H)$^+$].

Example M280

(RS)-[4-Chloro-5-(isopropyl-methyl-amino)-2-(3-oxo-3-{3-[2-(tetrahydro-pyran-2-yloxymethyl)-pyridin-4-yl]-phenyl}-propionylamino)-phenyl]-carbamic acid tert-butyl ester The title compound was obtained from [2-amino-4-chloro-5-(isopropyl-methyl-amino)-1-phenyl]-carbamic acid tert-butyl ester (Example J43) (314 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M as a light brown foam (360 mg, 55%).

MS (ISP) 649.5 [(M–H)$^-$].

Example M281

(RS)-[4-Chloro-5-(isobutyl-methyl-amino)-2-(3-oxo-3-{3-[2-(tetrahydro-pyran-2-yloxymethyl)-pyridin-4-yl]-phenyl}-propionylamino)-phenyl]-carbamic acid tert-butyl ester The title compound was obtained from [2-amino-4-chloro-5-(isobutyl-methyl-amino)-1-phenyl]-carbamic acid tert-butyl ester (Example J42) (328 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M as a light brown foam (350 mg, 53%).

MS (ISP) 663.5 [(M–H)$^-$].

Example M282

(RS)-[5-(Methyl-propyl-amino)-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester The title compound was obtained from [2-amino-5-(methyl-propyl-amino)-4-trifluoromethyl-phenyl]-carbamic acid tert-butyl ester (Example J17) (347 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M as a light red foam (260 mg, 38%).

MS (ISP) 683.4 [(M–H)$^-$].

Example M283

(RS)-[5-(Isopropyl-methyl-amino)-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester The title compound was obtained from [2-amino-5-(isopropyl-methyl-amino)-4-trifluoromethyl-phenyl]-carbamic acid tert-butyl ester (Example J41) (347 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M as a light yellow foam (520 mg, 76%).

MS (ISP) 683.4 [(M–H)$^-$].

Example M284

(RS)-[5-(Dimethyl-amino)-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester The title compound was obtained from [2-amino-5-(dimethyl-amino)-4-trifluoromethyl-phenyl]-carbamic acid tert-butyl ester (Example J1) (319 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) according to the general procedure M as a light red foam (470 mg, 72%).

MS (ISP) 655.5 [(M−H)$^-$].

Example M285

(2-{3-[3-(2-Methyl-pyridin-4-yl)-phenyl]-3-oxo-propionylamino}-5-morpholin-4-yl-4-trifluoromethyl-phenyl)-carbamic acid tert-butyl ester The title compound was prepared from (2-amino-5-morpholin-4-yl-4-trifluoromethyl-phenyl)-carbamic acid tert-butyl ester (Example J28) (271 mg, 0.75 mmol) and 3-[3-(2-methyl-pyridin-4-yl)-phenyl]-3-oxo-propionic acid tert-butyl ester (Example K12) (234 mg, 0.75 mmol) according to the general procedure M. Obtained as a light yellow foam (355 mg, 79%).

MS (ISN) 597.2 [(M−H)$^-$].

Example M286

(2-{3-[3-(2,6-Dimethyl-pyridin-4-yl)-phenyl]-3-oxo-propionylamino}-5-morpholin-4-yl-4-trifluoromethyl-phenyl)-carbamic acid tert-butyl ester The title compound was prepared from (2-amino-5-morpholin-4-yl-4-trifluoromethyl-phenyl)-carbamic acid tert-butyl ester (Example J28) (271 mg, 0.75 mmol) and 3-[3-(2,6-dimethyl-pyridin-4-yl)-phenyl]-3-oxo-propionic acid tert-butyl ester (Example K15) (244 mg, 0.75 mmol) according to the general procedure M.

Obtained as a light yellow foam (387 mg, 84%).

MS (ISN) 611.2 [(M−H)$^-$].

Example M287

(5-Ethoxy-2-{3-[3-(2-morpholin-4-yl-pyridin-4-yl)-phenyl]-3-oxo-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[3-(2-morpholin-4-yl-pyridin-4-yl)-phenyl]-3-oxo-propionic acid tert-butyl ester (Example K62) (286 mg, 0.75 mmol) according to the general procedure M. Obtained as a white solid (259 mg, 55%).

MS (ISN) 627.2 [(M−H)$^-$].

Example M288

[2-{3-[3-(2-Morpholin-4-yl-pyridin-4-yl)-phenyl]-3-oxo-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[3-(2-morpholin-4-yl-pyridin-4-yl)-phenyl]-3-oxo-propionic acid tert-butyl ester (Example K62) (286 mg, 0.75 mmol) according to the general procedure M. Obtained as a light brown foam (433 mg, 85%).

MS (ISN) 681.3 [(M−H)$^-$].

Example M289

(5-Methyl-2-{3-[3-(2-morpholin-4-yl-pyridin-4-yl)-phenyl]-3-oxo-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-[3-(2-morpholin-4-yl-pyridin-4-yl)-phenyl]-3-oxo-propionic acid tert-butyl ester (Example K62) (286 mg, 0.75 mmol) according to the general procedure M. Obtained as a light yellow foam (393 mg, 88%).

MS (ISN) 597.4 [(M−H)$^-$].

Example M290

(2-{3-Oxo-3-[3-(2-pyrrolidin-1-yl-pyridin-4-yl)-phenyl]-propionylamino}-4-trifluoromethyl-phenyl)-carbamic acid tert-butyl ester The title compound was prepared from (2-amino-4-trifluoromethyl-phenyl)-carbamic acid tert-butyl ester (Example J3) (214 mg, 0.75 mmol) and 3-oxo-3-[3-(2-pyrrolidin-1-yl-pyridin-4-yl)-phenyl]-propionic acid tert-butyl ester (Example K63) (275 mg, 0.75 mmol) according to the general procedure M. Obtained as an off-white amorphous substance (334 mg, 78%).

MS (ISN) 567 [(M−H)$^-$].

Example M291

(5-Methyl-2-{3-oxo-3-[3-(2-pyrrolidin-1-yl-pyridin-4-yl)-phenyl]-propionylamino}-4-trifluoromethyl-phenyl)-carbamic acid tert-butyl ester The title compound was prepared from (2-amino-5-methyl-4-trifluoromethyl-phenyl)-carbamic acid tert-butyl ester (Example J20) (218 mg, 0.75 mmol) and 3-oxo-3-[3-(2-pyrrolidin-1-yl-pyridin-4-yl)-phenyl]-propionic acid tert-butyl ester (Example K63) (275 mg, 0.75 mmol) according to the general procedure M. Obtained as an off-white amorphous substance (348 mg, 80%).

MS (ISN) 581 [(M−H)$^-$].

Example M292

(5-Ethoxy-2-{3-oxo-3-[3-(2-pyrrolidin-1-yl-pyridin-4-yl)-phenyl]-propionylamino}-4-trifluoromethyl-phenyl)-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-oxo-3-[3-(2-pyrrolidin-1-yl-pyridin-4-yl)-phenyl]-propionic acid tert-butyl ester (Example K63) (275 mg, 0.75 mmol) according to the general procedure M. Obtained as a light yellow amorphous substance (379 mg, 82%).

MS (ISN) 611 [(M−H)$^-$].

Example M293

[2-{3-Oxo-3-[3-(2-pyrrolidin-1-yl-pyridin-4-yl)-phenyl]-propionylamino}-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-oxo-3-[3-(2-pyrrolidin-1-yl-pyridin-4-yl)-phenyl]-propionic acid tert-butyl ester (Example K63) (275 mg, 0.75 mmol) according to the general procedure M. Obtained as a light yellow amorphous substance (419 mg, 84%).

MS (ISN) 665 [(M−H)⁻].

Example M294

[2-(3-[2,3']Bipyridinyl-4-yl-3-oxo-propionylamino)-4-trifluoromethyl-phenyl]-carbamic acid tert-butyl ester The title compound was prepared from (2-amino-4-trifluoromethyl-phenyl)-carbamic acid tert-butyl ester (Example J3) (214 mg, 0.75 mmol) and 3-[2,3']bipyridinyl-4-yl-3-oxo-propionic acid tert-butyl ester (Example K57) (224 mg, 0.75 mmol) according to the general procedure M. Obtained as a yellow foam (268 mg, 71%).

MS (ISN) 499 [(M−H)⁻].

Example M295

[2-(3-[2,3']Bipyridinyl-4-yl-3-oxo-propionylamino)-5-ethoxy-4-trifluoromethyl-phenyl]-carbamic acid tert-butyl ester The title compound was prepared from (2-amino-5-ethoxy-4-trifluoromethyl-phenyl)-carbamic acid tert-butyl ester (Example J8) (240 mg, 0.75 mmol) and 3-[2,3']bipyridinyl-4-yl-3-oxo-propionic acid tert-butyl ester (Example K57) (224 mg, 0.75 mmol) according to the general procedure M. Obtained as a yellow foam (319 mg, 78%).

MS (ISN) 543 [(M−H)⁻].

Example M296

[2-(3-[2,3']Bipyidinyl-4-yl-3-oxo-propionylamino)-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (281 mg, 0.75 mmol) and 3-[2,3']bipyridinyl-4-yl-3-oxo-propionic acid tert-butyl ester (Example K57) (224 mg, 0.75 mmol) according to the general procedure M. Obtained as a yellow foam (342 mg, 76%).

MS (ISN) 597 [(M−H)⁻].

Example M297

(RS)-[4-Chloro-5-methyl-2-(3-{3-[2-methyl-6-(tetrahydro-pyran-2-yloxymethyl)-pyridin-4-yl]-phenyl}-3-oxo-propionylamino)-phenyl]-carbamic acid tert-butyl ester The title compound was prepared from (2-amino-4-chloro-5-methyl-phenyl)-carbamic acid tert-butyl ester (Example J22) (257 mg, 1.0 mmol) and (RS)-3-{3-[2-methyl-6-(tetrahydro-pyran-2-yloxymethyl)-pyridin-4-yl]-phenyl}-3-oxo-propionic acid tert-butyl ester (Example K64) (426 mg, 1.0 mmol) according to the general procedure M. Obtained as a light yellow foam (460 mg, 76%).

MS (ISP) 608.3 [(M+H)⁺].

Example M298

(RS)-[5-Methyl-2-(3-{3-[2-methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester The title compound was prepared from (2-amino-5-methyl-4-trifluoromethyl-phenyl)-carbamic acid tert-butyl ester (Example J20) (290 mg, 1.0 mmol) and (RS)-3-{3-[2-methyl-6-(tetrahydro-pyran-2-yloxymethyl)-pyridin-4-yl]-phenyl}-3-oxo-propionic acid tert-butyl ester (Example K64) (426 mg, 1.0 mmol) according to the general procedure M. Obtained as a light yellow foam (510 mg, 79%).

MS (ISP) 642.4 [(M+H)⁺].

Example M299

(RS)-[5-Chloro-2-(3-{3-[2-methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester The title compound was prepared from (2-amino-5-chloro-4-trifluoromethyl-phenyl)-carbamic acid tert-butyl ester (Example J19) (311 mg, 1.0 mmol) and (RS)-3-}3-[2-methyl-6-(tetrahydro-pyran-2-yloxymethyl)-pyridin-4-yl]-phenyl}-3-oxo-propionic acid tert-butyl ester (Example K64) (426 mg, 1.0 mmol) according to the general procedure M. Obtained as a light yellow foam (420 mg, 63%).

MS (ISP) 662.3 [(M+H)⁺].

Example M300

(RS)-[2-(3-{3-[2-Methyl-6-(tetrahydro-pyran-2-yloxymethyl)-pyridin-4-yl]-phenyl}-3-oxo-propionylamino)-5-(2,2,2-trifluoro-ethoxy)-4-trifluoromethyl-phenyl]-carbamic acid tert-butyl ester The title compound was prepared from [2-amino-5-(2,2,2-trifluoro-ethoxy)-4-trifluoromethyl-phenyl]-carbamic acid tert-butyl ester (Example J6) (374 mg, 1.0 mmol) and (RS)-3-{3-[2-methyl-6-(tetrahydro-pyran-2-yloxymethyl)-pyridin-4-yl]-phenyl}-3-oxo-propionic acid tert-butyl ester (Example K64) (426 mg, 1.0 mmol) according to the general procedure M. Obtained as a light yellow foam (500 mg, 69%).

MS (ISP) 726.4 [(M+H)⁺].

Example M301

(RS)-[5-Ethoxy-2-(3-{3-[2-methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester The title compound was prepared from [2-amino-5-ethoxy-4-trifluoromethyl-phenyl]-carbamic acid tert-butyl ester (Example J6) (320 mg, 1.0 mmol) and (RS)-3-{3-[2-methyl-6-(tetrahydro-pyran-2-yloxymethyl)-pyridin-4-yl]-phenyl}-3-oxo-propionic acid tert-butyl ester (Example K64) (426 mg, 1.0 mmol) according to the general procedure M. Obtained as a light yellow foam (550 mg, 82%).

MS (ISP) 672.4 [(M+H)⁺].

Example M302

(RS)-[2-(3-{3-[2-Methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester The title compound was prepared from (2-amino-4-trifluoromethyl-phenyl)-carbamic acid tert-butyl ester (Example J3) (276 mg, 1.0 mmol) and (RS)-3-{3-[2-methyl-6-(tetrahydro-pyran-2-yloxymethyl)-pyridin-4-yl]-phenyl}-3-oxo-propionic acid tert-butyl ester (Example K64) (426 mg, 1.0 mmol) according to the general procedure M. Obtained as a light yellow foam (470 mg, 75%).

MS (ISP) 628.4 [(M+H)+].

Example M303

[2-{3-[3-(2,6-Dimethyl-pyridin-4-yl)-phenyl]-3-oxo-propionylamino}-5-(isobutyl-methyl-amino)-4-trifluoromethyl-phenyl]-carbamic acid tert-butyl ester The title compound was obtained from [2-amino-5-(isobutyl-methyl-amino)-4-trifluoromethyl-phenyl]-carbamic acid tert-butyl ester (Example J40) (361 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M as an off-white solid (380 mg, 62%).

MS (ISP) 611.4 [(M−H)−]; mp 175° C.

Example M304

(5-Dimethylamino-2-{3-[3-(2,6-dimethyl-pyridin-4-yl)-phenyl]-3-oxo-propionylamino}-4-trifluoromethyl-phenyl)-carbamic acid tert-butyl ester The title compound was obtained from [2-amino-5-dimethylamino-4-trifluoromethyl-phenyl]-carbamic acid tert-butyl ester (Example J1) (319 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M as a light brown solid (390 mg, 68%).

MS (ISP) 569.4 [(M−H)−]; mp 145° C.

Example M305

[4-Chloro-2-{3-[3-(2,6-dimethyl-pyridin-4-yl)-phenyl]-3-oxo-propionylamino}-5-(isobutyl-methyl-amino)-phenyl]-carbamic acid tert-butyl ester The title compound was obtained from (2-amino-4-chloro-5-(isobutyl-methyl-amino)-1-phenyl)-carbamic acid tert-butyl ester (Example J42) (328 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M as a light yellow solid (440 mg, 76%).

MS (ISP) 579.6 [(M+H)+]; mp 95° C.

Example M306

(2-{3-[3-(2,6-Dimethyl-pyridin-4-yl)-phenyl]-3-oxo-propionylamino}-5-pyrrolidin-1-yl-4-trifluoromethyl-phenyl)-carbamic acid tert-butyl ester RO4598802-000

The title compound was obtained from (2-amino-5-pyrrolidine-1-yl-4-trifluoromethyl-phenyl)-carbamic acid tert-butyl ester (Example J27) (345 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M as a yellow solid (470 mg, 79%).

MS (ISP) 597.4 [(M+H)+]; mp 161° C.

Example M307

[2-{3-[3-(2,6-Dimethyl-pyridin-4-yl)-phenyl]-3-oxo-propionylamino}-5-(isopropyl-methyl-amino)-4-trifluoromethyl-phenyl]-carbamic acid tert-butl ester The title compound was obtained from [2-amino-5-(isopropyl-methyl-amino)-4-trifluoromethyl-phenyl]-carbamic acid tert-butyl ester (Example J41) (347 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M as a light brown solid (440 mg, 73%).

MS (ISP) 599.4 [(M+H)+]; mp 187° C.

Example M308

[2-{3-[3-(2,6-Dimethyl-pyridin-4-yl)-phenyl]-3-oxo-propionylamino}-5-(methyl-propyl-amino)-4-trifluoromethyl-phenyl]-carbamic acid tert-butyl ester The title compound was obtained from [2-amino-5-(methyl-propyl-amino)-4-trifluoromethyl-phenyl]-carbamic acid tert-butyl ester (Example J17) (347 mg, 1.0 mmol) and 3-[3-(2,6-dimethyl-pyridin-4-yl)-phenyl]-3-oxo-propionic acid tert-butyl ester (Example K15) (325 mg, 1.0 mmol) according to the general procedure M as a light brown solid (420 mg, 70%).

MS (ISP) 599.4 [(M+H)+]; mp 123° C.

General Procedure N

Preparation of 4-aryl-1,3-dihydro-benzo[b][1,4]diazepin-2-ones

A solution or suspension of the {2-[3-aryl-3-oxo-propionylamino]-phenyl}-carbamic acid tert-butyl ester (1.0 mmol) in $CH_2Cl_2$ (5 mL) [anisole or 1,3-dimethoxybenzene (5–15 mmol) can be added if necessary]was treated with TFA (0.5–5.0 mL) at 0° C. and stirring was continued at 23° C. until tlc indicated complete consumption of the starting material.

Workup procedure a: The solvent was removed in vacuum, the residue treated with little ether, whereupon it crystallized. The solid was stirred with sat. $NaHCO_3$-solution or 1M $Na_2CO_3$-solution, filtered, washed with $H_2O$ and ether or mixtures of ether/THF/MeOH and was dried to give the title compound, which if necessary can be purified by crystallization from 1,4-dioxane or by silica gel column chromatography with cyclohexane/EtOAc or EtOAc/EtOH.

Workup procedure b: The reaction mixture was diluted with DCM or EtOAc, washed with sat. $NaHCO_3$-solution or 1M $Na_2CO_3$-solution, brine and dried over $MgSO_4$ or $Na_2SO_4$. Removal of the solvent in vacuum left a material, which could be triturated with ether or mixtures of ether/THF/MeOH to give the title compound, or which if necessary can be purified by crystallization from 1,4-dioxane or by silica gel column chromatography with cyclohexane/EtOAc or EtOAc/EtOH.

Example 1

7,8-Dichloro-4-(3-pyridin-3-yl-phenyl)-1,3-dihydro-benzo[b][1,4]diazepin-2-one

The title compound was prepared from 4,5-dichlorophenylenediamine (172 mg, 0.97 mmol) and 3-oxo-3-(3-pyridin-3-yl-phenyl)-propionic acid tert-butyl ester (Example K1) (289 mg, 0.97 mmol) by refluxing in xylene according to the general procedure M. Obtained as an off-white solid (310 mg).

MS (ISP) 382.2 [(M+H)+], 384 [(M+2+H)+] and 386 [(M+4+H)+]; mp 241° C.

Example 2

7,8-Dichloro-4-(3-pyridin-4-yl-phenyl)-1,3-dihydro-benzo[b][1,4]diazepin-2-one

The title compound was prepared from 4,5-dichlorophenylenediamine (177 mg, 1.0 mmol) and 3-oxo- 3-(3-pyridin-4-yl-phenyl)-propionic acid tert-butyl ester (Example K2) (297 mg, 1.0 mmol) by refluxing in xylene according to the general procedure M. Obtained as a brown solid (269 mg).

MS (ISP) 382.2 [(M+H)$^+$], 384 [(M+2+H)$^+$] and 386 [(M+4+H)$^+$]; mp 240° C.

Example 3

7-Dimethylamino-4-(3-pyridin-3-yl-phenyl)-8-trifluoromethyl-1,3-dihydro-benzo[b][1,4]diazepin-2-one The title compound was prepared from {5-dimethylamino-2-[3-oxo-3-(3-pyridin-3-yl-phenyl)-propionylamino]-4-trifluoromethyl-phenyl}-carbamic acid tert-butyl ester (Example M1) (306 mg, 0.56 mmol) by treatment with TFA in CH$_2$Cl$_2$ according to the general procedure N. Obtained as a yellow solid (162 mg).

MS (ISP) 425.4 [(M+H)$^+$]; mp 204° C.

Example 4

7-Dimethylamino-4-(3-pyridin-4-yl-phenyl)-8-trifluoromethyl-1,3-dihydro-benzo[b][1,4]diazepin-2-one Prepared from {5-dimethylamino-2-[3-oxo-3-(3-pyridin-4-yl-phenyl)-propionylamino]-4-trifluoromethyl-phenyl}-carbamic acid tert-butyl ester (Example M2) (284 mg, 0.52 mmol) by treatment with TFA in CH$_2$Cl$_2$ according to the general procedure N. Obtained as a yellow solid (158 mg).

MS (ISP) 425.4 [(M+H)$^+$]; mp 202° C.

Example 5

7,8-Dichloro-4-(3-pyridin-2-yl-phenyl)-1,3-dihydro-benzo[b][1,4]diazepin-2-one

The title compound was obtained from 4,5-dichlorophenylenediamine (177 mg, 1.0 mmol) and 3-oxo-3-(3-pyridin-2-yl-phenyl)-propionic acid tert-butyl ester (Example K3) (297 mg, 1.0 mmol) by refluxing in xylene according to the general procedure M as a pink solid (260 mg).

MS (ISP) 382.3 [(M+H)$^+$], 384 [(M+2+H)$^+$] and 386 [(M+4+H)$^+$]; mp 239° C.

Example 6

7-Dimethylamino-4-(3-pyridin-2-yl-phenyl)-8-trifluoromethyl-1,3-dihydro-benzo[b][1,4]diazepin-2-one The title compound was prepared from {5-dimethylamino-2-[3-oxo-3-(3-pyridin-2-yl-phenyl)-propionylamino]-4-trifluoromethyl-phenyl}-carbamic acid tert-butyl ester (Example M3) (253 mg, 0.466 mmol) by treatment with TFA in CH$_2$Cl$_2$ according to the general procedure N. Obtained as a light yellow solid (66 mg).

MS (ISP) 425.5 [(M+H)$^+$]; mp 201° C.

Example 7

8-Fluoro-4-(3-pyridin-3-yl-phenyl)-1,3-dihydro-benzo[b][1,4]diazepin-2-one

The title compound was prepared from {4-fluoro-2-[3-oxo-3-(3-pyridin-3-yl-phenyl)-propionylamino]-phenyl}-carbamic acid tert-butyl ester (Example M4) (94 mg, 0.21 mmol) by treatment with TFA in CH$_2$Cl$_2$ according to the general procedure N. Obtained as a light yellow solid (55 mg).

MS (ISP) 332 [(M+H)$^+$]; mp 210° C.

Example 8

8-Fluoro-4-(3-pyridin-4-yl-phenyl)-1,3-dihydro-benzo[b][1,4]diazepin-2-one

The title compound was prepared from {4-fluoro-2-[3-oxo-3-(3-pyridin-4-yl-phenyl)-propionylamino]-phenyl}-carbamic acid tert-butyl ester (Example M5) (245 mg, 0.75 mmol) by treatment with TFA in CH$_2$Cl$_2$ according to the general procedure N. Obtained as a light brown solid (145 mg).

MS (ISP) 332.2 [(M+H)$^+$]; mp 190–192° C.

Example 9

4-[3-(6-Methyl-pyridin-3-yl)-phenyl]-8-trifluoromethyl-1,3-dihydro-benzo[b][1,4]diazepin-2-one The title compound was prepared from (2-{3-[3-(6-methyl-pyridin-3-yl)-phenyl]-3-oxo-propionylamino}-4-trifluoromethyl-phenyl)-carbamic acid tert-butyl ester (Example M6) (390 mg, 0.75 mmol) by treatment with TFA in CH$_2$Cl$_2$ according to the general procedure N. Obtained as a light yellow solid (168 mg).

MS (ISP) 396.3 [(M+H)$^+$]; mp 215–218° C.

Example 10

7-Dimethylamino-4-[3-(6-methyl-pyridin-3-yl)-phenyl]-8-trifluoromethyl-1,3-dihydro-benzo[b][1,4]diazepin-2-one The title compound was prepared from (5-dimethylamino-2-{3-[3-(6-methyl-pyridin-3-yl)-phenyl]-3-oxo-propionylamino}-4-trifluoromethyl-phenyl)-carbamic acid tert-butyl ester (Example M7) (350 mg, 0.63 mmol) by treatment with TFA in CH$_2$Cl$_2$ according to the general procedure N. Obtained as a white solid (207 mg).

MS (ISP) 439.4 [(M+H)$^+$]; mp 233–237° C.

Example 11

8-Fluoro-4-[3-(6-methyl-pyridin-3-yl)-phenyl]-1,3-dihydro-benzo[b][1,4]diazepin-2-one The title compound was prepared from (4-fluoro-2-{3-[3-(6-methyl-pyridin-3-yl)-phenyl]-3-oxo-propionylamino}-phenyl)-carbamic acid tert-butyl ester (Example M8) (320 mg, 0.69 mmol) by treatment with TFA in CH$_2$Cl$_2$ according to the general procedure N. Obtained as a white solid (41 mg).

MS (ISP) 346.3 [(M+H)$^+$]; mp 225–226° C.

Example 12

8-(2-Fluoro-phenyl)-4-[3-(6-methyl-pyridin-3-yl)-phenyl]-1,3-dihydro-benzo[b][1,4]diazepin-2-one The title compound was prepared from (2'-fluoro-3-{3-[3-(6-methyl-pyridin-3-yl)-phenyl]-3-oxo-propionylamino}-biphenyl-4-yl)-carbamic acid tert-butyl ester (Example M9) (340 mg, 0.63 mmol) by treatment with TFA in CH₂Cl₂ according to the general procedure N. Obtained as a yellow solid (201 mg).

MS (ISP) 422.3 [(M+H)⁺]; mp 206–209° C.

Example 13

7-Dimethylamino-4-[3-(2-methyl-pyridin-3-yl)-phenyl]-8-trifluoromethyl-1,3-dihydro-benzo[b][1,4]diazepin-2-one The title compound was prepared from (5-dimethylamino-2-{3-[3-(2-methyl-pyridin-3-yl)-phenyl]-3-oxo-propionylamino}-4-trifluoromethyl-phenyl)-carbamic acid tert-butyl ester (Example M10) (380 mg, 0.683 mmol) by treatment with TFA in CH₂Cl₂ according to the general procedure N. Obtained as a light yellow solid (215 mg).

MS (ISP) 439.4 [(M+H)⁺]; mp 229–230° C.

Example 14

4-[3-(6-Methyl-pyridazin-3-yl)-phenyl]-8-trifluoromethyl-1,3-dihydro-benzo[b][1,4]diazepin-2-one The title compound was obtained from (2-{3-[3-(6-methyl-pyridazin-3-yl)-phenyl]-3-oxo-propionylamino}-4-trifluoromethyl-phenyl)-carbamic acid tert-butyl ester (Example M11) (286 mg, 0.56 mmol) by treatment with TFA in CH₂Cl₂ according to the general procedure N as a light yellow solid (176 mg).

MS (ISP) 397 [(M+H)⁺]; mp 233° C.

Example 15

7-Dimethylamino-4-[3-(6-methyl-pyridazin-3-yl)-phenyl]-8-trifluoromethyl-1,3-dihydro-benzo[b][1,4]diazepin-2-one The title compound was prepared from (5-dimethylamino-2-{3-[3-(6-methyl-pyridazin-3-yl)-phenyl]-3-oxo-propionylamino}-4-trifluoromethyl-phenyl)-carbamic acid tert-butyl ester (Example M12) (301 mg, 0.54 mmol) by treatment with TFA in CH₂Cl₂ according to the general procedure N. Obtained as a light yellow solid (189 mg).

MS (ISP) 440 [(M+H)⁺]; mp 174° C.

Example 16

8-(2-Fluoro-phenyl)-4-[3-(6-methyl-pyridazin-3-yl)-phenyl]-1,3-dihydro-benzo[b][1,4]diazepin-2-one The title compound was prepared from (2'-fluoro-3-{3-[3-(6-methyl-pyridazin-3-yl)-phenyl]-3-oxo-propionylamino}-biphenyl-4-yl)-carbamic acid tert-butyl ester (Example M13) (292 mg, 0.541 mmol) by treatment with TFA in CH₂Cl₂ according to the general procedure N. Obtained as a light yellow solid (181 mg).

MS (ISP) 423 [(M+H)⁺]; mp 225° C.

Example 17

4-[3-(2-Methyl-pyridin-3-yl)-phenyl]-8-trifluoromethyl-1,3-dihydro-benzo[b][1,4]diazepin-2-one The title compound was prepared from (2-{3-[3-(2-methyl-pyridin-3-yl)-phenyl]-3-oxo-propionylamino}-4-trifluoromethyl-phenyl)-carbamic acid tert-butyl ester (Example M14) (280 mg, 0.545 mmol) by treatment with TFA in CH₂Cl₂ according to the general procedure N. Obtained as a pink solid (163 mg).

MS (ISP) 396.3 [(M+H)⁺]; mp 219–220° C.

Example 18

8-Fluoro-4-[3-(2-methyl-pyridin-3-yl)-phenyl]-1,3-dihydro-benzo[b][1,4]diazepin-2-one The title compound was prepared from (4-fluoro-2-{3-[3-(2-methyl-pyridin-3-yl)-phenyl]-3-oxo-propionylamino}-phenyl)-carbamic acid tert-butyl ester (Example M15) (250 mg, 0.539 mmol) by treatment with TFA in CH₂Cl₂ according to the general procedure N. Obtained as a light yellow solid (143 mg).

MS (ISP) 346.4 [(M+H)⁺]; mp 219–220° C.

Example 19

8-(2-Fluoro-phenyl)-4-[3-(2-methyl-pyridin-3-yl)-phenyl]-1,3-dihydro-benzo[b][1,4]diazepin-2-one The title compound was prepared from (2'-fluoro-3-{3-[3-(2-methyl-pyridin-3-yl)-phenyl]-3-oxo-propionylamino}-biphenyl-4-yl)-carbamic acid tert-butyl ester (Example M16) (330 mg, 0.611 mmol) by treatment with TFA in CH₂Cl₂ according to the general procedure N. Obtained as a light yellow solid (211 mg).

MS (ISP) 422.4 [(M+H)⁺]; mp 192–194° C.

Example 20

4-(3-Pyridin-4-yl-phenyl)-8-trifluoromethyl-1,3-dihydro-benzo[b][1,4]diazepin-2-one The title compound was prepared from {2-[3-oxo-3-(3-pyridin-4-yl-phenyl)-propionylamino]-4-trifluoromethyl-phenyl}-carbamic acid tert-butyl ester (Example M17) by treatment with TFA in CH₂Cl₂ according to the general procedure N. Obtained as a white solid (176 mg).

MS (ISP) 382 [(M+H)⁺].

Example 21

8-(2-Fluoro-phenyl)-4-(3-pyridin-4-yl-phenyl)-1,3-dihydro-benzo[b][1,4]diazepin-2-one The title compound was prepared from {2'-fluoro-3-[3-oxo-3-(3-pyridin-4-yl-phenyl)-propionylamino]-biphenyl-4-yl}-carbamic acid tert-butyl ester (Example M18) by treatment with TFA in CH₂Cl₂ according to the general procedure N. Obtained as a light yellow solid (237 mg).

MS (ISP) 408 [(M+H)⁺].

Example 22

8-Chloro-4-(3-pyridin-4-yl-phenyl)-1,3-dihydro-benzo[b][1,4]diazepin-2-one

The title compound was obtained from {4-chloro-2-[3-oxo-3-(3-pyridin-4-yl-phenyl)-propionylamino]-phenyl}-carbamic acid tert-butyl ester (Example M19) by treatment with TFA in CH₂Cl₂ according to the general procedure N as a light brown solid (61 mg).

MS (ISP) 348 [(M+H)⁺] and 350 [(M+2+H)⁺]; mp 225–226° C.

Example 23

8-Chloro-7-fluoro-4-[3-(6-methyl-pyridin-3-yl)-phenyl]-1,3-dihydro-benzo[b][1,4]diazepin-2-one The title compound was prepared from (4-chloro-5-fluoro-2-{3-[3-(6-methyl-pyridin-3-yl)-phenyl]-3-oxopropionylamino}-phenyl)-carbamic acid tert-butyl ester (Example M20) (241 mg, 0.48 mmol) by treatment with TFA in $CH_2Cl_2$ according to the general procedure N. Obtained as an off-white solid (124 mg).

MS (ISP) 380.3 [(M+H)$^+$] and 382 [(M+2+H)$^+$]; mp 215–220° C.

Example 24

8-Chloro-7-fluoro-4-(3-pyridin-4-yl-phenyl)-1,3-dihydro-benzo[b [1,4]diazepin-2-one The title compound was prepared from {4-chloro-5-fluoro-2-[3-oxo-3-(3-pyridin-4-yl-phenyl)-propionylamino]-phenyl}-carbamic acid tert-butyl ester (Example M21) (239 mg, 0.49 mmol) by treatment with TFA in $CH_2Cl_2$ according to the general procedure N. Obtained as an off-white solid (149 mg).

MS (ISP) 366.2 [(M+H)$^+$] and 368 [(M+2+H)$^+$]; mp 235–240° C.

Example 25

8-Methyl-4-(3-pyridin-3-yl-phenyl)-7-trifluoromethyl-1,3-dihydro-benzo[b][1,4]diazepin-2-one The title compound was prepared from {4-methyl-2-[3-oxo-3-(3-pyridin-3-yl-phenyl)-propionylamino]-5-trifluoromethyl-phenyl}-carbamic acid tert-butyl ester (Example M22) by treatment with TFA in $CH_2Cl_2$ according to the general procedure N. Obtained as a white solid (162 mg).

MS (ISP) 396 [(M+H)$^+$]; mp 221° C.

Example 26

8-Chloro-7-methyl-4-(3-pyridin-3-yl-phenyl)-1,3-dihydro-benzo[b][1,4]diazepin-2-one The title compound was obtained from {4-chloro-5-methyl-2-[3-oxo-3-(3-pyridin-3-yl-phenyl)-propionylamino]-phenyl}-carbamic acid tert-butyl ester (Example M23) by treatment with TFA in $CH_2Cl_2$ according to the general procedure N as a light yellow solid (155 mg).

MS (ISP) 362 [(M+H)$^+$] and 364 [(M+2+H)$^+$]; mp 229° C.

Example 27

4-(3-Pyridin-3-yl-phenyl)-8-trifluoromethyl-1,3-dihydro-benzo[b][1,4]diazepin-2-one The title compound was prepared from {2-[3-oxo-3-(3-pyridin-3-yl-phenyl)-propionylamino]-4-trifluoromethyl-phenyl}-carbamic acid tert-butyl ester (Example M24) by treatment with TFA in $CH_2Cl_2$ according to the general procedure N. Obtained as a white solid (151 mg).

MS (ISP) 382 [(M+H)$^+$]; mp 216° C.

Example 28

8-Chloro-4-(3-pyridin-3-yl-phenyl)-1,3-dihydro-benzo[b][1,4]diazepin-2-one

The title compound was prepared from {4-chloro-2-[3-oxo-3-(3-pyridin-3-yl-phenyl)-propionylamino]-phenyl}-carbamic acid tert-butyl ester (Example M25) by treatment with TFA in $CH_2Cl_2$ according to the general procedure N. Obtained as a white solid (84 mg).

MS (ISP) 348 [(M+H)$^+$] and 350 [(M+2+H)$^+$]; mp 232° C.

Example 29

8-(2-Fluoro-phenyl)-4-(3-pyridin-3-yl-phenyl)-1,3-dihydro-benzo[b][1,4]diazepin-2-one The title compound was prepared from {2'-fluoro-3-[3-oxo-3-(3-pyridin-3-yl-phenyl)-propionylamino]-biphenyl-4-yl}-carbamic acid tert-butyl ester (Example M26) by treatment with TFA in $CH_2Cl_2$ according to the general procedure N. Obtained as a light brown solid (127 mg).

MS (ISP) 408 [(M+H)$^+$]; mp 208–209° C.

Example 30

4-(3-Pyridin-3-yl-phenyl)-7-(2,2,2-trifluoro-ethoxy)-8-trifluoromethyl-1,3-dihydro-benzo[b][1,4]diazepin-2-one The title compound was prepared from [2-[3-oxo-3-(3-pyridin-3-yl-phenyl)-propionylamino]-5-(2,2,2-trifluoro-ethoxy)-4-trifluoromethyl-phenyl]-carbamic acid tert-butyl ester (Example M27) by treatment with TFA in $CH_2Cl_2$ according to the general procedure N. Obtained as a white solid (173 mg).

MS (ISP) 480 [(M+H)$^+$]; mp 217° C.

Example 31

8-Chloro-4-[3-(6-methyl-pyridin-3-yl)-phenyl]-1,3-dihydro-benzo[b][1,4]diazepin-2-one The title compound was prepared from (4-chloro-2-{3-[3-(6-methyl-pyridin-3-yl)-phenyl]-3-oxo-propionylamino}-phenyl)-carbamic acid tert-butyl ester (Example M28) (282 mg, 0.59 mmol) by treatment with TFA in $CH_2Cl_2$ according to the general procedure N. Obtained as a light brown solid (163 mg).

MS (ISP) 362 [(M+H)$^+$] and 364 [(M+2+H)$^+$]; mp 230° C.

Example 32

8-Chloro-4-[3-(2-methyl-pyridin-3-yl)-phenyl]-1,3-dihydro-benzo[b][1,4]diazepin-2-one The title compound was prepared from (4-chloro-2-{3-[3-(2-methyl-pyridin-3-yl)-phenyl]-3-oxo-propionylamino}-phenyl)-carbamic acid tert-butyl ester (Example M29) (216 mg, 0.45 mmol) by treatment with TFA in $CH_2Cl_2$ according to the general procedure N. Obtained as a light brown solid (121 mg).

MS (ISP) 362 [(M+H)$^+$] and 364 [(M+2+H)$^+$]; mp 198° C.

Example 33

4-(3-Pyridin-2-yl-phenyl)-8-trifluoromethyl-1,3-dihydro-benzo[b][1,4]diazepin-2-one The title compound was prepared from {2-[3-oxo-3-(3-pyridin-2-yl-phenyl)-propionylamino]-4-trifluoromethyl-phenyl}-carbamic acid tert-butyl ester (Example M30) (275 mg, 0.551 mmol) by treatment with TFA in $CH_2Cl_2$ according to the general procedure N. Obtained as a white solid (141 mg).

MS (ISP) 382.3 [(M+H)$^+$]; mp 226–227° C.

Example 34

4-(3-Pyridin-3-yl-phenyl)-1,3-dihydro-benzo[b][1,4]diazepin-2-one

The title compound was prepared from 1,2-phenylenediamine (81 mg, 0.75 mmol) and 3-oxo-3-(3-pyridin-3-yl-phenyl)-propionic acid tert-butyl ester (Example K1) (223 mg, 0.75 mmol) by refluxing in xylene according to the general procedure M. Obtained as a white solid (204 mg).

MS (ISP) 314 [(M+H)$^+$]; mp 210–211° C.

Example 35

7-Methoxy-4-(3-pyridin-4-yl-phenyl)-8-trifluoromethyl-1,3-dihydro-benzo[b][1,4]diazepin-2-one The title compound was prepared from {5-methoxy-2-[3-oxo-3-(3-pyridin-4-yl-phenyl)-propionylamino]-4-trifluoromethyl-phenyl}-carbamic acid tert-butyl ester (Example M31) by treatment with TFA in CH$_2$Cl$_2$ according to the general procedure N. Obtained as a light yellow solid (183 mg).

MS (ISP) 412.3 [(M+H)$^+$]; mp 225° C. (dec.).

Example 36

7-Ethoxy-4-(3-pyridin-4-yl-phenyl)-8-trifluoromethyl-1,3-dihydro-benzo[b][1,4]diazepin-2-one The title compound was prepared from {5-ethoxy-2-[3-oxo-3-(3-pyridin-4-yl-phenyl)-propionylamino]-4-trifluoromethyl-phenyl}-carbamic acid tert-butyl ester (Example M32) by treatment with TFA in CH$_2$Cl$_2$ according to the general procedure N. Obtained as a light yellow solid (184 mg).

MS (ISP) 426.4 [(M+H)$^+$]; mp 206–207° C. (dec.).

Example 37

4-(3-Pyridin-4-yl-phenyl)-7-(2,2,2-trifluoro-ethoxy)-8-trifluoromethyl-1,3-dihydro-benzo[b][1,4]diazepin-2-one The title compound was prepared from [2-[3-oxo-3-(3-pyridin-4-yl-phenyl)-propionylamino]-5-(2,2,2-trifluoro-ethoxy)-4-trifluoromethyl-phenyl]-carbamic acid tert-butyl ester (Example M33) by treatment with TFA in CH$_2$Cl$_2$ according to the general procedure N. Obtained as a light yellow solid (175 mg).

MS (ISP) 480.3 [(M+H)$^+$]; mp 221–222° C. (dec.).

Example 38

8-Methoxy-4-(3-pyridin-4-yl-phenyl)-1,3-dihydro-benzo[b][1,4]diazepin-2-one

The title compound was prepared from {4-methoxy-2-[3-oxo-3-(3-pyridin-4-yl-phenyl)-propionylamino]-phenyl}-carbamic acid tert-butyl ester (Example M34) by treatment with TFA in CH$_2$Cl$_2$ according to the general procedure N. Obtained as a light yellow solid (160 mg).

MS (ISP) 344.4 [(M+H)$^+$]; mp 193–196° C.

Example 39

7-Dimethylamino-8-(2-fluoro-phenyl)-4-(3-pyridin-4-yl-phenyl)-1,3-dihydro-benzo[b][1,4]diazepin-2-one The title compound was prepared from {2-dimethylamino-2'-fluoro-5-(3-oxo-3-(3-pyridin-4-yl-phenyl)-propionylamino]-biphenyl-4-yl}-carbamic acid tert-butyl ester (Example M35) (302 mg, 0.531 mmol) by treatment with TFA in CH$_2$Cl$_2$ according to the general procedure N. Obtained as a yellow solid (208 mg).

MS (ISP) 451.4 [(M+H)$^+$]; mp 236–237° C.

Example 40

7-Dimethylamino-4-[3-(6-methoxy-pyridazin-3-yl)-phenyl]-8-trifluoromethyl-1,3-dihydro-benzo[b][1,4]diazepin-2-one The title compound was prepared from (5-dimethylamino-2-{3-[3-(6-methoxy-pyridazin-3-yl)-phenyl]-3-oxo-propionylamino}-4-trifluoromethyl-phenyl)-carbamic acid tert-butyl ester (Example M36) (282 mg, 0.49 mmol) by treatment with TFA in CH$_2$Cl$_2$ according to the general procedure N. Obtained as an off-white solid (214 mg).

MS (ISP) 456 [(M+H)$^+$]; mp 224° C.

Example 41

8-(2-Fluoro-phenyl)-4-[3-(6-methoxy-pyridazin-3-yl)-phenyl]-1,3-dihydro-benzo[b][1,4]diazepin-2-one The title compound was prepared from (2'-fluoro-3-{3-[3-(6-methoxy-pyridazin-3-yl)-phenyl]-3-oxo-propionylamino}-biphenyl-4-yl)-carbamic acid tert-butyl ester (Example M37) (308 mg, 0.55 mmol) by treatment with TFA in CH$_2$Cl$_2$ according to the general procedure N. Obtained as a light yellow solid (178 mg).

MS (ISP) 439 [(M+H)$^+$]; mp 220° C.

Example 42

7-Methoxy-4-(3-pyridin-2-yl-phenyl)-8-trifluoromethyl-1,3-dihydro-benzo[b][1,4]diazepin-2-one The title compound was prepared from {5-methoxy-2-[3-oxo-3-(3-pyridin-2-yl-phenyl)-propionylamino]-4-trifluoromethyl-phenyl}-carbamic acid tert-butyl ester (Example M38) (208 mg, 0.39 mmol) by treatment with TFA in CH$_2$Cl$_2$ according to the general procedure N. Obtained as an off-white solid (140 mg).

MS (ISN) 410 [(M−H)$^−$]; mp 240° C.

Example 43

7-Ethoxy-4-(3-pyridin-2-yl-phenyl)-8-trifluoromethyl-1,3-dihydro-benzo[b][1,4]diazepin-2-one The title compound was prepared from {5-ethoxy-2-[3-oxo-3-(3-pyridin-2-yl-phenyl)-propionylamino]-4-trifluoromethyl-phenyl}-carbamic acid tert-butyl ester (Example M39) (198 mg, 0.36 mmol) by treatment with TFA in CH$_2$Cl$_2$ according to the general procedure N. Obtained as an off-white solid (138 mg).

MS (ISN) 424 [(M−H)$^−$]; mp 229° C.

Example 44

4-(3-Pyridin-2-yl-phenyl)-7-(2,2,2-trifluoro-ethoxy)-8-trifluoromethyl-1,3-dihydro-benzo[b][1,4]diazepin-2-one The title compound was prepared from [2-[3-oxo-3-(3-pyridin-2-yl-phenyl)-propionylamino]-5-(2,2,2-trifluoroethoxy)-4-trifluoromethyl-phenyl]-carbamic acid tert-butyl ester (Example M40) (165 mg, 0.36 mmol) by treatment with TFA in $CH_2Cl_2$ according to the general procedure N. Obtained as an off-white solid (81 mg).

MS (ISN) 478 [(M−H)⁻]; mp 214° C.

Example 45

8-Chloro-7-methyl-4-(3-pyridin-2-yl-phenyl)-1,3-dihydro-benzo[b][1,4]diazepin-2-one The title compound was prepared from {4-chloro-5-methyl-2-[3-oxo-3-(3-pyridin-2-yl-phenyl)-propionylamino]-phenyl}-carbamic acid tert-butyl ester (Example M41) (269 mg, 0.561 mmol) by treatment with TFA in $CH_2Cl_2$ according to the general procedure N. Obtained as a white solid (161 mg).

MS (ISN) 360.1 [(M−H)⁻] and 362 [(M+2−H)⁻]; mp 222° C. (dec.).

Example 46

7-Methyl-4-(3-pyridin-2-yl-phenyl)-8-trifluoromethyl-1,3-dihydro-benzo[b][1,4]diazepin-2-one The title compound was prepared from {5-methyl-2-[3-oxo-3-(3-pyridin-2-yl-phenyl)-propionylamino]-4-trifluoromethyl-phenyl}-carbamic acid tert-butyl ester (Example M42) (245 mg, 0.476 mmol) by treatment with TFA in $CH_2Cl_2$ according to the general procedure N. Obtained as a light yellow solid (162 mg).

MS (ISN) 394.2 [(M−H)⁻]; mp 251–253° C.

Example 47

7-Dimethylamino-4-[3-(2,6-dimethyl-pyridin-3-yl)-phenyl]-8-trifluoromethyl-1,3-dihydro-benzo[b][1,4]diazepin-2-one The title compound was prepared from (5-dimethylamino-2-{3-[3-(2,6-dimethyl-pyridin-3-yl)-phenyl]-3-oxo-propionylamino}-4-trifluoromethyl-phenyl)-carbamic acid tert-butyl ester (Example M43) (190 mg, 0.333 mmol) by treatment with TFA in $CH_2Cl_2$ according to the general procedure N. Obtained as a brown solid (97 mg).

MS (ISP) 453.5 [(M+H)⁺]; mp 187–189° C.

Example 48

8-Chloro-7-methyl-4-(3-pyridazin-4-yl-phenyl)-1,3-dihydro-benzo[b][1,4]diazepin-2-one The title compound was prepared from {4-chloro-5-methyl-2-[3-oxo-3-(3-pyridazin-4-yl-phenyl)-propionylamino]-phenyl}-carbamic acid tert-butyl ester (Example M44) by treatment with TFA in $CH_2Cl_2$ according to the general procedure N. Obtained as a white solid (59 mg).

MS (ISP) 363 [(M+H)⁺] and 365 [(M+2+H)⁺]; mp 240° C. (dec.).

Example 49

7-Methyl-4-(3-pyridazin-4-yl-phenyl)-8-trifluoromethyl-1,3-dihydro-benzo[b][1,4]diazepin-2-one The title compound was prepared from {5-methyl-2-[3-oxo-3-(3-pyridazin-4-yl-phenyl)-propionylamino]-4-trifluoromethyl-phenyl}-carbamic acid tert-butyl ester (Example M45) by treatment with TFA in $CH_2Cl_2$ according to the general procedure N. Obtained as a white solid (110 mg).

MS (ISP) 397 [(M+H)⁺]; mp 223° C.

Example 50

4-[3-(6-Methoxy-pyridin-3-yl)-phenyl]-8-trifluoromethyl-1,3-dihydro-benzo[b][1,4]diazepin-2-one The title compound was prepared from (4-chloro-2-{3-[3-(6-methoxy-pyridin-3-yl)-phenyl]-3-oxo-propionylamino}-phenyl)-carbamic acid tert-butyl ester (Example M46) (270 mg, 0.54 mmol) by treatment with TFA in $CH_2Cl_2$ according to the general procedure N. Obtained as an off-white solid (79 mg).

MS (ISP) 412 [(M+H)⁺]; mp 210–215° C.

Example 51

8-Chloro-4-[3-(6-methoxy-pyridin-3-yl)-phenyl]-1,3-dihydro-benzo[b][1,4]diazepin-2-one The title compound was prepared from (4-chloro-2-{3-[3-(6-methoxy-pyridin-3-yl)-phenyl]-3-oxo-propionylamino}-phenyl)-carbamic acid tert-butyl ester (Example M47) (270 mg, 0.54 mmol) by treatment with TFA in $CH_2Cl_2$ according to the general procedure N. Obtained as an off-white solid (129 mg).

MS (ISP) 378 [(M+H)⁺] and 380 [(M+2+H)⁺]; mp 200–205° C.

Example 52

8-Chloro-7-fluoro-4-(3-pyridin-2-yl-phenyl)-1,3-dihydro-benzo[b][1,4]diazepin-2-one The title compound was prepared from {4-chloro-5-fluoro-2-[3-oxo-3-(3-pyridin-2-yl-phenyl)-propionylamino]-phenyl}-carbamic acid tert-butyl ester (Example M48) (270 mg, 0.54 mmol) by treatment with TFA in $CH_2Cl_2$ according to the general procedure N. Obtained as a light brown solid (174 mg).

MS (ISP) 366 [(M+H)⁺] and 368 [(M+2+H)⁺]; mp 197–198° C.

Example 53

8-(2-Fluoro-phenyl)-4-(3-pyridin-2-yl-phenyl)-1,3-dihydro-benzo[b][1,4]diazepin-2-one The title compound was prepared from {2'-fluoro-3-[3-oxo-3-(3-pyridin-2-yl-phenyl)-propionylamino]-biphenyl-4-yl}-carbamic acid tert-butyl ester (Example M49) (350 mg, 0.66 mmol) by treatment with TFA in $CH_2Cl_2$ according to the general procedure N. Obtained as a light yellow solid (153 mg).

MS (ISP) 408 [(M+H)⁺].

Example 54

4-(3-Pyridin-2-yl-phenyl)-8-pyrrol-1-yl-1,3-dihydro-benzo[b][1,4]diazepin-2-one

The title compound was prepared from {2-[3-oxo-3-(3-pyridin-2-yl-phenyl)-propionylamino]-4-pyrrol-1-yl-phenyl}-carbamic acid tert-butyl ester (Example M50) (290 mg, 0.58 mmol) by treatment with TFA in $CH_2Cl_2$ according to the general procedure N. Obtained as a light yellow solid (73 mg).

MS (ISP) 379 [(M+H)$^+$].

Example 55

7-Methoxy-4-(3-pyridin-3-yl-phenyl)-1,3-dihydro-benzo[b][1,4]diazepin-2-one

The title compound was prepared from {5-methoxy-2-[3-oxo-3-(3-pyridin-3-yl-phenyl)-propionylamino]-phenyl}-carbamic acid tert-butyl ester (Example M51) (229 mg, 0.50 mmol) by treatment with TFA in $CH_2Cl_2$ according to the general procedure N. Obtained as a light brown solid (159 mg).

MS (ISP) 344.4 [(M+H)$^+$]; mp 219° C. (dec.).

Example 56

4-(3-Pyridin-2-yl-phenyl)-7-(2,2,2-trifluoro-ethoxy)-1,3-dihydro-benzo[b][1,4]diazepin-2-one The title compound was prepared from [2-[3-oxo-3-(3-pyridin-2-yl-phenyl)-propionylamino]-5-(2,2,2-trifluoro-ethoxy)-phenyl]-carbamic acid tert-butyl ester (Example M52) (380 mg, 0.72 mmol) by treatment with TFA in $CH_2Cl_2$ according to the general procedure N. Obtained as a white solid (201 mg).

MS (ISP) 412 [(M+H)$^+$].

Example 57

4-(3-Pyridin-3-yl-phenyl)-7-(2,2,2-trifluoro-ethoxy)-1,3-dihydro-benzo[b][1,4]diazepin-2-one The title compound was prepared from [2-[3-oxo-3-(3-pyridin-3-yl-phenyl)-propionylamino]-5-(2,2,2-trifluoro-ethoxy)-phenyl]-carbamic acid tert-butyl ester (Example M53) (356 mg, 0.67 mmol) by treatment with TFA in $CH_2Cl_2$ according to the general procedure N. Obtained as a light yellow solid (190 mg).

MS (ISP) 412 [(M+H))$^+$].

Example 58

4-(3-Pyridin-4-yl-phenyl)-7-(2,2,2-trifluoro-ethoxy)-1,3-dihydro-benzo[b][1,4]diazepin-2-one The title compound was prepared from [2-[3-oxo-3-(3-pyridin-4-yl-phenyl)-propionylamino]-5-(2,2,2-trifluoro-ethoxy)-phenyl]-carbamic acid tert-butyl ester (Example M54) (250 mg, 0.47 mmol) by treatment with TFA in $CH_2Cl_2$ according to the general procedure N. Obtained as a light yellow solid (80 mg).

MS (ISP) 412 [(M+H)$^+$].

Example 59

7-Ethoxy-4-[3-(2-methyl-pyridin-4-yl)-phenyl]-1,3-dihydro-benzo[b][1,4]diazepin-2-one The title compound was prepared from (5-ethoxy-2-{3-[3-(2-methyl-pyridin-4-yl)-phenyl]-3-oxo-propionylamino}-phenyl)-carbamic acid tert-butyl ester (Example M55) (213 mg, 0.44 mmol) by treatment with TFA in $CH_2Cl_2$ according to the general procedure N. Obtained as a yellow solid (120 mg).

MS (ISP) 372 [(M+H)$^+$]; mp 163° C.

Example 60

7-Ethoxy-4-[3-(6-methyl-pyridin-3-yl)-phenyl]-1,3-dihydro-benzo[b][1,4]diazepin-2-one Prepared from (5-ethoxy-2-{3-[3-(2-methyl-pyridin-4-yl)-phenyl]-3-oxo-propionylamino}-phenyl)-carbamic acid tert-butyl ester (Example M56) (180 mg, 0.37 mmol) by treatment with TFA in $CH_2Cl_2$ according to the general procedure N. Obtained as a yellow solid (85 mg).

MS (ISP) 372 [(M+H)$^+$]; mp 173° C.

Example 61

7-Ethoxy-4-[3-(2-methyl-pyridin-4-yl)-phenyl]-8-trifluoromethyl-1,3-dihydro-benzo[b][1,4]diazepin-2-one The title compound was prepared from (5-ethoxy-2-{3-[3-(2-methyl-pyridin-4-yl)-phenyl]-3-oxo-propionylamino}-4-trifluoromethyl-phenyl)-carbamic acid tert-butyl ester (Example M57) (318 mg, 0.57 mmol) by treatment with TFA in $CH_2Cl_2$ according to the general procedure N. Obtained as an off-white solid (216 mg).

MS (ISP) 440 [(M+H)$^+$]; mp 236° C.

Example 62

7-(Cyclopropyl-methyl-amino)-4-(3-pyridin-3-yl-phenyl)-8-trifluoromethyl-1,3-dihydro-benzo[b][1,4]diazepin-2-one The title compound was prepared from {5-(cyclopropyl-methyl-amino)-2-[3-oxo-3-(3-pyridin-3-yl-phenyl)-propionylamino]-4-trifluoromethyl-phenyl}-carbamic acid tert-butyl ester (Example M58) (383 mg, 0.674 mmol) by treatment with TFA in $CH_2Cl_2$ according to the general procedure N. Obtained as a yellow solid (178 mg).

MS (ISP) 451.4 [(M+H)$^+$]; mp 196–198° C.

Example 63

7-Isobutylamino-4-(3-pyridin-4-yl-phenyl)-8-trifluoromethyl-1,3-dihydro-benzo[b][1,4]diazepin-2-one The title compound was prepared from {5-isobutylamino-2-[3-oxo-3-(3-pyridin-4-yl-phenyl)-propionylamino]-4-trifluoromethyl-phenyl}-carbamic acid tert-butyl ester (Example M59) (0.56 g, 0.98 mmol) by treatment with TFA in $CH_2Cl_2$ according to the general procedure N. Obtained as a light yellow solid (299 mg, 67%).

MS (ISP) 453.5 [(M+H)$^+$]; mp 198° C.

Example 64

8-Methyl-4-(3-pyridin-4-yl-phenyl)-7-trifluoromethyl-1,3-dihydro-benzo[b][1,4]diazepin-2-one The title compound was prepared from {4-methyl-2-[3-oxo-3-(3-pyridin-4-yl-phenyl)-propionylamino]-5-trifluoromethyl-phenyl}-carbamic acid tert-butyl ester (Example M61) (0.27 g, 0.53 mmol) by treatment with TFA in $CH_2Cl_2$ according to the general procedure N. Obtained as a light yellow solid (133 mg, 64%).

MS (ISP) 396.3 [(M+H)$^+$]; mp 217° C.

Example 65

7-Methyl-4-(3-pyridin-4-yl-phenyl)-8-trifluoromethyl-1,3-dihydro-benzo[b][1,4]diazepin-2-one The title compound was prepared from {5-methyl-2-[3-oxo-3-(3-pyridin-4-yl-phenyl)-propionylamino]-4- trifluoromethyl-phenyl}-carbamic acid tert-butyl ester (Example M60) (0.33 g, 0.64 mmol) by treatment with TFA in CH$_2$Cl$_2$ according to the general procedure N. Obtained as a light yellow solid (206 mg, 81%).

MS (ISP) 396.3 [(M+H)$^+$]; mp 229° C.

Example 66

7-Chloro-8-methyl-4-(3-pyridin-4-yl-phenyl)-1,3-dihydro-benzo[b][1,4]diazepin-2-one The title compound was prepared from {5-chloro-4-methyl-2-[3-oxo-3-(3-pyridin-4-yl-phenyl)-propionylamino]-phenyl}-carbamic acid tert-butyl ester (Example M63) (0.36 g, 0.75 mmol) by treatment with TFA in CH$_2$Cl$_2$ according to the general procedure N. Obtained as an off-white light solid (269 mg, 99%).

MS (ISP) 362.2 [(M+H)$^+$]; mp 236° C.

Example 67

8-Chloro-7-methyl-4-(3-pyridin-4-yl-phenyl)-1,3-dihydro-benzo[b][1,4]diazepin-2-one The title compound was prepared from {4-chloro-5-methyl-2-[3-oxo-3-(3-pyridin-4-yl-phenyl)-propionylamino]-phenyl}-carbamic acid tert-butyl ester (Example M62) (0.36 g, 0.75 mmol) by treatment with TFA in CH$_2$Cl$_2$ according to the general procedure N. Obtained as an off-white solid (234 mg, 86%).

MS (ISP) 362.2 [(M+H)$^+$]; mp 242° C.

Example 68

7-Chloro-4-(3-pyridin-4-yl-phenyl)-8-trifluoromethyl-1,3-dihydro-benzo[b][1,4]diazepin-2-one The title compound was obtained from {5-chloro-2-[3-oxo-3-(3-pyridin-4-yl-phenyl)-propionylamino]-4-trifluoromethyl-phenyl}-carbamic acid tert-butyl ester (Example M64) (0.39 g, 0.73 mmol) by treatment with TFA in CH$_2$Cl$_2$ according to the general procedure N as a light brown solid (122 mg, 40%).

MS (ISP) 414.1 [(M−H)$^-$]; mp 216° C.

Example 69

7,8-Dimethyl-4-(3-pyridin-4-yl-phenyl)-1,3-dihydro-benzo[b][1,4]diazepin-2-one

The title compound was prepared from commercially available 4,5-dimethyl-1,2-phenylendiamine (136 mg, 1.0 mmol) and 3-oxo-3-(3-pyridin-4-yl-phenyl)-propionic acid tert-butyl ester (Example K2) (297 mg, 1.0 mmol) in xylene (20 ml) under reflux conditions for 2 h according to the general procedure M. Obtained as a light brown solid (294 mg, 86%).

MS (ISP) 342.3 [(M+H)$^+$]; mp 231° C.

Example 70

7,8-Dichloro-4-[3-(2-methyl-pyridin-4-yl)-phenyl]-1,3-dihydro-benzo[b][1,4]diazepin-2-one The title compound was prepared from commercially available 4,5-dichloro-1,2-phenylendiamine (177 mg, 1.0 mmol) and 3-[3-(2-methyl-pyridin-4-yl)-phenyl]-3-oxo-propionic acid tert-butyl ester (Example K12) (311 mg, 1.0 mmol) in xylene (20 ml) under reflux conditions for 2 h according to the general procedure M. Obtained as a light red solid (274 mg, 69%).

MS (ISP) 394.1 [(M−H)$^-$]; mp 221° C.

Example 71

4-[3-(2-Methyl-pyridin-4-yl)-phenyl]-1,3-dihydro-benzo[b][1,4]diazepin-2-one

The title compound was prepared from commercially available 1,2-phenylendiamine (108 mg, 1.0 mmol) and 3-[3-(2-methyl-pyridin-4-yl)-phenyl]-3-oxo-propionic acid tert-butyl ester (Example K12) (311 mg, 1.0 mmol) in xylene (20 ml) under reflux conditions for 2 h according to the general procedure M. Obtained as an off-white solid (230 mg, 70%).

MS (ISP) 326.3 [(M−H)$^-$]; mp 192° C.

Example 72

8-(2-Fluoro-phenyl)-4-[3-(2-methyl-pyridin-4-yl)-phenyl]-1,3-dihydro-benzo[b][1,4]diazepin-2-one The title compound was prepared from (2'-fluoro-3-{3-[3-(2-methyl-pyridin-4-yl)-phenyl]-3-oxo-propionylamino}-biphenyl-4-yl)-carbamic acid tert-butyl ester (Example M65) (0.47 g, 0.87 mmol) by treatment with TFA in CH$_2$Cl$_2$ according to the general procedure N. Obtained as an off-white solid (305 mg, 83%).

MS (ISP) 420.2 [(M−H)$^-$]; mp 205° C.

Example 73

8-Chloro-7-methyl-4-[3-(2-methyl-pyridin-4-yl)-phenyl]-1,3-dihydro-benzo[b][1,4]diazepin-2-one The title compound was prepared from (4-chloro-5-methyl-2-{3-[3-(2-methyl-pyridin-4-yl)-phenyl]-3-oxo-propionylamino}-phenyl)-carbamic acid tert-butyl ester (Example M66) (0.46 g, 0.93 mmol) by treatment with TFA in CH$_2$Cl$_2$ according to the general procedure N. Obtained as a light brown solid (270 mg, 77%).

MS (ISP) 376.4 [(M+H)$^+$]; mp 215° C.

Example 74

8-Chloro-4-[3-(2-methyl-pyridin-4-yl)-phenyl]-1,3-dihydro-benzo[b][1,4]diazepin-2-one The title compound was prepared from (4-chloro-2-{3-[3-(2-methyl-pyridin-4-yl)-phenyl]-3-oxo-propionylamino}-phenyl)-carbamic acid tert-butyl ester (Example M67) (0.40 g, 0.83 mmol) by treatment with TFA in CH$_2$Cl$_2$ according to the general procedure N. Obtained as an off-white solid (239 mg, 79%).

MS (ISP) 362.2 [(M+H)$^+$]; mp 215° C.

Example 75

7-Methyl-4-[3-(2-methyl-pyridin-4-yl)-phenyl]-8-trifluoromethyl-1,3-dihydro benzo[b][1,4]diazepin-2-one The title compound was prepared from (5-methyl-2-{3-[3-(2-methyl-pyridin-4-yl)-phenyl]-3-oxo-propionylamino}-4-trifluoromethyl-phenyl)-carbamic acid tert-butyl ester (Example M68) (0.42 g, 0.80 mmol) by treatment with TFA in CH$_2$Cl$_2$ according to the general procedure N. Obtained as an off-white solid (242 mg, 74%).

MS (ISP) 410.4 [(M+H)$^+$]; mp 229° C.

Example 76

4-[3-(2-Methyl-pyridin-4-yl)-phenyl]-8-trifluoromethyl-1,3-dihydro benzo[b][1,4]diazepin-2-one The title compound was prepared from (2-{3-[3-(2-methyl-pyridin-4-yl)-phenyl]-3-oxo-propionylamino}-4-trifluoromethyl-phenyl)-carbamic acid tert-butyl ester (Example M69) (0.41 g, 0.80 mmol) by treatment with TFA in $CH_2Cl_2$ according to the general procedure N. Obtained as a light yellow solid (172 mg, 54%).

MS (ISP) 396.3 [(M+H)$^+$]; mp 208° C.

Example 77

8-Methyl-4-[3-(2-methyl-pyridin-4-yl)-phenyl]-7-trifluoromethyl-1,3-dihydro benzo[b][1,4]diazepin-2-one The title compound was prepared from (4-methyl-2-{3-[3-(2-methyl-pyridin-4-yl)-phenyl]-3-oxo-propionylamino}-5-trifluoromethyl-phenyl)-carbamic acid tert-butyl ester (Example M70) (0.32 g, 0.61 mmol) by treatment with TFA in $CH_2Cl_2$ according to the general procedure N. Obtained as an off white solid (120 mg, 48%).

MS (ISP) 410.4 [(M+H)$^+$]; mp 215° C.

Example 78

7-Dimethylamino-4-[3-(2-methyl-pyridin-4-yl)-phenyl]-8-trifluoromethyl-1,3-dihydro benzo[b][1,4]diazepin-2-one The title compound was prepared from (5-dimethylamino-2-{3-[3-(2-methyl-pyridin-4-yl)-phenyl]-3-oxo-propionylamino}-4-trifluoromethyl-phenyl)-carbamic acid tert-butyl ester (Example M71) (0.45 g, 0.81 mmol) by treatment with TFA in $CH_2Cl_2$ according to the general procedure N. Obtained as a light yellow solid (205 mg, 58%).

MS (ISP) 439.4 [(M+H)$^+$]; mp 225° C.

Example 79

8-Chloro-7-isobutylamino-4-[3-(2-methyl-pyridin-4-yl)-phenyl]-1,3-dihydro-benzo[b][1,4]diazepin-2-one The title compound was prepared from (4-chloro-5-isobutylamino-2-{3-[3-(2-methyl-pyridin-4-yl)-phenyl]-3-oxo-propionylamino}-phenyl)-carbamic acid tert-butyl ester (Example M72) (0.47 g, 0.85 mmol) by treatment with TFA in $CH_2Cl_2$ according to the general procedure N. Obtained as a light yellow solid (313 mg, 85%).

MS (ISP) 433.5 [(M+H)$^+$]; mp 220° C.

Example 80

7-(Methyl-propyl-amino)-4-[3-(2-methyl-pyridin-4-yl)-phenyl]-8-trifluoromethyl-1,3-dihydro benzo[b][1,4]diazepin-2-one The title compound was prepared from (5-(methyl-propyl-amino)-2-{3-[3-(2-methyl-pyridin-4-yl)-phenyl]-3-oxo-propionylamino}-4-trifluoromethyl-phenyl)-carbamic acid tert-butyl ester (Example M73) (0.46 g, 0.79 mmol) by treatment with TFA in $CH_2Cl_2$ according to the general procedure N. Obtained as a light brown solid (223 mg, 61%).

MS (ISP) 467.3 [(M+H)$^+$]; mp 192° C.

Example 81

7-(Methyl-propyl-amino)-4-(3-pyridin-4-yl-phenyl)-8-trifluoromethyl-1,3-dihydro-benzo[b][1,4]diazepin-2-one The title compound was prepared from {5-(methyl-propyl-amino)-2-[3-oxo-3-(3-pyridin-4-yl-phenyl)-propionylamino]-4-trifluoromethyl-phenyl}-carbamic acid tert-butyl ester (Example M74) (0.54 g, 0.95 mmol) by treatment with TFA in $CH_2Cl_2$ according to the general procedure N. Obtained as a light yellow solid (230 mg, 54%).

MS (ISP) 453.5 [(M+H)$^+$]; mp 192° C.

Example 82

7-Chloro-4-[3-(2-methyl-pyridin-4-yl)-phenyl]-8-trifluoromethyl-1,3-dihydro benzo[b][1,4]diazepin-2-one The title compound was prepared from (5-chloro-2-{3-[3-(2-methyl-pyridin-4-yl)-phenyl]-3-oxo-propionylamino}-4-trifluoromethyl-phenyl)-carbamic acid tert-butyl ester (Example M75) (0.34 g, 0.62 mmol) by treatment with TFA in $CH_2Cl_2$ according to the general procedure N. Obtained as an off-white solid (222 mg, 83%).

MS (ISP) 430.4 [(M+H)$^+$]; mp 221° C.

Example 83

The title compound was prepared from (4-fluoro-2-{3-[3-(2-methyl-pyridin-4-yl)-phenyl]-3-oxo-propionylamino}-phenyl)-carbamic acid tert-butyl ester (Example M76) (0.38 g, 0.82 mmol) by treatment with TFA in $CH_2Cl_2$ according to the general procedure N. Obtained as an off-white solid (230 mg, 81%).

MS (ISP) 346.3 [(M+H)$^+$]; mp 200° C.

Example 84

8-Chloro-7-methyl-4-[3-(2-methyl-pyridin-4-yl)-phenyl]-1,3-dihydro-benzo[b][1,4]diazepin-2-one The title compound was prepared from (5-chloro-4-methyl-2-{3-[3-(2-methyl-pyridin-4-yl)-phenyl]-3-oxo-propionylamino}-phenyl)-carbamic acid tert-butyl ester (Example M77) (0.36 g, 0.72 mmol) by treatment with TFA in $CH_2Cl_2$ according to the general procedure N. Obtained as a light yellow solid (220 mg, 81%).

MS (ISP) 376.4 [(M+H)$^+$]; mp 212° C.

Example 85

7-Dimethylamino-4-(3-pyrimidin-5-yl-phenyl)-8-trifluoromethyl-1,3-dihydro-benzo[b][1,4]diazepin-2-one The title compound was prepared from {5-dimethylamino-2-[3-oxo-3-(3-pyrimidin-5-yl-phenyl)-propionylamino]-4-trifluoromethyl-phenyl}-carbamic acid tert-butyl ester (Example M78) (0.35 g, 0.64 mmol) by treatment with TFA in $CH_2Cl_2$ according to the general procedure N. Obtained as a light yellow solid (170 mg, 62%).

MS (ISP) 426.4 [(M+H)$^+$]; mp 200° C.

Example 86

8-Chloro-7-methyl-4-(3-pyrazin-2-yl-phenyl)-1,3-dihydro-benzo[b][1,4]diazepin-2-one The title compound was prepared from {4-chloro-5-methyl-2-[3-oxo-3-(3-pyrazin-2-yl-phenyl)- propionylamino]-phenyl}-carbamic acid tert-butyl ester (Example M79) (0.31 g, 0.64 mmol) by treatment with TFA in CH$_2$Cl$_2$ according to the general procedure N. Obtained as an off-white solid (208 mg, 89%).

MS (ISP) 361.0 [(M−H)−]; mp 232° C.

Example 87

7-Methyl-4-(3-pyrazin-2-yl-phenyl)-8-trifluoromethyl-1,3-dihydro-benzo[b][1,4]diazepin-2-one The title compound was prepared from {5-methyl-2-[3-oxo-3-(3-pyrazin-2-yl-phenyl)-propionylamino]-4-trifluoromethyl-phenyl}-carbamic acid tert-butyl ester (Example M80) (0.34 g, 0.66 mmol) by treatment with TFA in CH$_2$Cl$_2$ according to the general procedure N. Obtained as a light yellow solid (211 mg, 81%).

MS (ISP) 397.3 [(M+H)+]; mp 237° C.

Example 88

7,8-Dichloro-4-(3-pyrazin-2-yl-phenyl)-1,3-dihydro-benzo[b][1,4]diazepin-2-one

The title compound was prepared from commercially available 4,5-dichloro-1,2-phenylendiamine (177 mg, 1.0 mmol) and 3-oxo-3-(3-pyrazin-2-yl-phenyl)-propionic acid tert-butyl ester (Example K13) (298 mg, 1.0 mmol) in xylene (20 ml) under reflux conditions for 2 h according to the general procedure M. Obtained as a light red solid (258 mg, 67%).

MS (ISP) 381.1 [(M−H)−]; mp 268° C.

Example 89

4-(3-Pyrazin-2-yl-phenyl)-8-trifluoromethyl-1,3-dihydro-benzo[b][1,4]diazepin-2-one The title compound was prepared from {2-[3-oxo-3-(3-pyrazin-2-yl-phenyl)-propionylamino]-4-trifluoromethyl-phenyl}-carbamic acid tert-butyl ester (Example M81) (0.33 g, 0.66 mmol) by treatment with TFA in CH$_2$Cl$_2$ according to the general procedure N. Obtained as an off-white solid (197 mg, 78%).

MS (ISP) 383.3 [(M+H)+]; mp 223° C.

Example 90

7-Dimethylamino-4-(3-pyrazin-2-yl-phenyl)-8-trifluoromethyl-1,3-dihydro-benzo[b][1,4]diazepin-2-one The title compound was prepared from {5-dimethylamino-2-[3-oxo-3-(3-pyrazin-2-yl-phenyl)-propionylamino]-4-trifluoromethyl-phenyl}-carbamic acid tert-butyl ester (Example M82) (0.36 g, 0.66 mmol) by treatment with TFA in CH$_2$Cl$_2$ according to the general procedure N. Obtained as a light yellow solid (163 mg, 58%).

MS (ISP) 426.4 [(M+H)+]; mp 204° C.

Example 91

7-Chloro-4-(3-pyrazin-2-yl-phenyl)-8-trifluoromethyl-1,3-dihydro-benzo[b][1,4]diazepin-2-one The title compound was prepared from {5-chloro-2-[3-oxo-3-(3-pyrazin-2-yl-phenyl)-propionylamino]-4-trifluoromethyl-phenyl}-carbamic acid tert-butyl ester (Example M83) (0.17 g, 0.32 mmol) by treatment with TFA in CH$_2$Cl$_2$ according to the general procedure N. Obtained as an off-white solid (98 mg, 74%).

MS (ISP) 415.1 [(M−H)−]; mp 235° C.

Example 92

8-(2-Fluoro-phenyl)-4-(3-pyrazin-2-yl-phenyl)-1,3-dihydro-benzo[b][1,4]diazepin-2-one The title compound was prepared from {2'-fluoro-3-[3-oxo-3-(3-pyrazin-2-yl-phenyl)-propionylamino]-biphenyl-4-yl}-carbamic acid tert-butyl ester (Example M84) (0.34 g, 0.65 mmol) by treatment with TFA in CH$_2$Cl$_2$ according to the general procedure N. Obtained as a light yellow solid (250 mg, 95%).

MS (ISP) 409.4 [(M+H)+]; mp 241° C.

Example 93

8-Methyl-4-(3-pyrazin-2-yl-phenyl)-7-trifluoromethyl-1,3-dihydro-benzo[b][1,4]diazepin-2-one The title compound was prepared from {4-methyl-2-[3-oxo-3-(3-pyrazin-2-yl-phenyl)-propionylamino]-5-trifluoromethyl-phenyl}-carbamic acid tert-butyl ester (Example M85) (0.28 g, 0.54 mmol) by treatment with TFA in CH$_2$Cl$_2$ according to the general procedure N. Obtained as a light yellow solid (146 mg, 68%).

MS (ISP) 397.2 [(M+H)+]; mp 216° C.

Example 94

8-Chloro-4-(3-pyrimidin-5-yl-phenyl)-1,3-dihydro-benzo[b][1,4]diazepin-2-one

The title compound was prepared from {4-chloro-2-[3-oxo-3-(3-pyrimidin-5-yl-phenyl)-propionylamino]-phenyl}-carbamic acid tert-butyl ester (Example M86) (0.35 g, 0.75 mmol) by treatment with TFA in CH$_2$Cl$_2$ according to the general procedure N. Obtained as a light brown solid (230 mg, 88%).

MS (ISP) 349.3 [(M+H)+]; mp 234° C.

Example 95

7-Chloro-4-(3-pyrimidin-5-yl-phenyl)-8-trifluoromethyl-1,3-dihydro-benzo[b][1,4]diazepin-2-one The title compound was prepared from {5-chloro-2-[3-oxo-3-(3-pyrimidin-5-yl-phenyl)-propionylamino]-4-trifluoromethyl-phenyl}-carbamic acid tert-butyl ester (Example M87) (0.42 g, 0.90 mmol) by treatment with TFA in CH$_2$Cl$_2$ according to the general procedure N. Obtained as a light red solid (230 mg, 61%).

MS (ISP) 415.1 [(M−H)−]; mp 222° C.

Example 96

8-Chloro-7-isobutylamino-4-(3-pyrimidin-5-yl-phenyl)-1,3-dihydro-benzo[b][1,4]diazepin-2-one The title compound was prepared from {4-chloro-5-isobutylamino-2-[3-oxo-3-(3-pyrimidin-5-yl-phenyl)-propionylamino]-phenyl}-carbamic acid tert-butyl ester (Example M88) (0.28 g, 0.52 mmol) by treatment with TFA in CH₂Cl₂ according to the general procedure N. Obtained as a yellow solid (200 mg, 92%).

MS (ISP) 420.4 [(M+H)⁺]; mp 241° C.

Example 97

7,8-Dichloro-4-(3-pyrimidin-5-yl-phenyl)-1,3-dihydro-benzo[b][1,4]diazepin-2-one The title compound was prepared from commercially available 4,5-dichloro-1,2-phenylendiamine (133 mg, 0.75 mmol) and 3-oxo-3-(3-pyrimidin-5-yl-phenyl)-propionic acid tert-butyl ester (Example K14) (223 mg, 0.75 mmol) in xylene (15 ml) under reflux conditions for 2 h according to the general procedure M. Obtained as a light red solid (250 mg, 87%).

MS (ISP) 381.3 [(M−H)⁻]; mp 272° C.

Example 98

7-Methyl-4-(3-pyrimidin-5-yl-phenyl)-8-trifluoromethyl-1,3-dihydro-benzo[b][1,4]diazepin-2-one The title compound was prepared from {5-methyl-2-[3-oxo-3-(3-pyrimidin-5-yl-phenyl)-propionylamino]-4-trifluoromethyl-phenyl}-carbamic acid tert-butyl ester (Example M89) (0.29 g, 0.56 mmol) by treatment with TFA in CH₂Cl₂ according to the general procedure N. Obtained as an off-white solid (170 mg, 76%).

MS (ISP) 495.4 [(M−H)⁻]; mp 233° C.

Example 99

7-(Methyl-propyl-amino)-4-(3-pyrimidin-5-yl-phenyl)-8-trifluoromethyl-1,3-dihydro-benzo[b][1,4]diazepin-2-one The title compound was prepared from {5-(methyl-propyl-amino)-2-[3-oxo-3-(3-pyrimidin-5-yl-phenyl)-propionylamino]-4-trifluoromethyl-phenyl}-carbamic acid tert-butyl ester (Example M90) (0.40 g, 0.70 mmol) by treatment with TFA in CH₂Cl₂ according to the general procedure N. Obtained as a light orange solid (210 mg, 66%).

MS (ISP) 454.5 [(M+H)⁺]; mp 197° C.

Example 100

8-Chloro-4-(3-pyridin-4-yl-phenyl)-7-trifluoromethyl-1,3-dihydro-benzo[b][1,4]diazepin-2-one The title compound was prepared from {4-chloro-2-[3-oxo-3-(3-pyridin-4-yl-phenyl)-propionylamino]-5-trifluoromethyl-phenyl}-carbamic acid tert-butyl ester (Example M92) (0.44 g, 0.82 mmol) by treatment with TFA in CH₂Cl₂ according to the general procedure N. Obtained as a light orange solid (120 mg, 35%).

MS (ISP) 416.3 [(M+H)⁺]; mp 200° C.

Example 101

8-Chloro-4-[3-(2-methyl-pyridin-4-yl)-phenyl]-7-trifluoromethyl-1,3-dihydro benzo[b][1,4]diazepin-2-one The title compound was prepared from (4-chloro-2-{3-[3-(2-methyl-pyridin-4-yl)-phenyl]-3-oxo-propionylamino}-5-trifluoromethyl-phenyl)-carbamic acid tert-butyl ester (Example M91) (0.36 g, 0.66 mmol) by treatment with TFA in CH₂Cl₂ according to the general procedure N. Obtained as a light yellow solid (250 mg, 88%).

MS (ISP) 430.4 [(M+H)⁺]; mp 201° C.

Example 102

7-(Methyl-propyl-amino)-4-(3-pyrazin-2-yl-phenyl)-8-trifluoromethyl-1,3-dihydro-benzo[b][1,4]diazepin-2-one The title compound was prepared from {5-(methyl-propyl-amino)-2-[3-oxo-3-(3-pyrazin-2-yl-phenyl)-propionylamino]-4-trifluoromethyl-phenyl}-carbamic acid tert-butyl ester (Example M93) (0.34 g, 0.59 mmol) by treatment with TFA in CH₂Cl₂ according to the general procedure N. Obtained as a light brown solid (176 mg, 65%).

MS (ISP) 454.5 [(M+H)⁺]; mp 201° C.

Example 103

7-Chloro-8-methyl-4-(3-pyrazin-2-yl-phenyl)-1,3-dihydro-benzo[b][1,4]diazepin-2-one The title compound was prepared from {5-chloro-4-methyl-2-[3-oxo-3-(3-pyrazin-2-yl-phenyl)-propionylamino]-phenyl}-carbamic acid tert-butyl ester (Example M94) (0.38 g, 0.79 mmol) by treatment with TFA in CH₂Cl₂ according to the general procedure N. Obtained as an off-white solid (240 mg, 84%).

MS (ISP) 363.1 [(M+H)⁺]; mp 218° C.

Example 104

8-Chloro-7-methyl-4-(3-pyrimidin-5-yl-phenyl)-1,3-dihydro-benzo[b][1,4]diazepin-2-one The title compound was prepared from {4-chloro-5-methyl-2-[3-oxo-3-(3-pyrimidin-5-yl-phenyl)-propionylamino]-phenyl}-carbamic acid tert-butyl ester (Example M95) (0.44 g, 0.92 mmol) by treatment with TFA in CH₂Cl₂ according to the general procedure N. Obtained as a light yellow solid (180 mg, 89%).

MS (ISP) 363.1 [(M+H)⁺]; mp 248° C.

Example 105

8-(2-Fluoro-phenyl)-4-(3-pyrimidin-5-yl-phenyl)-1,3-dihydro-benzo[b][1,4]diazepin-2-one The title compound was prepared from {2'-fluoro-3-[3-oxo-3-(3-pyrimidin-5-yl-phenyl)-propionylamino]-biphenyl-4-yl}-carbamic acid tert-butyl ester (Example M96) (0.42 g, 0.80 mmol) by treatment with TFA in CH₂Cl₂ according to the general procedure N. Obtained as a light yellow solid (230 mg, 71%).

MS (ISP) 407.3 [(M−H)⁻]; mp 223° C.

Example 106

8-Methyl-4-(3-pyrimidin-5-yl-phenyl)-7-trifluoromethyl-1,3-dihydro-benzo[b][1,4]diazepin-2-one The title compound was prepared from {4-methyl-2-[3-oxo-3-(3-pyrimidin-5-yl-phenyl)-propionylamino]-5-

Example 107

8-Chloro-4-(3-pyridin-2-yl-phenyl)-7-trifluoromethyl-1,3-dihydro-benzo[b][1,4]diazepin-2-one The title compound was prepared from {4-chloro-2-[3-oxo-3-(3-pyridin-2-yl-phenyl)-propionylamino]-5-trifluoromethyl-phenyl}-carbamic acid tert-butyl ester (Example M98) (0.27 g, 0.51 mmol) by treatment with TFA in CH$_2$Cl$_2$ according to the general procedure N. Obtained as a light brown solid (120 mg, 57%).

MS (ISP) 416.2 [(M+H)$^+$]; mp 208° C.

Example 108

4-[3-(2-Methyl-pyridin-4-yl)-phenyl]-8-pyrrol-1-yl-1,3-dihydro-benzo[b][1,4]diazepin-2-one Prepared from (2-{3-[3-(2-methyl-pyridin-4-yl)-phenyl]-3-oxo-propionylamino}-4-pyrrol-1-yl-phenyl)-carbamic acid tert-butyl ester (Example M99) (0.46 g, 0.90 mmol) by treatment with TFA in CH$_2$Cl$_2$ according to the general procedure N. Obtained as a light orange solid (220 mg, 62%).

MS (ISP) 393.3 [(M+H)$^+$]; mp 206° C.

Example 109

4-(3-Pyrazin-2-yl-phenyl)-8-pyrrol-1-yl-1,3-dihydro-benzo[b][1,4]diazepin-2-one

The title compound was prepared from {2-[3-oxo-3-(3-pyrazin-2-yl-phenyl)-propionylamino]-4-pyrrol-1-yl-phenyl}-carbamic acid tert-butyl ester (Example M100) (0.37 g, 0.74 mmol) by treatment with TFA in CH$_2$Cl$_2$ according to the general procedure N. Obtained as a light brown solid (170 mg, 60%).

MS (ISP) 380.4 [(M+H)$^+$]; mp 214° C.

Example 110

8-Chloro-4-(3-pyrazin-2-yl-phenyl)-7-trifluoromethyl-1,3-dihydro-benzo[b][1,4]diazepin-2-one The title compound was prepared from {4-chloro-2-[3-oxo-3-(3-pyrazin-2-yl-phenyl)-propionylamino]-5-trifluoromethyl-phenyl}-carbamic acid tert-butyl ester (Example M101) (0.28 g, 0.52 mmol) by treatment with TFA in CH$_2$Cl$_2$ according to the general procedure N. Obtained as a light brown solid (50 mg, 23%).

MS (ISP) 415.1 [(M−H)$^-$]; mp 214° C.

Example 111

8-Chloro-4-(3-pyrimidin-5-yl-phenyl)-7-trifluoromethyl-1,3-dihydro-benzo[b][1,4]diazepin-2-one The title compound was prepared from {4-chloro-2-[3-oxo-3-(3-pyrimidin-5-yl-phenyl)-propionylamino]-5-trifluoromethyl-phenyl}-carbamic acid tert-butyl ester (Example M102) (0.31 g, 0.58 mmol) by treatment with TFA in CH$_2$Cl$_2$ according to the general procedure N. Obtained as a light brown solid (110 mg, 46%).

MS (ISP) 415.1 [(M−H)$^-$]; mp 217° C.

Example 112

4-(3-Pyrazin-2-yl-phenyl)-7-(2,2,2-trifluoro-ethoxy)-8-trifluoromethyl-1,3-dihydro-benzo[b][1,4]diazepin-2-one The title compound was prepared from [2-[3-oxo-3-(3-pyrazin-2-yl-phenyl)-propionylamino]-5-(2,2,2-trifluoro-ethoxy)-4-trifluoromethyl-phenyl]-carbamic acid tert-butyl ester (Example M103) (0.37 g, 0.62 mmol) by treatment with TFA in CH$_2$Cl$_2$ according to the general procedure N. Obtained as a light yellow solid (220 mg, 74%).

MS (ISP) 481.2 [(M+H)$^+$]; mp 242° C.

Example 113

8-Chloro-4-(3-pyridin-3-yl-phenyl)-7-trifluoromethyl-1,3-dihydro-benzo[b][1,4]diazepin-2-one The title compound was prepared from {4-chloro-2-[3-oxo-3-(3-pyridin-3-yl-phenyl)-propionylamino]-5-trifluoromethyl-phenyl}-carbamic acid tert-butyl ester (Example M104) (0.23 g, 0.43 mmol) by treatment with TFA in CH$_2$Cl$_2$ according to the general procedure N. Obtained as a light orange solid (150 mg, 84%).

MS (ISP) 416.3 [(M+H)$^+$]; mp 208° C.

Example 114

4-[3-(2-Methyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-methyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M105) (0.41 g, 0.67 mmol) by treatment with TFA in CH$_2$Cl$_2$ according to the general procedure N. Obtained as a light brown solid (260 mg, 79%).

MS (ISP) 494.3 [(M+H)$^+$]; mp 223° C.

Example 115

7,8-Difluoro-4-[3-(2-methyl-pyridin-4-yl)-phenyl]-1,3-dihydro-benzo[b][1,4]diazepin-2-one The title compound was prepared from commercially available 4,5-difluoro-1,2-phenylendiamine (400 mg, 2.78 mmol) and 3-[3-(2-methyl-pyridin-4-yl)-phenyl]-3-oxo-propionic acid tert-butyl ester (Example K12) (864 mg, 2.78 mmol) in xylene (15 ml) under reflux conditions for 1.5 h according to the general procedure M. Obtained as a light brown solid (780 mg, 77%).

MS (ISP) 364.2 [(M+H)$^+$]; mp 217° C.

Example 116

7,8-Difluoro-4-(3-pyridin-3-yl-phenyl)-1,3-dihydro-benzo[b][1,4]diazepin-2-one

The title compound was prepared from commercially available 4,5-difluoro-1,2-phenylendiamine (144 mg, 1.0 mmol) and 3-oxo-3-(3-pyridin-3-yl-phenyl)-propionic acid tert-butyl ester (Example K1) (297 mg, 1.0 mmol) in xylene (6 ml) under reflux conditions for 1.5 h according to the general procedure M. Obtained as an off-white solid (224 mg, 64%).

MS (ISP) 350.2 [(M+H)$^+$]; mp 246° C.

Example 117

8-Chloro-4-[3-(2,6-dimethyl-pyridin-4-yl)-phenyl]-7-methyl-1,3-dihydro-benzo[b][1,4]diazepin-2-one The title compound was prepared from (4-chloro-2-{3-[3-(2,6-dimethyl-pyridin-4-yl)-phenyl]-5-methyl-3-oxo-propionylamino}-phenyl)-carbamic acid tert-butyl ester (Example M106) (0.28 g, 0.55 mmol) by treatment with TFA in CH$_2$Cl$_2$ according to the general procedure N. Obtained as an off-white solid (174 mg, 81%).

MS (ISP) 390.3 [(M+H)$^+$]; mp 226° C.

Example 118

8-Chloro-4-[3-(2,6-dimethyl-pyridin-4-yl)-phenyl]-1,3-dihydro-benzo[b][1,4]diazepin-2-one The title compound was prepared from (4-chloro-2-{3-[3-(2,6-dimethyl-pyridin-4-yl)-phenyl]-3-oxo-propionylamino}-phenyl)-carbamic acid tert-butyl ester (Example M107) (0.23 g, 0.47 mmol) by treatment with TFA in CH$_2$Cl$_2$ according to the general procedure N. Obtained as a light brown solid (133 mg, 76%).

MS (ISP) 376.4 [(M+H)$^+$]; mp 236° C.

Example 119

4-[3-(2,6-Dimethyl-pyridin-4-yl)-phenyl]-7-methyl-8-trifluoromethyl-1,3-dihydro benzo[b][1,4]diazepin-2-one The title compound was prepared from (2-{3-[3-(2,6-dimethyl-pyridin-4-yl)-phenyl]-5-methyl-3-oxo-propionylamino}-4-trifluoromethyl-phenyl)-carbamic acid tert-butyl ester (Example M108) (0.29 g, 0.54 mmol) by treatment with TFA in CH$_2$Cl$_2$ according to the general procedure N. Obtained as a light yellow solid (138 mg, 61%).

MS (ISP) 424.4 [(M+H)$^+$]; mp 229° C.

Example 120

4-[3-(2,6-Dimethyl-pyridin-4-yl)-phenyl]-8-trifluoromethyl-1,3-dihydro benzo[b][1,4]diazepin-2-one The title compound was prepared from (2-{3-[3-(2,6-dimethyl-pyridin-4-yl)-phenyl]-3-oxo-propionylamino}-4-trifluoromethyl-phenyl)-carbamic acid tert-butyl ester (Example M109) (0.26 g, 0.49 mmol) by treatment with TFA in CH$_2$Cl$_2$ according to the general procedure N. Obtained as a light yellow solid (110 mg, 55%).

MS (ISP) 410.4 [(M+H)$^+$]; mp 221° C.

Example 121

4-[3-(2,6-Dimethyl-pyridin-4-yl)-phenyl]-8-methyl-7-trifluoromethyl-1,3-dihydro benzo[b][1,4]diazepin-2-one The title compound was prepared from (2-{3-[3-(2,6-dimethyl-pyridin-4-yl)-phenyl]-4-methyl-3-oxo-propionylamino}-5-trifluoromethyl-phenyl)-carbamic acid tert-butyl ester (Example M110) (0.29 g, 0.54 mmol) by treatment with TFA in CH$_2$Cl$_2$ according to the general procedure N. Obtained as an off-white solid (176 mg, 78%).

MS (ISP) 424.5 [(M+H)$^+$]; mp 223° C.

Example 122

7-Chloro-4-[3-(2,6-dimethyl-pyridin-4-yl)-phenyl]-8-trifluoromethyl-1,3-dihydro benzo[b][1,4]diazepin-2-one The title compound was prepared from (5-chloro-2-{3-[3-(2,6-dimethyl-pyridin-4-yl)-phenyl]-3-oxo-propionylamino}-4-trifluoromethyl-phenyl)-carbamic acid tert-butyl ester (Example M111) (0.25 g, 0.44 mmol) by treatment with TFA in CH$_2$Cl$_2$ according to the general procedure N. Obtained as a light yellow solid (167 mg, 85%).

MS (ISP) 444.3 [(M+H)$^+$]; mp 229° C.

Example 123

8-Chloro-7-methyl-4-[3-(2,6-dimethyl-pyridin-4-yl)-phenyl]-1,3-dihydro-benzo[b][1,4]diazepin-2-one The title compound was prepared from (5-chloro-2-{3-[3-(2,6-dimethyl-pyridin-4-yl)-phenyl]-4-methyl-3-oxo-propionylamino}-phenyl)-carbamic acid tert-butyl ester (Example M112) (0.28 g, 0.55 mmol) by treatment with TFA in CH$_2$Cl$_2$ according to the general procedure N. Obtained as a light brown solid (204 mg, 95%).

MS (ISP) 390.3 [(M+H)$^+$]; mp 188° C.

Example 124

7,8-Dichloro-4-[3-(2,6-dimethyl-pyridin-4-yl)-phenyl]-1,3-dihydro-benzo[b][1,4]diazepin-2-one The title compound was prepared from commercially available 4,5-dichloro-1,2-phenylendiamine (109 mg, 0.61 mmol) and 3-[3-(2,6-dimethyl-pyridin-4-yl)-phenyl]-3-oxo-propionic acid tert-butyl ester (Example K15) (200 mg, 0.61 mmol) in xylene (10 ml) under reflux conditions for 2 h according to the general procedure M. Obtained as a light brown solid (173 mg, 69%).

MS (ISP) 410.3 [(M+H)$^+$]; mp 226° C.

Example 125

4-[3-(2,6-Dimethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2,6-dimethyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M114) (0.50 g, 0.80 mmol) by treatment with TFA in CH$_2$Cl$_2$ according to the general procedure N. Obtained as a light brown solid (274 mg, 68%).

MS (ISP) 508.3 [(M+H)$^+$]; mp 232° C.

Example 126

7,8-Difluoro-4-[3-(2,6-dimethyl-pyridin-4-yl)-phenyl]-1,3-dihydro-benzo[b][1,4]diazepin-2-one The title compound was prepared from commercially available 4,5-difluoro-1,2-phenylendiamine (400 mg, 2.78 mmol) and 3-[3-(2,6-dimethyl-pyridin-4-yl)-phenyl]-3-oxo-propionic acid tert-butyl ester (Example K15) (903 mg, 2.78 mmol) in xylene (15 ml) under reflux conditions for 1.5 h according to the general procedure M. Obtained as a light brown solid (860 mg, 82%).

MS (ISP) 378.2 [(M+H)+]; mp 252° C.

Example 127

4-[3-(2,6-Dimethyl-pyridin-4-yl)-phenyl]-7-ethoxy-8-trifluoromethyl-1,3-dihydro-benzo[b][1,4]diazepin-2-one The title compound was prepared from [2-{3-[3-(2,6-dimethyl-pyridin-4-yl)-phenyl]-3-oxo-propionylamino}-5-ethoxy-4-trifluoromethyl-phenyl]-carbamic acid tert-butyl ester (Example M115) (0.52 g, 0.91 mmol) by treatment with TFA in $CH_2Cl_2$ according to the general procedure N. Obtained as a light yellow solid (337 mg, 82%).

MS (ISP) 454.5 [(M+H)+]; mp 239° C.

Example 128

8-Chloro-4-[3-(2,6-dimethyl-pyridin-4-yl)-phenyl]-7-trifluoromethyl-1,3-dihydro benzo[b][1,4]diazepin-2-one The title compound was prepared from (4-chloro-2-{3-[3-(2,6-dimethyl-pyridin-4-yl)-phenyl]-3-oxo-propionylamino}-5-trifluoromethyl-phenyl)-carbamic acid tert-butyl ester (Example M113) (0.32 g, 0.57 mmol) by treatment with TFA in $CH_2Cl_2$ according to the general procedure N. Obtained as a light yellow solid (170 mg, 67%).

MS (ISP) 444.3 [(M+H)+]; mp 207° C.

Example 129

7-Methyl-4-[3-(6-methyl-pyrazin-2-yl)-phenyl]-8-trifluoromethyl-1,3-dihydro-benzo[b][1,4]diazepin-2-one The title compound was prepared from (5-methyl-2-{3-[3-(6-methyl-pyrazin-2-yl)-phenyl]-3-oxo-propionylamino}-4-trifluoromethyl-phenyl)-carbamic acid tert-butyl ester (Example M117) (0.46 g, 0.85 mmol) by treatment with TFA in $CH_2Cl_2$ according to the general procedure N. Obtained as an off-white solid (280 mg, 80%).

MS (ISP) 411.3 [(M+H)+]; mp 233° C.

Example 130

8-Methyl-4-[3-(6-methyl-pyrazin-2-yl)-phenyl]-7-trifluoromethyl-1,3-dihydro-benzo[b][1,4]diazepin-2-one The title compound was prepared from (4-methyl-2-{3-[3-(6-methyl-pyrazin-2-yl)-phenyl]-3-oxo-propionylamino}-5-trifluoromethyl-phenyl)-carbamic acid tert-butyl ester (Example M118) (0.39 g, 0.74 mmol) by treatment with TFA in $CH_2Cl_2$ according to the general procedure N. Obtained as an off-white solid (237 mg, 78%).

MS (ISP) 411.4 [(M+H)+]; mp 211° C.

Example 131

8-Chloro-7-methyl-4-[3-(6-methyl-pyrazin-2-yl)-phenyl]-1,3-dihydro-benzo[b][1,4]diazepin-2-one The title compound was prepared from (4-chloro-5-methyl-2-{3-[3-(6-methyl-pyrazin-2-yl)-phenyl]-3-oxo-propionylamino}-phenyl)-carbamic acid tert-butyl ester (Example M116) (0.46 g, 0.93 mmol) by treatment with TFA in $CH_2Cl_2$ according to the general procedure N. Obtained as a light brown solid (270 mg, 77%).

MS (ISP) 377.3 [(M+H)+]; mp 235° C.

Example 132

7-Chloro-8-methyl-4-[3-(6-methyl-pyrazin-2-yl)-phenyl]-1,3-dihydro-benzo[b][1,4]diazepin-2-one The title compound was prepared from (5-chloro-4-methyl-2-{3-[3-(6-methyl-pyrazin-2-yl)-phenyl]-3-oxo-propionylamino}-phenyl)-carbamic acid tert-butyl ester (Example M119) (0.39 g, 0.79 mmol) by treatment with TFA in $CH_2Cl_2$ according to the general procedure N. Obtained as a light yellow solid (260 mg, 88%).

MS (ISP) 377.4 [(M+H)+]; mp 254° C.

Example 133

7,8-Dichloro-4-[3-(6-methyl-pyrazin-2-yl)-phenyl]-1,3-dihydro-benzo[b][1,4]diazepin-2-one The title compound was prepared from commercially available 4,5-dichloro-1,2-phenylendiamine (177 mg, 1.0 mmol) and 3-[3-(6-methyl-pyrazin-2-yl)-phenyl]-3-oxo-propionic acid tert-butyl ester (Example K16) (312 mg, 1.0 mmol) in xylene (10 ml) under reflux conditions for 1.5 h according to the general procedure M. Obtained as a light red solid (329 mg, 83%).

MS (ISP) 395.1 [(M+H)+]; mp 265° C.

Example 134

8-Chloro-4-[3-(2,5-dimethyl-pyridin-4-yl)-phenyl]-7-methyl-1,3-dihydro-benzo[b][1,4]diazepin-2-one The title compound was prepared from (4-chloro-2-{3-[3-(2,5-dimethyl-pyridin-4-yl)-phenyl]-5-methyl-3-oxo-propionylamino}-phenyl)-carbamic acid tert-butyl ester (Example M120) (0.23 g, 0.45 mmol) by treatment with TFA in $CH_2Cl_2$ according to the general procedure N. Obtained as a light brown solid (150 mg, 85%).

MS (ISP) 390.3 [(M+H)+]; mp 208° C.

Example 135

4-[3-(2,5-Dimethyl-pyridin-4-yl)-phenyl]-7-methyl-8-trifluoromethyl-1,3-dihydro benzo[b][1,4]diazepin-2-one The title compound was prepared from (2-{3-[3-(2,5-dimethyl-pyridin-4-yl)-phenyl]-5-methyl-3-oxo-propionylamino}-4-trifluoromethyl-phenyl)-carbamic acid tert-butyl ester (Example M121) (0.36 g, 0.67 mmol) by treatment with TFA in $CH_2Cl_2$ according to the general procedure N. Obtained as a light yellow solid (210 mg, 75%).

MS (ISP) 424.5 [(M+H)+]; mp 211° C.

Example 136

7-Chloro-4-[3-(2,5-dimethyl-pyridin-4-yl)-phenyl]-8-trifluoromethyl-1,3-dihydro benzo[b][1,4]diazepin-2-one The title compound was prepared from (5-chloro-2-{3-[3-(2,5-dimethyl-pyridin-4-yl)-phenyl]-3-oxopropionylamino}-4-trifluoromethyl-phenyl)-carbamic acid tert-butyl ester (Example M122) (0.24 g, 0.43 mmol) by treatment with TFA in CH$_2$Cl$_2$ according to the general procedure N. Obtained as a light brown solid (110 mg, 58%).

MS (ISP) 444.3 [(M+H)$^+$]; mp 214° C.

Example 137

7,8-Dichloro-4-[3-(2,5-dimethyl-pyridin-4-yl)-phenyl]-1,3-dihydro-benzo[b][1,4]diazepin-2-one The title compound was prepared from commercially available 4,5-dichloro-1,2-phenylendiamine (133 mg, 0.75 mmol) and 3-[3-(2,5-dimethyl-pyridin-4-yl)-phenyl]-3-oxo-propionic acid tert-butyl ester (Example K17) (244 mg, 0.75 mmol) in xylene (15 ml) under reflux conditions for 2 h according to the general procedure M. Obtained as a light red solid (210 mg, 68%).

MS (ISP) 410.4 [(M+H)$^+$]; mp 208° C.

Example 138

4-[3-(2,5-Dimethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2,5-dimethyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M123) (0.29 g, 0.46 mmol) by treatment with TFA in CH$_2$Cl$_2$ according to the general procedure N. Obtained as a light yellow solid (220 mg, 94%).

MS (ISP) 508.4 [(M+H)$^+$]; mp 202° C.

Example 139

4-[3-(2,5-Dimethyl-pyridin-4-yl)-phenyl]-7-ethoxy-8-trifluoromethyl-1,3-dihydro-benzo[b][1,4]diazepin-2-one The title compound was prepared from [2-{3-[3-(2,5-dimethyl-pyridin-4-yl)-phenyl]-3-oxo-propionylamino}-5-ethoxy-4-trifluoromethyl-phenyl]-carbamic acid tert-butyl ester (Example M124) (0.25 g, 0.44 mmol) by treatment with TFA in CH$_2$Cl$_2$ according to the general procedure N. Obtained as a light yellow solid (170 mg, 86%).

MS (ISP) 454.5 [(M+H)$^+$]; mp 189° C.

Example 140

8-Chloro-4-[3-(2,3-dimethyl-pyridin-4-yl)-phenyl]-7-methyl-1,3-dihydro-benzo[b][1,4]diazepin-2-one The title compound was prepared from (4-chloro-2-{3-[3-(2,3-dimethyl-pyridin-4-yl)-phenyl]-5-methyl-3-oxo-propionylamino}-phenyl)-carbamic acid tert-butyl ester (Example M125) (0.27 g, 0.53 mmol) by treatment with TFA in CH$_2$Cl$_2$ according to the general procedure N. Obtained as a light yellow solid (140 mg, 68%).

MS (ISP) 390.1 [(M+H)$^+$]; mp 224° C.

Example 141

4-[3-(2,3-Dimethyl-pyridin-4-yl)-phenyl]-7-methyl-8-trifluoromethyl-1,3-dihydro benzo[b][1,4]diazepin-2-one The title compound was prepared from (2-{3-[3-(2,3-dimethyl-pyridin-4-yl)-phenyl]-5-methyl-3-oxo-propionylamino}-4-trifluoromethyl-phenyl)-carbamic acid tert-butyl ester (Example M126) (0.24 g, 0.44 mmol) by treatment with TFA in CH$_2$Cl$_2$ according to the general procedure N. Obtained as a light brown solid (130 mg, 69%).

MS (ISP) 424.3 [(M+H)$^+$]; mp 222° C.

Example 142

4-[3-(2,3-Dimethyl-pyridin-4-yl)-phenyl]-8-trifluoromethyl-1,3-dihydro benzo[b][1,4]diazepin-2-one The title compound was prepared from (2-{3-[3-(2,3-dimethyl-pyridin-4-yl)-phenyl]-3-oxo-propionylamino}-4-trifluoromethyl-phenyl)-carbamic acid tert-butyl ester (Example M127) (0.27 g, 0.51 mmol) by treatment with TFA in CH$_2$Cl$_2$ according to the general procedure N. Obtained as a light brown solid (100 mg, 48%).

MS (ISP) 410.3 [(M+H)$^+$]; mp 200° C.

Example 143

7-Chloro-4-[3-(2,3-dimethyl-pyridin-4-yl)-phenyl]-8-trifluoromethyl-1,3-dihydro benzo[b][1,4] diazepin-2-one The title compound was prepared from (5-chloro-2-{3-[3-(2,3-dimethyl-pyridin-4-yl)-phenyl]-3-oxo-propionylamino}-4-trifluoromethyl-phenyl)-carbamic acid tert-butyl ester (Example M128) (0.31 g, 0.55 mmol) by treatment with TFA in CH$_2$Cl$_2$ according to the general procedure N. Obtained as a light yellow solid (130 mg, 53%).

MS (ISP) 444.3 [(M+H)$^+$]; mp 212° C.

Example 144

7,8-Dichloro-4-[3-(2,3-dimethyl-pyridin-4-yl)-phenyl]-1,3-dihydro-benzo[b][1,4]diazepin-2-one The title compound was prepared from commercially available 4,5-dichloro-1,2-phenylendiamine (133 mg, 0.75 mmol) and 3-[3-(2,3-dimethyl-pyridin-4-yl)-phenyl]-3-oxo-propionic acid tert-butyl ester (Example K18) (244 mg, 0.75 mmol) in xylene (15 ml) under reflux conditions for 2 h according to the general procedure M. Obtained as a light brown solid (140 mg, 45%).

MS (ISP) 410.3 [(M+H)$^+$]; mp 219° C.

Example 145

4-[3-(2,3-Dimethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2,3-dimethyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M129) (0.32 g, 0.51 mmol) by treatment with TFA in CH$_2$Cl$_2$ according to the general procedure N. Obtained as a light brown solid (180 mg, 69%).

MS (ISP) 508.3 [(M+H)$^+$]; mp 222° C.

Example 146

4-[3-(2,3-Dimethyl-pyridin-4-yl)-phenyl]-7-ethoxy-8-trifluoromethyl-1,3-dihydro-benzo[b][1,4]diazepin-2-one The title compound was prepared from [2-{3-[3-(2,3-dimethyl-pyridin-4-yl)-phenyl]-3-oxo-propionylamino}-5- ethoxy-4-trifluoromethyl-phenyl]-carbamic acid tert-butyl ester (Example M130) (0.33 g, 0.58 mmol) by treatment with TFA in CH$_2$Cl$_2$ according to the general procedure N. Obtained as a light yellow solid (160 mg, 61%).

MS (ISP) 454.4 [(M+H)$^+$]; mp 217° C.

Example 147

8-Chloro-4-[3-(5-ethyl-2-methyl-pyridin-4-yl)-phenyl]-7-methyl-1,3-dihydro-benzo[b][1,4]diazepin-2-one The title compound was prepared from (4-chloro-2-{3-[3-(5-ethyl-2-methyl-pyridin-4-yl)-phenyl]-5-methyl-3-oxo-propionylamino}-phenyl)-carbamic acid tert-butyl ester (Example M131) (0.32 g, 0.61 mmol) by treatment with TFA in CH$_2$Cl$_2$ according to the general procedure N. Obtained as an off-white solid (170 mg, 69%).

MS (ISP) 404.4 [(M+H)$^+$]; mp 195° C.

Example 148

4-[3-(5-Ethyl-2-methyl-pyridin-4-yl)-phenyl]-7-methyl-8-trifluoromethyl-1,3-dihydro benzo[b][1,4]diazepin-2-one The title compound was prepared from (2-{3-[3-(5-ethyl-2-methyl-pyridin-4-yl)-phenyl]-5-methyl-3-oxo-propionylamino}-4-trifluoromethyl-phenyl)-carbamic acid tert-butyl ester (Example M132) (0.29 g, 0.52 mmol) by treatment with TFA in CH$_2$Cl$_2$ according to the general procedure N. Obtained as a light yellow solid (160 mg, 70%).

MS (ISP) 438.4 [(M+H)$^+$]; mp 182° C.

Example 149

4-[3-(5-Ethyl-2-methyl-pyridin-4-yl)-phenyl]-8-trifluoromethyl-1,3-dihydro benzo[b][1,4]diazepin-2-one The title compound was prepared from (2-{3-[3-(5-ethyl-2-methyl-pyridin-4-yl)-phenyl]-3-oxo-propionylamino}-4-trifluoromethyl-phenyl)-carbamic acid tert-butyl ester (Example M133) (0.26 g, 0.49 mmol) by treatment with TFA in CH$_2$Cl$_2$ according to the general procedure N. Obtained as an off-white solid (170 mg, 87%).

MS (ISP) 424.4 [(M+H)$^+$]; mp 183° C.

Example 150

7,8-Dichloro-4-[3-(5-ethyl-2-methyl-pyridin-4-yl)-phenyl]-1,3-dihydro-benzo[b][1,4]diazepin-2-one The title compound was prepared from commercially available 4,5-dichloro-1,2-phenylendiamine (133 mg, 0.75 mmol) and 3-[3-(5-ethyl-2-methyl-pyridin-4-yl)-phenyl]-3-oxo-propionic acid tert-butyl ester (Example K19) (255 mg, 0.75 mmol) in xylene (15 ml) under reflux conditions for 2 h according to the general procedure M. Obtained as a light brown solid (230 mg, 72%).

MS (ISP) 424.3 [(M+H)$^+$]; mp 191° C.

Example 151

4-[3-(5-ethyl-2-methyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(5-ethyl-2-methyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M134) (0.29 g, 0.45 mmol) by treatment with TFA in CH$_2$Cl$_2$ according to the general procedure N. Obtained as an off-white solid (220 mg, 93%).

MS (ISP) 522.3 [(M+H)$^+$]; mp 169° C.

Example 152

4-[3-(5-Ethyl-2-methyl-pyridin-4-yl)-phenyl]-7-ethoxy-8-trifluoromethyl-1,3-dihydro-benzo[b][1,4]diazepin-2-one The title compound was prepared from [2-{3-[3-(5-ethyl-2-methyl-pyridin-4-yl)-phenyl]-3-oxo-propionylamino}-5-ethoxy-4-trifluoromethyl-phenyl]-carbamic acid tert-butyl ester (Example M135) (0.30 g, 0.51 mmol) by treatment with TFA in CH$_2$Cl$_2$ according to the general procedure N. Obtained as an off-white solid (220 mg, 92%).

MS (ISP) 468.5 [(M+H)$^+$]; mp 191° C.

Example 153

8-Chloro-4-[3-(2-ethyl-pyridin-4-yl)-phenyl]-7-methyl-1,3-dihydro-benzo[b][1,4]diazepin-2-one The title compound was prepared from (4-chloro-2-{3-[3-(2-ethyl-pyridin-4-yl)-phenyl]-5-methyl-3-oxo-propionylamino}-phenyl)-carbamic acid tert-butyl ester (Example M136) (0.26 g, 0.51 mmol) by treatment with TFA in CH$_2$Cl$_2$ according to the general procedure N. Obtained as an off-white solid (147 mg, 74%).

MS (ISP) 390.2 [(M+H)$^+$]; mp 195° C.

Example 154

4-[3-(2-Ethyl-pyridin-4-yl)-phenyl]-7-methyl-8-trifluoromethyl-1,3-dihydro benzo[b][1,4]diazepin-2-one The title compound was prepared from (2-{3-[3-(2-ethyl-pyridin-4-yl)-phenyl]-5-methyl-3-oxo-propionylamino}-4-trifluoromethyl-phenyl)-carbamic acid tert-butyl ester (Example M137) (0.28 g, 0.52 mmol) by treatment with TFA in CH$_2$Cl$_2$ according to the general procedure N. Obtained as an off-white solid (192 mg, 88%).

MS (ISP) 424.4 [(M+H)$^+$]; mp 228° C.

Example 155

4-[3-(2-Ethyl-pyridin-4-yl)-phenyl]-8-trifluoromethyl-1,3-dihydro benzo[b][1,4]diazepin-2-one The title compound was prepared from (2-{3-[3-(2-ethyl-pyridin-4-yl)-phenyl]-3-oxo-propionylamino}-4-trifluoromethyl-phenyl)-carbamic acid tert-butyl ester (Example M138) (0.27 g, 0.51 mmol) by treatment with TFA in CH$_2$Cl$_2$ according to the general procedure N. Obtained as an off-white solid (158 mg, 78%).

MS (ISP) 410.3 [(M+H)$^+$]; mp 208° C.

Example 156

7-Chloro-4-[3-(2-ethyl-pyridin-4-yl)-phenyl]-8-trifluoromethyl-1,3-dihydro benzo[b][1,4]diazepin-2-one The title compound was prepared from (5-chloro-2-{3-[3-(2-ethyl-pyridin-4-yl)-phenyl]-3-oxo-propionylamino}-

4-trifluoromethyl-phenyl)-carbamic acid tert-butyl ester (Example M139) (0.27 g, 0.48 mmol) by treatment with TFA in $CH_2Cl_2$ according to the general procedure N. Obtained as an off-white solid (165 mg, 77%).

MS (ISP) 444.3 [(M+H)$^+$]; mp 217° C.

Example 157

7,8-Dichloro-4-[3-(2-ethyl-pyridin-4-yl)-phenyl]-1,3-dihydro-benzo[b][1,4]diazepin-2-one The title compound was prepared from commercially available 4,5-dichloro-1,2-phenylendiamine (133 mg, 0.75 mmol) and 3-[3-(2-ethyl-pyridin-4-yl)-phenyl]-3-oxo-propionic acid tert-butyl ester (Example K20) (244 mg, 0.75 mmol) in xylene (7.5 ml) under reflux conditions for 1.5 h according to the general procedure M. Obtained as a light red solid (236 mg, 77%).

MS (ISP) 410.3 [(M+H)$^+$]; mp 216° C.

Example 158

4-[3-(2-Ethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-ethyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M140) (0.34 g, 0.54 mmol) by treatment with TFA in $CH_2Cl_2$ according to the general procedure N. Obtained as a light brown solid (239 mg, 87%).

MS (ISP) 508.4 [(M+H)$^+$]; mp 232° C.

Example 159

4-[3-(2-Ethyl-pyridin-4-yl)-phenyl]-7-ethoxy-8-trifluoromethyl-1,3-dihydro-benzo[b][1,4]diazepin-2-one The title compound was prepared from [2-{3-[3-(2-ethyl-pyridin-4-yl)-phenyl]-3-oxo-propionylamino}-5-ethoxy-4-trifluoromethyl-phenyl]-carbamic acid tert-butyl ester (Example M141) (0.33 g, 0.58 mmol) by treatment with TFA in $CH_2Cl_2$ according to the general procedure N. Obtained as a light brown solid (230 mg, 88%).

MS (ISP) 454.5 [(M+H)$^+$]; mp 244° C.

Example 160

7-Dimethylamino-4-[3-(6-methyl-pyridin-2-yl)-phenyl]-8-trifluoromethyl-1,3-dihydro-benzo[b][1,4]diazepin-2-one The title compound was prepared from (5-dimethylamino-2-{3-[3-(6-methyl-pyridin-2-yl)-phenyl]-3-oxo-propionylamino}-4-trifluoromethyl-phenyl)-carbamic acid tert-butyl ester (Example M142) (244 mg, 0.44 mmol) by treatment with TFA in $CH_2Cl_2$ according to the general procedure N. Obtained as a yellow solid (168 mg, 87%).

MS (ISP) 439 [(M+H)$^+$]; mp 195° C.

Example 161

8-Chloro-4-[3-(6-cyclopropyl-pyridin-3-yl)-phenyl]-7-methyl-1,3-dihydro-benzo[b][1,4]diazepin-2-one The title compound was prepared from (4-chloro-2-{3-[3-(6-cyclopropyl-pyridin-3-yl)-phenyl]-3-oxo-propionylamino}-5-methyl-phenyl)-carbamic acid tert-butyl ester (Example M143) (332 mg, 0.638 mmol) by treatment with TFA in $CH_2Cl_2$ according to the general procedure N. Obtained as a white solid (163 mg, 64%).

MS (ISP) 402.4 [(M+H)$^+$] and 404 [(M+2+H)$^+$]; mp 198–199° C.

Example 162

7-Ethoxy-4-(3-pyridin-3-yl-phenyl)-1,3-dihydro-benzo[b][1,4]diazepin-2-one

The title compound was prepared from {5-ethoxy-2-[3-oxo-3-(3-pyridin-3-yl-phenyl)-propionylamino]-phenyl}-carbamic acid tert-butyl ester (Example M144) (170 mg, 0.36 mmol) by treatment with TFA in $CH_2Cl_2$ according to the general procedure N. Obtained as a brown solid (84 mg, 65%).

MS (ISP) 358.3 [(M+H)$^+$]; mp 166–169° C.

Example 163

7-Ethoxy-4-(3-pyridin-4-yl-phenyl)-1,3-dihydro-benzo[b][1,4]diazepin-2-one

The title compound was prepared from {5-ethoxy-2-[3-oxo-3-(3-pyridin-4-yl-phenyl)-propionylamino]-phenyl}-carbamic acid tert-butyl ester (Example M145) (193 mg, 0.41 mmol) by treatment with TFA in $CH_2Cl_2$ according to the general procedure N. Obtained as a brown solid (105 mg, 72%).

MS (ISP) 358.3 [(M+H)$^+$]; mp 180–185° C.

Example 164

8-Phenylethynyl-4-(3-pyridin-2-yl-phenyl)-1,3-dihydro-benzo[b][1,4]diazepin-2-one The title compound was prepared from {2-[3-oxo-3-(3-pyridin-2-yl-phenyl)-propionylamino]-4-phenylethynyl-phenyl}-carbamic acid tert-butyl ester (Example M146) (276 mg, 0.52 mmol) by treatment with TFA in $CH_2Cl_2$ according to the general procedure N. Obtained as an off-white solid (200 mg, 93%).

MS (ISP) 414 [(M+H)$^+$]; mp 242° C.

Example 165

8-(4-Fluoro-phenylethynyl)-4-(3-pyridin-2-yl-phenyl)-1,3-dihydro-benzo[b][1,4]diazepin-2-one The title compound was prepared from {4-(4-fluoro-phenylethynyl)-2-[3-oxo-3-(3-pyridin-2-yl-phenyl)-propionylamino]-phenyl}-carbamic acid tert-butyl ester (Example M147) (287 mg, 0.52 mmol) by treatment with TFA in $CH_2Cl_2$ according to the general procedure N. Obtained as an off-white solid (197 mg, 88%).

MS (ISP) 432 [(M+H)$^+$]; mp 249° C.

Example 166

4-[3-(6-Cyclopropyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-cyclopropyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M148) (334 mg, 0.524 mmol) by treatment with TFA in CH$_2$Cl$_2$ according to the general procedure N. Obtained as a white solid (201 mg, 74%).

MS (ISP) 520.2 [(M+H)$^+$]; mp 213–214° C.

Example 167

4-[3-(6-Cyclopropyl-pyridin-3-yl)-phenyl]-7-methyl-8-trifluoromethyl-1,3-dihydro-benzo[b][1,4]diazepin-2-one The title compound was prepared from (2-{3-[3-(6-cyclopropyl-pyridin-3-yl)-phenyl]-3-oxo-propionylamino}-5-methyl-4-trifluoromethyl-phenyl)-carbamic acid tert-butyl ester (Example M149) (310 mg, 0.56 mmol) by treatment with TFA in CH$_2$Cl$_2$ according to the general procedure N. Obtained as a white solid (192 mg, 79%).

MS (ISP) 436.4 [(M+H)$^+$]; mp 220–221° C.

Example 168

4-[3-(6-Methoxy-pyridin-3-yl)-phenyl]-7-methyl-8-trifluoromethyl-1,3-dihydro-benzo[b][1,4]diazepin-2-one The title compound was prepared from (2-{3-[3-(6-methoxy-pyridin-3-yl)-phenyl]-3-oxo-propionylamino}-5-methyl-4-trifluoromethyl-phenyl)-carbamic acid tert-butyl ester (Example M150) (232 mg, 0.43 mmol) by treatment with TFA in CH$_2$Cl$_2$ according to the general procedure N. Obtained as a white solid (113 mg, 62%).

MS (ISP) 426.4 [(M+H)$^+$]; mp 219–224° C.

Example 169

4-[3-(6-Methoxy-pyridin-3-yl)-phenyl]-7-(2,2,2-trifluoro-ethoxy)-1,3-dihydro-benzo[b][1,4]diazepin-2-one The title compound was prepared from [2-{3-[3-(6-methoxy-pyridin-3-yl)-phenyl]-3-oxo-propionylamino}-5-(2,2,2-trifluoro-ethoxy)-phenyl]-carbamic acid tert-butyl ester (Example M151) (245 mg, 0.44 mmol) by treatment with TFA in CH$_2$Cl$_2$ according to the general procedure N. Obtained as a light brown solid (101 mg, 52%).

MS (ISP) 442.3 [(M+H)$^+$]; mp 186° C.

Example 170

4-[3-(6-Methoxy-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-methoxy-pyridin-3-yl)-phenyl]-3-oxo-propionylamino}-5-(2,2,2-trifluoro-ethoxy)-4-trifluoromethyl-phenyl]-carbamic acid tert-butyl ester (Example M152) (377 mg, 0.60 mmol) by treatment with TFA in CH$_2$Cl$_2$ according to the general procedure N. Obtained as an off-white solid (118 mg, 39%).

MS (ISP) 510.3 [(M+H)$^+$]; mp 220–225° C.

Example 171

4-[3-(6-Cyclopropyl-pyridin-3-yl)-phenyl]-8-trifluoromethyl-1,3-dihydro-benzo[b][1,4]diazepin-2-one The title compound was prepared from (2-{3-[3-(6-cyclopropyl-pyridin-3-yl)-phenyl]-3-oxo-propionylamino}-4-trifluoromethyl-phenyl)-carbamic acid tert-butyl ester (Example M153) (300 mg, 0.556 mmol) by treatment with TFA in CH$_2$Cl$_2$ according to the general procedure N. Obtained as a white solid (125 mg, 53%).

MS (ISP) 422.3 [(M+H)$^+$]; mp 179–181° C.

Example 172

7-Methyl-4-(3-pyridin-3-yl-phenyl)-8-trifluoromethyl-1,3-dihydro-benzo[b][1,4]diazepin-2-one The title compound was prepared from {5-methyl-2-[3-oxo-3-(3-pyridin-3-yl-phenyl)-propionylamino]-4-trifluoromethyl-phenyl}-carbamic acid tert-butyl ester (Example M154) (260 mg, 0.506 mmol) by treatment with TFA in CH$_2$Cl$_2$ according to the general procedure N. Obtained as a white solid (166 mg, 83%).

MS (ISP) 396.3 [(M+H)$^+$]; mp 206–207° C.

Example 173

7-Methoxy-4-(3-pyridin-3-yl-phenyl)-8-trifluoromethyl-1,3-dihydro-benzo[b][1,4]diazepin-2-one The title compound was prepared from {5-methoxy-2-[3-oxo-3-(3-pyridin-3-yl-phenyl)-propionylamino]-4-trifluoromethyl-phenyl}-carbamic acid tert-butyl ester (Example M155) (320 mg, 0.604 mmol) by treatment with TFA in CH$_2$Cl$_2$ according to the general procedure N. Obtained as a light yellow solid (164 mg, 66%).

MS (ISP) 412.3 [(M+H)$^+$]; mp 209–211° C.

Example 174

8-(4-Fluoro-phenylethynyl)-4-(3-pyridin-3-yl-phenyl)-1,3-dihydro-benzo[b][1,4]diazepin-2-one The title compound was prepared from {4-(4-fluoro-phenylethynyl)-2-[3-oxo-3-(3-pyridin-3-yl-phenyl)-propionylamino]-phenyl}-carbamic acid tert-butyl ester (Example M156) (304 mg, 0.553 mmol) by treatment with TFA in CH$_2$Cl$_2$ according to the general procedure N. Obtained as a light yellow solid (207 mg, 87%).

MS (ISP) 432.4 [(M+H)$^+$]; mp 228–230° C.

Example 175

8-Phenylethynyl-4-(3-pyridin-3-yl-phenyl)-1,3-dihydro-benzo[b][1,4]diazepin-2-one The title compound was prepared from {2-[3-oxo-3-(3-pyridin-3-yl-phenyl)-propionylamino]-4-phenylethynyl-phenyl}-carbamic acid tert-butyl ester (Example M157) (310 mg, 0.583 mmol) by treatment with TFA in CH$_2$Cl$_2$ according to the general procedure N. Obtained as a light yellow solid (180 mg, 75%).

MS (ISP) 414.3 [(M+H)$^+$]; mp 241° C.

Example 176

4-[3-(6-Cyclopropyl-pyridin-3-yl)-phenyl]-7-(2,2,2-trifluoro-ethoxy)-1,3-dihydro-benzo[b][1,4]diazepin-2-one The title compound was prepared from [2-{3-[3-(5-cyclopropyl-pyridin-2-yl)-phenyl]-3-oxo-propionylamino}-5-(2,2,2-trifluoro-ethoxy)-phenyl]-carbamic acid tert-butyl ester (Example M158) (310 mg, 0.583 mmol) by treatment with TFA in $CH_2Cl_2$ according to the general procedure N. Obtained as a light yellow solid (177 mg, 52%).

MS (ISP) 452.4 [(M+H)$^+$]; mp 178–180° C.

Example 177

4-[3-(6-Isopropyl-pyridin-3-yl)-phenyl]-8-trifluoromethyl-1,3-dihydro-benzo[b][1,4]diazepin-2-one The title compound was prepared from (2-{3-[3-(6-isopropyl-pyridin-3-yl)-phenyl]-3-oxo-propionylamino}-4-trifluoromethyl-phenyl)-carbamic acid tert-butyl ester (Example M159) (260 mg, 0.506 mmol) by treatment with TFA in $CH_2Cl_2$ according to the general procedure N. Obtained as an off-white solid (94 mg, 53%).

MS (ISP) 424 [(M+H)$^+$]; mp 194° C.

Example 178

4-[3-(6-Isopropyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-isopropyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M160) (339 mg, 0.53 mmol) by treatment with TFA in $CH_2Cl_2$ according to the general procedure N. Obtained as an off-white solid (203 mg, 73%).

MS (ISP) 522 [(M+H)$^+$]; mp 197° C.

Example 179

8-Chloro-4-[3-(6-isopropyl-pyridin-3-yl)-phenyl]-7-methyl-1,3-dihydro-benzo[b][1,4]diazepin-2-one The title compound was prepared from (4-chloro-2-{3-[3-(6-isopropyl-pyridin-3-yl)-phenyl]-3-oxo-propionylamino}-5-methyl-phenyl)-carbamic acid tert-butyl ester (Example M161) (133 mg, 0.26 mmol) by treatment with TFA in $CH_2Cl_2$ according to the general procedure N. Obtained as an off-white solid (61 mg, 58%).

MS (ISP) 404 [(M+H)$^+$] and 406 [(M+2+H)$^+$]; mp 190° C.

Example 180

4-[3-(6-Isopropyl-pyridin-3-yl)-phenyl]-7-methyl-8-trifluoromethyl-1,3-dihydro-benzo[b][1,4]diazepin-2-one The title compound was prepared from (2-{3-[3-(6-isopropyl-pyridin-3-yl)-phenyl]-3-oxo-propionylamino}-5-methyl-4-trifluoromethyl-phenyl)-carbamic acid tert-butyl ester (Example M162) (167 mg, 0.30 mmol) by treatment with TFA in $CH_2Cl_2$ according to the general procedure N. Obtained as an off-white solid (91 mg, 69%).

MS (ISP) 438 [(M+H)$^+$]; mp 199° C.

Example 181

8-Chloro-7-ethoxy-4-(3-pyridin-3-yl-phenyl)-1,3-dihydro-benzo[b][1,4]diazepin-2-one The title compound was prepared from {4-chloro-5-ethoxy-2-[3-oxo-3-(3-pyridin-3-yl-phenyl)-propionylamino]-phenyl}-carbamic acid tert-butyl ester (Example M163) (111 mg, 0.22 mmol) by treatment with TFA in $CH_2Cl_2$ according to the general procedure N. Obtained as an off-white solid (62 mg, 72%).

MS (ISP) 392 [(M+H)$^+$] and 394 [(M+2+H)$^+$]; mp 210° C.

Example 182

8-Chloro-7-ethoxy-4-[3-(2-methyl-pyridin-4-yl)-phenyl]-1,3-dihydro-benzo[b][1,4]diazepin-2-one The title compound was prepared from (4-chloro-5-ethoxy-2-{3-[3-(2-methyl-pyridin-4-yl)-phenyl]-3-oxo-propionylamino}-phenyl)-carbamic acid tert-butyl ester (Example M164) (244 mg, 0.47 mmol) by treatment with TFA in $CH_2Cl_2$ according to the general procedure N. Obtained as an off-white solid (157 mg, 82%).

MS (ISP) 406 [(M+H)$^+$] and 408 [(M+2+H)$^+$]; mp 185° C.

Example 183

7-Chloro-4-(3-pyridin-3-yl-phenyl)-8-trifluoromethyl-1,3-dihydro-benzo[b][1,4]diazepin-2-one The title compound was prepared from {5-chloro-2-[3-oxo-3-(3-pyridin-3-yl-phenyl)-propionylamino]-4-trifluoromethyl-phenyl}-carbamic acid tert-butyl ester (Example M165) (250 mg, 0.468 mmol) by treatment with TFA in $CH_2Cl_2$ according to the general procedure N. Obtained as a white solid (154 mg, 79%).

MS (ISP) 416.3 [(M+H)$^+$] and 418 [(M+2+H)$^+$]; mp 226–227° C.

Example 184

7-Ethoxy-4-(3-pyridin-3-yl-phenyl)-8-trifluoromethyl-1,3-dihydro-benzo[b][1,4]diazepin-2-one The title compound was prepared from {5-ethoxy-2-[3-oxo-3-(3-pyridin-3-yl-phenyl)-propionylamino]-4-trifluoromethyl-phenyl}-carbamic acid tert-butyl ester (Example M166) (265 mg, 0.488 mmol) by treatment with TFA in $CH_2Cl_2$ according to the general procedure N. Obtained as a white solid (154 mg, 74%).

MS (ISP) 426.4 [(M+H)$^+$]; mp 219–224° C.

Example 185

4-(3-Pyridin-3-yl-phenyl)-8-trifluoromethoxy-1,3-dihydro-benzo[b][1,4]diazepin-2-one The title compound was prepared from {2-[3-oxo-3-(3-pyridin-3-yl-phenyl)-propionylamino]-4-trifluoromethoxy-phenyl}-carbamic acid tert-butyl ester (Example M167) (238 mg, 0.46 mmol) by treatment with TFA in $CH_2Cl_2$ according to the general procedure N. Obtained as an off-white solid (137 mg, 75%).

MS (ISP) 398 [(M+H)$^+$]; mp 207° C.

Example 186

4-[3-(2-Methyl-pyridin-4-yl)-phenyl]-8-trifluoromethoxy-1,3-dihydro-benzo[b][1,4]diazepin-2-one The title compound was prepared from (2-{3-[3-(2-methyl-pyridin-4-yl)-phenyl]-3-oxo-propionylamino}-4- trifluoromethoxy-phenyl)-carbamic acid tert-butyl ester (Example M168) (236 mg, 0.45 mmol) by treatment with TFA in $CH_2Cl_2$ according to the general procedure N. Obtained as an off-white solid (72 mg, 39%).

MS (ISP) 412 [(M+H)$^+$]; mp 200° C.

Example 187

4-(3-Pyridin-3-yl-phenyl)-7-pyrrolidin-1-yl-8-trifluoromethyl-1,3-dihydro-benzo[b][1,4]diazepin-2-one The title compound was prepared from {2-[3-oxo-3-(3-pyridin-3-yl-phenyl)-propionylamino]-5-pyrrolidin-1-yl-4-trifluoromethyl-phenyl}-carbamic acid tert-butyl ester (Example M169) (249 mg, 0.438 mmol) by treatment with TFA in $CH_2Cl_2$ according to the general procedure N. Obtained as a yellow solid (129 mg, 65%).

MS (ISP) 451.4 [(M+H)$^+$]; mp 219–221° C.

Example 188

7-Morpholin-4-yl-4-(3-pyridin-3-yl-phenyl)-8-trifluoromethyl-1,3-dihydro-benzo[b][1,4]diazepin-2-one The title compound was prepared from {5-morpholin-4-yl-2-[3-oxo-3-(3-pyridin-3-yl-phenyl)-propionylamino]-4-trifluoromethyl-phenyl}-carbamic acid tert-butyl ester (Example M170) (336 mg, 0.575 mmol) by treatment with TFA in $CH_2Cl_2$ according to the general procedure N. Obtained as a yellow solid (155 mg, 58%).

MS (ISP) 467.3 [(M+H)$^+$]; mp 198–201° C.

Example 189

8-Chloro-4-[3-(6-ethyl-pyridin-3-yl)-phenyl]-7-methyl-1,3-dihydro-benzo[b][1,4]diazepin-2-one The title compound was prepared from (4-chloro-2-{3-[3-(6-ethyl-pyridin-3-yl)-phenyl]-3-oxo-propionylamino}-5-methyl-phenyl)-carbamic acid tert-butyl ester (Example M171) (290 mg, 0.57 mmol) by treatment with TFA in $CH_2Cl_2$ according to the general procedure N. Obtained as a light yellow solid (145 mg, 65%).

MS (ISP) 390.3 [(M+H)$^+$] and 392 [(M+2+H)$^+$]; mp 182–185° C.

Example 190

7-Ethoxy-4-[3-(6-ethyl-pyridin-3-yl)-phenyl]-8-trifluoromethyl-1,3-dihydro-benzo[b][1,4]diazepin-2-one The title compound was prepared from (5-ethoxy-2-{3-[3-(6-ethyl-pyridin-3-yl)-phenyl]-3-oxo-propionylamino}-4-trifluoromethyl-phenyl)-carbamic acid tert-butyl ester (Example M172) (214 mg, 0.374 mmol) by treatment with TFA in $CH_2Cl_2$ according to the general procedure N. Obtained as an off-white solid (167 mg, 98%).

MS (ISP) 454.5 [(M+H)$^+$]; mp 218–219° C.

Example 191

4-[3-(6-Ethyl-pyridin-3-yl)-phenyl]-8-trifluoromethyl-1,3-dihydro-benzo[b][1,4]diazepin-2-one The title compound was prepared from (2-{3-[3-(6-ethyl-pyridin-3-yl)-phenyl]-3-oxo-propionylamino}-4-trifluoromethyl-phenyl)-carbamic acid tert-butyl ester (Example M173) (257 mg, 0.49 mmol) by treatment with TFA in $CH_2Cl_2$ according to the general procedure N. Obtained as an off-white solid (134 mg, 67%).

MS (ISP) 410 [(M+H)$^+$]; mp 211° C.

Example 192

4-[3-(6-Ethyl-pyridin-3-yl)-phenyl]-8-trifluoromethyl-1,3-dihydro-benzo[b][1,4]diazepin-2-one The title compound was prepared from (2-{3-[3-(6-ethyl-pyridin-3-yl)-phenyl]-3-oxo-propionylamino}-5-methyl-4-trifluoromethyl-phenyl)-carbamic acid tert-butyl ester (Example M174) (287 mg, 0.53 mmol) by treatment with TFA in $CH_2Cl_2$ according to the general procedure N. Obtained as an off-white solid (184 mg, 82%).

MS (ISP) 424 [(M+H)$^+$]; mp 225° C.

Example 193

4-[3-(6-Ethyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-ethyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M175) (387 mg, 0.619 mmol) by treatment with TFA in $CH_2Cl_2$ according to the general procedure N. Obtained as an off-white solid (191 mg, 61%).

MS (ISP) 508 [(M+H)$^+$]; mp 191° C.

Example 194

7-Cyclopropylmethoxy-4-(3-pyridin-3-yl-phenyl)-8-trifluoromethyl-1,3-dihydro-benzo[b][1,4]diazepin-2-one The title compound was prepared from {5-cyclopropylmethoxy-2-[3-oxo-3-(3-pyridin-3-yl-phenyl)-propionylamino]-4-trifluoromethyl-phenyl}-carbamic acid tert-butyl ester (Example M176) (275 mg, 0.48 mmol) by treatment with TFA in $CH_2Cl_2$ according to the general procedure N. Obtained as an off-white solid (170 mg, 78%).

MS (ISP) 452 [(M+H)$^+$]; mp 197° C.

Example 195

7-Cyclopropylmethoxy-4-[3-(2-methyl-pyridin-4-yl)-phenyl]-8-trifluoromethyl-1,3-dihydro-benzo[b][1,4]diazepin-2-one The title compound was prepared from (5-cyclopropylmethoxy-2-{3-[3-(2-methyl-pyridin-4-yl)-phenyl]-3-oxo-propionylamino}-4-trifluoromethyl-phenyl)-carbamic acid tert-butyl ester (Example M177) (279 mg, 0.48 mmol) by treatment with TFA in $CH_2Cl_2$ according to the general procedure N. Obtained as an off-white solid (144 mg, 64%).

MS (ISP) 466 [(M+H)$^+$]; mp 203° C.

Example 196

7-Cyclopropylmethoxy-4-[3-(6-cyclopropyl-pyridin-3-yl)-phenyl]-8-trifluoromethyl-1,3-dihydro-benzo[b][1,4]diazepin-2-one The title compound was prepared from (5-cyclopropylmethoxy-2-{3-[3-(6-cyclopropyl-pyridin-3- yl)-phenyl]-3-oxo-propionylamino}-4-trifluoromethyl-phenyl)-carbamic acid tert-butyl ester (Example M178) (240 mg, 0.39 mmol) by treatment with TFA in $CH_2Cl_2$ according to the general procedure N. Obtained as an off-white solid (74 mg, 39%).

MS (ISP) 492 [(M+H)$^+$]; mp 223° C.

Example 197

4-(3-Pyridin-3-yl-phenyl)-8-(2,2,2-trifluoro-ethoxy)-1,3-dihydro-benzo[b][1,4]diazepin-2-one The title compound was prepared from [2-[3-oxo-3-(3-pyridin-3-yl-phenyl)-propionylamino]-4-(2,2,2-trifluoro-ethoxy)-phenyl]-carbamic acid tert-butyl ester (Example M179) (266 mg, 0.5 mmol) by treatment with TFA in $CH_2Cl_2$ according to the general procedure N. Obtained as an off-white solid (175 mg, 85%).

MS (ISP) 412 [(M+H)$^+$]; mp 156° C.

Example 198

4-[3-(4-Oxo-7-trifluoromethyl-4,5-dihydro-3H-benzo[b][1,4]diazepin-2-yl)-phenyl]-pyridine-2-carbonitrile The title compound was prepared from (2-{3-[3-(2-cyano-pyridin-4-yl)-phenyl]-3-oxo-propionylamino}-4-trifluoromethyl-phenyl)-carbamic acid tert-butyl ester (Example M180) (304 mg, 0.58 mmol) by treatment with TFA in $CH_2Cl_2$ according to the general procedure N. Obtained as a white solid (147 mg, 62%).

MS (EI) 406.2 (M$^+$); mp 239–240° C.

Example 199

4-[3-(8-Methyl-4-oxo-7-trifluoromethyl-4,5-dihydro-3H-benzo[b][1,4]diazepin-2-yl)-phenyl]-pyridine-2-carbonitrile The title compound was prepared from (2-{3-[3-(2-cyano-pyridin-4-yl)-phenyl]-3-oxo-propionylamino}-5-methyl-4-trifluoromethyl-phenyl)-carbamic acid tert-butyl ester (Example M181) (265 mg, 0.492 mmol) by treatment with TFA in $CH_2Cl_2$ according to the general procedure N. Obtained as a white solid (122 mg, 59%).

MS (EI) 420.3 (M$^+$); mp 205–211° C.

Example 200

4-[3-(6-Amino-pyridin-3-yl)-phenyl]-8-trifluoromethyl-1,3-dihydro-benzo[b][1,4]diazepin-2-one The title compound was prepared by the following sequence: 1.) To a solution of 3-[3-(6-Amino-pyridin-3-yl)-phenyl]-3-oxo-propionic acid tert-butyl ester (Example K25) (1.0 g, 3.2 mmol) and DMAP (8 mg, 0.064 mmol) in THF (6.4 mL) was added $Boc_2O$ (699 mg, 3.2 mmol) and mixture was stirred for 26.5 h at 23° C., poured onto sat. $NaHCO_3$-solution (20 mL), extracted with EtOAc (twice 25 mL). The combined organic layers were washed with 0.5 M HCl (20 mL) and brine (20 mL), dried over $Na_2SO_4$. Removal of the solvent in vacuum left a light brown foam (1.273 g). 2.) Part of this material (206 mg, 0.5 mmol) and (2-amino-4-trifluoromethyl-phenyl)-carbamic acid tert-butyl ester (Example J3) (214 mg, 0.75 mmol) were refluxed in toluene (3 mL) for 8 h, then the reaction mixture was cooled to 23° C., the precipitate was filtered off and washed with $Et_2O$ (10 mL) to give a light brown solid (96.5 mg). 3.) Part of the obtained material (88.9 mg, 0.145 mmol) was converted into the title compound by treatment with TFA in $CH_2Cl_2$ according to the general procedure N. Obtained as a light brown solid (35.2 mg, 61%).

MS (ISN) 395.2 [(M–H)$^-$].

Example 201

4-[3-(6-Amino-pyridin-3-yl)-phenyl]-7-methyl-8-trifluoromethyl-1,3-dihydro-benzo[b][1,4]diazepin-2-one The title compound was prepared by the following sequence: 1.) To a solution of 3-[3-(6-Amino-pyridin-3-yl)-phenyl]-3-oxo-propionic acid tert-butyl ester (Example K25) (1.0 g, 3.2 mmol) and DMAP (8 mg, 0.064 mmol) in THF (6.4 mL) was added $Boc_2O$ (699 mg, 3.2 mmol) and mixture was stirred for 26.5 h at 23° C., poured onto sat. $NaHCO_3$-solution (20 mL), extracted with EtOAc (twice 25 mL). The combined organic layers were washed with 0.5 M HCl (20 mL) and brine (20 mL), dried over $Na_2SO_4$. Removal of the solvent in vacuum left a light brown foam (1.273 g). 2.) Part of this material (206 mg, 0.5 mmol) and (2-amino-5-methyl-4-trifluoromethyl-phenyl)-carbamic acid tert-butyl ester (Example J20) (218 mg, 0.75 mmol) were refluxed in toluene (3 mL) for 8 h, then the reaction mixture was cooled to 23° C., the precipitate was filtered off and washed with $Et_2O$ (10 mL) to give a yellow solid (70.8 mg). 3.) Part of the obtained material (63.7 mg, 0.101 mmol) was converted into the title compound by treatment with TFA in $CH_2Cl_2$ according to the general procedure N. Obtained as a light yellow solid (25.2 mg, 61%).

MS (ISP) 411.3 [(M+H)$^+$].

Example 202

8-Chloro-4-(3-pyridin-3-yl-phenyl)-7-(2,2,2-trifluoro-ethoxy)-1,3-dihydro-benzo[b][1,4]diazepin-2-one The title compound was prepared from [4-chloro-2-[3-oxo-3-(3-pyridin-3-yl-phenyl)-propionylamino]-5-(2,2,2-trifluoro-ethoxy)-phenyl]-carbamic acid tert-butyl ester (Example M182) (272 mg, 0.482 mmol) by treatment with TFA in $CH_2Cl_2$ according to the general procedure N. Obtained as a yellow solid (150 mg, 70%).

MS (ISP) 446.3 [(M+H)$^+$] and 448 [(M+2+H)$^+$]; mp 203–204° C.

Example 203

4-{3-[7-Chloro-4-oxo-8-(2,2,2-trifluoro-ethoxy)-4,5-dihydro-3H-benzo[b][1,4]diazepin-2-yl]-phenyl}-pyridine-2-carbonitrile The title compound was prepared from [4-chloro-2-{3-[3-(2-cyano-pyridin-4-yl)-phenyl]-3-oxo-propionylamino}-5-(2,2,2-trifluoro-ethoxy)-phenyl]-carbamic acid tert-butyl ester (Example M183) (239 mg, 0.406 mmol) by treatment with TFA in $CH_2Cl_2$ according to the general procedure N. Obtained as a yellow solid (120 mg, 63%).

MS (ISP) 471.2 [(M+H)$^+$] and 473 [(M+2+H)$^+$]; mp 224–225° C.

Example 204

5-[3-(4-Oxo-7-trifluoromethyl-4,5-dihydro-3H-benzo[b][1,4]diazepin-2-yl)-phenyl]-pyridine-2-carbonitrile The title compound was prepared from (2-{3-[3-(6-cyano-pyridin-3-yl)-phenyl]-3-oxo-propionylamino}-4- trifluoromethyl-phenyl)-carbamic acid tert-butyl ester (Example M184) (295 mg, 0.562 mmol) by treatment with TFA in CH₂Cl₂ according to the general procedure N. Obtained as a white solid (125 mg, 55%).

MS (ISP) 407.4 [(M+H)⁺]; mp 234–237° C.

Example 205

4-(3-Pyridazin-3-yl-phenyl)-8-trifluoromethyl-1,3-dihydro-benzo[b][1,4]diazepin-2-one The title compound was prepared from {2-[3-oxo-3-(3-pyridazin-3-yl-phenyl)-propionylamino]-4-trifluoromethyl-phenyl}-carbamic acid tert-butyl ester (Example M185) (245 mg, 0.49 mmol) by treatment with TFA in CH₂Cl₂ according to the general procedure N. Obtained as a yellow solid (144 mg, 77%).

MS (ISP) 383.3 [(M+H)⁺]; mp 238–240° C.

Example 206

4-Methyl-8-trifluoromethoxy-1,3-dihydro-benzo[b][1,4]diazepin-2-one; Compound with 2-phenyl-pyridine The title compound was prepared from {2-[3-oxo-3-(3-pyridin-2-yl-phenyl)-propionylamino]-4-trifluoromethoxy-phenyl}-carbamic acid tert-butyl ester (Example M186) (255 mg, 0.495 mmol) by treatment with TFA in CH₂Cl₂ according to the general procedure N. Obtained as a light yellow solid (137 mg, 70%).

MS (ISP) 398.4 [(M+H)⁺]; mp 221–222° C.

Example 207

4-[3-(6-Cyclopropyl-pyridin-3-yl)-phenyl]-8-trifluoromethoxy-1,3-dihydro-benzo[b][1,4]diazepin-2-one The title compound was prepared from (2-{3-[3-(6-cyclopropyl-pyridin-3-yl)-phenyl]-3-oxo-propionylamino}-4-trifluoromethoxy-phenyl)-carbamic acid tert-butyl ester (Example M187) (242 mg, 0.436 mmol) by treatment with TFA in CH₂Cl₂ according to the general procedure N. Obtained as a white solid (93 mg, 49%).

MS (ISP) 438.4 [(M+H)⁺]; mp 190–191° C.

Example 208

7-(2-Methoxy-ethoxy)-4-(3-pyridin-3-yl-phenyl)-8-trifluoromethyl-1,3-dihydro-benzo[b][1,4]diazepin-2-one The title compound was prepared from {5-(2-methoxy-ethoxy)-2-[3-oxo-3-(3-pyridin-3-yl-phenyl)-propionylamino]-4-trifluoromethyl-phenyl}-carbamic acid tert-butyl ester (Example M188) (278 mg, 0.49 mmol) by treatment with TFA in CH₂Cl₂ according to the general procedure N. Obtained as a light yellow solid (153 mg, 69%).

MS (ISP) 456 [(M+H)⁺]; mp 190–191° C.

Example 209

4-{3-[8-(2-Methoxy-ethoxy)-4-oxo-7-trifluoromethyl-4,5-dihydro-3H-benzo[b][1,4]diazepin-2-yl]-phenyl}-pyridine-2-carbonitrile The title compound was prepared from [2-{3-[3-(2-cyano-pyridin-4-yl)-phenyl]-3-oxo-propionylamino}-5-(2-methoxy-ethoxy)-4-trifluoromethyl-phenyl]-carbamic acid tert-butyl ester (Example M189) (278 mg, 0.46 mmol) by treatment with TFA in CH₂Cl₂ according to the general procedure N. Obtained as a light yellow solid (185 mg, 84%).

MS (ISP) 481 [(M+H)⁺]; mp 212–213° C.

Example 210

4-[3-(8-Ethyl-4-oxo-7-trifluoromethyl-4,5-dihydro-3H-benzo[b][1,4]diazepin-2-yl)-phenyl]-pyridine-2-carbonitrile The title compound was prepared from (2-{3-[3-(2-cyano-pyridin-4-yl)-phenyl]-3-oxo-propionylamino}-5-ethyl-4-trifluoromethyl-phenyl)-carbamic acid tert-butyl ester (Example M190) (300 mg, 0.54 mmol) by treatment with TFA in CH₂Cl₂ according to the general procedure N. Obtained as a white solid (158 mg, 67%).

MS (ISP) 435 [(M+H)⁺]; mp 210–217° C.

Example 211

7-Ethyl-4-(3-pyridin-3-yl-phenyl)-8-trifluoromethyl-1,3-dihydro-benzo[b][1,4]diazepin-2-one The title compound was prepared from {5-ethyl-2-[3-oxo-3-(3-pyridin-3-yl-phenyl)-propionylamino]-4-trifluoromethyl-phenyl}-carbamic acid tert-butyl ester (Example M191) (365 mg, 0.69 mmol) by treatment with TFA in CH₂Cl₂ according to the general procedure N. Obtained as a white solid (122 mg, 43%).

MS (ISP) 410 [(M+H)⁺]; mp 197–198° C.

Example 212

4-[3-(6-Methoxy-pyridin-3-yl)-phenyl]-8-trifluoromethoxy-1,3-dihydro-benzo[b][1,4]diazepin-2-one The title compound was prepared from (2-{3-[3-(6-methoxy-pyridin-3-yl)-phenyl]-3-oxo-propionylamino}-4-trifluoromethoxy-phenyl)-carbamic acid tert-butyl ester (Example M192) (216 mg, 0.396 mmol) by treatment with TFA in CH₂Cl₂ according to the general procedure N. Obtained as a light yellow solid (37 mg, 22%).

MS (ISP) 428.5 [(M+H)⁺]; mp 186° C.

Example 213

4-[3-(2,6-Dimethyl-pyridin-4-yl)-phenyl]-8-trifluoromethoxy-1,3-dihydro-benzo[b][1,4]diazepin-2-one The title compound was prepared from (2-{3-[3-(2,6-dimethyl-pyridin-4-yl)-phenyl]-3-oxo-propionylamino}-4-trifluoromethoxy-phenyl)-carbamic acid tert-butyl ester (Example M193) (230 mg, 0.423 mmol) by treatment with TFA in CH₂Cl₂ according to the general procedure N. Obtained as a white solid (97 mg, 54%).

MS (ISP) 426.4 [(M+H)⁺]; mp 190–193° C.

Example 214

4-(3-Pyridin-3-yl-phenyl)-8-trifluoromethyl-7-vinyl-1,3-dihydro-benzo[b][1,4]diazepin-2-one The title compound was prepared from {2-[3-oxo-3-(3-pyridin-3-yl-phenyl)-propionylamino]-4-trifluoromethyl-5- vinyl-phenyl}-carbamic acid tert-butyl ester (Example M194) (273 mg, 0.52 mmol) by treatment with TFA in CH₂Cl₂ according to the general procedure N. Obtained as a white solid (127 mg, 60%).

MS (ISP) 408 [(M+H)⁺]; mp 208–209° C.

Example 215

7-Propoxy-4-(3-pyridin-3-yl-phenyl)-8-trifluoromethyl-1,3-dihydro-benzo[b][1,4]diazepin-2-one The title compound was prepared from {2-[3-oxo-3-(3-pyridin-3-yl-phenyl)-propionylamino]-5-propoxy-4-trifluoromethyl-phenyl}-carbamic acid tert-butyl ester (Example M195) (359 mg, 0.626 mmol) by treatment with TFA in CH₂Cl₂ according to the general procedure N. Obtained as a white solid (223 mg, 81%).

MS (ISN) 438.2 [(M−H)⁻]; mp 219–221° C.

Example 216

4-[3-(6-Cyclopropyl-pyridin-3-yl)-phenyl]-7-propoxy-8-trifluoromethyl-1,3-dihydro-benzo[b][1,4]diazepin-2-one The title compound was prepared from (2-{3-[3-(6-cyclopropyl-pyridin-3-yl)-phenyl]-3-oxo-propionylamino}-5-propoxy-4-trifluoromethyl-phenyl)-carbamic acid tert-butyl ester (Example M196) (362 mg, 0.59 mmol) by treatment with TFA in CH₂Cl₂ according to the general procedure N. Obtained as an off-white solid (153 mg, 54%).

MS (ISN) 478.2 [(M−H)⁻]; mp 209–210° C.

Example 217

4-[3-(6-Dimethylamino-pyridin-3-yl)-phenyl]-7-methyl-8-trifluoromethyl-1,3-dihydro-benzo[b][1,4]diazepin-2-one The title compound was prepared from (2-{3-[3-(6-dimethylamino-pyridin-3-yl)-phenyl]-3-oxo-propionylamino}-5-methyl-4-trifluoromethyl-phenyl)-carbamic acid tert-butyl ester (Example M197) (298 mg, 0.53 mmol) by treatment with TFA in CH₂Cl₂ according to the general procedure N. Obtained as an off-white solid (198 mg, 83%).

MS (ISN) 439 [(M−H)⁻]; mp 231–233° C.

Example 218

4-[3-(6-Dimethylamino-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-dimethylamino-pyridin-3-yl)-phenyl]-3-oxo-propionylamino}-5-(2,2,2-trifluoro-ethoxy)-4-trifluoromethyl-phenyl]-carbamic acid tert-butyl ester (Example M198) (397 mg, 0.62 mmol) by treatment with TFA in CH₂Cl₂ according to the general procedure N. Obtained as a yellow solid (248 mg, 77%).

MS (ISP) 523 [(M+H)⁺]; mp 240–241° C.

Example 219

4-[3-(2,6-Dimethyl-pyridin-4-yl)-phenyl]-7-propoxy-8-trifluoromethyl-1,3-dihydro-benzo[b][1,4]diazepin-2-one The title compound was prepared from (2-{3-[3-(2,6-dimethyl-pyridin-4-yl)-phenyl]-3-oxo-propionylamino}-5-propoxy-4-trifluoromethyl-phenyl)-carbamic acid tert-butyl ester (Example M199) (319 mg, 0.545 mmol) by treatment with TFA in CH₂Cl₂ according to the general procedure N. Obtained as a light yellow solid (172 mg, 68%).

MS (ISP) 468.2 [(M+H)⁺]; mp 205–206° C.

Example 220

4-[3-(2-Cyclopropyl-pyridin-3-yl)-phenyl]-8-trifluoromethyl-1,3-dihydro-benzo[b][1,4]diazepin-2-one The title compound was prepared from (2-{3-[3-(2-cyclopropyl-pyridin-3-yl)-phenyl]-3-oxo-propionylamino}-4-trifluoromethyl-phenyl)-carbamic acid tert-butyl ester (Example M200) (223 mg, 0.413 mmol) by treatment with TFA in CH₂Cl₂ according to the general procedure N. Obtained as a light yellow solid (107 mg, 61%).

MS (ISP) 422.3 [(M+H)⁺]; mp 171–173° C.

Example 221

4-[3-(2-Cyclopropyl-pyridin-3-yl)-phenyl]-7-methyl-8-trifluoromethyl-1,3-dihydro-benzo[b][1,4]diazepin-2-one The title compound was prepared from (2-{3-[3-(2-cyclopropyl-pyridin-3-yl)-phenyl]-3-oxo-propionylamino}-5-methyl-4-trifluoromethyl-phenyl)-carbamic acid tert-butyl ester (Example M201) (245 mg, 0.443 mmol) by treatment with TFA in CH₂Cl₂ according to the general procedure N. Obtained as a light brown solid (122 mg, 63%).

MS (ISP) 436.4 [(M+H)⁺]; mp 173–175° C.

Example 222

4-[3-(2-Methyl-pyridin-4-yl)-phenyl]-7-propyl-8-trifluoromethyl-1,3-dihydro-benzo[b][1,4]diazepin-2-one The title compound was prepared from (2-{3-[3-(2-methyl-pyridin-4-yl)-phenyl]-3-oxo-propionylamino}-5-propyl-4-trifluoromethyl-phenyl)-carbamic acid tert-butyl ester (Example M202) (285 mg, 0.51 mmol) by treatment with TFA in CH₂Cl₂ according to the general procedure N. Obtained as a light yellow solid (67 mg, 29%).

MS (ISP) 438 [(M+H)⁺].

Example 223

7-Ethyl-4-[3-(2-methyl-pyridin-4-yl)-phenyl]-8-trifluoromethyl-1,3-dihydro-benzo[b][1,4]diazepin-2-one The title compound was prepared from (2-{3-[3-(2-methyl-pyridin-4-yl)-phenyl]-3-oxo-propionylamino}-5-propyl-4-trifluoromethyl-phenyl)-carbamic acid tert-butyl ester (Example M203) (204 mg, 0.38 mmol) by treatment with TFA in CH₂Cl₂ according to the general procedure N. Obtained as a light yellow solid (94 mg, 58%).

MS (ISP) 424 [(M+H)⁺].

Example 224

4-[3-(6-Cyclopropyl-pyridin-3-yl)-phenyl]-7-propyl-8-trifluoromethyl-1,3-dihydro-benzo[b][1,4]diazepin-2-one The title compound was prepared from (2-{3-[3-(6-cyclopropyl-pyridin-3-yl)-phenyl]-3-oxo-propionylamino}-

5-propyl-4-trifluoromethyl-phenyl)-carbamic acid tert-butyl ester (Example M204) (266 mg, 0.46 mmol) by treatment with TFA in CH$_2$Cl$_2$ according to the general procedure N. Obtained as a light yellow solid (75 mg, 35%).
MS (ISP) 464 [(M+H)$^+$].

Example 225

4-[3-(6-Cyclopropyl-pyridin-3-yl)-phenyl]-7-ethyl-8-trifluoromethyl-1,3-dihydro-benzo[b][1,4]diazepin-2-one The title compound was prepared from (2-{3-[3-(6-cyclopropyl-pyridin-3-yl)-phenyl]-3-oxo-propionylamino}-5-ethyl-4-trifluoromethyl-phenyl)-carbamic acid tert-butyl ester (Example M205) (201 mg, 0.35 mmol) by treatment with TFA in CH$_2$Cl$_2$ according to the general procedure N. Obtained as a light yellow solid (98 mg, 62%).
MS (ISP) 450 [(M+H)$^+$].

Example 226

4-[3-(4-Methyl-pyridin-3-yl)-phenyl]-8-trifluoromethyl-1,3-dihydro-benzo[b][1,4]diazepin-2-one The title compound was prepared from (2-{3-[3-(6-cyclopropyl-pyridin-3-yl)-phenyl]-3-oxo-propionylamino}-5-ethyl-4-trifluoromethyl-phenyl)-carbamic acid tert-butyl ester (Example M206) (266 mg, 0.518 mmol) by treatment with TFA in CH$_2$Cl$_2$ according to the general procedure N. Obtained as a white solid (162 mg, 79%).
MS (ISP) 396.3 [(M+H)$^+$]; mp 220–221° C.

Example 227

4-[3-(2-Cyclopropyl-pyridin-3-yl)-phenyl]-7-ethoxy-8-trifluoromethyl-1,3-dihydro-benzo[b][1,4]diazepin-2-one The title compound was prepared from (2-{3-[3-(2-cyclopropyl-pyridin-3-yl)-phenyl]-3-oxo-propionylamino}-5-ethoxy-4-trifluoromethyl-phenyl)-carbamic acid tert-butyl ester (Example M207) (200 mg, 0.343 mmol) by treatment with TFA in CH$_2$Cl$_2$ according to the general procedure N. Obtained as a light brown solid (63 mg, 39%).
MS (ISP) 466.3 [(M+H)$^+$]; mp 187–188° C.

Example 228

4-[3-(2,6-Dimethyl-pyridin-4-yl)-phenyl]-7-ethyl-8-trifluoromethyl-1,3-dihydro-benzo[b][1,4]diazepin-2-one The title compound was prepared from (2-{3-[3-(2,6-dimethyl-pyridin-4-yl)-phenyl]-3-oxo-propionylamino}-5-ethyl-4-trifluoromethyl-phenyl)-carbamic acid tert-butyl ester (Example M208) (155 mg, 0.28 mmol) by treatment with TFA in CH$_2$Cl$_2$ according to the general procedure N. Obtained as an off-white solid (72 mg, 59%).
MS (ISP) 438 [(M+H)$^+$]; mp 231° C.

Example 229

4-[3-(2,6-Dimethyl-pyridin-4-yl)-phenyl]-7-propyl-8-trifluoromethyl-1,3-dihydro-benzo[b][1,4]diazepin-2-one The title compound was prepared from (2-{3-[3-(2,6-Dimethyl-pyridin-4-yl)-phenyl]-3-oxo-propionylamino}-5-propyl-4-trifluoromethyl-phenyl)-carbamic acid tert-butyl ester (Example M209) (295 mg, 0.52 mmol) by treatment with TFA in CH$_2$Cl$_2$ according to the general procedure N. Obtained as an off-white solid (197 mg, 84%).
MS (ISP) 452 [(M+H)$^+$]; mp 216° C.

Example 230

7-Propyl-4-(3-pyridin-3-yl-phenyl)-8-trifluoromethyl-1,3-dihydro-benzo[b][1,4]diazepin-2-one The title compound was prepared from {2-[3-oxo-3-(3-pyridin-3-yl-phenyl)-propionylamino]-5-propyl-4-trifluoromethyl-phenyl}-carbamic acid tert-butyl ester (Example M210) (165 mg, 0.31 mmol) by treatment with TFA in CH$_2$Cl$_2$ according to the general procedure N. Obtained as a yellow solid (77 mg, 59%).
MS (ISP) 424 [(M+H)$^+$]; mp 162° C.

Example 231

7-Ethoxy-4-[3-(4-methyl-pyridin-3-yl)-phenyl]-8-trifluoromethyl-1,3-dihydro-benzo[b][1,4]diazepin-2-one The title compound was prepared from (5-ethoxy-2-{3-[3-(4-methyl-pyridin-3-yl)-phenyl]-3-oxo-propionylamino}-4-trifluoromethyl-phenyl)-carbamic acid tert-butyl ester (Example M211) (304 mg, 0.545 mmol) by treatment with TFA in CH$_2$Cl$_2$ according to the general procedure N. Obtained as a light yellow solid (177 mg, 74%).
MS (ISP) 440.4 [(M+H)$^+$]; mp 213–214° C.

Example 232

4-[3-(4-Methyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(4-methyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M212) (304 mg, 0.545 mmol) by treatment with TFA in CH$_2$Cl$_2$ according to the general procedure N. Obtained as an off-white solid (180 mg, 60%).
MS (ISP) 494.2 [(M+H)$^+$]; mp 198–200° C.

Example 233

7-Methyl-4-[3-(4-methyl-pyridin-3-yl)-phenyl]-8-trifluoromethyl-1,3-dihydro-benzo[b][1,4]diazepin-2-one The title compound was prepared from (5-methyl-2-{3-[3-(4-methyl-pyridin-3-yl)-phenyl]-3-oxo-propionylamino}-4-trifluoromethyl-phenyl)-carbamic acid tert-butyl ester (Example M213) (291 mg, 0.552 mmol) by treatment with TFA in CH$_2$Cl$_2$ according to the general procedure N. Obtained as a white solid (182 mg, 81%).
MS (ISP) 410.4 [(M+H)$^+$]; mp 205–207° C.

Example 234

4-[3-(2-Ethyl-pyridin-3-yl)-phenyl]-7-methyl-8-trifluoromethyl-1,3-dihydro-benzo[b][1,4]diazepin-2-one The title compound was prepared from (2-{3-[3-(2-ethyl-pyridin-3-yl)-phenyl]-3-oxo-propionylamino}-5-methyl-4- trifluoromethyl-phenyl)-carbamic acid tert-butyl ester (Example M214) (312 mg, 0.58 mmol) by treatment with TFA in CH$_2$Cl$_2$ according to the general procedure N. Obtained as a white solid (190 mg, 77%).

MS (ISP) 424 [(M+H)$^+$]; mp 213° C.

Example 235

7-Ethoxy-4-[3-(2-ethyl-pyridin-3-yl)-phenyl]-8-trifluoromethyl-1,3-dihydro-benzo[b][1,4]diazepin-2-one The title compound was prepared from (5-ethoxy-2-{3-[3-(2-ethyl-pyridin-3-yl)-phenyl]-3-oxo-propionylamino}-4-trifluoromethyl-phenyl)-carbamic acid tert-butyl ester (Example M215) (255 mg, 0.45 mmol) by treatment with TFA in CH$_2$Cl$_2$ according to the general procedure N. Obtained as a light yellow solid (148 mg, 73%).

MS (ISP) 454 [(M+H)$^+$]; mp 214° C.

Example 236

4-[3-(2-Ethyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-ethyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M216) (335 mg, 0.536 mmol) by treatment with TFA in CH$_2$Cl$_2$ according to the general procedure N. Obtained as an off-white solid (159 mg, 58%).

MS (ISP) 508 [(M+H)$^+$]; mp 184° C.

Example 237

7-Methyl-4-[3-(6-methyl-pyridin-3-yl)-phenyl]-8-trifluoromethyl-1,3-dihydro-benzo[b][1,4]diazepin-2-one The title compound was prepared from (5-methyl-2-{3-[3-(6-methyl-pyridin-3-yl)-phenyl]-3-oxo-propionylamino}-4-trifluoromethyl-phenyl)-carbamic acid tert-butyl ester (Example M217) (299 mg, 0.57 mmol) by treatment with TFA in CH$_2$Cl$_2$ according to the general procedure N. Obtained as a light yellow solid (194 mg, 83%).

MS (ISP) 410 [(M+H)$^+$]; mp 235° C.

Example 238

7-Ethoxy-4-[3-(6-methyl-pyridin-3-yl)-phenyl]-8-trifluoromethyl-1,3-dihydro-benzo[b][1,4]diazepin-2-one The title compound was prepared from (5-ethoxy-2-{3-[3-(6-methyl-pyridin-3-yl)-phenyl]-3-oxo-propionylamino}-4-trifluoromethyl-phenyl)-carbamic acid tert-butyl ester (Example M218) (260 mg, 0.47 mmol) by treatment with TFA in CH$_2$Cl$_2$ according to the general procedure N. Obtained as a yellow solid (137 mg, 66%).

MS (ISP) 440 [(M+H)$^+$]; mp 210° C.

Example 239

4-[3-(6-Methyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-methyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M219) (191 mg, 0.31 mmol) by treatment with TFA in CH$_2$Cl$_2$ according to the general procedure N. Obtained as a light yellow solid (95 mg, 62%).

MS (ISP) 494 [(M+H)$^+$]; mp 159° C.

Example 240

4-[3-(2,6-Dimethyl-pyridin-4-yl)-phenyl]-7-fluoro-8-trifluoromethyl-1,3-dihydro-benzo[b][1,4]diazepin-2-one The title compound was prepared from (2-{3-[3-(2,6-dimethyl-pyridin-4-yl)-phenyl]-3-oxo-propionylamino}-5-fluoro-4-trifluoromethyl-phenyl)-carbamic acid tert-butyl ester (Example M220) (291 mg, 0.533 mmol) by treatment with TFA in CH$_2$Cl$_2$ according to the general procedure N. Obtained as a white solid (169 mg, 74%).

MS (ISP) 428.5 [(M+H)$^+$]; mp 251–252° C.

Example 241

4-[3-(2,6-Dimethyl-pyridin-4-yl)-phenyl]-8-trifluoromethyl-7-vinyl-1,3-dihydro-benzo[b][1,4]diazepin-2-one The title compound was prepared from (2-{3-[3-(2,6-dimethyl-pyridin-4-yl)-phenyl]-3-oxo-propionylamino}-4-trifluoromethyl-5-vinyl-phenyl)-carbamic acid tert-butyl ester (Example M221) (175 mg, 0.316 mmol) by treatment with TFA in CH$_2$Cl$_2$ according to the general procedure N. Obtained as a light yellow solid (104 mg, 76%).

MS (ISP) 436.4 [(M+H)$^+$]; mp 225–226° C.

Example 242

7-(2-Methoxy-ethoxy)-4-[3-(2-methyl-pyridin-4-yl)-phenyl]-8-trifluoromethyl-1,3-dihydro-benzo[b][1,4]diazepin-2-one The title compound was prepared from (5-(2-methoxy-ethoxy)-2-{3-[3-(2-methyl-pyridin-4-yl)-phenyl]-3-oxo-propionylamino}-4-trifluoromethyl-phenyl)-carbamic acid tert-butyl ester (Example M222) (340 mg, 0.58 mmol) by treatment with TFA in CH$_2$Cl$_2$ according to the general procedure N. Obtained as a light brown solid (196 mg, 72%).

MS (ISP) 470 [(M+H)$^+$]; mp 198–199° C.

Example 243

4-[3-(2,6-Dimethyl-pyridin-4-yl)-phenyl]-7-(2-methoxy-ethoxy)-8-trifluoromethyl-1,3-dihydro-benzo[b][1,4]diazepin-2-one The title compound was prepared from [2-{3-[3-(2,6-dimethyl-pyridin-4-yl)-phenyl]-3-oxo-propionylamino}-5-(2-methoxy-ethoxy)-4-trifluoromethyl-phenyl]-carbamic acid tert-butyl ester (Example M223) (320 mg, 0.53 mmol) by treatment with TFA in CH$_2$Cl$_2$ according to the general procedure N. Obtained as a light brown solid (183 mg, 71%).

MS (ISP) 484 [(M+H)$^+$]; mp 213–214° C.

Example 244

4-[3-(2-Methyl-pyridin-4-yl)-phenyl]-8-trifluoromethyl-7-vinyl-1,3-dihydro-benzo[b][1,4]diazepin-2-one The title compound was prepared from (2-{3-[3-(2-methyl-pyridin-4-yl)-phenyl]-3-oxo-propionylamino}-4- trifluoromethyl-5-vinyl-phenyl)-carbamic acid tert-butyl ester (Example M224) (300 mg, 0.56 mmol) by treatment with TFA in CH$_2$Cl$_2$ according to the general procedure N. Obtained as a light brown solid (133 mg, 56%).

MS (ISP) 422 [(M+H)$^+$]; mp 200–201° C.

Example 245

4-[3-(4,6-Dimethyl-pyridin-3-yl)-phenyl]-7-methyl-8-trifluoromethyl-1,3-dihydro-benzo[b][1,4]diazepin-2-one The title compound was prepared from (2-{3-[3-(4,6-dimethyl-pyridin-3-yl)-phenyl]-3-oxo-propionylamino}-5-methyl-4-trifluoromethyl-phenyl)-carbamic acid tert-butyl ester (Example M225) (312 mg, 0.576 mmol) by treatment with TFA in CH$_2$Cl$_2$ according to the general procedure N. Obtained as a white solid (182 mg, 75%).

MS (ISP) 424.4 [(M+H)$^+$]; mp 218–219° C.

Example 246

4-[3-(6-Cyclopropyl-4-methyl-pyridin-3-yl)-phenyl]-7-methyl-8-trifluoromethyl-1,3-dihydro-benzo[b][1,4]diazepin-2-one The title compound was prepared from (2-{3-[3-(6-cyclopropyl-4-methyl-pyridin-3-yl)-phenyl]-3-oxo-propionylamino}-5-methyl-4-trifluoromethyl-phenyl)-carbamic acid tert-butyl ester (Example M226) (279 mg, 0.49 mmol) by treatment with TFA in CH$_2$Cl$_2$ according to the general procedure N. Obtained as an off-white solid (116 mg, 53%).

MS (ISP) 450 [(M+H)$^+$]; mp 195° C.

Example 247

4-[3-(6-Cyclopropyl-4-methyl-pyridin-3-yl)-phenyl]-7-ethoxy-8-trifluoromethyl-1,3-dihydro-benzo[b][1,4]diazepin-2-one The title compound was prepared from (2-{3-[3-(6-cyclopropyl-4-methyl-pyridin-3-yl)-phenyl]-3-oxo-propionylamino}-5-ethoxy-4-trifluoromethyl-phenyl)-carbamic acid tert-butyl ester (Example M227) (305 mg, 0.51 mmol) by treatment with TFA in CH$_2$Cl$_2$ according to the general procedure N. Obtained as an off-white solid (160 mg, 65%).

MS (ISP) 480 [(M+H)$^+$]; mp 202° C.

Example 248

4-[3-(6-Cyclopropyl-4-methyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-cyclopropyl-4-methyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M228) (305 mg, 0.47 mmol) by treatment with TFA in CH$_2$Cl$_2$ according to the general procedure N. Obtained as an off-white solid (206 mg, 82%).

MS (ISP) 534 [(M+H)$^+$]; mp 206° C.

Example 249

4-[3-(2-Ethyl-6-methyl-pyridin-4-yl)-phenyl]-7-methyl-8-trifluoromethyl-1,3-dihydro-benzo[b][1,4]diazepin-2-one The title compound was prepared from (2-{3-[3-(2-ethyl-6-methyl-pyridin-4-yl)-phenyl]-3-oxo-propionylamino}-5-methyl-4-trifluoromethyl-phenyl)-carbamic acid tert-butyl ester (Example M229) (292 mg, 0.53 mmol) by treatment with TFA in CH$_2$Cl$_2$ according to the general procedure N. Obtained as an off-white solid (188 mg, 81%).

MS (ISP) 438 [(M+H)$^+$]; mp 212° C.

Example 250

7-Ethoxy-4-[3-(2-ethyl-6-methyl-pyridin-4-yl)-phenyl]-8-trifluoromethyl-1,3-dihydro-benzo[b][1,4]diazepin-2-one The title compound was prepared from (5-ethoxy-2-{3-[3-(2-ethyl-6-methyl-pyridin-4-yl)-phenyl]-3-oxo-propionylamino}-4-trifluoromethyl-phenyl)-carbamic acid tert-butyl ester (Example M230) (282 mg, 0.48 mmol) by treatment with TFA in CH$_2$Cl$_2$ according to the general procedure N. Obtained as an off-white solid (205 mg, 91%).

MS (ISP) 468 [(M+H)$^+$]; mp 215° C.

Example 251

4-[3-(2-Ethyl-6-methyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-ethyl-6-methyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M231) (366 mg, 0.57 mmol) by treatment with TFA in CH$_2$Cl$_2$ according to the general procedure N. Obtained as an off-white solid (242 mg, 81%).

MS (ISP) 522 [(M+H)$^+$]; mp 209° C.

Example 252

4-[3-(4,6-Dimethyl-pyridin-3-yl)-phenyl]-7-ethoxy-8-trifluoromethyl-1,3-dihydro-benzo[b][1,4]diazepin-2-one The title compound was prepared from (2-{3-[3-(4,6-dimethyl-pyridin-3-yl)-phenyl]-3-oxo-propionylamino}-5-ethoxy-4-trifluoromethyl-phenyl)-carbamic acid tert-butyl ester (Example M232) (340 mg, 0.595 mmol) by treatment with TFA in CH$_2$Cl$_2$ according to the general procedure N. Obtained as a white solid (148 mg, 55%).

MS (ISP) 454.5 [(M+H)$^+$]; mp 226–228° C.

Example 253

4-[3-(4,6-Dimethyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(4,6-dimethyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M233) (378 mg, 0.604 mmol) by treatment with TFA in CH$_2$Cl$_2$ according to the general procedure N. Obtained as a white solid (269 mg, 88%).

MS (ISP) 508.4 [(M+H)$^+$]; mp 176–180° C.

Example 254

4-[3-(6-Ethyl-4-methyl-pyridin-3-yl)-phenyl]-7-methyl-8-trifluoromethyl-1,3-dihydro-benzo[b][1,4]diazepin-2-one The title compound was prepared from (2-{3-[3-(6-ethyl-4-methyl-pyridin-3-yl)-phenyl]-3-oxo-propionylamino}-5- methyl-4-trifluoromethyl-phenyl)-carbamic acid tert-butyl ester (Example M234) (156 mg, 0.28 mmol) by treatment with TFA in CH$_2$Cl$_2$ according to the general procedure N. Obtained as an off-white solid (73 mg, 60%).

MS (ISP) 438 [(M+H)$^+$]; mp 200° C.

Example 255

7-Ethoxy-4-[3-(6-ethyl-4-methyl-pyridin-3-yl)-phenyl]-8-trifluoromethyl-1,3-dihydro-benzo[b][1,4]diazepin-2-one The title compound was prepared from (5-ethoxy-2-{3-[3-(6-ethyl-4-methyl-pyridin-3-yl)-phenyl]-3-oxo-propionylamino}-4-trifluoromethyl-phenyl)-carbamic acid tert-butyl ester (Example M235) (151 mg, 0.26 mmol) by treatment with TFA in CH$_2$Cl$_2$ according to the general procedure N. Obtained as an off-white solid (84 mg, 69%).

MS (ISP) 468 [(M+H)$^+$]; mp 205° C.

Example 256

4-[3-(6-Ethyl-4-methyl-pyridin-3-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(6-Ethyl-4-methyl-pyridin-3-yl)-phenyl]-3-oxo-propionylamino}-5-(2,2,2-trifluoro-ethoxy)-4-trifluoromethyl-phenyl]-carbamic acid tert-butyl ester (Example M236) (176 mg, 0.28 mmol) by treatment with TFA in CH$_2$Cl$_2$ according to the general procedure N. Obtained as a yellow solid (43 mg, 29%).

MS (ISP) 522 [(M+H)$^+$]; mp 145–160° C.

Example 257

4-[3-(2-Cyclopropyl-6-methyl-pyridin-4-yl)-phenyl]-7-methyl-8-trifluoromethyl-1,3-dihydro-benzo[b][1,4]diazepin-2-one The title compound was prepared from (2-{3-[3-(2-cyclopropyl-6-methyl-pyridin-4-yl)-phenyl]-3-oxo-propionylamino}-5-methyl-4-trifluoromethyl-phenyl)-carbamic acid tert-butyl ester (Example M237) (273 mg, 0.48 mmol) by treatment with TFA in CH$_2$Cl$_2$ according to the general procedure N. Obtained as an off-white solid (177 mg, 82%).

MS (ISP) 450 [(M+H)$^+$]; mp 257° C.

Example 258

4-[3-(2-Cyclopropyl-6-methyl-pyridin-4-yl)-phenyl]-7-ethoxy-8-trifluoromethyl-1,3-dihydro-benzo[b][1,4]diazepin-2-one The title compound was prepared from (2-{3-[3-(2-cyclopropyl-6-methyl-pyridin-4-yl)-phenyl]-3-oxo-propionylamino}-5-ethoxy-4-trifluoromethyl-phenyl)-carbamic acid tert-butyl ester (Example M238) (244 mg, 0.41 mmol) by treatment with TFA in CH$_2$Cl$_2$ according to the general procedure N. Obtained as an off-white solid (150 mg, 76%).

MS (ISP) 480 [(M+H)$^+$]; mp 232° C.

Example 259

4-[3-(2-Cyclopropyl-6-methyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-cyclopropyl-6-methyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M239) (308 mg, 0.47 mmol) by treatment with TFA in CH$_2$Cl$_2$ according to the general procedure N. Obtained as an off-white solid (199 mg, 79%).

MS (ISP) 534 [(M+H)$^+$]; mp 200° C.

Example 260

7-Methyl-4-[3-(2-methyl-pyridin-3-yl)-phenyl]-8-trifluoromethyl-1,3-dihydro-benzo[b][1,4]diazepin-2-one The title compound was prepared from (5-methyl-2-{3-[3-(2-methyl-pyridin-3-yl)-phenyl]-3-oxo-propionylamino}-4-trifluoromethyl-phenyl)-carbamic acid tert-butyl ester (Example M240) (416 mg, 0.79 mmol) by treatment with TFA in CH$_2$Cl$_2$ according to the general procedure N. Obtained as a light yellow solid (246 mg, 76%).

MS (ISP) 410.4 [(M+H)$^+$]; mp 246° C.

Example 261

7-Hydroxymethyl-4-[3-(2-methyl-pyridin-4-yl)-phenyl]-8-trifluoromethyl-1,3-dihydro-benzo[b][1,4]diazepin-2-one The title compound was prepared from [2-{3-[3-(2-methyl-pyridin-4-yl)-phenyl]-3-oxo-propionylamino}-5-(tetrahydro-pyran-2-yloxymethyl)-4-trifluoromethyl-phenyl]-carbamic acid tert-butyl ester (Example M241) (156 mg, 0.28 mmol) by treatment with TFA in CH$_2$Cl$_2$ according to the general procedure N. Obtained as a light yellow solid (50 mg, 42%).

MS (ISP) 426 [(M+H)$^+$]; mp 218° C.

Example 262

4-[3-(2-Isobutyl-pyridin-4-yl)-phenyl]-7-methyl-8-trifluoromethyl-1,3-dihydro benzo[b][1,4]diazepin-2-one The title compound was prepared from (2-{3-[3-(2-isobutyl-pyridin-4-yl)-phenyl]-5-methyl-3-oxo-propionylamino}-4-trifluoromethyl-phenyl)-carbamic acid tert-butyl ester (Example M242) (0.28 g, 0.49 mmol) by treatment with TFA in CH$_2$Cl$_2$ according to the general procedure N. Obtained as a light brown solid (160 mg, 72%).

MS (ISP) 452.5 [(M+H)$^+$]; mp 209° C.

Example 263

4-[3-(2-Ethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-isobutyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M243) (0.31 g, 0.47 mmol) by treatment with TFA in CH$_2$Cl$_2$ according to the general procedure N. Obtained as a light brown solid (140 mg, 55%).

MS (ISP) 536.4 [(M+H)$^+$]; mp 183° C.

Example 264

8-Chloro-7-methyl-4-[3-(2-trifluoromethyl-pyridin-4-yl)-phenyl]-1,3-dihydro-benzo[b][1,4]diazepin-2-one The title compound was prepared from (4-chloro-5-methyl-2-{3-oxo-3-[3-(2-trifluoromethyl-pyridin-4-yl)- phenyl]-propionylamino}-phenyl)-carbamic acid tert-butyl ester (Example M244) (0.26 g, 0.47 mmol) by treatment with TFA in CH$_2$Cl$_2$ according to the general procedure N. Obtained as an off-white solid (200 mg, 98%).

MS (ISP) 428.2 [(M–H)$^-$]; mp 247° C.

Example 265

7-Methyl-8-trifluoromethyl-4-[3-(2-trifluoromethyl-pyridin-4-yl)-phenyl]-1,3-dihydro-benzo[b][1,4]diazepin-2-one The title compound was prepared from (5-methyl-2-{3-oxo-3-[3-(2-trifluoromethyl-pyridin-4-yl)-phenyl]-propionylamino}-4-trifluoromethyl-phenyl)-carbamic acid tert-butyl ester (Example M245) (0.28 g, 0.48 mmol) by treatment with TFA in CH$_2$Cl$_2$ according to the general procedure N. Obtained as an off-white solid (220 mg, 99%).

MS (ISP) 462.1 [(M–H)$^-$]; mp 247° C.

Example 266

7-Chloro-8-trifluoromethyl-4-[3-(2-trifluoromethyl-pyridin-4-yl)-phenyl]-1,3-dihydro-benzo[b][1,4]diazepin-2-one The title compound was prepared from (5-chloro-2-{3-oxo-3-[3-(2-trifluoromethyl-pyridin-4-yl)-phenyl]-propionylamino}-4-trifluoromethyl-phenyl)-carbamic acid tert-butyl ester (Example M246) (0.24 g, 0.40 mmol) by treatment with TFA in CH$_2$Cl$_2$ according to the general procedure N. Obtained as a light brown solid (150 mg, 78%).

MS (ISP) 482.2 [(M–H)$^-$]; mp 229° C.

Example 267

7,8-Dichloro-4-[3-(2-trifluoromethyl-pyridin-4-yl)-phenyl]-1,3-dihydro-benzo[b][1,4]diazepin-2-one The title compound was prepared from commercially available 4,5-dichloro-1,2-phenylendiamine (133 mg, 0.75 mmol) and 3-oxo-3-[3-(2-trifluoromethyl-pyridin-4-yl)-phenyl]-propionic acid tert-butyl ester (Example K38) (274 mg, 0.75 mmol) in xylene (15 ml) under reflux conditions for 2 h according to the general procedure M. Obtained as a light red solid (290 mg, 86%).

MS (ISP) 448.0 [(M–H)$^-$]; mp 226° C.

Example 268

7-(2,2,2-Trifluoro-ethoxy)-8-trifluoromethyl-4-[3-(2-trifluoromethyl-pyridin-4-yl)-phenyl]-1,3-dihydro-benzo[b][1,4]diazepin-2-one The title compound was prepared from [2-{3-oxo-3-[3-(2-trifluoromethyl-pyridin-4-yl)-phenyl]-propionylamino}-5-(2,2,2-trifluoro-ethoxy)-4-trifluoromethyl-phenyl]-carbamic acid tert-butyl ester (Example M247) (0.43 g, 0.65 mmol) by treatment with TFA in CH$_2$Cl$_2$ according to the general procedure N. Obtained as a light brown solid (260 mg, 74%).

MS (ISP) 546.2 [(M–H)$^-$]; mp 220° C.

Example 269

7-Ethoxy-8-trifluoromethyl-4-[3-(2-trifluoromethyl-pyridin-4-yl)-phenyl]-1,3-dihydro-benzo[b][1,4]diazepin-2-one The title compound was prepared from (5-ethoxy-2-{3-oxo-3-[3-(2-trifluoromethyl-pyridin-4-yl)-phenyl]-propionylamino}-4-trifluoromethyl-phenyl)-carbamic acid tert-butyl ester (Example M248) (0.30 g, 0.49 mmol) by treatment with TFA in CH$_2$Cl$_2$ according to the general procedure N. Obtained as a light yellow solid (220 mg, 91%).

MS (ISP) 492.1 [(M–H)$^-$]; mp 251° C.

Example 270

8-Chloro-4-[3-(2-isopropyl-pyridin-4-yl)-phenyl]-7-methyl-1,3-dihydro-benzo[b][1,4]diazepin-2-one The title compound was prepared from (4-chloro-2-{3-[3-(2-isopropyl-pyridin-4-yl)-phenyl]-5-methyl-3-oxo-propionylamino}-phenyl)-carbamic acid tert-butyl ester (Example M249) (0.32 g, 0.61 mmol) by treatment with TFA in CH$_2$Cl$_2$ according to the general procedure N. Obtained as a light yellow solid (200 mg, 81%).

MS (ISP) 404.4 [(M+H)$^+$]; mp 196° C.

Example 271

4-[3-(2-Isopropyl-pyridin-4-yl)-phenyl]-7-methyl-8-trifluoromethyl-1,3-dihydro benzo[b][1,4]diazepin-2-one The title compound was prepared from (2-{3-[3-(2-isopropyl-pyridin-4-yl)-phenyl]-5-methyl-3-oxo-propionylamino}-4-trifluoromethyl-phenyl)-carbamic acid tert-butyl ester (Example M250) (0.21 g, 0.38 mmol) by treatment with TFA in CH$_2$Cl$_2$ according to the general procedure N. Obtained as an off-white solid (150 mg, 91%).

MS (ISP) 438.4 [(M+H)$^+$]; mp 205° C.

Example 272

4-[3-(2-Isopropyl-pyridin-4-yl)-phenyl]-8-trifluoromethyl-1,3-dihydro benzo[b][1,4]diazepin-2-one The title compound was prepared from (2-{3-[3-(2-isopropyl-pyridin-4-yl)-phenyl]-3-oxo-propionylamino}-4-trifluoromethyl-phenyl)-carbamic acid tert-butyl ester (Example M251) (0.23 g, 0.43 mmol) by treatment with TFA in CH$_2$Cl$_2$ according to the general procedure N. Obtained as a light yellow solid (150 mg, 83%).

MS (ISP) 422.2 [(M+–H)$^-$]; mp 168° C.

Example 273

7-Chloro-4-[3-(2-isopropyl-pyridin-4-yl)-phenyl]-8-trifluoromethyl-1,3-dihydro benzo[b][1,4]diazepin-2-one The title compound was prepared from (5-chloro-2-{3-[3-(2-isopropyl-pyridin-4-yl)-phenyl]-3-oxo-propionylamino}-4-trifluoromethyl-phenyl)-carbamic acid tert-butyl ester (Example M252) (0.22 g, 0.38 mmol) by treatment with TFA in CH$_2$Cl$_2$ according to the general procedure N. Obtained as a light yellow solid (150 mg, 86%).

MS (ISP) 456.3 [(M–H)$^-$]; mp 200° C.

Example 274

7,8-Dichloro-4-[3-(2-isopropyl-pyridin-4-yl)-phenyl]-1,3-dihydro-benzo[b][1,4]diazepin-2-one The title compound was prepared from commercially available 4,5-dichloro-1,2-phenylendiamine (133 mg, 0.75 mmol) and 3-[3-(2-isopropyl-pyridin-4-yl)-phenyl]-3-oxo-propionic acid tert-butyl ester (Example K39) (255 mg, 0.75 mmol) in xylene (15 ml) under reflux conditions for 1.5 h according to the general procedure M. Obtained as a light red solid (220 mg, 69%).

MS (ISP) 424.3 [(M−H)⁻]; mp 195° C.

Example 275

4-[3-(2-Isopropyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-isopropyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M253) (0.33 g, 0.52 mmol) by treatment with TFA in CH$_2$Cl$_2$ according to the general procedure N. Obtained as a light brown solid (230 mg, 85%).

MS (ISP) 520.2 [(M−H)⁻]; mp 202° C.

Example 276

4-[3-(2-Isopropyl-pyridin-4-yl)-phenyl]-7-ethoxy-8-trifluoromethyl-1,3-dihydro-benzo[b][1,4]diazepin-2-one The title compound was prepared from [2-{3-[3-(2-isopropyl-pyridin-4-yl)-phenyl]-3-oxo-propionylamino}-5-ethoxy-4-trifluoromethyl-phenyl]-carbamic acid tert-butyl ester (Example M254) (0.32 g, 0.55 mmol) by treatment with TFA in CH$_2$Cl$_2$ according to the general procedure N. Obtained as an off-white solid (200 mg, 78%).

MS (ISP) 466.2 [(M−H)⁻]; mp 217° C.

Example 277

8-Chloro-4-[3-(2-isobutyl-pyridin-4-yl)-phenyl]-7-methyl-1,3-dihydro-benzo[b][1,4]diazepin-2-one The title compound was prepared from (4-chloro-2-{3-[3-(2-isobutyl-pyridin-4-yl)-phenyl]-5-methyl-3-oxo-propionylamino}-phenyl)-carbamic acid tert-butyl ester (Example M256) (0.29 g, 0.54 mmol) by treatment with TFA in CH$_2$Cl$_2$ according to the general procedure N. Obtained as a light yellow solid (170 mg, 75%).

MS (ISP) 416.2 [(M−H)⁻]; mp 198° C.

Example 278

7-Chloro-4-[3-(2-isobutyl-pyridin-4-yl)-phenyl]-8-trifluoromethyl-1,3-dihydro benzo[b][1,4]diazepin-2-one The title compound was prepared from (5-chloro-2-{3-[3-(2-isobutyl-pyridin-4-yl)-phenyl]-3-oxo-propionylamino}-4-trifluoromethyl-phenyl)-carbamic acid tert-butyl ester (Example M255) (0.31 g, 0.53 mmol) by treatment with TFA in CH$_2$Cl$_2$ according to the general procedure N. Obtained a light yellow solid (220 mg, 89%).

MS (ISP) 470.1 [(M−H)⁻]; mp 213° C.

Example 279

7,8-Dichloro-4-[3-(2-isobutyl-pyridin-4-yl)-phenyl]-1,3-dihydro-benzo[b][1,4]diazepin-2-one The title compound was prepared from commercially available 4,5-dichloro-1,2-phenylendiamine (133 mg, 0.75 mmol) and 3-[3-(2-isobutyl-pyridin-4-yl)-phenyl]-3-oxo-propionic acid tert-butyl ester (Example K37) (265 mg, 0.75 mmol) in xylene (15 ml) under reflux conditions for 2 h according to the general procedure M. Obtained as a light brown solid (230 mg, 70%).

MS (ISP) 436.2 [(M−H)⁻]; mp 204° C.

Example 280

4-[3-(2-Isobutyl-pyridin-4-yl)-phenyl]-7-ethoxy-8-trifluoromethyl-1,3-dihydro-benzo[b][1,4]diazepin-2-one The title compound was prepared from [2-{3-[3-(2-isobutyl-pyridin-4-yl)-phenyl]-3-oxo-propionylamino}-5-ethoxy-4-trifluoromethyl-phenyl]-carbamic acid tert-butyl ester (Example M257) (0.30 g, 0.50 mmol) by treatment with TFA in CH$_2$Cl$_2$ according to the general procedure N. Obtained as an off-white solid (210 mg, 87%).

MS (ISP) 480.3 [(M−H)⁻]; mp 203° C.

Example 281

4-[3-(2-Isobutyl-pyridin-4-yl)-phenyl]-8-trifluoromethyl-1,3-dihydro benzo[b][1,4]diazepin-2-one The title compound was prepared from (2-{3-[3-(2-isobutyl-pyridin-4-yl)-phenyl]-3-oxo-propionylamino}-4-trifluoromethyl-phenyl)-carbamic acid tert-butyl ester (Example M258) (0.25 g, 0.45 mmol) by treatment with TFA in CH$_2$Cl$_2$ according to the general procedure N. Obtained as a light yellow solid (180 mg, 91%).

MS (ISP) 436.3 [(M−H)⁻]; mp 181° C.

Example 282

8-Chloro-4-[3-(2-hydroxymethyl-pyridin-4-yl)-phenyl]-7-methyl-1,3-dihydro-benzo[b][1,4]diazepin-2-one The title compound was prepared from (RS)-[4-chloro-5-methyl-2-(3-oxo-3-{3-[2-(tetrahydro-pyran-2-yloxymethyl)-pyridin-4-yl]-phenyl}-propionylamino)-phenyl]-carbamic acid tert-butyl ester (Example M259) (0.50 g, 0.84 mmol) by treatment with TFA in CH$_2$Cl$_2$ according to the general procedure N. Obtained as an off-white solid (182 mg, 55%).

MS (ISP) 392.2 [(M+H)⁺]; mp 234° C.

Example 283

4-[3-(2-Hydroxymethyl-pyridin-4-yl)-phenyl]-7-methyl-8-trifluoromethyl-1,3-dihydro benzo[b][1,4]diazepin-2-one The title compound was prepared from (RS)-[5-methyl-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester (Example M260) (6.20 g, 98.8 mmol) by treatment with TFA in CH$_2$Cl$_2$ according to the general procedure N. Obtained as a light brown solid (2.74 g, 65%).

MS (ISP) 424.2 [(M−H)⁻]; mp 215° C.

Example 284

7-Chloro-4-[3-(2-hydroxymethyl-pyridin-4-yl)-phenyl]-8-trifluoromethyl-1,3-dihydro benzo[b][1,4]diazepin-2-one The title compound was prepared from (RS)-[5-chloro-2-(3-oxo-3-{3-[2-(tetrahydro-pyran-2-yloxymethyl)- pyridin-4-yl]-phenyl}-propionylamino)-4-trifluoromethyl-phenyl]-carbamic acid tert-butyl ester (Example M261) (0.54 g, 0.83 mmol) by treatment with TFA in $CH_2Cl_2$ according to the general procedure N. Obtained as a light yellow solid (170 mg, 46%).

MS (ISP) 446.2 [(M+H)$^+$]; mp 199° C.

Example 285

7,8-Dichloro-4-[3-(2-hydroxymethyl-pyridin-4-yl)-phenyl]-1,3-dihydro-benzo[b][1,4]diazepin-2-one The title compound was prepared from commercially available 4,5-dichloro-1,2-phenylendiamine (177 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) in xylene (15 ml) under reflux conditions for 1.5 h according to the general procedure M and subsequent treatment with TFA in $CH_2Cl_2$ according to the general procedure N. Obtained as a light brown solid (220 mg, 53%).

MS (ISP) 410.1 [(M−H)$^-$]; mp 224° C.

Example 286

4-[3-(2-Hydroxymethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from (RS)-[2-(3-oxo-3-{3-[2-(tetrahydro-pyran-2-yloxymethyl)-pyridin-4-yl]-phenyl}-propionylamino)-5-(2,2,2-trifluoro-ethoxy)-4-trifluoromethyl-phenyl]-carbamic acid tert-butyl ester (Example M262) (0.48 g, 0.67 mmol) by treatment with TFA in $CH_2Cl_2$ according to the general procedure N.

Obtained as a light brown solid (240 mg, 70%).

MS (ISP) 508.2 [(M−H)$^-$]; mp 201° C.

Example 287

4-[3-(2-Hydroxymethyl-pyridin-4-yl)-phenyl]-7-ethoxy-8-trifluoromethyl-1,3-dihydro-benzo[b][1,4]diazepin-2-one The title compound was prepared from (RS)-[5-ethoxy-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester (Example M263) (0.48 g, 0.73 mmol) by treatment with TFA in $CH_2Cl_2$ according to the general procedure N. Obtained as a light yellow solid (270 mg, 81%).

MS (ISP) 454.3 [(M−H)$^-$]; mp 216° C.

Example 288

4-[3-(6-Methyl-pyridin-3-yl)-phenyl]-8-pyrrol-1-yl-1,3-dihydro-benzo[b][1,4]diazepin-2-one The title compound was prepared from (2-amino-4-pyrrol-1-yl-phenyl)-carbamic acid tert-butyl ester (Example J11) (273 mg, 1 mmol) and 3-[3-(6-methyl-pyridin-3-yl)-phenyl]-3-oxo-propionic acid tert-butyl ester (Example K4) (311 mg, 1 mmol) according to the general procedure M and subsequent treatment of the crude product according to the general procedure N. Obtained as a yellow solid (195 mg).

MS (ISP) 393.2 [(M+H)$^+$]; mp 213–214° C.

Example 289

4-[3-(2-Methyl-pyridin-3-yl)-phenyl]-8-pyrrol-1-yl-1,3-dihydro-benzo[b][1,4]diazepin-2-one The title compound was prepared from (2-amino-4-pyrrol-1-yl-phenyl)-carbamic acid tert-butyl ester (Example J11) (273 mg, 1 mmol) and 3-[3-(2-methyl-pyridin-3-yl)-phenyl]-3-oxo-propionic acid tert-butyl ester (Example K5) (311 mg, 1 mmol) according to the general procedure M and subsequent treatment of the crude product according to the general procedure N. Obtained as a light yellow solid (146 mg).

MS (ISP) 393.2 [(M+H)$^+$]; mp 215–216° C.

Example 290

4-[2,3']Bipyridinyl-4-yl-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (116 mg, 0.4 mmol) and 3-[2,3']bipyridinyl-4-yl-3-oxo-propionic acid tert-butyl ester (Example K57) (119 mg, 0.4 mmol) according to the general procedure M and subsequent treatment of the crude product according to the general procedure N. Obtained as a light yellow solid (95 mg).

MS (ISP) 397.2 [(M+H)$^+$]; mp 218–220° C.

Example 291

4-[2,3']Bipyridinyl-4-yl-8-chloro-7-methyl-1,3-dihydro-benzo[b][1,4]diazepin-2-one The title compound was prepared from (2-amino-4-chloro-5-methyl-phenyl)-carbamic acid tert-butyl ester (Example J22) (102 mg, 0.4 mmol) and 3-[2,3']bipyridinyl-4-yl-3-oxo-propionic acid tert-butyl ester (Example K57) (119 mg, 0.4 mmol) according to the general procedure M and subsequent treatment of the crude product according to the general procedure N. Obtained as a light yellow solid (120 mg).

MS (ISP) 363.1 [(M+H)$^+$]; mp 229–231° C.

Example 292

4-[2,4']Bipyridinyl-4-yl-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (116 mg, 0.4 mmol) and 3-[2,4']bipyridinyl-4-yl-3-oxo-propionic acid tert-butyl ester (Example K58) (119 mg, 0.4 mmol) according to the general procedure M and subsequent treatment of the crude product according to the general procedure N. Obtained as a light yellow solid (86 mg).

MS (ISN) 394.9 [(M−H)$^-$]; mp 224–226° C.

Example 293

4-[2,4']Bipyridinyl-4-yl-8-chloro-7-methyl-1,3-dihydro-benzo[b][1,4]diazepin-2-one The title compound was prepared from (2-amino-4-chloro-5-methyl-phenyl)-carbamic acid tert-butyl ester (Example J22) (90 mg, 0.35 mmol) and 3-[2,4']bipyridinyl-4-yl-3-oxo-propionic acid tert-butyl ester (Example K58) (104 mg, 0.35 mmol) according to the general procedure M and subsequent treatment of the crude product according to the general procedure N. Obtained as a light yellow solid (120 mg).

MS (ISP) 363.1 [(M+H)$^+$]; mp 233–235° C.

Example 294

7-Methyl-4-(2'-methyl-[2,4']bipyridinyl-4-yl)-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (102 mg, 0.35 mmol) and 3-(2'-methyl-[2,4']bipyridinyl-4-yl)-3-oxo-propionic acid tert-butyl ester (Example K59) (109 mg, 0.35 mmol) according to the general procedure M and subsequent treatment of the crude product according to the general procedure N. Obtained as a light yellow solid (80 mg).

MS (ISN) 409.5 [(M−H)−]; mp 238–240° C.

Example 295

8-Chloro-7-methyl-4-(2'-methyl-[2,4']bipyridinyl-4-yl)-1,3-dihydro-benzo[b][1,4]diazepin-2-one The title compound was prepared from (2-amino-4-chloro-5-methyl-phenyl)-carbamic acid tert-butyl ester (Example J22) (67 mg, 0.26 mmol) and 3-(2'-methyl-[2,4'] bipyri-dinyl-4-yl)-3-oxo-propionic acid tert-butyl ester (Example K59) (81 mg, 0.26 mmol) according to the general procedure M and subsequent treatment of the crude product according to the general procedure N. Obtained as a light yellow solid (69 mg).

MS (ISP) 377.2 [(M+H)+]; mp 225–227° C.

Example 296

8-Chloro-7-methyl-4-(2'-methyl-[2,4']bipyridinyl-4-yl)-1,3-dihydro-benzo[b][1,4]diazepin-2-one The title compound was prepared from (2-amino-5-methyl-4-trifluoromethyl-phenyl)-carbamic acid tert-butyl ester (Example J20) (87 mg, 0.3 mmol) and 3-oxo-3-(3-pyrimidin-4-yl-phenyl)-propionic acid tert-butyl ester (Example K43) (99 mg, 0.3 mmol) according to the general procedure M and subsequent treatment of the crude product according to the general procedure N. Obtained as a light yellow solid (73 mg).

MS (ISP) 397.3 [(M+H)+]; mp 222–225° C.

Example 297

8-Chloro-7-methyl-4-(3-pyrimidin-4-yl-phenyl)-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-oxo-3-(3-pyrimidin-4-yl-phenyl)-propionic acid tert-butyl ester (Example K43) (179 mg, 0.6 mmol) according to the general procedure M and subsequent treatment of the crude product according to the general procedure N. Obtained as a light yellow solid (115 mg).

MS (ISP) 363.1 [(M+H)+]; mp 242–247° C.

Example 298

7-Dimethylamino-4-(3-pyrimidin-4-yl-phenyl)-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (160 mg, 0.5 mmol) and 3-oxo-3-(3-pyrimidin-4-yl-phenyl)-propionic acid tert-butyl ester (Example K43) (179 mg, 0.6 mmol) according to the general procedure M and subsequent treatment of the crude product according to the general procedure N. Obtained as a light yellow solid (112 mg).

MS (ISP) 426.3 [(M+H)+]; mp 209–210° C.

Example 299

8-Chloro-4-(3-pyrimidin-4-yl-phenyl)-1,3-dihydro-benzo[b][1,4]diazepin-2-one

The title compound was prepared from (2-amino-4-chloro-phenyl)-carbamic acid tert-butyl ester (Example J4) (121 mg, 0.5 mmol) and 3-oxo-3-(3-pyrimidin-4-yl-phenyl)-propionic acid tert-butyl ester (Example K4) (164 mg, 0.55 mmol) according to the general procedure M and subsequent treatment of the crude product according to the general procedure N. Obtained as a light yellow solid (96 mg).

MS (ISP) 349.2 [(M+H)+]; mp 220–233° C.

Example 300

7,8-Dichloro-4-(3-pyrimidin-4-yl-phenyl)-1,3-dihydro-benzo[b][1,4]diazepin-2-one The title compound was prepared from 4,5-dichlorophenylenediamine (89 mg, 0.5 mmol) and 3-oxo-3-(3-pyrimidin-4-yl-phenyl)-propionic acid tert-butyl ester (Example K43) (164 mg, 0.55 mmol) by refluxing in xylene according to the general procedure M. Obtained as a light yellow solid (63 mg).

MS (ISP) 383.0 [(M+H)+]; mp 234–237° C.

Example 301

7-Methyl-4-[3-(2-methyl-pyrimidin-4-yl)-phenyl]-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (87 mg, 0.3 mmol) and 3-[3-(2-methyl-pyrimidin-4-yl)-phenyl]-3-oxo-propionic acid tert-butyl ester (Example K42) (112 mg, 0.36 mmol) according to the general procedure M and subsequent treatment of the crude product according to the general procedure N. Obtained as a light yellow solid (41 mg).

MS (ISP) 411.2 [(M+H)+]; mp 230–232° C.

Example 302

8-Chloro-7-methyl-4-[3-(2-methyl-pyrimidin-4-yl)-phenyl]-1,3-dihydro-benzo[b][1,4]diazepin-2-one The title compound was prepared from (2-amino-4-chloro-5-methyl-phenyl)-carbamic acid tert-butyl ester (Example J22) (77 mg, 0.3 mmol) and 3-[3-(2-methyl-pyrimidin-4-yl)-phenyl]-3-oxo-propionic acid tert-butyl ester (Example K42) (112 mg, 0.36 mmol) according to the general procedure M and subsequent treatment of the crude product according to the general procedure N. Obtained as a light yellow solid (59 mg).

MS (ISP) 377.2 [(M+H)+].

Example 303

7-Dimethylamino-4-[3-(2-methyl-pyrimidin-4-yl)-phenyl]-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (160 mg, 0.5 mmol) and 3-[3-(2-methyl-pyrimidin-4-yl)-phenyl]-3-oxo-propionic acid tert-butyl ester (Example K42) (187 mg, 0.6 mmol) according to the general procedure M and subsequent treatment of the crude product according to the general procedure N. Obtained as a light yellow solid (152 mg).

MS (ISP) 440.3 [(M+H)+]; mp 211–212° C.

Example 304

4-[3-(2-Methyl-pyrimidin-4-yl)-phenyl]-8-trifluoromethyl-1,3-dihydro-benzo[b][1,4]diazepin-2-one The title compound was prepared from (2-amino-4-trifluoromethyl-phenyl)-carbamic acid tert-butyl ester (Example J3) (138 mg, 0.5 mmol) and 3-[3-(2-methyl-pyrimidin-4-yl)-phenyl]-3-oxo-propionic acid tert-butyl ester (Example K42) (187 mg, 0.6 mmol) according to the general procedure M and subsequent treatment of the crude product according to the general procedure N. Obtained as a light yellow solid (46 mg).

MS (ISP) 397.3 [(M+H)$^+$]; mp 212–226° C.

Example 305

8-Chloro-4-[3-(2-methyl-pyrimidin-4-yl)-phenyl]-1,3-dihydro-benzo[b][1,4]diazepin-2-one The title compound was prepared from (2-amino-4-chloro-phenyl)-carbamic acid tert-butyl ester (Example J4) (121 mg, 0.5 mmol) and 3-[3-(2-methyl-pyrimidin-4-yl)-phenyl]-3-oxo-propionic acid tert-butyl ester (Example K42) (187 mg, 0.6 mmol) according to the general procedure M and subsequent treatment of the crude product according to the general procedure N. Obtained as a light yellow solid (49 mg).

MS (ISP) 363.1 [(M+H)$^+$]; mp 215–220° C.

Example 306

7,8-Dichloro-4-[3-(2-methyl-pyrimidin-4-yl)-phenyl]-1,3-dihydro-benzo[b][1,4]diazepin-2-one The title compound was prepared from 4,5-dichlorophenylenediamine (89 mg 0.5 mmol) and 3-[3-(2-methyl-pyrimidin-4-yl)-phenyl]-3-oxo-propionic acid tert-butyl ester (Example K42) (172 mg, 0.55 mmol) by refluxing in xylene according to the general procedure M. Obtained as a light yellow solid (131 mg).

MS (ISN) 394.8/397.0 [(M–H)$^-$]; mp 241–242° C.

Example 307

4-[3-(2-Methyl-pyrimidin-4-yl)-phenyl]-8-pyrrol-1-yl-1,3-dihydro-benzo[b][1,4]diazepin-2-one The title compound was prepared from (2-amino-4-pyrrol-1-yl-phenyl)-carbamic acid tert-butyl ester (Example J11) (137 mg, 0.5 mmol) and 3-[3-(2-methyl-pyrimidin-4-yl)-phenyl]-3-oxo-propionic acid tert-butyl ester (Example K42) (187 mg, 0.6 mmol) according to the general procedure M and subsequent treatment of the crude product according to the general procedure N. Obtained as a light yellow solid (30 mg).

MS (ISP) 394.3 [(M+H)$^+$]; mp 209–212° C.

Example 308

7-Methyl-4-[3-(6-methyl-pyrimidin-4-yl)-phenyl]-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (145 mg, 0.5 mmol) and 3-[3-(6-methyl-pyrimidin-4-yl)-phenyl]-3-oxo-propionic acid tert-butyl ester (Example K41) (187 mg, 0.6 mmol) according to the general procedure M and subsequent treatment of the crude product according to the general procedure N. Obtained as a light yellow solid (59 mg).

MS (ISP) 411.2 [(M+H)$^+$]; mp 227–230° C.

Example 309

8-Chloro-7-methyl-4-[3-(6-methyl-pyrimidin-4-yl)-phenyl]-1,3-dihydro-benzo[b][1,4]diazepin-2-one The title compound was prepared from (2-amino-4-chloro-5-methyl-phenyl)-carbamic acid tert-butyl ester (Example J22) (77 mg, 0.3 mmol) and 3-[3-(6-methyl-pyrimidin-4-yl)-phenyl]-3-oxo-propionic acid tert-butyl ester (Example K41) (112 mg, 0.36 mmol) according to the general procedure M and subsequent treatment of the crude product according to the general procedure N. Obtained as a light yellow solid (61 mg).

MS (ISP) 377.2 [(M+H)$^+$]; mp 226–227° C.

Example 310

7-Dimethylamino-4-[3-(6-methyl-pyrimidin-4-yl)-phenyl]-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (160 mg, 0.5 mmol) and 3-[3-(6-methyl-pyrimidin-4-yl)-phenyl]-3-oxo-propionic acid tert-butyl ester (Example K41) (187 mg, 0.6 mmol) according to the general procedure M and subsequent treatment of the crude product according to the general procedure N. Obtained as a light yellow solid (139 mg).

MS (ISP) 440.3 [(M+H)$^+$]; mp 232–236° C.

Example 311

4-[3-(6-Methyl-pyrimidin-4-yl)-phenyl]-8-trifluoromethyl-1,3-dihydro-benzo[b][1,4]diazepin-2-one The title compound was prepared from (2-amino-4-trifluoromethyl-phenyl)-carbamic acid tert-butyl ester (Example J3) (138 mg, 0.5 mmol) and 3-[3-(6-methyl-pyrimidin-4-yl)-phenyl]-3-oxo-propionic acid tert-butyl ester (Example K41) (187 mg, 0.6 mmol) according to the general procedure M and subsequent treatment of the crude product according to the general procedure N. Obtained as a light yellow solid (44 mg).

MS (ISP) 397.3 [(M+H)$^+$]; mp 219–220° C.

Example 312

8-Chloro-4-[3-(6-methyl-pyrimidin-4-yl)-phenyl]-1,3-dihydro-benzo[b][1,4]diazepin-2-one The title compound was prepared from (2-amino-4-chloro-phenyl)-carbamic acid tert-butyl ester (Example J4) (121 mg, 0.5 mmol) and 3-[3-(6-methyl-pyrimidin-4-yl)-phenyl]-3-oxo-propionic acid tert-butyl ester (Example K41) (187 mg, 0.6 mmol) according to the general procedure M and subsequent treatment of the crude product according to the general procedure N. Obtained as a light yellow solid (37 mg).

MS (ISP) 363.0 [(M+H)$^+$]; mp 199–200° C.

Example 313

7,8-Dichloro-4-[3-(6-methyl-pyrimidin-4-yl)-phenyl]-1,3-dihydro-benzo[b][1,4]diazepin-2-one The title compound was prepared from 4,5-dichlorophenylenediamine (89 mg, 0.5 mmol) and 3-[3-(6-methyl-pyrimidin-4-yl)-phenyl]-3-oxo-propionic acid tert-butyl ester (Example K41) (172 mg, 0.55 mmol) by refluxing in xylene according to the general procedure M. Obtained as a light yellow solid (63 mg).

MS (ISP) 397.1/399.3 [(M+H)$^+$]; mp 220–222° C.

Example 314

4-[3-(6-Methyl-pyrimidin-4-yl)-phenyl]-8-pyrrol-1-yl-1,3-dihydro-benzo[b][1,4]diazepin-2-one The title compound was prepared from (2-amino-4-pyrrol-1-yl-phenyl)-carbamic acid tert-butyl ester (Example J11) (137 mg, 0.5 mmol) and 3-[3-(6-methyl-pyrimidin-4-yl)-phenyl]-3-oxo-propionic acid tert-butyl ester (Example K41) (172 mg, 0.55 mmol) according to the general procedure M and subsequent treatment of the crude product according to the general procedure N. Obtained as a light yellow solid (40 mg).

MS (ISP) 394.2 [(M+H)$^+$]; mp 242–243° C.

Example 315

4-[3-(2-Amino-6-methyl-pyrimidin-4-yl)-phenyl]-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (145 mg, 0.5 mmol) and 3-[3-(2-amino-6-methyl-pyrimidin-4-yl)-phenyl]-3-oxo-propionic acid tert-butyl ester (Example K45) (180 mg, 0.55 mmol) according to the general procedure M and subsequent treatment of the crude product according to the general procedure N. Obtained as a light yellow solid (64 mg).

MS (ISP) 426.3 [(M+H)$^+$]; mp 248–250° C.

Example 316

4-[3-(2-Amino-6-methyl-pyrimidin-4-yl)-phenyl]-8-chloro-7-methyl-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-[3-(2-amino-6-methyl-pyrimidin-4-yl)-phenyl]-3-oxo-propionic acid tert-butyl ester (Example K45) (180 mg, 0.55 mmol) according to the general procedure M and subsequent treatment of the crude product according to the general procedure N. Obtained as a light yellow solid (108 mg).

MS (ISP) 392.1 [(M+H)$^+$]; mp 242–243° C.

Example 317

4-[3-(2-Amino-6-methyl-pyrimidin-4-yl)-phenyl]-7-dimethylamino-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (96 mg, 0.3 mmol) and 3-[3-(2-amino-6-methyl-pyrimidin-4-yl)-phenyl]-3-oxo-propionic acid tert-butyl ester (Example K45) (118 mg, 0.36 mmol) according to the general procedure M and subsequent treatment of the crude product according to the general procedure N. Obtained as a light yellow solid (31 mg).

MS (ISP) 455.3 [(M+H)$^+$]; mp 250–253° C.

Example 318

7-Methyl-4-[3-(6-methyl-2-methylamino-pyrimidin-4-yl)-phenyl]-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (135 mg, 0.5 mmol) and 3-[3-(6-methyl-2-methylamino-pyrimidin-4-yl)-phenyl]-3-oxo-propionic acid tert-butyl ester (Example K48) (171 mg, 0.5 mmol) according to the general procedure M and subsequent treatment of the crude product according to the general procedure N. Obtained as a light yellow solid (82 mg).

MS (ISP) 440.2 [(M+H)$^+$]; mp 241–243° C.

Example 319

8-Chloro-7-methyl-4-[3-(6-methyl-2-methylamino-pyrimidin-4-yl)-phenyl]-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-[3-(6-methyl-2-methylamino-pyrimidin-4-yl)-phenyl]-3-oxo-propionic acid tert-butyl ester (Example K48) (188 mg, 0.55 mmol) according to the general procedure M and subsequent treatment of the crude product according to the general procedure N. Obtained as a light yellow solid (88 mg).

MS (ISP) 406.2 [(M+H)$^+$]; mp 235–237° C.

Example 320

4-[3-(2-Dimethylamino-6-methyl-pyrimidin-4-yl)-phenyl]-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (116 mg, 0.4 mmol) and 3-[3-(2-dimethylamino-6-methyl-pyrimidin-4-yl)-phenyl]-3-oxo-propionic acid tert-butyl ester (Example K49) (171 mg, 0.48 mmol) according to the general procedure M and subsequent treatment of the crude product according to the general procedure N. Obtained as a light yellow solid (114 mg).

MS (ISP) 454.3 [(M+H)$^+$]; mp 248–252° C.

Example 321

8-Chloro-4-[3-(2-dimethylamino-6-methyl-pyrimidin-4-yl)-phenyl]-7-methyl-1,3-dihydro-benzo[b][1,4]diazepin-2-one The title compound was prepared from (2-amino-4-chloro-5-methyl-phenyl)-carbamic acid tert-butyl ester (Example J22) (103 mg, 0.4 mmol) and 3-[3-(2-dimethylamino-6-methyl-pyrimidin-4-yl)-phenyl]-3-oxo-propionic acid tert-butyl ester (Example K49) (171 mg, 0.48 mmol) according to the general procedure M and subsequent treatment of the crude product according to the general procedure N. Obtained as a light yellow solid (133 mg).

MS (ISP) 420.2 [(M+H)$^+$]; mp 248–250° C.

Example 322

4-{3-[2-(2-Hydroxy-ethylamino)-6-methyl-pyrimidin-4-yl]-phenyl}-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (145 mg, 0.5 mmol) and 3-{3-[2-(2-hydroxy-ethylamino)-6-methyl-pyrimidin-4-yl]-phenyl}-3-oxo-propionic acid tert-butyl ester (Example K50) (250 mg, 0.55 mmol) according to the general procedure M and subsequent treatment of the crude product according to the general procedure N. Obtained as a light yellow solid (100 mg).

MS (ISP) 470.1 [(M+H)$^+$]; mp 228–230° C.

Example 323

8-Chloro-4-{3-[2-(2-hydroxy-ethylamino)-6-methyl-pyrimidin-4-yl]-phenyl}-7-methyl-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-{3-[2-(2-hydroxy-ethylamino)-6-methyl-pyrimidin-4-yl]-phenyl}-3-oxo-propionic acid tert-butyl ester (Example K50) (251 mg, 0.55 mmol) according to the general procedure M and subsequent treatment of the crude product according to the general procedure N. Obtained as a light yellow solid (136 mg).

MS (ISP) 436.2 [(M+H)$^+$]; mp 197–199° C.

Example 324

4-{3-[2-(2-Methoxy-ethylamino)-6-methyl-pyrimidin-4-yl]-phenyl}-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (145 mg, 0.5 mmol) and 3-{3-[2-(2-methoxy-ethylamino)-6-methyl-pyrimidin-4-yl]-phenyl}-3-oxo-propionic acid tert-butyl ester (Example K51) (212 mg, 0.55 mmol) according to the general procedure M and subsequent treatment of the crude product according to the general procedure N. Obtained as a light yellow solid (169 mg).

MS (ISP) 484.3 [(M+H)$^+$]; mp 236–238° C.

Example 325

8-Chloro-4-{3-[2-(2-methoxy-ethylamino)-6-methyl-pyrimidin-4-yl]-phenyl}-7-methyl-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-{3-[2-(2-methoxy-ethylamino)-6-methyl-pyrimidin-4-yl]-phenyl}-3-oxo-propionic acid tert-butyl ester (Example K51) (212 mg, 0.55 mmol) according to the general procedure M and subsequent treatment of the crude product according to the general procedure N. Obtained as a light yellow solid (122 mg).

MS (ISP) 450.2 [(M+H)$^+$]; mp 222–224° C.

Example 326

7-Dimethylamino-4-{3-[2-(2-methoxy-ethylamino)-6-methyl-pyrimidin-4-yl]-phenyl}-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (160 mg, 0.5 mmol) and 3-{3-[2-(2-methoxy-ethylamino)-6-methyl-pyrimidin-4-yl]-phenyl}-3-oxo-propionic acid tert-butyl ester (Example K51) (212 mg, 0.55 mmol) according to the general procedure M and subsequent treatment of the crude product according to the general procedure N. Obtained as a light yellow solid (84 mg).

MS (ISP) 513.3 [(M+H)$^+$]; mp 200–203° C.

Example 327

8-Chloro-7-methyl-4-[3-(6-methyl-2-morpholin-4-yl-pyrimidin-4-yl)-phenyl]-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-{3-[2-(2-methoxy-ethylamino)-6-methyl-pyrimidin-4-yl]-phenyl}-3-oxo-propionic acid tert-butyl ester (Example K51) (219 mg, 0.55 mmol) according to the general procedure M and subsequent treatment of the crude product according to the general procedure N. Obtained as a light yellow solid (126 mg).

MS (ISN) 460.1 [(M–H)$^-$]; mp 252–256° C.

Example 328

4-[3-(6-Amino-pyrimidin-4-yl)-phenyl]-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (116 mg, 0.4 mmol) and 3-[3-(6-amino-pyrimidin-4-yl)-phenyl]-3-oxo-propionic acid tert-butyl ester (Example K53) (138 mg, 0.44 mmol) according to the general procedure M and subsequent treatment of the crude product according to the general procedure N. Obtained as a light yellow solid (90 mg).

MS (ISP) 412.2 [(M+H)$^+$]; mp 201–205° C.

Example 329

4-[3-(6-Amino-pyrimidin-4-yl)-phenyl]-8-chloro-7-methyl-1,3-dihydro-benzo[b][1,4]diazepin-2-one The title compound was prepared from (2-amino-4-chloro-5-methyl-phenyl)-carbamic acid tert-butyl ester (Example J22) (103 mg, 0.4 mmol) and 3-[3-(6-amino-pyrimidin-4-yl)-phenyl]-3-oxo-propionic acid tert-butyl ester (Example K53) (138 mg, 0.44 mmol) according to the general procedure M and subsequent treatment of the crude product according to the general procedure N. Obtained as a light yellow solid (126 mg).

MS (ISP) 378.2 [(M+H)$^+$]; mp 228–233° C.

Example 330

7-Methyl-4-[3-(6-methylamino-pyrimidin-4-yl)-phenyl]-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (145 mg, 0.5 mmol) and 3-[3-(6-methylamino-pyrimidin-4-yl)-phenyl]-3-oxo-propionic acid tert-butyl ester (Example K54) (180 mg, 0.55 mmol) according to the general procedure M and subsequent treatment of the crude product according to the general procedure N. Obtained as a light yellow solid (166 mg).

MS (ISP) 426.2 [(M+H)$^+$]; mp 232–233° C.

Example 331

8-Chloro-7-methyl-4-[3-(6-methylamino-pyrimidin-4-yl)-phenyl]-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-[3-(6-methylamino-pyrimidin-4-yl)-phenyl]-3-oxo-propionic acid tert-butyl ester (Example K54) (180 mg, 0.55 mmol) according to the general procedure M and subsequent treatment of the crude product according to the general procedure N. Obtained as a light yellow solid (132 mg).

MS (ISP) 392.1 [(M+H)$^+$]; mp 240–243° C.

Example 332

4-[3-(6-Dimethylamino-pyrimidin-4-yl)-phenyl]-7-methyl-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (116 mg, 0.4 mmol) and 3-[3-(6-dimethylamino-pyrimidin-4-yl)-phenyl]-3-oxo-propionic acid tert-butyl ester (Example K55) (150 mg, 0.44 mmol) according to the general procedure M and subsequent treatment of the crude product according to the general procedure N. Obtained as a light yellow solid (143 mg).

MS (ISP) 440.2 [(M+H)$^+$]; mp 239–242° C.

Example 333

8-Chloro-4-[3-(6-dimethylamino-pyrimidin-4-yl)-phenyl]-7-methyl-1,3-dihydro-benzo[b][1,4]diazepin-2-one The title compound was prepared from (2-amino-4-chloro-5-methyl-phenyl)-carbamic acid tert-butyl ester (Example J22) (103 mg, 0.4 mmol) and 3-[3-(6-dimethylamino-pyrimidin-4-yl)-phenyl]-3-oxo-propionic acid tert-butyl ester (Example K55) (150 mg, 0.44 mmol) according to the general procedure M and subsequent treatment of the crude product according to the general procedure N. Obtained as a light yellow solid (109 mg).

MS (ISP) 406.2 [(M+H)$^+$]; mp 226–228° C.

Example 334

8-Chloro-4-{3-[6-(2-methoxy-ethylamino)-pyrimidin-4-yl]-phenyl}-7-methyl-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-{3-[6-(2-methoxy-ethylamino)-pyrimidin-4-yl]-phenyl}-3-oxo-propionic acid tert-butyl ester (Example K56) (204 mg, 0.55 mmol) according to the general procedure M and subsequent treatment of the crude product according to the general procedure N. Obtained as a light yellow solid (118 mg).

MS (ISP) 436.2 [(M+H)$^+$]; mp 211–213° C.

Example 335

8-Chloro-7-methyl-4-(3-pyrimidin-2-yl-phenyl)-1,3-dihydro-benzo[b][1,4]diazepin-2-one The title compound was prepared from (2-amino-4-chloro-5-methyl-phenyl)-carbamic acid tert-butyl ester (Example J22) (128 mg, 0.5 mmol) and 3-oxo-3-(3-pyrimidin-2-yl-phenyl)-propionic acid tert-butyl ester (Example K44) (179 mg, 0.6 mmol) according to the general procedure M and subsequent treatment of the crude product according to the general procedure N. Obtained as a light yellow solid (81 mg).

MS (ISP) 363.1 [(M+H)$^+$]; mp 223–227° C.

Example 336

4-(3-Pyrimidin-2-yl-phenyl)-8-trifluoromethyl-1,3-dihydro-benzo[b][1,4]diazepin-2-one The title compound was prepared from (2-amino-5-methyl-4-trifluoromethyl-phenyl)-carbamic acid tert-butyl ester (Example J20) (145 mg, 0.5 mmol) and 3-oxo-3-(3-pyrimidin-2-yl-phenyl)-propionic acid tert-butyl ester (Example K44) (179 mg, 0.6 mmol) according to the general procedure M and subsequent treatment of the crude product according to the general procedure N. Obtained as a light yellow solid (80 mg).

MS (ISP) 397.2 [(M+H)$^+$]; mp 230–236° C.

Example 337

7-Dimethylamino-4-(3-pyrimidin-2-yl-phenyl)-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (160 mg, 0.5 mmol) and 3-oxo-3-(3-pyrimidin-2-yl-phenyl)-propionic acid tert-butyl ester (Example K44) (179 mg, 0.6 mmol) according to the general procedure M and subsequent treatment of the crude product according to the general procedure N. Obtained as a light yellow solid (43 mg).

MS (ISP) 426.4 [(M+H)$^+$]; mp 221–223° C.

Example 338

4-(3-Pyrimidin-2-yl-phenyl)-8-trifluoromethyl-1,3-dihydro-benzo[b][1,4]diazepin-2-one The title compound was prepared from (2-amino-4-trifluoromethyl-phenyl)-carbamic acid tert-butyl ester (Example J3) (138 mg, 0.5 mmol) and 3-oxo-3-(3-pyrimidin-2-yl-phenyl)-propionic acid tert-butyl ester (Example K44) (164 mg, 0.55 mmol) according to the general procedure M and subsequent treatment of the crude product according to the general procedure N. Obtained as a light yellow solid (75 mg).

MS (ISN) 381.0 [(M–H)$^-$]; mp 236–237° C.

Example 339

8-Chloro-4-(3-pyrimidin-2-yl-phenyl)-1,3-dihydro-benzo[b][1,4]diazepin-2-one

The title compound was prepared from (2-amino-4-chloro-phenyl)-carbamic acid tert-butyl ester (Example J4) (121 mg, 0.5 mmol) and 3-oxo-3-(3-pyrimidin-2-yl-phenyl)-propionic acid tert-butyl ester (Example K44) (164 mg, 0.55 mmol) according to the general procedure M and subsequent treatment of the crude product according to the general procedure N. Obtained as a light yellow solid (102 mg).

MS (ISP) 349.2 [(M+H)$^+$]; mp 217–222° C.

Example 340

7,8-Dichloro-4-(3-pyrimidin-2-yl-phenyl)-1,3-dihydro-benzo[b][1,4]diazepin-2-one The title compound was prepared from 4,5-dichlorophenylenediamine (89 mg 0.5 mmol) and 3-oxo-3-(3-pyrimidin-2-yl-phenyl)-propionic acid tert-butyl ester (Example K44) (164 mg, 0.55 mmol) by refluxing in xylene according to the general procedure M. Obtained as a light yellow solid (127 mg).

MS (ISP) 383.1/385.1 [(M+H)$^+$]; mp 227–230° C.

Example 341

7-Dimethylamino-4-[3-(3-methyl-[1,2,4]triazin-6-yl)-phenyl]-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (160 mg, 0.5 mmol) and 3-[3-(3-methyl-[1,2,4]triazin-6-yl)-phenyl]-3-oxo-propionic acid tert-butyl ester (Example K46) (180 mg, 0.55 mmol) according to the general procedure M and subsequent treatment of the crude product according to the general procedure N. Obtained as a light yellow solid (8 mg).

MS (ISP) 441.2 [(M+H)$^+$].

Example 342

4-[3-(3-Methyl-[1,2,4]triazin-6-yl)-phenyl]-8-trifluoromethyl-1,3-dihydro-benzo[b][1,4]diazepin-2-one The title compound was prepared from (2-amino-4-trifluoromethyl-phenyl)-carbamic acid tert-butyl ester (Example J3) (83 mg, 0.3 mmol) and 3-[3-(3-methyl-[1,2,4]triazin-6-yl)-phenyl]-3-oxo-propionic acid tert-butyl ester (Example K46) (113 mg, 0.36 mmol) according to the general procedure M and subsequent treatment of the crude product according to the general procedure N. Obtained as a light yellow solid (18 mg).

MS (ISP) 398.3 [(M+H)$^+$].

Example 343

7-Dimethylamino-4-[3-(5,6-dimethyl-[1,2,4]triazin-3-yl)-phenyl]-8-trifluoromethyl-1,3-dihydro-benzo[b][1,4]diazepin-2-one The title compound was prepared from (2-amino-5-dimethylamino-4-trifluoromethyl-phenyl)-carbamic acid tert-butyl ester (Example J1) (160 mg, 0.5 mmol) and 3-[3-(5,6-dimethyl-[1,2,4]triazin-3-yl)-phenyl]-3-oxo-propionic acid tert-butyl ester (Example K47) (180 mg, 0.55 mmol) according to the general procedure M and subsequent treatment of the crude product according to the general procedure N. Obtained as a light yellow solid (26 mg).

MS (ISP) 455.3 [(M+H)$^+$]; mp 233–236° C.

Example 344

4-[3-(6-Cyclopropyl-4-methyl-pyridin-3-yl)-phenyl]-8-trifluoromethyl-1,3-dihydro-benzo[b][1,4]diazepin-2-one The title compound was prepared from (2-{3-[3-(6-cyclopropyl-4-methyl-pyridin-3-yl)-phenyl]-3-oxo-propionylamino}-4-trifluoromethyl-phenyl)-carbamic acid tert-butyl ester (Example M264) (260 mg, 0.47 mmol) by treatment with TFA in CH$_2$Cl$_2$ according to the general procedure N. Obtained as an off-white solid (67 mg, 33%).

MS (ISN) 434 [(M−H)$^-$]; mp 119° C.

Example 345

4-[3-(4,6-Dimethyl-pyridin-3-yl)-phenyl]-8-trifluoromethyl-1,3-dihydro-benzo[b[[1,4]diazepin-2-one The title compound was prepared from (2-{3-[3-(4,6-dimethyl-pyridin-3-yl)-phenyl]-3-oxo-propionylamino}-4-trifluoromethyl-phenyl)-carbamic acid tert-butyl ester (Example M265) (289 mg, 0.55 mmol) by treatment with TFA in CH$_2$Cl$_2$ according to the general procedure N. Obtained as an off-white solid (146 mg, 65%).

MS (ISN) 408 [(M−H)$^-$]; mp 203° C.

Example 346

4-[3-(2-Cyclopropyl-pyridin-4-yl)-phenyl]-8-trifluoromethyl-1,3-dihydro-benzo[b][1,4]diazepin-2-one The title compound was prepared from (2-{3-[3-(2-cyclopropyl-pyridin-4-yl)-phenyl]-3-oxo-propionylamino}-4-trifluoromethyl-phenyl)-carbamic acid tert-butyl ester (Example M266) (274 mg, 0.51 mmol) by treatment with TFA in CH$_2$Cl$_2$ according to the general procedure N. Obtained as an off-white solid (168 mg, 78%).

MS (ISN) 420 [(M−H)$^-$]; mp 181° C.

Example 347

4-[3-(2-Cyclopropyl-pyridin-4-yl)-phenyl]-7-methyl-8-trifluoromethyl-1,3-dihydro-benzo[b][1,4]diazepin-2-one The title compound was prepared from (2-{3-[3-(2-cyclopropyl-pyridin-4-yl)-phenyl]-3-oxo-propionylamino}-5-methyl-4-trifluoromethyl-phenyl)-carbamic acid tert-butyl ester (Example M267) (286 mg, 0.52 mmol) by treatment with TFA in CH$_2$Cl$_2$ according to the general procedure N. Obtained as a light yellow solid (198 mg, 87%).

MS (ISN) 434 [(M−H)$^-$]; mp 232° C.

Example 348

4-[3-(2-Cyclopropyl-pyridin-4-yl)-phenyl]-7-ethoxy-8-trifluoromethyl-1,3-dihydro-benzo[b][1,4]diazepin-2-one The title compound was prepared from (2-{3-[3-(2-cyclopropyl-pyridin-4-yl)-phenyl]-3-oxo-propionylamino}-5-ethoxy-4-trifluoromethyl-phenyl)-carbamic acid tert-butyl ester (Example M268) (298 mg, 0.51 mmol) by treatment with TFA in CH$_2$Cl$_2$ according to the general procedure N. Obtained as a light yellow solid (179 mg, 75%).

MS (ISP) 466 [(M+H)$^+$]; mp 244° C.

Example 349

4-[3-(2-Cyclopropyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-cyclopropyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M269) (349 mg, 0.55 mmol) by treatment with TFA in CH$_2$Cl$_2$ according to the general procedure N. Obtained as a light yellow solid (230 mg, 81%).

MS (ISN) 518 [(M−H)$^-$]; mp 218° C.

Example 350

7-Cyclopropyl-4-[3-(2-methyl-pyridin-4-yl)-phenyl]-8-trifluoromethyl-1,3-dihydro-benzo[b][1,4]diazepin-2-one The title compound was prepared from (5-cyclopropyl-2-{3-[3-(2-methyl-pyridin-4-yl)-phenyl]-3-oxo-propionylamino}-4-trifluoromethyl-phenyl)-carbamic acid tert-butyl ester (Example M270) (349 mg, 0.63 mmol) by treatment with TFA in CH$_2$Cl$_2$ according to the general procedure N. Obtained as a light yellow solid (91 mg, 33%).

MS (ISN) 434.2 [(M−H)$^-$]; mp 205–211° C.

Example 351

4-[3-(2-Cyclopentyl-pyridin-4-yl)-phenyl]-7-methyl-8-trifluoromethyl-1,3-dihydro-benzo[b][1,4]diazepin-2-one The title compound was prepared from (2-{3-[3-(2-cyclopentyl-pyridin-4-yl)-phenyl]-3-oxo-propionylamino}-

5-methyl-4-trifluoromethyl-phenyl)-carbamic acid tert-butyl ester (Example M271) (360 mg, 0.619 mmol) by treatment with TFA in $CH_2Cl_2$ according to the general procedure N. Obtained as a light yellow solid (135 mg, 47%).

MS (ISP) 464.3 [(M+H)+]; mp 218–219° C.

Example 352

4-[3-(2-Cyclopentyl-pyridin-4-yl)-phenyl]-8-trifluoromethyl-1,3-dihydro-benzo[b][1,4]diazepin-2-one The title compound was prepared from (2-{3-[3-(2-cyclopentyl-pyridin-4-yl)-phenyl]-3-oxo-propionylamino}-4-trifluoromethyl-phenyl)-carbamic acid tert-butyl ester (Example M272) (300 mg, 0.529 mmol) by treatment with TFA in $CH_2Cl_2$ according to the general procedure N. Obtained as an off-white solid (143 mg, 60%).

MS (ISP) 450.2 [(M+H)+]; mp 165–167° C.

Example 353

4-[3-(2-Cyclopentyl-pyridin-4-yl)-phenyl]-7-ethoxy-8-trifluoromethyl-1,3-dihydro-benzo[b][1,4]diazepin-2-one The title compound was prepared from (2-{3-[3-(2-cyclopentyl-pyridin-4-yl)-phenyl]-3-oxo-propionylamino}-5-ethoxy-4-trifluoromethyl-phenyl)-carbamic acid tert-butyl ester (Example M273) (360 mg, 0.589 mmol) by treatment with TFA in $CH_2Cl_2$ according to the general procedure N. Obtained as a yellow solid (198 mg, 68%).

MS (ISP) 494.3 [(M+H)+]; mp 192–193° C.

Example 354

4-[3-(2-Cyclopentyl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-cyclopentyl-pyridin-4-yl)-phenyl]-3-oxo-propionylamino}-5-(2,2,2-trifluoro-ethoxy)-4-trifluoromethyl-phenyl]-carbamic acid tert-butyl ester (Example M274) (400 mg, 0.601 mmol) by treatment with TFA in $CH_2Cl_2$ according to the general procedure N. Obtained as a light brown solid (195 mg, 59%).

MS (ISP) 548.3 [(M+H)+]; mp 147–148° C.

Example 355

4-[3-(1-Oxy-pyridin-3-yl)-phenyl]-8-trifluoromethyl-1,3-dihydro-benzo[b][1,4]diazepin-2-one The title compound was prepared from 4-(3-pyridin-3-yl-phenyl)-8-trifluoromethyl-1,3-dihydro-benzo[b][1,4]diazepin-2-one (Example 27) (381 mg, 1.0 mmol) by treatment with mCPBA (3-chloro-perbenzoic acid, 370 mg, 1.5 mmol) in $CH_2Cl_2$ (60 mL) at 23° C. until tlc indicated complete conversion. Evaporated to dryness, suspended in $Na_2S_2O_3$-sol.+$NaHCO_3$-sol., filtered precipitate off, washed thoroughly with water, triturated with ether and dried in high vacuum. Obtained as a yellow solid (330 mg, 83%).

MS (ISP) 398.2 [(M+H)+]; mp 230–231° C.

Example 356

7-Methyl-4-[3-(1-oxy-pyridin-3-yl)-phenyl]-8-trifluoromethyl-1,3-dihydro-benzo[b][1,4]diazepin-2-one The title compound was prepared from 7-methyl-4-(3-pyridin-3-yl-phenyl)-8-trifluoromethyl-1,3-dihydro-benzo[b][1,4]diazepin-2-one (Example 172) (381 mg, 1.0 mmol) by treatment with mCPBA in $CH_2Cl_2$ at 23° C. as described for Example 355. Obtained as a light yellow solid (317 mg, 77%).

MS (ISP) 412.3 [(M+H)+]; mp 235–236° C.

Example 357

4-[3-(1-Oxy-pyridin-3-yl)-phenyl]-7-(2,2,2-trifluoro-ethoxy)-8-trifluoromethyl-1,3-dihydro-benzo[b][1,4]diazepin-2-one The title compound was prepared from 4-(3-pyridin-3-yl-phenyl)-7-(2,2,2-trifluoro-ethoxy)-8-trifluoromethyl-1,3-dihydro-benzo[b][1,4]diazepin-2-one (Example 30) (479 mg, 1.0 mmol) by treatment with mCPBA in $CH_2Cl_2$ at 23° C. as described for Example 355. Obtained as a yellow solid (371 mg, 75%).

MS (ISP) 496 [(M+H)+]; mp 226° C.

Example 358

7-Hydroxymethyl-4-[3-(2-methyl-1-oxy-pyridin-4-yl)-phenyl]-8-trifluoromethyl-1,3-dihydro-benzo[b][1,4]diazepin-2-one The title compound was prepared from 7-hydroxymethyl-4-[3-(2-methyl-pyridin-4-yl)-phenyl]-8-trifluoromethyl-1,3-dihydro-benzo[b][1,4]diazepin-2-one (Example 261) (100 mg, 0.24 mmol) by treatment with mCPBA in $CH_2Cl_2$ at 23° C. as described for Example 355. Obtained as a light yellow solid (46 mg, 43%).

MS (ISP) 442 [(M+H)+]; mp 185° C. (dec.).

Example 359

7-Ethoxy-4-[3-(2-methyl-1-oxy-pyridin-4-yl)-phenyl]-8-trifluoromethyl-1,3-dihydro-benzo[b][1,4]diazepin-2-one The title compound was prepared from 7-ethoxy-4-[3-(2-methyl-pyridin-4-yl)-phenyl]-8-trifluoromethyl-1,3-dihydro-benzo[b][1,4]diazepin-2-one (Example 61) (439 mg, 1.0 mmol) by treatment with mCPBA in $CH_2Cl_2$ at 23° C. as described for Example 355. Obtained as a light yellow solid (295 mg, 65%).

MS (ISP) 456 [(M+H)+]; mp 227° C.

Example 360

4-(3-{2-[(Isobutyl-methyl-amino)-methyl]-pyridin-4-yl}-phenyl)-7-methyl-8-trifluoromethyl-1,3-dihydro-benzo[b][1,4]diazepin-2-one A stirred suspension of 4-[3-(2-hydroxymethyl-pyridin-4-yl)-phenyl]-7-methyl-8-trifluoromethyl-1,3-dihydro-benzo[b][1,4]diazepin-2-one (Example 283) (213 mg, 0.50 mmol) and thionyl chloride (0.11 ml, 1.50 mmol) in $CH_2Cl_2$ was refluxed for 45 min, evaporated to dryness and dissolved in DMF (3 ml). To the stirred solution N-isobutyl-methyl-amine (436 mg, 5.0 mmol) was added and the reaction mixture was stirred at RT for 1 h. Aqueous work-up ($CH_2Cl_2$) and further purification by column chromatography on silica gel ($CH_2Cl_2$/MeOH 15:1) yielded the title compound as a light yellow solid (142 mg, 57%).

MS (ISP) 495.4 [(M+H)+]; mp 188° C.

Example 361

4-[3-(2-Methoxymethyl-pyridin-4-yl)-phenyl]-7-methyl-8-trifluoromethyl-1,3-dihydro-benzo[b][1,4]diazepin-2-one The title compound was prepared from 4-[3-(2-hydroxymethyl-pyridin-4-yl)-phenyl]-7-methyl-8- trifluoromethyl-1,3-dihydro-benzo[b][1,4]diazepin-2-one (Example 283) (213 mg, 0.50 mmol) by reaction with thionylchloride in $CH_2Cl_2$ and subsequent treatment of the corresponding crude chloride with sodium methanolate (5.4M, 1 ml) in MeOH (5 ml)/$CH_2Cl_2$ (5 ml) according to the general procedure of example 288. Obtained as an off-white solid (101 mg, 46%).

MS (ISP) 438.3 [(M–H)⁻]; mp 225° C.

Example 362

7-(Isobutyl-methyl-amino)-4-[3-(2-methyl-pyridin-4-yl)-phenyl]-8-trifluoromethyl-1,3-dihydro-benzo[b][1,4]diazepin-2-one The title compound was prepared from (5-(isobutyl-methyl-amino)-2-{3-[3-(2-methyl-pyridin-4-yl)-phenyl]-3-oxo-propionylamino}-4-trifluoromethyl-phenyl)-carbamic acid tert-butyl ester (Example M275) (0.44 g, 0.73 mmol) by treatment with TFA in $CH_2Cl_2$ according to the general procedure N. Obtained as a light brown solid (186 mg, 53%).

MS (ISP) 481.3 [(M+H)⁺]; mp 189° C.

Example 363

7-(Isopropyl-methyl-amino)-4-[3-(2-methyl-pyridin-4-yl)-phenyl]-8-trifluoromethyl-1,3-dihydro-benzo[b][1,4]diazepin-2-one The title compound was prepared from (5-(isopropyl-methyl-amino)-2-{3-[3-(2-methyl-pyridin-4-yl)-phenyl]-3-oxo-propionylamino}-4-trifluoromethyl-phenyl)-carbamic acid tert-butyl ester (Example M276) (0.44 g, 0.75 mmol) by treatment with TFA in $CH_2Cl_2$ according to the general procedure N. Obtained as an off-white solid (252 mg, 72%).

MS (ISP) 467.3 [(M+H)⁺]; mp 207° C.

Example 364

7-(Isopropyl-methyl-amino)-4-[3-(2-methyl-pyridin-4-yl)-phenyl]-8-trifluoromethyl-1,3-dihydro-benzo[b][1,4]diazepin-2-one The title compound was prepared from (4-chloro-5-(isobutyl-methyl-amino)-2-{3-[3-(2-methyl-pyridin-4-yl)-phenyl]-3-oxo-propionylamino}-phenyl)-carbamic acid tert-butyl ester (Example M277) (0.40 g, 0.71 mmol) by treatment with TFA in $CH_2Cl_2$ according to the general procedure N. Obtained as an off-white solid (269 mg, 85%).

MS (ISP) 447.3 [(M+H)⁺]; mp 122° C.

Example 365

4-[3-(2-Methyl-pyridin-4-yl)-phenyl]-7-pyrrolidin-1-yl-8-trifluoromethyl-1,3-dihydro-benzo[b][1,4]diazepin-2-one The title compound was prepared from (2-{3-[3-(2-methyl-pyridin-4-yl)-phenyl]-3-oxo-propionylamino}-5-pyrrolidin-1-yl-4-trifluoromethyl-phenyl)-carbamic acid tert-butyl ester (Example M278) (0.34 g, 0.58 mmol) by treatment with TFA in $CH_2Cl_2$ according to the general procedure N. Obtained as a yellow solid (217 mg, 80%).

MS (ISP) 463.3 [(M–H)⁻]; mp 223° C.

Example 366

4-[3-(2-Hydroxymethyl-pyridin-4-yl)-phenyl]-7-(isobutyl-methyl-amino)-8-trifluoromethyl-1,3-dihydro-benzo[b][1,4]diazepin-2-one The title compound was prepared from (RS)-[5-(isobutyl-methyl-amino)-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester (Example M279) (5.82 g, 8.34 mmol) by treatment with TFA in $CH_2Cl_2$ according to the general procedure N. Obtained as a light yellow solid (2.84 g, 69%).

MS (ISP) 497.4 [(M+H)⁺]; mp 130° C.

Example 367

8-Chloro-4-[3-(2-hydroxymethyl-pyridin-4-yl)-phenyl]-7-(isopropyl-methyl-amino)-1,3-dihydro-benzo[b][1,4]diazepin-2-one The title compound was prepared from (RS)-[4-chloro-5-(isopropyl-methyl-amino)-2-(3-oxo-3-{3-[2-(tetrahydro-pyran-2-yloxymethyl)-pyridin-4-yl]-phenyl}-propionylamino)-phenyl]-carbamic acid tert-butyl ester (Example M280) (0.35 g, 0.54 mmol) by treatment with TFA in $CH_2Cl_2$ according to the general procedure N. Obtained as a yellow solid (162 mg, 67%).

MS (ISP) 449.3 [(M+H)⁺]; mp 143° C.

Example 368

8-Chloro-4-[3-(2-hydroxymethyl-pyridin-4-yl)-phenyl]-7-(isobutyl-methyl-amino)-1,3-dihydro-benzo[b][1,4]diazepin-2-one The title compound was prepared from (RS)-[4-chloro-5-(isobutyl-methyl-amino)-2-(3-oxo-3-{3-[2-(tetrahydro-pyran-2-yloxymethyl)-pyridin-4-yl]-phenyl}-propionylamino)-phenyl]-carbamic acid tert-butyl ester (Example M281) (0.34 g, 0.51 mmol) by treatment with TFA in $CH_2Cl_2$ according to the general procedure N. Obtained as a light brown solid (152 mg, 64%).

MS (ISP) 463.3 [(M+H)⁺]; mp 161° C.

Example 369

4-[3-(2-Hydroxymethyl-pyridin-4-yl)-phenyl]-7-(methyl-propyl-amino)-8-trifluoromethyl-1,3-dihydro-benzo[b][1,4]diazepin-2-one The title compound was prepared from (RS)-[5-(methyl-propyl-amino)-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester (Example M282) (0.25 g, 0.36 mmol) by treatment with TFA in $CH_2Cl_2$ according to the general procedure N. Obtained as a light brown solid (109 mg, 62%).

MS (ISP) 483.4 [(M+H)⁺]; mp 97° C.

Example 370

4-[3-(2-Hydroxymethyl-pyridin-4-yl)-phenyl]-7-(isopropyl-methyl-amino)-8-trifluoromethyl-1,3-dihydro-benzo[b][1,4]diazepin-2-one The title compound was prepared from (RS)-[5-isopropyl-methyl-amino)-2-(3-oxo-3-{3-[2-(tetrahydro-pyran-2-yloxymethyl)-pyridin-4-yl]-phenyl}-propionylamino)-4-trifluoromethyl-phenyl]-carbamic acid tert-butyl ester (Example M283) (0.51 g, 0.74 mmol) by treatment with TFA in $CH_2Cl_2$ according to the general procedure N. Obtained as a yellow solid (221 mg, 61%).

MS (ISP) 483.5 [(M+H)⁺]; mp 124° C.

Example 371

7-Dimethylamino-4-[3-(2-hydroxymethyl-pyridin-4-yl)-phenyl]-8-trifluoromethyl-1,3-dihydro-benzo[b][1,4]diazepin-2-one The title compound was prepared from (RS)-[5-(dimethyl-amino)-2-(3-oxo-3-{3-[2-(tetrahydro-pyran-2- yloxymethyl)-pyridin-4-yl]-phenyl}-propionylamino)-4-trifluoromethyl-phenyl]-carbamic acid tert-butyl ester (Example M284) (0.46 g, 0.70 mmol) by treatment with TFA in CH$_2$Cl$_2$ according to the general procedure N.

Obtained as a light yellow solid (212 mg, 67%).
MS (ISP) 455.5 [(M+H)$^+$]; mp 223° C.

Example 372

7-Methyl-4-[3-(2-methyl-1-oxy-pyridin-4-yl)-phenyl]-8-trifluoromethyl-1,3-dihydro-benzo[b][1,4]diazepin-2-one To a stirred solution of 7-methyl-4-[3-(2-methyl-pyridin-4-yl)-phenyl]-8-trifluoromethyl-1,3-dihydro-benzo[b][1,4]diazepin-2-one (Example 75) (100 mg, 0.24 mmol) in CH$_2$Cl$_2$ (10 ml) and MeOH (0.35 ml) was added at RT 3-chloro-perbenzoic acid (54.7 mg, 0.32 mmol). The reaction mixture was stirred at RT for 5 h and evaporated. Diethyl ether (5 ml) and sat. NaHCO$_3$ solution (5 ml) was added, the mixture was stirred at RT for 1 h and the solid was collected by filtration to yield the product as a light brown solid (101 mg, 97%).

MS (ISP) 426.4 [(M+H)$^+$]; mp 237° C.

Example 373

4-[3-(2-Hydroxymethyl-1-oxy-pyridin-4-yl)-phenyl]-7-methyl-8-trifluoromethyl-1,3-dihydro-benzo[b][1,4]diazepin-2-one The title compound was prepared from 4-[3-(2-hydroxymethyl-pyridin-4-yl)-phenyl]-7-methyl-8-trifluoromethyl-1,3-dihydro-benzo[b][1,4]diazepin-2-one (Example 283) (0.20 g, 0.47 mmol) by treatment with 3-chloro-perbenzoic acid in MeOH/CH$_2$Cl$_2$ according to the general procedure of example 373. Obtained as an off-white solid (68 mg, 33%).

MS (ISP) 442.3 [(M+H)$^+$]; mp 231° C.

Example 374

4-[3-(2,6-Dimethyl-1-oxy-pyridin-4-yl)-phenyl]-7-(2,2,2-trifluoro-ethoxy)-8-trifluoromethyl-1,3-dihydro-benzo[b][1,4]diazepin-2-one The title compound was prepared from 4-[3-(2,6-dimethyl-pyridin-4-yl)-phenyl]-7-(2,2,2-trifluoro-ethoxy)-8-trifluoromethyl-1,3-dihydro-benzo[b][1,4]diazepin-2-one (Example 125) (0.30 g, 0.59 mmol) by treatment with 3-chloro-perbenzoic acid in MeOH/CH$_2$Cl$_2$ according to the general procedure of example 355. Obtained as a yellow solid (178 mg, 58%).

MS (ISP) 522.3 [(M–H)$^-$]; mp 231° C.

Example 375

4-[3-(2,6-Dimethyl-1-oxy-pyridin-4-yl)-phenyl]-7-methyl-8-trifluoromethyl-1,3-dihydro-benzo[b][1,4]diazepin-2-one The title compound was prepared from 4-[3-(2,6-dimethyl-pyridin-4-yl)-phenyl]-7-methyl-8-trifluoromethyl-1,3-dihydro-benzo[b][1,4]diazepin-2-one (Example 119) (0.30 g, 0.71 mmol) by treatment with 3-chloro-perbenzoic acid in MeOH/CH$_2$Cl$_2$ according to the general procedure of example 355. Obtained as a light yellow solid (144 mg, 46%).

MS (ISP) 438.3 [(M–H)$^-$]; mp 231° C.

Example 376

7,8-Dichloro-4-[3-(2,6-dimethyl-1-oxy-pyridin-4-yl)-phenyl]-1,3-dihydro-benzo[b][1,4]diazepin-2-one The title compound was prepared 7,8-dichloro-4-[3-(2,6-dimethyl-pyridin-4-yl)-phenyl]-1,3-dihydro-benzo[b][1,4]diazepin-2-one (Example 124) (0.30 g, 0.73 mmol) by treatment with 3-chloro-perbenzoic acid in MeOH/CH$_2$Cl$_2$ according to the general procedure of example 355. Obtained as a light red solid (140 mg, 45%).

MS (ISP) 424.2 [(M–H)$^-$]; mp 225° C.

Example 377

8-Chloro-4-3-(2,6-dimethyl-1-oxy-pyridin-4-yl)-phenyl]-7-methyl-1,3-dihydro-benzo[b][1,4]diazepin-2-one The title compound was prepared 8-chloro-4-[3-(2,6-dimethyl-pyridin-4-yl)-phenyl]-7-methyl-1,3-dihydro-benzo[b][1,4]diazepin-2-one (Example 117) (0.30 g, 0.77 mmol) by treatment with 3-chloro-perbenzoic acid in MeOH/CH$_2$Cl$_2$ according to the general procedure of example 355. Obtained as a light yellow solid (113 mg, 36%).

MS (ISP) 406.3 [(M+H)$^+$]; mp 192° C.

Example 378

8-Chloro-4-[3-(2-cyclopropylaminomethyl-pyridin-4-yl)-phenyl]-7-methyl-1,3-dihydro-benzo[b][1,4]diazepin-2-one The title compound was prepared from 8-chloro-4-[3-(2-hydroxymethyl-pyridin-4-yl)-phenyl]-7-methyl-1,3-dihydro-benzo[b][1,4]diazepin-2-one (Example 282) (196 mg, 0.50 mmol) by reaction with thionylchloride in CH$_2$Cl$_2$ and subsequent treatment of the corresponding crude chloride with cyclopropylamine in DMF according to the general procedure of example 288. Obtained as a light brown (96 mg, 45%).

MS (ISP) 431.3 [(M–H)$^-$]; mp 171° C.

Example 379

4-[3-(2-Cyclopropylaminomethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from 4-[3-(2-hydroxymethyl-pyridin-4-yl)-phenyl]-7-(2,2,2-trifluoro-ethoxy)-8-trifluoromethyl-1,3-dihydro-benzo[b][1,4]diazepin-2-one (Example 286) (255 mg, 0.50 mmol) by reaction with thionylchloride in CH$_2$Cl$_2$ and subsequent treatment of the corresponding crude chloride with cyclopropylamine in DMF according to the general procedure of example 288. Obtained as a light brown solid (152 mg, 55%).

MS (ISP) 547.3 [(M–H)$^-$]; mp 150° C.

Example 380

4-[3-(2-Pyrrolidin-1-ylmethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from 4-[3-(2-hydroxymethyl-pyridin-4-yl)-phenyl]-7-(2,2,2-trifluoro-ethoxy)-8-trifluoromethyl-1,3-dihydro-benzo[b][1,4]

diazepin-2-one (Example 286) (255 mg, 0.50 mmol) by reaction with thionylchloride in $CH_2Cl_2$ and subsequent treatment of the corresponding crude chloride with pyrrolidine in DMF according to the general procedure of example 288. Obtained as a light brown solid (225 mg, 80%).

MS (ISP) 563.4 [(M+H)$^+$]; mp 182° C.

Example 381

4-[3-(2-Azetidin-1-ylmethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from 4-[3-(2-hydroxymethyl-pyridin-4-yl)-phenyl]-7-(2,2,2-trifluoro-ethoxy)-8-trifluoromethyl-1,3-dihydro-benzo[b][1,4] diazepin-2-one (Example 286) (255 mg, 0.50 mmol) by reaction with thionylchloride in $CH_2Cl_2$ and subsequent treatment of the corresponding crude chloride with azetidine in DMF according to the general procedure of example 288. Obtained as an off-white solid (153 mg, 56%).

MS (ISP) 549.4 [(M+H)$^+$]; mp 190° C.

Example 382

4-(3-{2-[(Methyl-propyl-amino)-methyl]-pyridin-4-yl}-phenyl)-7-(2,2,2-trifluoro-ethoxy)-8-trifluoromethyl-1,3-dihydro-benzo[b][1,4]diazepin-2-one The title compound was prepared from 4-[3-(2-hydroxymethyl-pyridin-4-yl)-phenyl]-7-(2,2,2-trifluoro-ethoxy)-8-trifluoromethyl-1,3-dihydro-benzo[b][1,4] diazepin-2-one (Example 286) (255 mg, 0.50 mmol) by reaction with thionylchloride in $CH_2Cl_2$ and subsequent treatment of the corresponding crude chloride with methyl-propyl-amine in DMF according to the general procedure of example 288. Obtained as an off-white solid (207 mg, 73%).

MS (ISP) 565.3 [(M+H)$^+$]; mp 155° C.

Example 383

4-[3-(2-Ethyl-6-methyl-pyridin-4-yl)-phenyl]-7-(2,2,2-trifluoro-ethoxy)-8-trifluoromethyl-1,3-dihydro-benzo[b][1,4]diazepin-2-one The title compound was prepared from (2-{3-[3-(2-methyl-pyridin-4-yl)-phenyl]-3-oxo-propionylamino}-5-morpholin-4-yl-4-trifluoromethyl-phenyl)-carbamic acid tert-butyl ester (Example M285) (345 mg, 0.576 mmol) by treatment with TFA in $CH_2Cl_2$ according to the general procedure N. Obtained as a light yellow solid (175 mg, 63%).

MS (ISP) 481.4 [(M+H)$^+$]; mp 191–196° C.

Example 384

4-[3-(2,6-Dimethyl-pyridin-4-yl)-phenyl]-7-morpholin-4-yl-8-trifluoromethyl-1,3-dihydro-benzo[b][1,4]diazepin-2-one The title compound was prepared from (2-{3-[3-(2-methyl-pyridin-4-yl)-phenyl]-3-oxo-propionylamino}-5-morpholin-4-yl-4-trifluoromethyl-phenyl)-carbamic acid tert-butyl ester (Example M286) (377 mg, 0.615 mmol) by treatment with TFA in $CH_2Cl_2$ according to the general procedure N. Obtained as a yellow solid (211 mg, 69%).

MS (ISP) 495.3 ((M+H)$^+$]; mp 251–252° C.

Example 385

7-Ethoxy-4-[3-(2-morpholin-4-yl-pyridin-4-yl)-phenyl]-8-trifluoromethyl-1,3-dihydro-benzo[b][1,4]diazepin-2-one The title compound was prepared from (5-ethoxy-2-{3-[3-(2-morpholin-4-yl-pyridin-4-yl)-phenyl]-3-oxo-propionylamino}-4-trifluoromethyl-phenyl)-carbamic acid tert-butyl ester (Example M287) (249 mg, 0.397 mmol) by treatment with TFA in $CH_2Cl_2$ according to the general procedure N. Obtained as a white solid (162 mg, 80%).

MS (ISP) 511.3 [(M+H)$^+$]; mp 199–200° C.

Example 386

4-[3-(2-Morpholin-4-yl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-[3-(2-morpholin-4-yl-pyridin-4-yl)-phenyl]-3-oxo-propionylamino}-5-(2,2,2-trifluoro-ethoxy)-4-trifluoromethyl-phenyl]-carbamic acid tert-butyl ester (Example M288) (423 mg, 0.62 mmol) by treatment with TFA in $CH_2Cl_2$ according to the general procedure N. Obtained as a light brown solid (214 mg, 61%).

MS (ISN) 563.2 [(M–H)$^-$]; mp 189–190° C.

Example 387

7-Methyl-4-[3-(2-morpholin-4-yl-pyridin-4-yl)-phenyl]-8-trifluoromethyl-1,3-dihydro-benzo[b][1,4]diazepin-2-one The title compound was prepared from (5-methyl-2-{3-[3-(2-morpholin-4-yl-pyridin-4-yl)-phenyl]-3-oxo-propionylamino}-4-trifluoromethyl-phenyl)-carbamic acid tert-butyl ester (Example M289) (383 mg, 0.64 mmol) by treatment with TFA in $CH_2Cl_2$ according to the general procedure N. Obtained as a light yellow solid (230 mg, 75%).

MS (ISP) 481.3 [(M+H)$^+$]; mp 240–242° C.

Example 388

4-[3-(2-Pyrrolidin-1-yl-pyridin-4-yl)-phenyl]-8-trifluoromethyl-1,3-dihydro-benzo[b][1,4]diazepin-2-one The title compound was prepared from (2-{3-oxo-3-[3-(2-pyrrolidin-1-yl-pyridin-4-yl)-phenyl]-propionylamino}-4-trifluoromethyl-phenyl)-carbamic acid tert-butyl ester (Example M290) (294 mg, 0.52 mmol) by treatment with TFA in $CH_2Cl_2$ according to the general procedure N. Obtained as a yellow solid (191 mg, 82%).

MS (ISP) 451 [(M+H)$^+$]; mp 224° C.

Example 389

7-Methyl-4-[3-(2-pyrrolidin-1-yl-pyridin-4-yl)-phenyl]-8-trifluoromethyl-1,3-dihydro-benzo[b][1,4]diazepin-2-one The title compound was prepared from (5-methyl-2-{3-oxo-3-[3-(2-pyrrolidin-1-yl-pyridin-4-yl)-phenyl]-propionylamino}-4-trifluoromethyl-phenyl)-carbamic acid tert-butyl ester (Example M291) (311 mg, 0.53 mmol) by treatment with TFA in $CH_2Cl_2$ according to the general procedure N. Obtained as a yellow solid (154 mg, 63%).

MS (ISP) 465 [(M+H)$^+$]; mp 190° C.

Example 390

7-Ethoxy-4-[3-(2-pyrrolidin-1-yl-pyridin-4-yl)-phenyl]-8-trifluoromethyl-1,3-dihydro-benzo[b][1,4]diazepin-2-one The title compound was prepared from (5-ethoxy-2-{3-oxo-3-[3-(2-pyrrolidin-1-yl-pyridin-4-yl)-phenyl]- propionylamino}-4-trifluoromethyl-phenyl)-carbamic acid tert-butyl ester (Example M292) (337 mg, 0.55 mmol) by treatment with TFA in $CH_2Cl_2$ according to the general procedure N. Obtained as a yellow solid (142 mg, 52%).

MS (ISP) 495 [(M+H)$^+$]; mp 215° C.

Example 391

4-[3-(2-Pyrrolidin-1-yl-pyridin-4-yl)-phenyl]-7-(2,2,2-trifluoro-ethoxy)-8-trifluoromethyl-1,3-dihydro-benzo[b][1,4]diazepin-2-one The title compound was prepared from [2-{3-oxo-3-[3-(2-pyrrolidin-1-yl-pyridin-4-yl)-phenyl]-propionylamino}-5-(2,2,2-trifluoro-ethoxy)-4-trifluoromethyl-phenyl]-carbamic acid tert-butyl ester (Example M293) (376 mg, 0.61 mmol) by treatment with TFA in $CH_2Cl_2$ according to the general procedure N. Obtained as a yellow solid (111 mg, 33%).

MS (ISP) 549 [(M+H)$^+$]; mp 165° C.

Example 392

4 4-[2,3']Bipyridinyl-4-yl-8-trifluoromethyl-1,3-dihydro-benzo[b][1,4]diazepin-2-one The title compound was prepared from [2-(3-[2,3']bipyridinyl-4-yl-3-oxo-propionylamino)-4-trifluoromethyl-phenyl]-carbamic acid tert-butyl ester (Example M294) (230 mg, 0.46 mmol) by treatment with TFA in $CH_2Cl_2$ according to the general procedure N. Obtained as a yellow solid (147 mg, 84%).

MS (ISP) 383 [(M+H)$^+$]; mp 227° C.

Example 393

4-[2,3']Bipyridinyl-4-yl-7-ethoxy-8-trifluoromethyl-1,3-dihydro-benzo[b][1,4]diazepin-2-one The title compound was prepared from [2-(3-[2,3']bipyridinyl-4-yl-3-oxo-propionylamino)-5-ethoxy-4-trifluoromethyl-phenyl]-carbamic acid tert-butyl ester (Example M295) (288 mg, 0.53 mmol) by treatment with TFA in $CH_2Cl_2$ according to the general procedure N. Obtained as a yellow solid (195 mg, 86%).

MS (ISP) 427 [(M+H)$^+$]; mp 249° C.

Example 394

4-[2,3']Bipyridinyl-4-yl-7-(2,2,2-trifluoro-ethoxy)-8-trifluoromethyl-1,3-dihydro-benzo[b][1,4]diazepin-2-one The title compound was prepared from [2-(3-[2,3']bipyridinyl-4-yl-3-oxo-propionylamino)-5-(2,2,2-trifluoro-ethoxy)-4-trifluoromethyl-phenyl]-carbamic acid tert-butyl ester (Example M296) (305 mg, 0.51 mmol) by treatment with TFA in $CH_2Cl_2$ according to the general procedure N. Obtained as a yellow solid (201 mg, 82%).

MS (ISP) 481 [(M+H)$^+$]; mp 197° C.

Example 395

7-(Isobutyl-methyl-amino)-4-(3-{2-[(isobutyl-methyl-amino)-methyl]-pyridin-4-yl}-phenyl)-8-trifluoromethyl-1,3-dihydro-benzo[b][1,4]diazepin-2-one The title compound was prepared from 4-[3-(2-hydroxymethyl-pyridin-4-yl)-phenyl]-7-(isobutyl-methyl-amino)-8-trifluoromethyl-1,3-dihydro-benzo[b][1,4]diazepin-2-one (Example 366) (248 mg, 0.50 mmol) by reaction with thionylchloride in $CH_2Cl_2$ and subsequent treatment of the corresponding crude chloride with isobutyl-methyl-amine in DMF according to the general procedure of Example 288. Obtained as an off-white solid (176 mg, 45%).

MS (ISP) 566.5 [(M+H)$^+$]; mp 190° C.

Example 396

8-Chloro-4-(3-{2-[(isobutyl-methyl-amino)-methyl]-pyridin-4-yl}-phenyl)-7-methyl-1,3-dihydro-benzo[b][1,4]diazepin-2-one The title compound was prepared from 8-chloro-4-[3-(2-hydroxymethyl-pyridin-4-yl)-phenyl]-7-methyl-1,3-dihydro-benzo[b][1,4]diazepin-2-one (Example 282) (196 mg, 0.50 mmol) by reaction with thionylchloride in $CH_2Cl_2$ and subsequent treatment of the corresponding crude chloride with isobutyl-methyl-amine in DMF according to the general procedure of Example 288. Obtained as a light brown solid (141 mg, 61%).

MS (ISP) 461.3 [(M+H)$^+$]; mp 151° C.

Example 397

4-(3-{2-[(Isobutyl-methyl-amino)-methyl]-pyridin-4-yl}-phenyl)-7-(2,2,2-trifluoro-ethoxy)-8-trifluoromethyl-1,3-dihydro-benzo[b][1,4]diazepin-2-one The title compound was prepared from 4-[3-(2-hydroxymethyl-pyridin-4-yl)-phenyl]-7-(2,2,2-trifluoro-ethoxy)-8-trifluoromethyl-1,3-dihydro-benzo[b][1,4]diazepin-2-one (Example 286) (255 mg, 0.50 mmol) by reaction with thionylchloride in $CH_2Cl_2$ and subsequent treatment of the corresponding crude chloride with isobutyl-methyl-amine in DMF according to the general procedure of Example 288. Obtained as a light brown solid (199 mg, 69%).

MS (ISP) 579.4 [(M+H)$^+$]; mp 166° C.

Example 398

7-(Isobutyl-methyl-amino)-4-[3-(2-methoxymethyl-pyridin-4-yl)-phenyl]-8-trifluoromethyl-1,3-dihydro-benzo[b][1,4]diazepin-2-one The title compound was prepared from 4-[3-(2-hydroxymethyl-pyridin-4-yl)-phenyl]-7-(isobutyl-methyl-amino)-8-trifluoromethyl-1,3-dihydro-benzo[b][1,4]diazepin-2-one (Example 366) (248 mg, 0.50 mmol) by reaction with thionylchloride in $CH_2Cl_2$ and subsequent treatment of the corresponding crude chloride with sodium methanolate (5.4M, 1 ml) in MeOH (5 ml)/$CH_2Cl_2$ (5 ml) according to the general procedure of Example 288. Obtained as a light yellow solid (58 mg, 23%).

MS (ISP) 511.4 [(M+H)$^+$]; mp 141° C.

Example 399

8-Chloro-4-[3-(2-methoxymethyl-pyridin-4-yl)-phenyl]-7-methyl-1,3-dihydro-benzo[b][1,4]diazepin-2-one The title compound was prepared from 8-chloro-4-[3-(2-hydroxymethyl-pyridin-4-yl)-phenyl]-7-methyl-1,3-dihydro-benzo[b][1,4]diazepin-2-one (Example 282) (196 mg, 0.50 mmol) by reaction with thionylchloride in $CH_2Cl_2$ and subsequent treatment of the corresponding crude chloride with sodium methanolate (5.4M, 1 ml) in MeOH (5 ml)/CH$_2$Cl$_2$ (5 ml) according to the general procedure of Example 288. Obtained as an off-white solid (72 mg, 35%).

MS (ISP) 406.3 [(M+H)$^+$]; mp 216° C.

Example 400

4-[3-(2-Methoxymethyl-pyridin-4-yl)-phenyl]-7-(2,2,2-trifluoro-ethoxy)-8-trifluoromethyl-1,3-dihydro-benzo[b][1,4]diazepin-2-one The title compound was prepared from 4-[3-(2-hydroxymethyl-pyridin-4-yl)-phenyl]-7-(2,2,2-trifluoro-ethoxy)-8-trifluoromethyl-1,3-dihydro-benzo[b][1,4]diazepin-2-one (Example 286) (255 mg, 0.50 mmol) by reaction with thionylchloride in CH$_2$Cl$_2$ and subsequent treatment of the corresponding crude chloride with sodium methanolate (5.4M, 1 ml) in MeOH (5 ml)/CH$_2$Cl$_2$ (5 ml) according to the general procedure of Example 288. Obtained as an off-white solid (94 mg, 36%).

MS (ISP) 524.3 [(M+H)$^+$]; mp 225° C.

Example 401

8-Chloro-4-[3-(2-hydroxymethyl-6-methyl-pyridin-4-yl)-phenyl]-7-methyl-1,3-dihydro-benzo[b][1,4]diazepin-2-one The title compound was prepared from (RS)-[4-chloro-5-methyl-2-(3-{3-[2-methyl-6-(tetrahydro-pyran-2-yloxymethyl)-pyridin-4-yl]-phenyl}-3-oxo-propionylamino)-phenyl]-carbamic acid tert-butyl ester (Example M297) (0.45 g, 0.74 mmol) by treatment with TFA in CH$_2$Cl$_2$ according to the general procedure N. Obtained as a light brown solid (200 mg, 67%).

MS (ISP) 406.3 [(M+H)$^+$]; mp 202° C.

Example 402

4-[3-(2-Hydroxymethyl-6-methyl-pyridin-4-yl)-phenyl]-7-methyl-8-trifluoromethyl-1,3-dihydro-benzo[b][1,4]diazepin-2-one The title compound was prepared from (RS)-[5-methyl-2-(3-{3-[2-methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester (Example M298) (0.49 g, 0.76 mmol) by treatment with TFA in CH$_2$Cl$_2$ according to the general procedure N. Obtained as a light yellow solid (200 mg, 60%).

MS (ISP) 440.3 [(M+H)$^+$]; mp 200° C.

Example 403

7-Chloro-4-[3-(2-hydroxymethyl-6-methyl-pyridin-4-yl)-phenyl]-8-trifluoromethyl-1,3-dihydro-benzo[b][1,4]diazepin-2-one The title compound was prepared from (RS)-[5-chloro-2-(3-{3-[2-methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester (Example M299) (0.41 g, 0.62 mmol) by treatment with TFA in CH$_2$Cl$_2$ according to the general procedure N. Obtained as a light yellow solid (150 mg, 53%).

MS (ISP) 460.2 [(M+H)$^+$]; mp 163° C.

Example 404

7,8-Dichloro-4-[3-(2-hydroxymethyl-6-methyl-pyridin-4-yl)-phenyl]-1,3-dihydro-benzo[b][1,4]diazepin-2-one The title compound was prepared from commercially available 4,5-dichloro-1,2-phenylendiamine (177 mg, 1.0 mmol) and (RS)-3-{3-[2-methyl-6-(tetrahydro-pyran-2-yloxymethyl)-pyridin-4-yl]-phenyl}-3-oxo-propionic acid tert-butyl ester (Example K64) (426 mg, 1.0 mmol) in xylene (20 ml) under reflux conditions for 1.5 h according to the general procedure M and subsequent treatment with TFA in CH$_2$Cl$_2$ according to the general procedure N. Obtained as a light brown solid (140 mg, 35%).

MS (ISP) 426.0 [(M+H)$^+$]; mp 234° C.

Example 405

4-[3-(2-Hydroxymethyl-6-methyl-pyridin-4-yl)-phenyl]-7-(2,2,2-trifluoro-ethoxy)-8-trifluoromethyl-1,3-dihydro-benzo[b][1,4]diazepin-2-one The title compound was prepared from (RS)-[2-(3-{3-[2-methyl-6-(tetrahydro-pyran-2-yloxymethyl)-pyridin-4-yl]-phenyl}-3-oxo-propionylamino)-5-(2,2,2-trifluoro-ethoxy)-4-trifluoromethyl-phenyl]-carbamic acid tert-butyl ester (Example M300) (0.49 g, 0.67 mmol) by treatment with TFA in CH$_2$Cl$_2$ according to the general procedure N. Obtained as a light brown solid (230 mg, 65%).

MS (ISP) 524.3 [(M+H)$^+$]; mp 227° C.

Example 406

7-Ethoxy-4-[3-(2-hydroxymethyl-6-methyl-pyridin-4-yl)-phenyl]-8-trifluoromethyl-1,3-dihydro-benzo[b][1,4]diazepin-2-one The title compound was prepared from (RS)-[5-ethoxy-2-(3-{3-[2-methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester (Example M301) (0.54 g, 0.80 mmol) by treatment with TFA in CH$_2$Cl$_2$ according to the general procedure N. Obtained as a light red solid (240 mg, 64%).

MS (ISP) 470.3 [(M+H)$^+$]; mp 225° C.

Example 407

4-[3-(2-Hydroxymethyl-6-methyl-pyridin-4-yl)-phenyl]-8-trifluoromethyl-1,3-dihydro-benzo[b][1,4]diazepin-2-one The title compound was prepared from (RS)-[2-(3-{3-[2-methyl-6-(tetrahydro-pyran-2-yloxymethyl)-pyridin-4-yl]-phenyl}-3-oxo-propionylamino)-4-trifluoromethyl-phenyl]-carbamic acid tert-butyl ester (Example M302) (0.46 g, 0.73 mmol) by treatment with TFA in CH$_2$Cl$_2$ according to the general procedure N. Obtained as a light yellow solid (210 mg, 67%).

MS (ISP) 426.1 [(M+H)$^+$]; mp 228° C.

Example 408

4-[3-(2,6-Dimethyl-pyridin-4-yl)-phenyl]-7-(isobutyl-methyl-amino)-8-trifluoromethyl-1,3-dihydro-benzo[b][1,4]diazepin-2-one The title compound was prepared from [2-{3-[3-(2,6-dimethyl-pyridin-4-yl)-phenyl]-3-oxo-propionylamino}-5-(isobutyl-methyl-amino)-4-trifluoromethyl-phenyl]-carbamic acid tert-butyl ester (Example M303) (0.37 g, 0.60 mmol) by treatment with TFA in CH$_2$Cl$_2$ according to the general procedure N. Obtained as an off-white solid (262 mg, 88%).

MS (ISP) 495.4 [(M+H)$^+$]; mp 215° C.

Example 409

7-Dimethylamino-4-[3-(2,6-dimethyl-pyridin-4-yl)-phenyl]-8-trifluoromethyl-1,3-dihydro-benzo[b][1,4]diazepin-2-one The title compound was prepared from (5-dimethylamino-2-{3-[3-(2,6-dimethyl-pyridin-4-yl)- phenyl]-3-oxo-propionylamino}-4-trifluoromethyl-phenyl)-carbamic acid tert-butyl ester (Example M304) (0.38 g, 0.67 mmol) by treatment with TFA in CH$_2$Cl$_2$ according to the general procedure N. Obtained as an off-white solid (203 mg, 67%).

MS (ISP) 453.2 [(M+H)$^+$]; mp 256° C.

Example 410

8-Chloro-4-[3-(2,6-dimethyl-pyridin-4-yl)-phenyl]-7-(isobutyl-methyl-amino)-1,3-dihydro-benzo[b][1,4]diazepin-2-one The title compound was prepared from [4-chloro-2-{3-[3-(2,6-dimethyl-pyridin-4-yl)-phenyl]-3-oxo-propionylamino}-5-(isobutyl-methyl-amino)-phenyl]-carbamic acid tert-butyl ester (Example M305) (0.43 g, 0.74 mmol) by treatment with TFA in CH$_2$Cl$_2$ according to the general procedure N. Obtained as an off-white solid (282 mg, 82%).

MS (ISP) 461.3 [(M+H)$^+$]; mp 229° C.

Example 411

4-[3-(2,6-Dimethyl-pyridin-4-yl)-phenyl]-7-pyrrolidin-1-yl-8-trifluoromethyl-1,3-dihydro-benzo[b][1,4]diazepin-2-one The title compound was prepared from (2-{3-[3-(2,6-dimethyl-pyridin-4-yl)-phenyl]-3-oxo-propionylamino}-5-pyrrolidin-1-yl-4-trifluoromethyl-phenyl)-carbamic acid tert-butyl ester (Example M306) (0.46 g, 0.77 mmol) by treatment with TFA in CH$_2$Cl$_2$ according to the general procedure N. Obtained as a yellow solid (344 mg, 93%).

MS (ISP) 479.2 [(M+H)$^+$]; mp 233° C.

Example 412

4-[3-(2,6-Dimethyl-pyridin-4-yl)-phenyl]-7-(isopropyl-methyl-amino)-8-trifluoromethyl-1,3-dihydro-benzo[b][1,4]diazepin-2-one The title compound was prepared from [2-{3-[3-(2,6-dimethyl-pyridin-4-yl)-phenyl]-3-oxo-propionylamino}-5-(isopropyl-methyl-amino)-4-trifluoromethyl-phenyl]-carbamic acid tert-butyl ester (Example M307) (0.43 g, 0.72 mmol) by treatment with TFA in CH$_2$Cl$_2$ according to the general procedure N. Obtained as a light brown solid (310 mg, 90%).

MS (ISP) 481.3 [(M+H)$^+$]; mp 232° C.

Example 413

4-[3-(2,6-Dimethyl-pyridin-4-yl)-phenyl]-7-(methyl-propyl-amino)-8-trifluoromethyl-1,3-dihydro-benzo[b][1,4]diazepin-2-one The title compound was prepared from [2-{3-[3-(2,6-dimethyl-pyridin-4-yl)-phenyl]-3-oxo-propionylamino}-5-(methyl-propyl-amino)-4-trifluoromethyl-phenyl]-carbamic acid tert-butyl ester (Example M308) (0.41 g, 0.68 mmol) by treatment with TFA in CH$_2$Cl$_2$ according to the general procedure N. Obtained as a light brown solid (267 mg, 81%).

MS (ISP) 481.3 [(M+H)$^+$]; mp 233° C.

Example 414

4-[3-(2-Methyl-pyridin-4-yl)-phenyl]-7,8-bis-trifluoromethyl-1,3-dihydro-benzo[b][1,4]diazepin-2-one The title compound was prepared from 4,5-bis-trifluoromethyl-benzene-1,2-diamine [CAS-No. 30454-92-3] (244 mg, 1.0 mmol) and 3-[3-(2-methyl-pyridin-4-yl)-phenyl]-3-oxo-propionic acid tert-butyl ester (Example K12) (311 mg, 1.0 mmol) in toluene (10 ml) under reflux conditions for 2 h according to the general procedure M and subsequent treatment with TFA in CH$_2$Cl$_2$ according to the general procedure N. Obtained as a light yellow solid (304 mg, 66%).

MS (ISP) 464.2 [(M+H)$^+$]; mp 209° C.

Example 415

4-[3-(2,6-Dimethyl-pyridin-4-yl)-phenyl]-7,8-bis-trifluoromethyl-1,3-dihydro-benzo[b][1,4]diazepin-2-one The title compound was prepared from 4,5-bis-trifluoromethyl-benzene-1,2-diamine [CAS-No. 30454-92-3] (244 mg, 1.0 mmol) and 3-[3-(2,6-dimethyl-pyridin-4-yl)-phenyl]-3-oxo-propionic acid tert-butyl ester (Example K15) (325 mg, 1.0 mmol) in toluene (10 ml) under reflux conditions for 2 h according to the general procedure M and subsequent treatment with TFA in CH$_2$Cl$_2$ according to the general procedure N. Obtained as an off-white solid (132 mg, 28%).

MS (ISP) 478.3 [(M+H)$^+$]; mp 220° C.

Example 416

4-(3-Pyridin-3-yl-phenyl)-7,8-bis-trifluoromethyl-1,3-dihydro-benzo[b][1,4]diazepin-2-one The title compound was prepared from 4,5-bis-trifluoromethyl-benzene-1,2-diamine [CAS-No. 30454-92-3] (244 mg, 1.0 mmol) and 3-oxo-3-(3-pyridin-3-yl-phenyl)-propionic acid tert-butyl ester (Example K1) (297 mg, 1.0 mmol) in toluene (10 ml) under reflux conditions for 2 h according to the general procedure M and subsequent treatment with TFA in CH$_2$Cl$_2$ according to the general procedure N. Obtained as a light brown solid (315 mg, 70%).

MS (ISP) 450.2 [(M+H)$^+$]; mp 210° C.

Example 417

4-[3-(2-Hydroxymethyl-pyridin-4-yl)-phenyl]-7,8-bis-trifluoromethyl-1,3-dihydro-benzo[b][1,4]diazepin-2-one The title compound was prepared from 4,5-bis-trifluoromethyl-benzene-1,2-diamine [CAS-No. 30454-92-3] (244 mg, 1.0 mmol) and (RS)-3-oxo-3-{3-[2-(tetrahydro-pyran-2-yloxymethyl)-pyridin-4-yl]-phenyl}-propionic acid tert-butyl ester (Example K40) (412 mg, 1.0 mmol) in toluene (10 ml) under reflux conditions for 2 h according to the general procedure M and subsequent treatment with TFA in CH$_2$Cl$_2$ according to the general procedure N. Obtained as a light yellow solid (291 mg, 61%).

MS (ISP) 480.2 [(M+H)$^+$]; mp 209° C.

Example I

Tablets of the following composition are produced in a conventional manner:

| mg/Tablet | |
|---|---|
| Active ingredient | 100 |
| Powdered. lactose | 95 |
| White corn starch | 35 |

-continued

| mg/Tablet | |
|---|---|
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

| mg/Tablet | |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

| mg/Capsule | |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

What is claimed is:

1. A compound of formula I

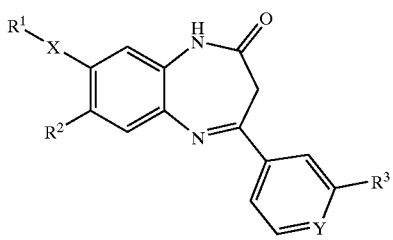

I wherein
X is a single bond or an ethynediyl group; and wherein in case X is a single bond,
$R^1$ is hydrogen,
cyano,
halogen,
lower alkyl,
lower alkoxy,
fluoro-lower alkyl,
fluoro-lower alkoxy,
pyrrol-1-yl, or
phenyl, which is unsubstituted or substituted by one or two substituents selected from the group consisting of halogen, lower alkyl or fluoro-lower alkyl;
or in case X is an ethynediyl group,
$R^1$ is phenyl, which is unsubstituted or substituted by one or two substituents selected from the group consisting of halogen, lower alkyl or fluoro-lower alkyl;
and wherein
$R^2$ is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;
m is 1, 2, 3 or 4;
R' is hydrogen, lower alkyl or $C_3$–$C_6$-cycloalkyl;
R" is hydrogen, lower alkyl or $C_3$–$C_6$-cycloalkyl;
Y is —CH= or =N—;
$R^3$ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
whereby R' and R" have the meaning specified above;
n is 0, 1, 2, 3 or 4;
or a pharmaceutically acceptable addition salt thereof.

2. The compound of formula I according to claim 1

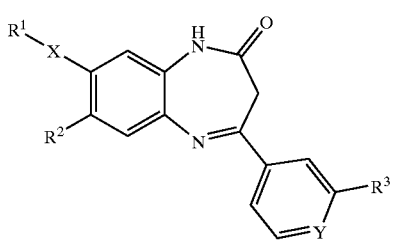

I wherein
X is a single bond,
$R^1$ is hydrogen,
cyano,
halogen,
lower alkyl,
lower alkoxy,
fluoro-lower alkyl, fluoro-lower alkoxy,
pyrrol-1-yl, or
phenyl, which is unsubstituted or substituted by one or two substituents selected from the group consisting of halogen, lower alkyl or fluoro-lower alkyl;
$R^2$ is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;
m is 1, 2, 3 or 4;
R' is hydrogen, lower alkyl or $C_3$–$C_6$-cycloalkyl;
R" is hydrogen, lower alkyl or $C_3$–$C_6$-cycloalkyl;
Y is —CH= or =N—;
$R^3$ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
whereby R' and R" have the meaning specified above;
n is 0, 1, 2, 3 or 4;
or a pharmaceutically acceptable addition salt thereof.

3. The compound according to claim 2, wherein Y is —CH=.

4. The compound according to claim 3, wherein $R^3$ is pyridyl, which is unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and R' and R" are independently from each other selected from hydrogen, lower alkyl or $C_3$–$C_6$-cycloalkyl.

5. The compound according to claim 4, wherein $R^1$ is hydrogen, halogen, lower alkyl or fluoro-lower alkyl.

6. The compound according to claim 5, wherein $R^1$ is hydrogen or lower alkyl.

7. The compound according to claim 6, which compound is selected from the group consisting of
8-methyl-4-(3-pyridin-3-yl-phenyl)-7-trifluoromethyl-1,3-dihydro-benzo[b][1,4]diazepin-2-one,
8-methyl-4-[3-(2-methyl-pyridin-4-yl)-phenyl]-7-trifluoromethyl-1,3-dihydro benzo[b][1,4]diazepin-2-one,
4-(3-pyridin-3-yl-phenyl)-7-(2,2,2-trifluoro-ethoxy)-1,3-dihydro-benzo[b][1,4]diazepin-2-one, and
4-[3-(2,6-dimethyl-pyridin-4-yl)-phenyl]-8-methyl-7-trifluoromethyl-1,3-dihydro benzo[b][1,4]diazepin-2-one.

8. The compound according to claim 5, wherein $R^1$ is halogen.

9. The compound according to claim 8, which compound is selected from the group consisting of
7,8-dichloro-4-(3-pyridin-3-yl-phenyl)-1,3-dihydro-benzo[b][1,4]diazepin-2-one,
8-chloro-4-(3-pyridin-4-yl-phenyl)-1,3-dihydro-benzo[b][1,4]diazepin-2-one,
7,8-dichloro-4-(3-pyridin-4-yl-phenyl)-1,3-dihydro-benzo[b][1,4]diazepin-2-one,
8-chloro-7-methyl-4-(3-pyridin-3-yl-phenyl)-1,3-dihydro-benzo[b][1,4]diazepin-2-one,
8-chloro-4-(3-pyridin-3-yl-phenyl)-1,3-dihydro-benzo[b][1,4]diazepin-2-one,
8-chloro-4-[3-(6-methyl-pyridin-3-yl)-phenyl]-1,3-dihydro-benzo[b][1,4]diazepin-2-one,
8-chloro-4-[3-(2-methyl-pyridin-3-yl)-phenyl]-1,3-dihydro-benzo[b][1,4]diazepin-2-one,
8-chloro-7-methyl-4-(3-pyridin-4-yl-phenyl)-1,3-dihydro-benzo[b][1,4]diazepin-2-one,
7,8-dichloro-4-[3-(2-methyl-pyridin-4-yl)-phenyl]-1,3-dihydro-benzo[b][1,4]diazepin-2-one,
8-chloro-7-methyl-4-[3-(2-methyl-pyridin-4-yl)-phenyl]-1,3-dihydro-benzo[b][1,4]diazepin-2-one,
8-fluoro-4-[3-(2-methyl-pyridin-4-yl)-phenyl]-1,3-dihydro-benzo[b][1,4]diazepin-2-one,
8-chloro-4-[3-(2-methyl-pyridin-4-yl)-phenyl]-7-trifluoromethyl-1,3-dihydro benzo[b][1,4]diazepin-2-one,
8-chloro-4-[3-(2,6-dimethyl-pyridin-4-yl)-phenyl]-7-methyl-1,3-dihydro-benzo[b][1,4]diazepin-2-one, and
7,8-dichloro-4-[3-(2,6-dimethyl-pyridin-4-yl)-phenyl]-1,3-dihydro-benzo[b][1,4]diazepin-2-one.

10. The compound according to claim 5, wherein $R^1$ is trifluoromethyl.

11. The compound according to claim 10, which compound is selected from the group consisting of
7-dimethylamino-4-(3-pyridin-3-yl-phenyl)-8-trifluoromethyl-1,3-dihydro-benzo[b][1,4]diazepin-2-one,
7-dimethylamino-4-(3-pyridin-4-yl-phenyl)-8-trifluoromethyl-1,3-dihydro-benzo[b][1,4]diazepin-2-one,
4-(3-pyridin-4-yl-phenyl)-8-trifluoromethyl-1,3-dihydro-benzo[b][1,4]diazepin-2-one,
4-(3-pyridin-3-yl-phenyl)-8-trifluoromethyl-1,3-dihydro-benzo[b][1,4]diazepin-2-one,
4-(3-pyridin-3-yl-phenyl)-7-(2,2,2-trifluoro-ethoxy)-8-trifluoromethyl-1,3-dihydro-benzo[b][1,4]diazepin-2-one,
7-ethoxy-4-(3-pyridin-4-yl-phenyl)-8-trifluoromethyl-1,3-dihydro-benzo[b][1,4]diazepin-2-one,
4-(3-pyridin-4-yl-phenyl)-7-(2,2,2-trifluoro-ethoxy)-8-trifluoromethyl-1,3-dihydro-benzo[b][1,4]diazepin-2-one,
7-methyl-4-(3-pyridin-4-yl-phenyl)-8-trifluoromethyl-1,3-dihydro-benzo[b][1,4]diazepin-2-one,
8-methyl-4-(3-pyridin-4-yl-phenyl)-7-trifluoromethyl-1,3-dihydro-benzo[b][1,4]diazepin-2-one,
7-chloro-4-(3-pyridin-4-yl-phenyl)-8-trifluoromethyl-1,3-dihydro-benzo[b][1,4]diazepin-2-one, 7-methyl-4-[3-(2-methyl-pyridin-4-yl)-phenyl]-8-trifluoromethyl-1,3-dihydro benzo[b][1,4]diazepin-2-one, 4-[3-(2-methyl-pyridin-4-yl)-phenyl]-8-trifluoromethyl-1,3-dihydro benzo[b][1,4]diazepin-2-one, 7-dimethylamino-4-[3-(2-methyl-pyridin-4-yl)-phenyl]-8-trifluoromethyl-1,3-dihydro benzo[b][1,4]diazepin-2-one, 4-[3-(2,6-dimethyl-pyridin-4-yl)-phenyl]-7-methyl-8-trifluoromethyl-1,3-dihydro benzo[b][1,4]diazepin-2-one, and 4-[3-(2,6-dimethyl-pyridin-4-yl)-phenyl]-8-trifluoromethyl-1,3-dihydro benzo[b][1,4]diazepin-2-one.

12. The compound according to claim 10, which compound is selected from the group consisting of 7-chloro-4-[3-(2,6-dimethyl-pyridin-4-yl)-phenyl]-8-trifluoromethyl-1,3-dihydro benzo[b][1,4]diazepin-2-one, 4-[3-(2,6-dimethyl-pyridin-4-yl)-phenyl]-7-(2,2,2-trifluoro-ethoxy)-8-trifluoromethyl-1,3-dihydro-benzo[b][1,4]diazepin-2-one, 4-[3-(2,6-dimethyl-pyridin-4-yl)-phenyl]-7-ethoxy-8-trifluoromethyl-1,3-dihydro-benzo[b][1,4]diazepin-2-one, 4-[3-(2-ethyl-pyridin-4-yl)-phenyl]-7-methyl-8-trifluoromethyl-1,3-dihydro benzo[b][1,4]diazepin-2-one, 4-[3-(6-cyclopropyl-pyridin-3-yl)-phenyl]-8-trifluoromethyl-1,3-dihydro-benzo[b][1,4]diazepin-2-one, 7-methyl-4-(3-pyridin-3-yl-phenyl)-8-trifluoromethyl-1,3-dihydro-benzo[b][1,4]diazepin-2-one, 7-methoxy-4-(3-pyridin-3-yl-phenyl)-8-trifluoromethyl-1,3-dihydro-benzo[b][1,4]diazepin-2-one, 7-ethoxy-4-(3-pyridin-3-yl-phenyl)-8-trifluoromethyl-1,3-dihydro-benzo[b][1,4]diazepin-2-one, 7-cyclopropylmethoxy-4-[3-(2-methyl-pyridin-4-yl)-phenyl]-8-trifluoromethyl-1,3-dihydro-benzo[b][1,4]diazepin-2-one, 7-ethyl-4-[3-(2-methyl-pyridin-4-yl)-phenyl]-8-trifluoromethyl-1,3-dihydro-benzo[b][1,4]diazepin-2-one, 4-[3-(2,6-dimethyl-pyridin-4-yl)-phenyl]-7-ethyl-8-trifluoromethyl-1,3-dihydro-benzo[b][1,4]diazepin-2-one, 4-[3-(2-ethyl-6-methyl-pyridin-4-yl)-phenyl]-7-methyl-8-trifluoromethyl-1,3-dihydro-benzo[b][1,4]diazepin-2-one, and 4-[3-(2-hydroxymethyl-pyridin-4-yl)-phenyl]-7-methyl-8-trifluoromethyl-1,3-dihydro benzo[b][1,4]diazepin-2-one.

13. The compound according to claim 4, wherein $R^1$ is pyrrol-1-yl or phenyl, which is unsubstituted or substituted by one or two substituents selected from the group consisting of halogen, lower alkyl or fluoro-lower alkyl.

14. The compound according to claim 13, which compound is selected from the group consisting of 8-(2-fluoro-phenyl)-4-[3-(2-methyl-pyridin-3-yl)-phenyl]-1,3-dihydro-benzo[b][1,4]diazepin-2-one, 8-(2-fluoro-phenyl)-4-(3-pyridin-4-yl-phenyl)-1,3-dihydro-benzo[b][1,4]diazepin-2-one, 8-(2-fluoro-phenyl)-4-(3-pyridin-3-yl-phenyl)-1,3-dihydro-benzo[b][1,4]diazepin-2-one, and 8-(2-fluoro-phenyl)-4-[3-(2-methyl-pyridin-4-yl)-phenyl]-1,3-dihydro-benzo[b][1,4]diazepin-2-one.

15. The compound according to claim 4, wherein $R^1$ is fluoro-lower alkoxy.

16. The compound according to claim 15, which compound is

4-[3-(2-methyl-pyridin-4-yl)-phenyl]-8-trifluoromethoxy-1,3-dihydro-benzo[b][1,4]diazepin-2-one.

17. The compound according to claim 3, wherein $R^3$ is pyrazinyl, which is unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and R' and R" are independently from each other selected from hydrogen, lower alkyl or $C_3$–$C_6$-cycloalkyl.

18. The compound according to claim 17, which compound is selected from the group consisting of 8-chloro-7-methyl-4-(3-pyrazin-2-yl-phenyl)-1,3-dihydro-benzo[b][1,4]diazepin-2-one, 7-methyl-4-(3-pyrazin-2-yl-phenyl)-8-trifluoromethyl-1,3-dihydro-benzo[b][1,4]diazepin-2-one, and 7-(methyl-propyl-amino)-4-(3-pyrazin-2-yl-phenyl)-8-trifluoromethyl-1,3-dihydro-benzo[b][1,4]diazepin-2-one.

19. The compound according to claim 3, wherein $R^3$ is pyrimidinyl or pyridazinyl, which are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —$(CH_2)_n$—C(O)—OR", —$(CH_2)_n$—C(O)—NR'R", —$(CH_2)_n$—SO$_2$—NR'R", —$(CH_2)_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and R' and R" are independently from each other selected from hydrogen, lower alkyl or $C_3$–$C_6$-cycloalkyl.

20. The compound according to claim 19, which compound is selected from the group consisting of 8-chloro-7-methyl-4-(3-pyridazin-4-yl-phenyl)-1,3-dihydro-benzo[b][1,4]diazepin-2-one, 7-methyl-4-(3-pyridazin-4-yl-phenyl)-8-trifluoromethyl-1,3-dihydro-benzo[b][1,4]diazepin-2-one, 8-(2-fluoro-phenyl)-4-(3-pyrimidin-5-yl-phenyl)-1,3-dihydro-benzo[b][1,4]diazepin-2-one, and 4-[3-(6-methyl-pyrimidin-4-yl)-phenyl]-8-trifluoromethyl-1,3-dihydro-benzo[b][1,4]diazepin-2-one.

21. The compound according to claim 3, wherein $R^3$ is pyridine-N-oxide, which is unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —$(CH_2)_n$—C(O)—OR", —$(CH_2)_n$—C(O)—NR'R", —$(CH_2)_n$—SO$_2$—NR'R", —(CH$_2$)$_n$—C(NH$_2$)=NR", hydroxy, lower alkoxy, lower alkylthio, C$_3$–C$_6$-cycloalkyl and lower alkyl, which is optionally substituted by fluoro, —NR'R", hydroxy, lower alkoxy, pyrrolidin-1-yl, azetidin-1-yl, cyano or carbamoyloxy, and R' and R" are independently from each other selected from hydrogen, lower alkyl or C$_3$–C$_6$-cycloalkyl.

22. The compound according to claim 2, wherein Y is —N═.

23. The compound according to claim 22, which compound is selected from the group consisting of
4-[2,3']bipyridinyl-4-yl-7-methyl-8-trifluoromethyl-1,3-dihydro-benzo[b][1,4]diazepin-2-one, and
7-methyl-4-(2'-methyl-[2,4']bipyridinyl-4-yl)-8-trifluoromethyl-1,3-dihydro-benzo[b][1,4]diazepin-2-one.

24. The compound of formula I according to claim 1

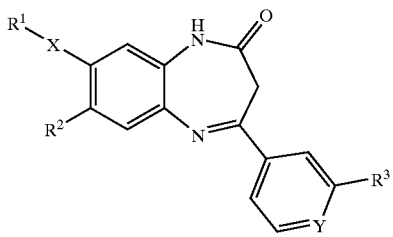

wherein
X is an ethynediyl group;
R$^1$ is phenyl, which is unsubstituted or substituted by one or two substituents selected from the group consisting of halogen, lower alkyl or fluoro-lower alkyl;
R$^2$ is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;
m is 1, 2, 3 or 4;
R' is hydrogen, lower alkyl or C$_3$–C$_6$-cycloalkyl;
R" is hydrogen, lower alkyl or C$_3$–C$_6$-cycloalkyl;
Y is —CH═ or ═N—;
R$^3$ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)═NR", hydroxy, lower alkoxy, lower alkylthio, C$_3$–C$_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
whereby R' and R" have the meaning specified above;
n is 0, 1, 2, 3 or 4;
or its pharmaceutically acceptable addition salt thereof.

25. A pharmaceutical composition comprising one or more compound of formula I

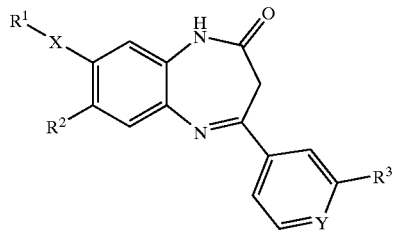

wherein
X is a single bond,
R$^1$ is hydrogen,
cyano,
halogen,
lower alkyl,
lower alkoxy,
fluoro-lower alkyl,
fluoro-lower alkoxy,
pyrrol-1-yl, or
phenyl, which is unsubstituted or substituted by one or two substituents selected from the group consisting of halogen, lower alkyl or fluoro-lower alkyl;
R$^2$ is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;
m is 1, 2, 3 or 4;
R' is hydrogen, lower alkyl or C$_3$–C$_6$-cycloalkyl;
R" is hydrogen, lower alkyl or C$_3$–C$_6$-cycloalkyl;
Y is —CH═ or ═N—;
R$^3$ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)═NR", hydroxy, lower alkoxy, lower alkylthio, C$_3$–C$_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
whereby R' and R" have the meaning specified above;
n is 0, 1, 2, 3 or 4;
or its pharmaceutically acceptable addition salt thereof,
and a pharmaceutically acceptable excipient.

26. A process for preparing compounds of formula I

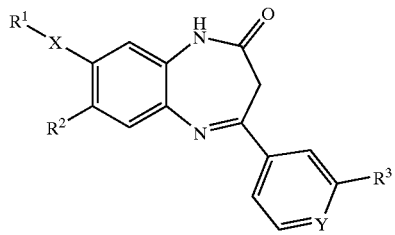

wherein

X is a single bond,

R¹ is hydrogen,
  cyano,
  halogen,
  lower alkyl,
  lower alkoxy,
  fluoro-lower alkyl,
  fluoro-lower alkoxy,
  pyrrol-1-yl, or
  phenyl, which is unsubstituted or substituted by one or two substituents selected from the group consisting of halogen, lower alkyl or fluoro-lower alkyl;

R² is hydrogen,
  lower alkyl,
  lower alkenyl
  lower alkoxy,
  halogen,
  —NR'R",
  pyrrolidin-1-yl,
  piperidin-1-yl,
  morpholine-4-yl,
  fluoro-lower alkyl,
  fluoro-lower alkoxy, or
  lower alkoxy-(ethoxy)$_m$;

m is 1, 2, 3 or 4;

R' is hydrogen, lower alkyl or $C_3$–$C_6$-cycloalkyl;

R" is hydrogen, lower alkyl or $C_3$–$C_6$-cycloalkyl;

Y is —CH= or =N—;

R³ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
  whereby R' and R" have the meaning specified above;

n is 0, 1, 2, 3 or 4;

or its pharmaceutically acceptable addition salt thereof, which process comprises reacting a compound of formula II

with a compound of formula

or

wherein R is ethyl or butyl, to a compound of formula III

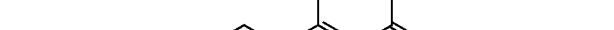

which subsequently undergoes deprotection of the amino group and cyclization, to obtain a compound of formula

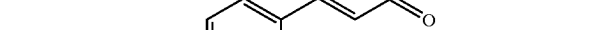

wherein R¹, R², R³, X and Y are as described above.

27. The process according to claim 26 further comprises converting the compound obtained into a pharmaceutically acceptable acid addition salt.

28. A method of treating psychosis or schizophrenia comprising administering to a patient in need of such treatment a therapeutically effective amount of at least one compound of formula I

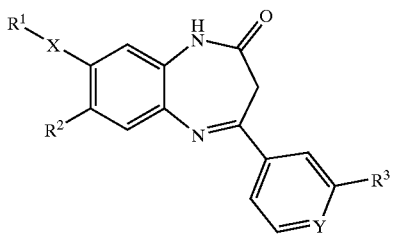

wherein

X is a single bond,

R¹ is hydrogen,
cyano,
halogen,
lower alkyl,
lower alkoxy,
fluoro-lower alkyl,
fluoro-lower alkoxy,
pyrrol-1-yl, or
phenyl, which is unsubstituted or substituted by one or two substituents selected from the group consisting of halogen, lower alkyl or fluoro-lower alkyl;

R² is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;

m is 1, 2, 3 or 4;

R' is hydrogen, lower alkyl or $C_3$–$C_6$-cycloalkyl;

R" is hydrogen, lower alkyl or $C_3$–$C_6$-cycloalkyl;

Y is —CH= or =N—;

R³ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
whereby R' and R" have the meaning specified above;

n is 0, 1, 2, 3 or 4;

or a pharmaceutically acceptable addition salt thereof.

29. A pharmaceutical composition comprising one or more compound of formula I

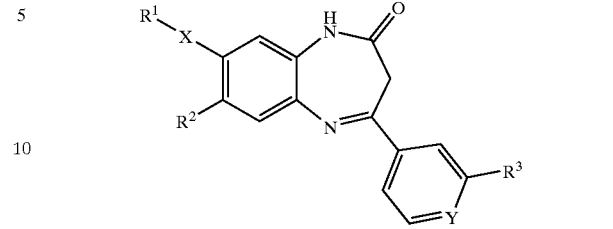

wherein

X is an ethynediyl group;

R¹ is phenyl, which is unsubstituted or substituted by one or two substituents selected
from the group consisting of halogen, lower alkyl or fluoro-lower alkyl;

R² is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;

m is 1, 2, 3 or 4;

R' is hydrogen, lower alkyl or $C_3$–$C_6$-cycloalkyl;

R" is hydrogen, lower alkyl or $C_3$–$C_6$-cycloalkyl;

Y is —CH= or =N—;

R³ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
whereby R' and R" have the meaning specified above;

n is 0, 1, 2, 3 or 4;

or its pharmaceutically acceptable addition salt thereof, and a pharmaceutically acceptable excipient.

30. A process for preparing compounds of formula I

[Structure of formula I: benzodiazepinone with R¹–X on one ring position, R² on another, and a phenyl group with R³ and Y substituents]

wherein

X is an ethynediyl group;

R¹ is phenyl, which is unsubstituted or substituted by one or two substituents selected from the group consisting of halogen, lower alkyl or fluoro-lower alkyl;

R² is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;

m is 1, 2, 3 or 4;

R' is hydrogen, lower alkyl or $C_3$–$C_6$-cycloalkyl;

R" is hydrogen, lower alkyl or $C_3$–$C_6$-cycloalkyl;

Y is —CH= or =N—;

R³ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy, whereby R' and R" have the meaning specified above;

n is 0, 1, 2, 3 or 4;

or its pharmaceutically acceptable addition salt thereof, which process comprises reacting a compound of formula II

[Structure of formula II: benzene ring with R¹–X, R², NH₂, and NHBoc substituents]

with a compound of formula

[Structure of formula IV: dioxinone with pyridyl group bearing Y and R³]

or

[Structure of formula IVa: aryl ketone with CO₂R group, Y and R³ substituents]

wherein R is ethyl or butyl, to a compound of formula III

[Structure of formula III: intermediate with R¹–X, R², NHBoc, amide linkage to ketone bearing pyridyl with Y and R³]

which subsequently undergoes deprotection of the amino group and cyclization, to obtain a compound of formula

[Structure of formula I]

wherein R¹, R², R³, X and Y are as described above.

31. The process according to claim 30 further comprises converting the compound obtained into a pharmaceutically acceptable acid addition salt.

32. A method of treating psychosis or schizophrenia comprising administering to a patient in need of such treatment a therapeutically effective amount of at least one compound of formula I

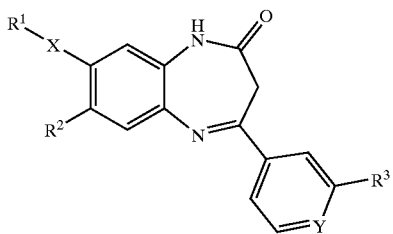

wherein
X is an ethynediyl group;
R¹ is phenyl, which is unsubstituted or substituted by one or two substituents selected from the group consisting of halogen, lower alkyl or fluoro-lower alkyl;
R² is hydrogen,
lower alkyl,
lower alkenyl
lower alkoxy,
halogen,
—NR'R",
pyrrolidin-1-yl,
piperidin-1-yl,
morpholine-4-yl,
fluoro-lower alkyl,
fluoro-lower alkoxy, or
lower alkoxy-(ethoxy)$_m$;
m is 1, 2, 3 or 4;
R' is hydrogen, lower alkyl or $C_3$–$C_6$-cycloalkyl;
R" is hydrogen, lower alkyl or $C_3$–$C_6$-cycloalkyl;
Y is —CH= or =N—;
R³ is a six-membered aromatic heterocycle containing 1 to 3 nitrogen atoms or a pyridine-N-oxide, which rings are unsubstituted or substituted by one or two substituents selected from the group consisting of halogen, fluoro-lower alkyl, fluoro-lower alkoxy, cyano, amino, lower alkylamino, lower alkoxy-lower alkylamino, lower hydroxy-lower alkylamino, —(CH$_2$)$_n$—C(O)—OR", —(CH$_2$)$_n$—C(O)—NR'R", —(CH$_2$)$_n$—SO$_2$—NR'R", —(CH$_2$)$_n$—C(NH$_2$)=NR", hydroxy, lower alkoxy, lower alkylthio, $C_3$–$C_6$-cycloalkyl and lower alkyl, which is optionally substituted by fluoro, —NR'R", hydroxy, lower alkoxy, pyrrolidin-1-yl, azetidin-1-yl, cyano or carbamoyloxy,
whereby R' and R" have the meaning specified above;
n is 0, 1, 2, 3 or 4;
or its pharmaceutically acceptable addition salt thereof.

* * * * *

UNITED STATES PATENT AND TRADEMARK OFFICE
CERTIFICATE OF CORRECTION

PATENT NO.   : 6,949,542 B2
DATED        : September 27, 2005
INVENTOR(S)  : Geo Adam et al.

It is certified that error appears in the above-identified patent and that said Letters Patent is hereby corrected as shown below:

Title page,
Item [73], Assignee, "Hoffman-La Roche Inc.,..." should be -- Hoffmann-La Roche Inc.,... --.

Signed and Sealed this

Fourteenth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,949,542 B2
APPLICATION NO. : 10/350713
DATED : September 27, 2005
INVENTOR(S) : Adam et al.

It is certified that error appears in the above-identified patent and that said Letters Patent is hereby corrected as shown below:

IN THE SPECIFICATION:
* Column 65, lines 35-36, the title of Example M20 reads
"(4-Chloro-5-fluoro-2-{3-[3-(6-methyl-pyridin-3-yl)-phenyl]-3-oxo-propionylamino}-"
The title of Example M20 should read -- (4-Chloro-5-fluoro-2-{3-[3-(6-methyl-pyridin-3-yl)-phenyl]-3-oxo-propionylamino}-phenyl)-carbamic acid tert-butyl ester --.

* Column 73, lines 38-39, the title of Example M60 reads
"{5-Methyl-2-[3-oxo-3-(3-pyridin-4-yl-phenyl)-propionylamino]-4-trifluoromethyl-".
The title of Example M60 should read -- {5-Methyl-2-[3-oxo-3-(3-pyridin-4-yl-phenyl)-propionylamino]-4-trifluoromethyl-phenyl}-carbamic acid tert-butyl ester --.

* Column 78, lines 23-24, the title of Example M84 reads
"{2'-Fluoro-3-[3-oxo-3-(3-pyrazin-2-yl-phenyl)-propionylamino]-biphenyl-4-yl}-carbamic". The title of Example M84 should read -- {2'-Fluoro-3-[3-oxo-3-(3-pyrazin-2-yl-phenyl)-propionylamino]-biphenyl-4-yl}-carbamic-acid tert-butyl ester --.

- Column 90, lines 62-64, the title of Example M147 reads
"{4-(4-Fluoro-phenylethynyl)-2-[3-oxo-3-(3-pyridin-2-yl-phenyl)-propionylamino}-phenyl]-carbamic acid tert-butyl ester". The title of Example M147 should read
-- {4-(4-Fluoro-phenylethynyl)-2- [3-oxo-3-(3-pyridin-2-yl-phenyl)-propionylamino]-phenyl}-carbamic acid tert-butyl ester --.

* Column 110, lines 32-34, the title of Example M244 reads
"(4-Chloro-5-methyl-2-{3-oxo-3-[3-(2-trifluoromethyl-pyridin-4-yl)-phenyl]-". The title of Example M244 should read -- (4-Chloro-5-methyl-2-{3-oxo-3-[3-(2-trifluoromethyl-pyridin-4-yl)- phenyl]-propionylamino }-phenyl)-carbamic acid tert-butyl ester --.

UNITED STATES PATENT AND TRADEMARK OFFICE
CERTIFICATE OF CORRECTION

PATENT NO.       : 6,949,542 B2
APPLICATION NO. : 10/350713
DATED            : September 27, 2005
INVENTOR(S)      : Adam et al.

It is certified that error appears in the above-identified patent and that said Letters Patent is hereby corrected as shown below:

\* Column 140, line 28, the title of Example 83 is missing and should read
-- 8-Fluoro-4-[3-(2-methyl-pyridin-4-yl)-phenyl]-1,3-dihydro-benzo[b][1,4]diazepin-2-one --.

Signed and Sealed this

Twenty-fourth Day of April, 2007

JON W. DUDAS
*Director of the United States Patent and Trademark Office*